US009328386B2

(12) United States Patent
Schaab et al.

(10) Patent No.: US 9,328,386 B2
(45) Date of Patent: May 3, 2016

(54) MARKERS FOR SUSCEPTIBILITY TO AN INHIBITOR OF AN SRC-FAMILY KINASE

(75) Inventors: Christoph Schaab, Martinsried (DE); Klaus Godl, Martinsried (DE); Martin Klammer, Martinsried (DE); Andreas Tebbe, Martinsried (DE); Stefan Müller, Martinsried (DE)

(73) Assignee: Evotec (München) GmbH, Martinsried (DE)

( * ) Notice: Subject to any disclaimer, the term of this patent is extended or adjusted under 35 U.S.C. 154(b) by 0 days.

(21) Appl. No.: 14/239,067

(22) PCT Filed: Aug. 16, 2012

(86) PCT No.: PCT/EP2012/066055
§ 371 (c)(1),
(2), (4) Date: Feb. 14, 2014

(87) PCT Pub. No.: WO2013/024144
PCT Pub. Date: Feb. 21, 2013

(65) Prior Publication Data

US 2014/0302172 A1 Oct. 9, 2014

(30) Foreign Application Priority Data

Aug. 16, 2011 (EP) .................................... 11177711
Aug. 16, 2011 (EP) .................................... 11177726
Aug. 18, 2011 (EP) .................................... 11178024
May 8, 2012 (EP) .................................... 12167185

(51) Int. Cl.
*G01N 33/53* (2006.01)
*C12Q 1/68* (2006.01)
*G01N 33/574* (2006.01)
*G01N 33/569* (2006.01)

(52) U.S. Cl.
CPC ........ *C12Q 1/6881* (2013.01); *G01N 33/56966* (2013.01); *G01N 33/574* (2013.01); *G01N 2333/70546* (2013.01)

(58) Field of Classification Search
None
See application file for complete search history.

(56) References Cited

FOREIGN PATENT DOCUMENTS

WO WO 2008/086342 A2 7/2008

OTHER PUBLICATIONS

Desgrosellier, J. et al. "Integrins in cancer: biological implications and therapeutic opportunities". *Nature Reviews Cancer*, vol. 10 No. 1, Jan. 2010, pp. 9-22.
Huang, F. et al. "Identification of Candidate Molecular Markers Prediction Sensitivity in Solid Tumors to Dasatinib: Rational for Patient Selection". *Cancer Research*, vol. 67 No. 5, Mar. 2007, pp. 2226-2238.
Wu, C. et al. "A Predictive Phosphorylation Signature of Lung Cancer". *PLoS One*, vol. 4 No. 11, Nov. 2009, pp. 1-9.
Klammer, M. et al. "Identifying differentially regulated subnetworks from phosphoproteomic data". *BMC Bioinformatics*, vol. 11, Jun. 2010, 13 pgs.
Klammer, M. et al. "Phophosignature Predicts Dasatinib Response in Non-small Cell Lung Cancer". *Molecular and Cellular Proteomics*, vol. 11 No. 9, May 2012, pp. 651-668.
Sos, M. et al. "Predicting drug susceptibility of non-small cell lung cancers based on genetic lesions". *The Journal of Clinical Investigation*, vol. 119 No. 6, Jun. 2009, pp. 1727-1740.
International Search Report and Written Opinion mailed Oct. 17, 2012 in PCT/EP2012/066055 (12 pgs.).

*Primary Examiner* — James Martinell
(74) *Attorney, Agent, or Firm* — Foley & Lardner LLP

(57) ABSTRACT

The present invention relates to a method for predicting the responsiveness of a mammalian tumor cell or cancer cell to an inhibitor of a kinase of the Src family, such as dasatinib, bosutinib, saracatinib or ponatinib. The present invention also provides for a method for predicting the responsiveness of an individual to an inhibitor of a kinase of the Src family, whereby the individual is suspected to suffer from cancer. These methods involve the evaluation of the status of integrin β4, wherein said status is indicative for the responsiveness to the inhibitor. Furthermore, a kit useful for carrying out the methods described herein as well as an oligo—or polynucleotide and/or antibodies capable of detecting the expression level of integrin β4 for predicting the responsiveness to the inhibitor are provided.

20 Claims, 12 Drawing Sheets

* all four ITGB4 phosphorylation sites

Figure 1:
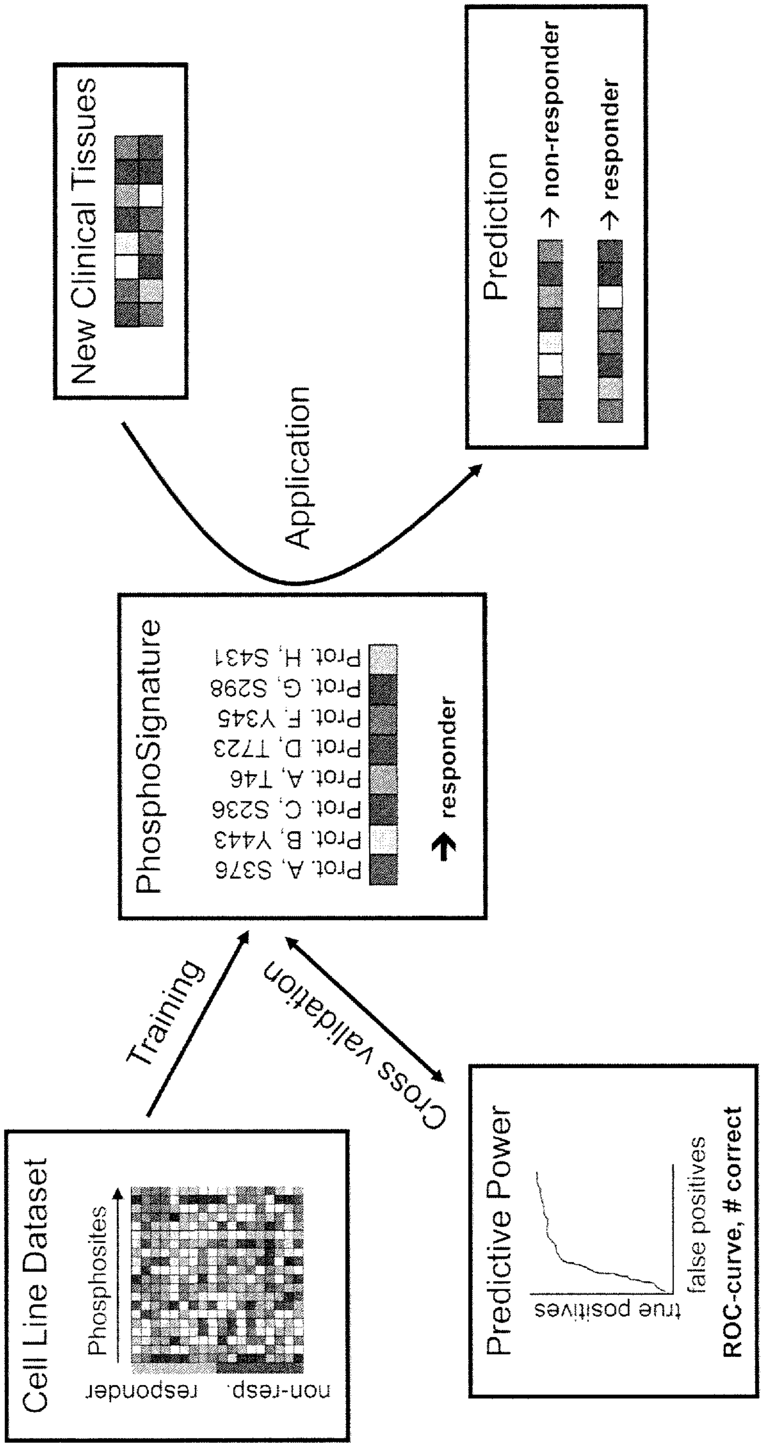

| | ITGB4* | BAIAP2 | GPCR5A | ITPR3 | TNKS1BP1 | ARHGEF18 | IASPP | APG16L | TPD52L2 |
|---|---|---|---|---|---|---|---|---|---|
| ITGB4* | 17.8 | | | | | | | | |
| BAIAP2 | 18 | 14 | | | | | | | |
| GPCR5A | 18 | 17.8 | 17 | | | | | | |
| ITPR3 | 19 | 16.8 | 17 | 13.4 | | | | | |
| TNKS1BP1 | 19 | 18 | 18 | 18 | 17 | | | | |
| ARHGEF18 | 18.8 | 17.8 | 19 | 19 | 18 | 17 | | | |
| IASPP | 18 | 16 | 17.4 | 17 | 18 | 19 | 13.2 | | |
| APG16L | 18.8 | 17 | 17 | 16 | 18 | 17.8 | 16 | 13 | |
| TPD52L2 | 19 | 17.6 | 17 | 18 | 18 | 17.2 | 15.6 | 14.6 | 13.8 |

C

MARKERS FOR SUSCEPTIBILITY TO AN INHIBITOR OF AN SRC-FAMILY KINASE

SEQUENCE LISTING

The instant application contains a Sequence Listing which has been submitted electronically in ASCII format and is hereby incorporated by reference in its entirety. Said ASCII copy, created on Mar. 20, 2014, is named 028622-0282_SL.txt and is 190,378 bytes in size.

The present invention relates to a method for predicting the responsiveness of a mammalian tumor cell or cancer cell to an inhibitor of a kinase of the Src family, such as dasatinib, bosutinib, saracatinib or ponatinib, especially of dasatinib, bosutinib or saracatinib. The present invention also provides for a method for predicting the responsiveness of an individual to an inhibitor of a kinase of the Src family, whereby the individual is suspected to suffer from cancer. These methods involve the evaluation of the status of integrin β4, wherein said status is indicative for the responsiveness to the inhibitor. Furthermore, a kit useful for carrying out the methods described herein as well as an oligo- or polynucleotide and/or antibodies capable of detecting the expression level of integrin β4 for predicting the responsiveness to the inhibitor are provided.

Targeted drugs are less toxic than traditional chemotherapeutic therapies; however, the proportion of patients that benefit from these drugs is often smaller. A marker that confidently predicts the patient's response to a specific therapy would allow an individual therapy selection most likely to benefit the patient. The introduction of targeted drugs for treating cancer is a major biomedical achievement of the past decade (Reichert and Valge-Archer, 2007; Katzel, Fanucchi et al., 2009). Since these drugs selectively block molecular pathways that are typically over-activated in tumour cells, they are more precise and less toxic than traditional chemotherapy therapeutics. However, while many cancer patients benefit from a specific targeted therapy, many others do not. Therefore, predictive molecular markers are needed to confidently predict the patient's response to a specific therapy. Such markers would facilitate therapy personalization, where the selected therapy is based on the molecular profile of the patient.

Predictive tests currently used in the clinic are frequently based on one particular marker that is often linked to the target of the drug. A well-known example for such predictive tests is assessing HER2/neu overexpression using immunohistochemistry or fluorescent in situ hybridization to predict the response to therapy with trastuzumab (Herceptin®, Roche) (see Cobleigh, Vogel et al., 1999; Ross and Fletcher, 1999). However, there is still a need in the art for means and methods allowing the identification of individuals/patients that are responsive to a given therapy.

The stratification of responsive individuals would, in particular, be desirable for patients suffering from cancer, such as lung cancer or breast cancer. Approximately 391,000 incidences and 342,000 deaths from lung cancer were estimated in Europe in 2008 (Ferlay, Parkin et al., 2010), accounting for nearly 20% of all cancer deaths in Europe.

Inhibitors of a kinase of the Src family, such as dasatinib, bosutinib, saracatinib or ponatinib, are used in the treatment of cancer, in particular lung cancer. Approximately 85% of all lung cancer incidences are non-small cell lung cancer (NSCLC) (Jemal, Siegel et al., 2008). Non-small cell lung cancer (NSCLC) is one of the two main types of lung carcinoma, non-small cell (80.4%) and small-cell (16.8%) lung carcinoma, the classification being based on histological criteria. The non-small cell lung carcinomas have a similar prognosis and similar management and comprise three subtypes: squamous cell lung carcinoma, adenocarcinoma and large cell lung carcinoma. Squamous cell lung carcinoma (31.1% of lung cancers) often starts near a central bronchus and commonly shows cavitation and necrosis within the center of the cancer. Adenocarcinoma (29.4% of lung cancers) mostly originates in peripheral lung tissue and is usually associated with smoking. Large cell lung carcinoma (10.7% of lung cancers) is a fast-growing form that develops near the surface of the lung. Common treatments of NSCLC include surgery, chemotherapy, and radiation therapy. In particular, NSCLC is treated with adjuvant chemotherapy (i.e. chemotherapy after surgery). Wu (2009) describes phosphorylation patterns in lung cancer (see Wu (2009) PloS ONE 4 (11) e7994).

Dasatinib (Sprycel®, Bristol-Myers Squibb) is a multi-kinase inhibitor targeting BCR-ABL, the Src-kinase family, c-Kit, ephrin receptors, and PDGFRβ (Bantscheff, Eberhard et al., 2007; Sharma, Weber et al., 2009). It is currently approved for chronic myelogenous leukaemia and Philadelphia chromosome-positive acute lymphoblastic leukaemia. Recently, dasatinib was clinically evaluated in patients with advanced NSCLC. Dasatinib had modest clinical activity, with only one partial response and eleven metabolic responses among thirty-four patients. Neither Src family kinase activation nor EGFR and Kras mutations could predict the response to dasatinib (Johnson, Bekele et al., 2010).

US 2010/0120788 investigated, inter alia, the gene expression pattern in prostate cancer cell lines which were known to be sensitive or resistant to dasatinib. 174 differentially regulated genes were identified and all these genes are, in a speculative manner, proposed as markers for sensitivity to dasatinib. Some of the speculative 174 markers proposed in US 2010/0120788 do indeed not predict responsiveness to dasatinib. US 2010/0120788 reduced the list of 174 marker genes by additionally investigating the effect of treatment with dasatinib on their expression level. Ten genes with modulated expression (SCEL, ANXA3. CST6, LAMC2, ZBED2, EREG, AXL, FHL2, PLAU, and ARNTL2) were selected as predictive markers. US 2010/0120788 also proposes that the expression level of androgen receptor (AR), kallikrein 3, cytokeratin 5, uPA and EphA2 can be used to predict responsiveness. US 2010/0120788 does not speculate, let alone show that the phosphorylation status might be useful as a marker for responsiveness to dasatinib.

The corresponding scientific paper Wang (2007) (Genome Biology 8:R255) identifies five genes (androgen receptor (AR), kallikrein 3, cytokeratin 5, uPA and EphA2) which could be used to stratify patients which are sensitive to dasatinib. In a further paper markers for sensitivity to dasatinib in lung and breast cancer cell lines were investigated (Huang 2007). 67, 2226-2238). A set of six genes, namely Epha2, CAV1. CAV2, ANXA1, PTRF and IGFB2 was identified.

Yet, none of the above documents provides reliable data showing that ITGB4 could be used as marker for responsiveness to dasatinib. In contrast, the data provided herein was verified in clinical samples; see appended examples.

Thus, the technical problem underlying the present invention is the provision of reliable means and methods for the evaluation of cells, in particular tumor cells, and/or individuals for their responsiveness to anti-cancer treatment with inhibitors of kinases of the Src family.

Accordingly, the present invention relates to a method for predicting the responsiveness of a mammalian tumor or cancer cell to an inhibitor of a kinase of the Src-family, said method comprising evaluating, the status of integrin β4

(ITGB4) in/of said cell, wherein said status is indicative of the responsiveness of said cell to the inhibitor.

It is to be understood that the cell to be evaluated may be part of a sample (like a biopsy sample) and that also different cells from a given sample (like a biopsy sample) may be evaluated/assessed/scrutinized without referring from the gist of this invention. Accordingly, the status of integrin β4 may be assessed in cellular or tissue lysates as well as in whole tissue samples (again like biopsy samples etc.).

The term "status of integrin β4 (ITGB4) in a cell/sample/tissue/etc." is also meant to comprise "status of integrin β4 (ITGB4) of a cell/sample/tissue/etc.".

The present invention also relates to a method for predicting the responsiveness of an individual suspected to suffer from, suffering from or being prone to suffer from cancer, to an inhibitor of a kinase of the Src-family, said method comprising evaluating the status of integrin β4 (ITGB4) in/of a sample of said individual wherein said status is indicative of a responsive individual to the inhibitor.

In the present invention it has surprisingly been found that the status of integrin β4 (ITGB4) (for example the expression level or activity of integrin β4 and/or the status of phosphorylation or the phosphosignature of integrin β4) allows the identification of tumor cells/cancer cells or individuals suffering from a cancer that are responsive to an inhibitor of a kinase of the Src family. Recently, several studies tried to identify molecular signatures comprising multiple markers for response predictions, usually based on gene expression profiling (e.g. Dressman, Berchuck et al., 2007; Huang, Reeves et al., 2007). However, no study identified a signature from global phosphoproteomic profiles. Thus, it has been found herein for the first time that the phosphorylation status of a protein can be used as marker for responsiveness to treatment with an inhibitor of a kinase of the Src family. Moreover, the expression level of integrin β4 has unexpectedly been identified as potent and reliable marker for responsiveness to treatment with an inhibitor of a kinase of the Src family. Integrin β4 is a protein that mediates cell-matrix or cell-cell adhesion. Desgrosellier (2010) Nature Reviews reports on the role of integrins in cancer. It has not been proposed in the art that studying Integrin β4 might be useful for predicting responsiveness to anti-cancer treatment.

The data provided herein have been generated using a NSCLC (non small cell lung cancer) cell line collection; in addition, the experiments were validated in a breast cell line collection. Thus, the herein provided means allow the identification of cancer patients which are responsive to an inhibitor of a kinase of the Src family.

In the herein provided experiments. NSCLC cell lines were tested for their response to dasatinib. The identical cell lines were profiled in a global, unbiased, phosphoproteomics study and the phosphoproteome profiles obtained were used to assemble a biomarker signature of 12 phosphorylation sites. The performance of this signature was evaluated in a cross-validation set-up and the robustness of the selected predictive features was investigated. Finally, the predictive power of the signature was confirmed in an independent set of breast cancer cell lines.

Quantitative mass spectrometry was used to globally profile the basal phosphoproteome of a panel of non-small cell lung cancer cell lines. The effect of the kinase inhibitor dasatinib on cellular growth was tested against the same panel. From the phosphoproteome profiles, a signature of twelve phosphorylation sites was identified that can accurately predict dasatinib sensitivity. Surprisingly, it was found that four of the phosphorylation sites belong to integrin β4, a protein that mediates cell-matrix or cell-cell adhesion. The signature was evaluated in cross-validation and label-switch experiments, and in six independently profiled breast cancer cell lines. The use of a pool of cell lines as a common reference enabled the accurate quantification of the detected sites. The accuracy and reproducibility of the phosphoproteomic workflow was demonstrated in label switch experiments. These results show that predictive phosphorylation signatures from global, quantitative phosphoproteomic data were identified as reliable markers for responsiveness to an inhibitor of a kinase of the Src family. As mentioned, the accuracy of the prediction was validated in a leave-one-out cross-validation procedure. 18 out of 19 cell lines could be classified correctly. The obtained prediction accuracy was surprisingly high (94%), the area under the curve was 92%.

The 12 phosphorylation sites were located on 9 different proteins (see Table 1). Unexpectedly, four of the phosphorylation sites are located on Integrin β4 (ITGB4 or CD104). In general, integrins mediate cell-matrix or cell-cell adhesion and are involved in transducing, signals to regulate transcription and cell growth. The subunit β4 associates with α6 and the resulting integrin α6β4 is a receptor for the laminin family of extracellular matrix proteins. Integrin β4 is linked to various signalling pathways such as the MAPK, PI3K-Akt, and Src-Fak pathways (Dans, Gagnoux-Palacios et al., 2001; Chung, Bachelder et al., 2002; Dutta and Shaw. 2008). Though expression of α6β4 is associated with poor patient prognosis in various cancers (Van Waes, Kozarsky et al., 1991; Tagliabue, Ghirelli et al., 1998; Lu, Simin et al., 2008) a role of Integrin β4 in the prediction to responsiveness to anti-cancer treatment has not been proposed. According to the PhosphoSite database (Hornbeck, Chabra et al., 2004) the sites S1457 and S1518 were detected in previous mass spectrometry experiments, but the physiological function for any of the four sites identified herein has not been described so far. All four sites are stronger phosphorylated in the dasatinib sensitive cells than the dasatinib resistant cells.

Besides the sites on integrin β4, the signature comprised eight other phosphorylation sites on eight other proteins. Like integrin β4, the brain-specific angiogenesis inhibitor 1-associated protein 2 (BAIAP2) and the Rho guanine nucleotide exchange factor 18 (ARHGEF8) are involved in regulating the actin cytoskeleton. BAIAP2 (also called insulin receptor substrate p53. IRSp53) serves as an adaptor linking a Ras-related protein Rac1 with a Wiskott-Aldrich syndrome protein family member 2 (WAVE2). The recruitment of WAVE2 induces Cdc42 and the formation of filopodia (Miki, Yamaguchi et al., 2000; Yamagishi, Masuda et al., 2004). ARGHEF18 acts as a guanine nucleotide exchange factor for the GTPases RhoA and Rac1 (Blomquist, Schworer et al., 2000; Niu, Profirovic et al., 2003). Activation of RhoA induces actin stress fibres and cell rounding.

The RelA-associated inhibitor (PPP1R13L, also called inhibitor of ASPP protein, IASPP) and the G-protein coupled receptor family C group 5 member A (GPRC5A, also called retinoic acid-induced protein 3. RAI3) are functionally connected to the tumour suppressor p53. The term "retinoic acid-induced protein 3. RAI3" as used herein is also called GPCR5A. The terms GPRC5A and GPCR5A are, accordingly, used interchangeably herein. PPP1R13L (also known as IASPP) binds to p53 and inhibits its activation by ASPP1 and ASPP2 (Bergamaschi, Samuels et al., 2006). On the other hand, p53 was demonstrated to bind to the promoter of GPRC5A and negatively regulate its expression (Wu, Ding et al., 2005).

The tumour suppressor p53 is associated with at least two signature proteins. At the same time, p53 is inactivated by mutations in a large proportion of tumour cell lines. Therefore, one might assume that the p53-status alone might be predictive of a response to dasatinib. According to the IARC TP53 database (Petitjean, Mathe et al., 2007). 6 out of 7 sensitive and 3 out of 5 non-sensitive cell lines have a mutation in the p53 protein (7 cell lines were not listed, see also Table 2). 19 cell lines that had consistent sensitivity, as determined in this study and previously (Sos, Michel et al., 2009) were used herein. Since the effect on function is not known for all mutations, it was assumed that any mutation, apart from neutral or silent mutations, was functionally relevant. The null-hypothesis that sensitivity to treatment with dasatinib does not differ between p53-mutated and p53-wildtype cell lines cannot be rejected (Fisher's exact test p-value is 0.52). Therefore, the mutation status of p53 is, in contrast to the herein provided markers, not a good predictor of dasatinib sensitivity. This shows that the selection of the phosphorylation sites of the herein provided marker proteins for responsiveness to anti-cancer treatment is counterintuitive.

Further, there is no link between the other four proteins inositol 1,4,5-triphosphate receptor type 3 (ITPR3), 182 kDa tankyrase-1-binding protein (TNKS1BP1), autophagy-related protein 16-1 (APG16L), tumour protein D54 (TPD52L2), and the main dasatinib targets. The protein "autophagy-related protein 16-1" (short "APG16L") is also termed herein "ATG16L1"; both terms can be used interchangeably herein.

It was found herein that the predictor, in particular the newly defined phophosignature predictor, identified from a panel of NSCLC-cell lines can also be used in other cancer cell lines. As shown in the appended examples, 5 out of 6 breast cancer cell lines were correctly predicted (prediction accuracy 83%). Only one resistant cell line (MDA-MB-468) was predicted to be sensitive.

Furthermore, it was found that the herein provided methods allow for the prediction of the responsiveness to various inhibitors of the Src-family like dasatinib, saracatinib and bosutinib. As shown herein in relation to cancer cell lines representing, cancer types like NSCLC and breast cancer, the prediction accuracy of the herein provided methods is high, usually above 80%. Accordingly, the herein provided methods are highly predictive for responsiveness to inhibitors of the Src-family, having a prediction accuracy of preferably 70%, 75%, or more, more preferably 80%, 85%, 90% or more, and most preferably 95% or more. For example, the herein provided methods usually have a prediction accuracy of more than 80%, more preferably 85%, 90%, 91%, 92%, 93%, 94% or more and most preferably of 95% or more, and up to 100% in relation to responsiveness to dasatinib.

Herein, the phosphorylation data were globally normalized, assuming that the overall phosphoproteome is fairly well conserved between the different cell lines. However, this strategy is no longer applicable to targeted detection of the selected phosphosites, since all phosphosites will be regulated. We provide an alternative normalization strategy using the expression of eight non-regulated ribosomal proteins. It was demonstrated that the prediction of sensitivity using the phospho-signature is stable for the application of the alternative normalization strategy.

The identified phospho-signature having twelve phosphorylation sites is therefore highly predictive for the sensitivity to treatment with an inhibitor of a kinase of the Src family (such as dasatinib) in NSCLC cell lines as well as breast cancer cell lines. Subsets or individual markers thereof are also suitable for predicting the responsiveness to an inhibitor of a kinase of the Src family. While it was demonstrated that the method permits identifying a highly predictive phosphorylation signature for response to dasatinib treatment in NSCLC cell lines, it is evident that the method can also be applied to other drugs, particularly other kinase inhibitors, and to other tumor types.

In a recent study, Andersen et al. identified phosphorylation sites predicting response to phosphatidylinositol 3-kinase (PI3K) inhibitors (Andersen. Sathyanarayanan et al., 2010). Their study differs in two aspects from the experiments underlying the present invention. First, the authors focused on the PI3K and MAPK pathways by immunoprecipitating phosphorylated peptides with antibodies directed against corresponding phospho-motifs. In contrast, herein an unbiased approach was followed, where no hypothesis about the involved signalling pathways had to be made. Second, the authors first investigated the regulation of phosphorylation sites upon drug treatment in one sensitive cell line, and subsequently confirmed the applicability of one site to response prediction by evaluating its basal phosphorylation in a panel of cell lines. In contrast, the experiments provided herein started directly by investigating a panel of responsive and non-responsive cell lines.

In sum, the identification of the status of integrin β4 as marker for susceptibility of (a) tumor or cancer cell(s) to an inhibitor of a kinase of the Src family provides an effective therapeutic approach for patients suffering from cancer. Treatment of susceptible patients with such an inhibitor may lead to an increase in clinical response rate and/or an increase in survival.

As disclosed herein, the present invention provides for means and methods that allow the prediction of the responsiveness (of a mammalian tumor or cancer cell or of a mammalian tumor or cancer tissue) to inhibitors of the Src-kinases/inhibitors of a kinase of the Src-family. Therefore, also comprised are means and methods for the elucidation of the responders (individuals/patients) to inhibitors of the Src-kinases/inhibitors of a kinase of the Src-family. These means and methods comprise the evaluation/measurement/assessment/scrutinization/determination of the status of integrin β4 (ITGB4) in a (tumor or cancer) cell or in a sample (like in a tumor or cancer sample), wherein said status is indicative of the responsiveness of said cell or said sample. In other words, in accordance with this invention, the status of integrin β4 (ITGB4) is evaluated/measured/assessed/scrutinized/determined and, depending on said status, it can be determined whether or not the tumor or cancer cell or the tumor or cancer (of an individual, like a patient) is responsive to a treatment with (an) inhibitor(s) of the Src-kinases/(an) inhibitor(s) of a kinase of the Src-family. The status of integrin β4 (ITGB4) to be assessed/evaluated/scrutinized in accordance with this invention comprises the expression status (like mRNA status or protein status) or the phosphorylation status (or the "phosphosignature") of integrin β4 (ITGB4). It is to be understood that the term "phosphosignature" does comprise individual phosphorylations/phosphorylation sites of individual proteins (like one or more phosphorylation sites as defined herein on ITGB4) as well as all phosphorylations and/or phosphorylation sites on individual proteins and also phosphorylations and/or phosphorylation sites on different proteins within any given cell or any given sample.

In context of this invention it is evident for the skilled artisan that terms like "evaluating the status of integrin b4 (ITGB4) in a tumor or cancer cell or a sample"" or "evaluating the phosphorylation of integrin b4 (ITGB4) in a tumor or cancer cell or a sample" comprise and mean also the evaluation or assessment of the status of such a cell or of such a sample. Accordingly, it is to be understood that the present invention does not only comprise the direct measurements of these statuses in the corresponding cells, tissues and/or samples, but does also comprise the measurement/evaluation etc in corresponding processed samples, like cell or tissue lysates, purified cell or tissue lysates, etc. Therefore, and in accordance with this invention, it is evident that the expression status as well as the phosphorylation status can be evaluated/measured/assessed/scrutinized/determined in or on the same (cellular or tissue) sample but can also be evaluated/measured/assessed/scrutinized/determined in or on different samples (for example different cell or tissue samples from the same individual, like the same patient). It is also envisaged in context of this invention that different samples originating from the same tissue (for example biopsy tissue) be assessed in accordance with this invention. Such a sample may, accordingly, be divided in order to evaluate/measure/assess/scrutinized/determine the status/the statuses of integrin b4 (ITGB4) in said sample. The present invention also provides for means and methods that allow the prediction of the responsiveness (of a mammalian tumor or cancer cell or of a mammalian tumor or cancer tissue) to inhibitors of the Src-kinases/inhibitors of a kinase of the Src-family, wherein one or more of the following phosphorylation site(s) are determined: S509 of BAIAP2; S345 of GPRC5A; S916 of ITPR3; S429 of TNKS1BP1; S1101 of ARHGEF18; S102 of IASPP; S269 of APG16L; and/or S161 of TPD52L2. Again, an increase in the phosphorylation of one or more of these phosphorylation sites in comparison to a control is (also) indicative of the responsiveness of a (tumor or cancer) cell to the inhibitors of the Src-kinases/inhibitors of a kinase of the Src-family. Such an increase in a sample or cell of an individual/patient is (also) indicative of the responsiveness an individual/patient to said inhibitor Furthermore, it is to be understood that in accordance with this invention these evaluation, etc. of the status or the statuses of integrin b4 (ITGB4), may comprise an individual measurement, like the measurement of the expression status or the measurement of the phosphorylation status but also concomitant/concurrently measurements are envisaged. The measurement can, if desired also take place in a sequential manner, i.e. the expression status may be determined before the phosphorylation status or vice versa. Again, also individual measurements of the status of integrin b4 (ITGB4) (like the individual evaluation of the phosphorylation status or the individual evaluation of the expression status" is within the gist of the present invention and give conclusive information of the responsiveness of a mammalian tumor or cancer cell to inhibitors of the Src-kinases/inhibitors of a kinase of the Src-family.

As used herein, a kinase "inhibitor" or "inhibitor of a kinase" refers to any compound capable of downregulating, decreasing, suppressing or otherwise regulating the amount and/or activity of a kinase. Inhibition of these kinases can be achieved by any of a variety of mechanisms known in the art, including, but not limited to binding directly to the kinase polypeptide, denaturing or otherwise inactivating the kinase, or inhibiting the expression of the gene (e.g., transcription to mRNA, translation to a nascent polypeptide, and/or final polypeptide modifications to a mature protein), which encodes the kinase. Generally, kinase inhibitors may be proteins, polypeptides, nucleic acids, small molecules, or other chemical moieties.

As used herein the term "inhibiting" or "inhibition" refers to the ability of a compound to downregulate, decrease, reduce, suppress, inactivate, or inhibit at least partially the activity of an enzyme, or the expression of an enzyme or protein The term "inhibitor of a kinase of the Src family" means accordingly in this context a compound capable of inhibiting the expression and/or activity of a kinase of the Src family as defined herein. An "inhibitor of a kinase of the Src family" may, for example, interfere with transcription of a gene encoding such a kinase, processing (e.g. splicing, export from the nucleus and the like) of the gene product (e.g. unspliced or partially spliced mRNA) and/or translation of the gene product (e.g. mature mRNA). The inhibitor of a kinase of the Src family may also interfere with further modification (like phosphorylation) of the polypeptide/protein encoded by the kinase gene and thus completely or partially inhibit the activity of the kinase. Furthermore, the inhibitor of a kinase of the Src family inhibitor may interfere with interactions of the kinase with other proteins. It is particularly preferred that inhibitors to be used in accordance with the invention show a high potency (demonstrated by a low $IC_{50}$ value) for inhibiting kinase activity.

The Src family kinase is a family of non-receptor tyrosine kinases that includes Src, Yes, Fyn, and Fgr, forming the SrcA subfamily, Lck, Hck, Blk, and Lyn in the SrcB subfamily, and Frk in its own subfamily. The SrcA and SrcB subfamilies are specific to vertebrates, accordingly, the use of inhibitors of (a) kinase(s) of the SrcA and/or SrcB subfamilies is preferred herein. The affinity of an inhibitor of a kinase of the Src family in the meaning of the present invention to said kinase is preferably higher than the affinity of said inhibitor to the inhibitor of nuclear factor κ-B subunits β and γ (IKBKB and IKBKG); see Example 6. For example, the affinity of the inhibitor of a kinase of the Src family to said kinase is preferably at least 5-fold higher, preferably at least 10-fold higher than the affinity of the inhibitor to the inhibitor of nuclear factor κ-B subunits β and γ (IKBKB and IKBKG). Examples of inhibitors of a kinase of the Src-family which have a higher affinity to said kinase than to the inhibitor of nuclear factor κ-B subunits β and γ (IKBKB and IKBKG) are dasatinib, bosutinib (SKI-606), or saracatinib (AZD530).

Thus, the present invention relates to a method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein the affinity of the inhibitor of a kinase of the Src family to said kinase is preferably at least 5-fold higher, preferably at least 10-fold higher than the affinity of said inhibitor to the inhibitor of nuclear factor κ-B subunits β and γ (IKBKB or IKBKG).

Accordingly, the present invention relates to a method for predicting the responsiveness of an individual to an inhibitor of a kinase of the Src-family, said method comprising evaluating the status of integrin β4 (ITGB4) in/of a sample of an individual suspected to suffer from cancer, suffering from cancer or being prone to suffer from cancer, wherein said status is indicative of a responsive individual to the inhibitor, wherein the affinity of the inhibitor of a kinase of the Src family to said kinase is preferably at least 5-fold higher, preferably at least 10-fold higher than the affinity of said inhibitor to the inhibitor of nuclear factor κ-B subunits β and γ (IKBKB or IKBKG).

All explanations given herein in relation to "responsiveness of a mammalian tumor or cancer cell", "responsiveness of an individual", "evaluation of the status of integrin β4", "cancer" or "tumor", and the like, apply mutatis mutandis to the above aspects of the present invention. Corresponding items provided herein can be combined with the above aspects of the present invention.

The following inhibitors of (a) kinase(s) of the Src family are preferably used in accordance with the present invention: dasatinib, bosutinib (SKI-606), saracatinib (AZD530), and/ or posatinib (AP24534) and/or pharmaceutically acceptable salts, solvates, and/or hydrates of these inhibitors. The use of dasatinib, bosutinib (SKI-606), or saracatinib (AZD530) is particularly preferred herein. Also the use of the corresponding pharmaceutically acceptable salts, solvates, and/or hydrates thereof is particularly preferred.

Most preferably, dasatinib or (a) pharmaceutically acceptable salt(s), solvate(s), and/or hydrate(s) thereof is used. These and further exemplary inhibitors and pharmaceutically acceptable salts, solvates, and/or hydrates of these inhibitors to be used herein are described in more detail below.

Brand Name: dasatinib (Trade name Sprycel)

Code name: BMS-354825

Structure

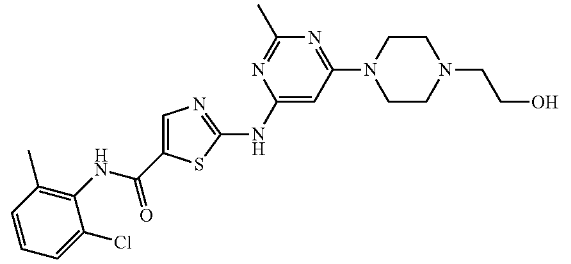 [SMILES: Cc1nc(Nc2ncc(C(=O)Nc3c(C)cccc3Cl)s2)cc(N2CCN(CCO)CC2)n1]

IUPAC Name: N-(2-chloro-6-methylphenyl)-2-[[6-[4-(2-hydroxyethyl)piperazin-1-yl]-2-methylpyrimidin-4-yl]amino]-1,3-thiazole-5-carboxamide Affinities (basic outline): Ephrin receptors≈SFK≈ABL, PDGFR, CSFIR. KIT, DDR1

Molecule Group Thiazol

Clinical Phase: Approved for Imatinib Resistant CML and Ph+ ALL; Phase II (NSCLC, prostate cancer. AML, breast cancer, head and neck Cancer, colorectal cancer)

Developer: BMS

Brand Name: bosutinib

Code Name: SKI-606

Structure:

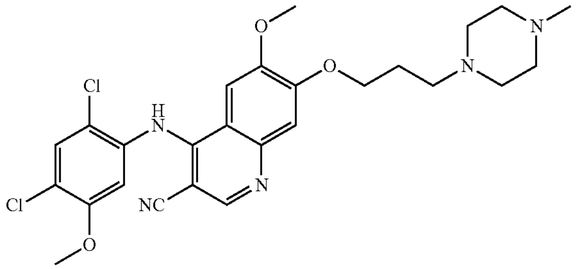 [SMILES: COc1cc(Nc2c(C#N)cnc3cc(OCCCN4CCN(C)CC4)c(OC)cc23)c(Cl)cc1Cl]

IUPAC Name: 4-(2,4-dichloro-5-methoxyphenylamino)-6-methoxy-7-(3-(4-methylpiperazin-1-yl)propoxy)quinoline-3-carbonitrile Affinities (basic outline): ABL≈SFK>BTK fam>STE20 fam Selectivity/affinity source: QCP, KinaseProfiler Molecule Group: quinoline Clinical Phase: I-II (Advanced solid tumor) II (Breast Cancer)

Developer: Pfizer

Brand Name: saracatinib

Code Name: AZD530

Structure:

AZD0530

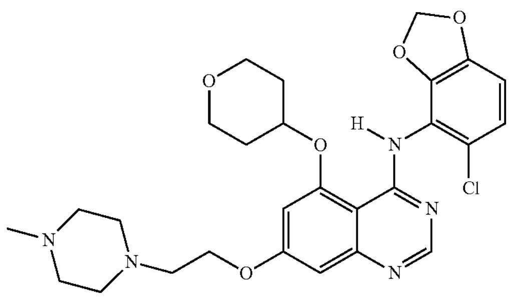

IUPAC Name: N-(5-Chloro-1,3-benzodioxol-4-yl)-7-[2-(4-methyl-1-piperazinyl)ethoxy]-5-[(tetrahydro-2H-pyran-4-yl)oxy]-4-quinazolinamine Affinities (basic outline): SFK>mutEGFR(L858R L861Q)>ABL>>KIT>>CSK>EGFR 13 of 23 tested submicromolar Selectivity/affinity source: IVKA Molecule Group: quinazoline Clinical Phase: I (Advanced solid tumor), I-II (Pancreatic Cancer), II (Ovarian, Prostate, Osteosarcoma, Melanoma, Colon Cancer . . . )

Developer: Astra Zeneca

Brand Name: ponatinib

Code Name: AP24534

Structure:

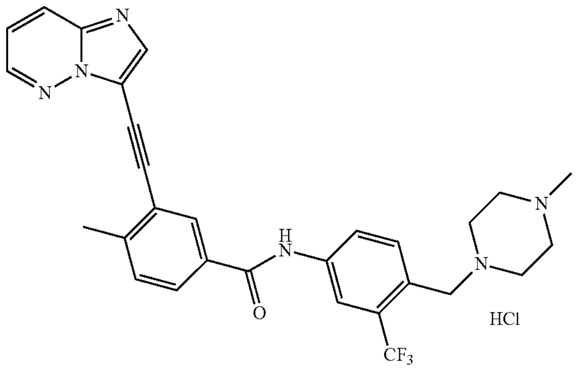 [SMILES: Cc1ccc(C(=O)Nc2ccc(CN3CCN(C)CC3)c(C(F)(F)F)c2)cc1C#Cc1cnc2cccnn12 ; Cl]

IUPAC Name: 3-(imidazo[1,2-b]pyridazin-3-ylethynyl)-4-methyl-N-(4-((4-methylpiperazin-1-yl)methyl)-3-(trifluoromethyl)phenyl)benzamide Affinities (basic outline): SFK>ABL>EPHRs>PDGFRa>VEGFR>FGFR>KIT Selectivity/affinity source: rather broad spectrum/Kinase Hotspot assay (>100 kinases)

Molecule Group: purine

Clinical Phase: II (ALL,CML)

Developer: ARIAD

Brand Name: bafetinib

Code Name: INNO-406

Structure:

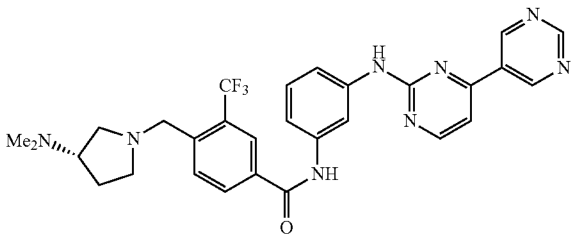 [SMILES: CN(C)[C@H]1CCN(Cc2ccc(C(=O)Nc3cccc(Nc4nccc(-c5cncnc5)n4)c3)cc2C(F)(F)F)C1]

IUPAC Name: N-[3-([5,5'-Bipyrimidin]-2-ylamino)-4-methylphenyl]-4-[[(3S)-3-(dimethylamino)-1-pyrrolidinyl]methyl]-3-(trifluoromethyl)benzamide Affinities (basic outline): ABL>LYN,LCK>residual SFK>KIT=PDGFR (kinases possess an ic50<1 μM)

Selectivity/affinity source: KinaseProfiler (272 kinases)[11]

Molecule Group: 2-phenylaminopyrimidine

Clinical Phase: I (ALL,CML) II (B-CCL)

Developer: CytRx

Code Name: M475271

Structure:

M475271

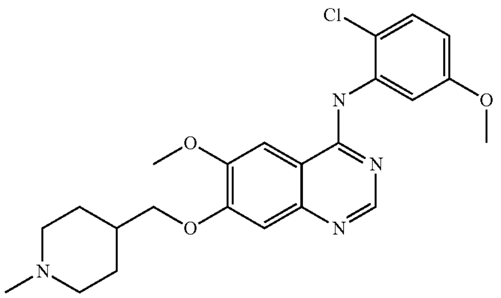

IUPAC Name: 4-quinazolinamine, N-(2-chloro-5-methoxyphenyl)-6-methoxy-7-[(1-methyl-4-piperidinyl)methoxy]-(9Cl)

Affinities (basic outline):

YES(10)>SRC(25 nM)>LCK(200 nM)>VEGFR(500 nM)>EGFR(600 nM)>>CSK(7600 nM)>>FGFR1(20 μM)

Selectivity/affinity source: IVKA

Molecule Group: quinazoline

Clinical Phase: I-II PC

Developer: Astra Zeneca

Code Name: CGP76030

Structure:

7

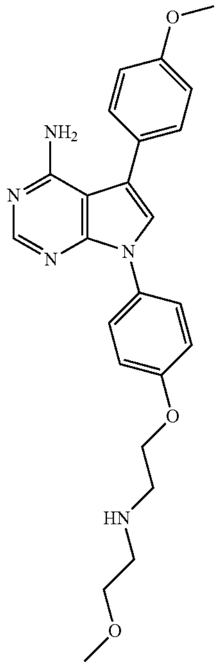

CGP-76030

IUPAC Name: 7-{4-[2-(2-Methoxy-ethylamino)-ethyl]-phenyl}-5-(4-methoxy-phenyl)-7H-pyrrolo[2,3-d]pyrimidin-4-ylamine Affinities (basic outline):

YES(2 nM)>SRC>FGR>LYN>ABL(180 nM)>LCK(250 nM)>EGFR(260 nM)>PYK2(500 nM)>CSK(560 nM)>VEGFR(2.7 μM)

Selectivity/affinity source: IVKA

Molecule Group: pyrrolo-pyrimidine

Clinical Phase: preclinical

Developer: Novartis

Code Name: AP23846

Structure:

AP23846

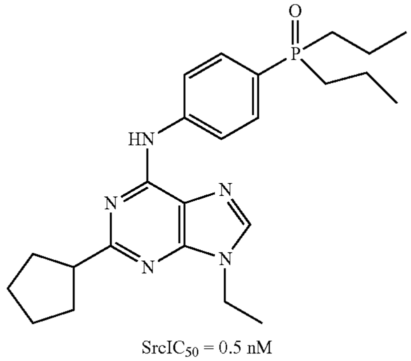

Src$IC_{50}$ = 0.5 nM

IUPAC Name: [2-cyclopentyl-N-(4-(dimethylphosphoryl)phenyl)-9-ethyl-9H-purin-6-amine]

Affinities (basic outline):

SFK(all<1 nM)>FLT3>FGR>ABL(21 nM)>FLT1>IR>VEGFR>KIT(193 nM)>PDGFRa(247nM)>PDGFRb(413 nM)>EGFR(>3 μM)

Selectivity/affinity source: IVKA

Molecule Group: purine

Clinical Phase: toxic[17]

Developer: ARIAD

Code Name: SU6656

Structure:

SU6656

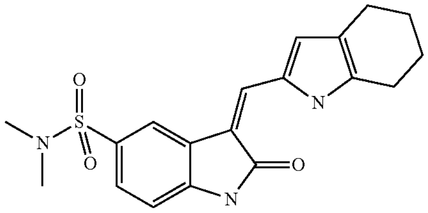

IUPAC Name: (2-oxo-3-(4,5,6,7-tetrahydro-1H-indol-2-ylmethylene)-2,3-dihydro-1H-indole-5-sulfonic acid dimethylamide)

Affinities (basic outline): SFK(0.02-6.88 nM)>ABL>FGFR1>MET(3 nM)>FRK>CSK(7 nM)

Selectivity/affinity source: IVKA

Molecule Group: indolinone

Developer: SUGEN

Brand Name: kxo-I

Code Name: KX2-391

Structure:

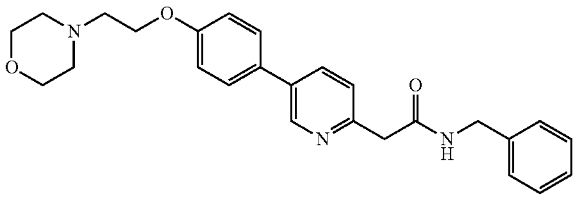 [SMILES: O=C(Cc1ccc(-c2ccc(OCCN3CCOCC3)cc2)cn1)NCc1ccccc1]

IUPAC Name: (E)-(4-(2-(1H-indazol-3-yl)vinyl)phenyl)(piperazin-1-yl)methanone

Affinities (basic outline): Targeting substrate binding site

Clinical Phase: I (Advanced solid tumor, Lymphoma)

Developer: Kinex

Code Name XL999

Structure:

XL-999

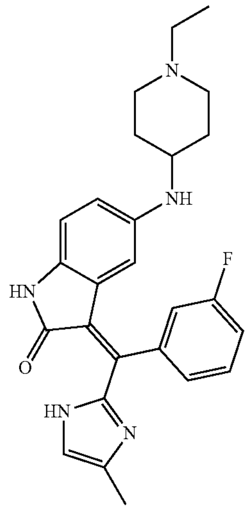

IUPAC Name: 5-(1-Ethyl-piperidin-4-ylamino)-3-[1-(3-fluoro-phenyl)-1-(4-methyl-1H-imidazol-2-yl)-meth-(Z)-ylidene]-1,3-dihydro-indol-2-one Affinities (basic outline): Targeting substrate binding site Developer: Exelixis Code Name XL-647

Structure:

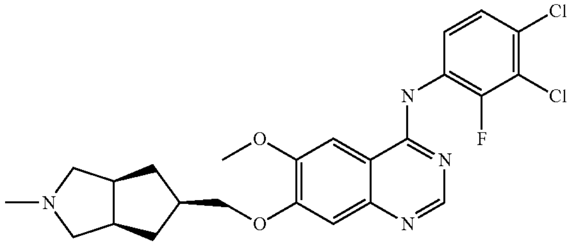 [SMILES: COc1cc2c(Nc3ccc(Cl)c(Cl)c3F)ncnc2cc1OC[C@@H]1C[C@@H]2CN(C)C[C@@H]2C1]

IUPAC Name: N-(3,4-Dichloro-2-fluorophenyl)-6-methoxy-7-[[(3aR,5r,6aS)-2-methyloctahydrocyclopenta[c]pyrrol-5-yl]methoxy]quinazolin-4-anine Affinities (basic outline): EGFR, EphB4, HER2, Src, VEGFR-2 VEGFR-3

Clinical Phase: III (NSCLC)

Developer: Kadmon

As described in more detail below, use of inhibitors of a kinase of the Src family in accordance with the present invention is not limited to the herein described or further known inhibitors. Accordingly, also yet unknown inhibitors may be used in accordance with the present invention. Such inhibitors may be identified by the methods described and provided herein and methods known in the art, like high-throughput screening using biochemical assays for inhibition of kinases of the Src family.

Assays for screening of potential inhibitors and, in particular, for identifying inhibitors as defined herein, comprise, for example, in vitro competition binding assays to quantitatively measure interactions between test compounds and recombinantly expressed kinases[1]. Hereby, competition with immobilized capture compounds and free test compounds is performed. Test compounds that bind the kinase active site will reduce the amount of kinase captured on solid support, whereas test molecules that do not bind the kinase have no effect on the amount of kinase captured on the solid support. Furthermore, inhibitor selectivity can also be assessed in parallel enzymatic assays for a set of recombinant protein kinases.[2,3] These assays are based on the measurement of the inhibitory effect of a kinase inhibitor and determine the concentration of compound required for 50% inhibition of the protein kinases of interest. Proteomics methods are also an efficient tool to identify cellular targets of kinase inhibitors. Kinases are enriched from cellular lysates by immobilized capture compounds, so the native target spectrum of a kinase inhibitor can be determined.[4]

Assays for screening of potential inhibitors and, in particular, for identifying inhibitors as defined herein, are, for example, described in the following papers (which have also been cited above):

Fabian et al; Nat. Biotechnol. 2005 23(3):329-36

Davies et al.; Biochem. J. 2000 351: 95-105.

Bain et al.; Biochem. J. 2003 371: 199-204.

Godl et al; Proc Natl Acad Sci USA. 2003 100(26):15434-9.

Based on his general knowledge a person skilled in the art is in the position to identify inhibitors or verify the inhibiting activity of compounds suspected of being inhibitors. These tests may be employed on cell(s) or cell culture(s) described in the appended example, but also further cell(s)/tissue(s)/cell culture(s) may be used, such as cell(s)/tissue(s)/cell culture(s) derived from biopsies.

The herein provided methods for predicting or determining the responsiveness of a mammalian tumor or cancer cell to an inhibitor of a kinase of the Src-family or methods for predicting the responsiveness of an individual to an inhibitor of a kinase of the Src-family comprise the evaluation of the status of integrin β4 (ITGB4). The status is indicative of the responsiveness of said cell to the inhibitor or of a responsive individual to the inhibitor, respectively.

The status of integrin β4 (ITGB4) may be determined using a sample of an individual suffering from, suspected to suffer from or being prone to suffer from cancer. Said sample may, for example, be obtained by (a) biopsy (biopsies). Preferably, said sample is obtained from a patient suffering from, suspected to suffer from or being prone to suffer from lung cancer (such as NSCLC) or breast cancer. It is preferred herein that said sample is obtained from (a) tumor(s) and, accordingly, is (a) tumor cell(s) or (a) tumor tissue(s) suspected of being for example a NSCLC tumor, a breast tumor and the like. A person skilled in the art is in the position to identify such tumors and/or individuals/patients suffering from corresponding cancer using standard techniques known in the art and methods disclosed herein.

It is also envisaged herein that two or more different inhibitors (i.e. inhibitors having different chemical formulae, optionally non-structurally related inhibitors) may be tested simultaneously. However, it is preferred herein that only one inhibitor is tested at one time.

Preferred inhibitors to be used and tested in the present invention are described herein.

As mentioned, it has been found herein that the expression level of integrin β4 can be used to evaluate whether an individual or a cell and the like respond to an inhibitor of a kinase of the Src family. Accordingly, the status of integrin β4 can be the expression level of integrin β4, wherein an increase in said expression level in comparison to the control is indicative of the responsiveness of said cell or a responsive individual to the inhibitor. Preferably, the expression level of integrin β4 is at least 2.5-fold, preferably at least 5-fold, even more preferably at least 10-fold increased in comparison to the control. The activity of integrin β4 can also be measured and evaluated in addition or in the alternative to the expression level of integrin β4 in accordance with the present invention.

In accordance with the above, the present invention relates to the following aspects:

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said status is the expression level of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said status is the expression level of integrin β4, wherein an increase in said expression level in comparison to the control is indicative of the responsiveness of said cell to the inhibitor.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4, wherein an increase in said expression level in comparison to the control is indicative of the responsiveness of said cell to the inhibitor.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4, wherein an increase in said expression level in comparison to the control is indicative of the responsiveness of said cell to the inhibitor.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4, wherein an increase in said expression level in comparison to the control is indicative of the responsiveness of said cell to the inhibitor.

In a preferred embodiment, the expression level of integrin β4 is the mRNA expression level of integrin β4. A person skilled in the art is aware of corresponding means and methods for detecting and evaluating the integrin β4 expression level and/or activity. Exemplary methods to be used include but are not limited to molecular assessments such as Western Blots, Northern Blots, Real-Time PCR and the like.

If the gene product is an RNA, in particular an mRNA (e.g. unspliced, partially spliced or spliced mRNA), determination can be performed by taking advantage of northern blotting techniques, in situ hybridization, hybridization on microarrays or DNA chips equipped with one or more probes or probe sets specific for mRNA transcripts or PCR techniques, like, quantitative PCR techniques, such as Real time PCR. These and other suitable methods for binding (specific) mRNA are well known in the art and are, for example, described in Sambrook and Russell (2001, loc. cit.). A skilled person is capable of determining the amount of the component, in particular said gene products, by taking advantage of a correlation, preferably a linear correlation, between the intensity of a detection signal and the amount of the gene product to be determined.

Accordingly, the present invention relates to the following aspects:

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said status is the expression level of integrin β4, wherein the expression level of integrin β4 is the mRNA expression level of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4, wherein the expression level of integrin β4 is the mRNA expression level of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4, wherein the expression level of integrin β4 is the mRNA expression level of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4, wherein the expression level of integrin β4 is the mRNA expression level of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4, wherein an increase in said expression level in comparison to the control is indicative of the responsiveness of said cell to the inhibitor, wherein the expression level of integrin β4 is the mRNA expression level of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4, wherein an increase in said expression level in comparison to the control is indicative of the responsiveness of said cell to the inhibitor, wherein the expression level of integrin β4 is the mRNA expression level of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4, wherein an increase in said expression level in comparison to the control is indicative of the responsiveness of said cell to the inhibitor, wherein the expression level of integrin β4 is the mRNA expression level of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said status is the expression level of integrin β4, wherein an increase in said expression level in comparison to the control is indicative of the responsiveness of said cell to the inhibitor, wherein the expression level of integrin β4 is the mRNA expression level of integrin β4.

In a further preferred embodiment, the expression level of integrin β4 to be assessed in context of this invention is the protein expression level of integrin β4. Quantification of the protein expression level can be performed by taking advantage of the well known techniques such as Western blotting techniques, immunoassays, gel- or blot-based methods, IHC, mass spectrometry, flow cytometry, FACS and the like.

Generally, a person skilled in the art is aware of methods for the quantitation of (a) polypeptide(s)/protein(s). Amounts of purified polypeptide in solution can be determined by physical methods, e.g. photometry. Methods of quantifying a particular polypeptide in a mixture may rely on specific binding, e.g. of antibodies. Antibodies to be used for quantification and detection of the expression of integrin β4 are known in the art, like commercially available anti integrin β4 antibodies, such as anti-integrin beta 4 antibody [M126] (ab29042, Abcam), CAB005258 (sc-9090, Santa Cruz Biotechnology), NB100-78102 (Novus Biologicals), #4707 (Cell Signaling Technology) or SAB4501588 (Sigma-Aldrich). Such antibodies may be used in the herein provided detection and quantitation methods. Specific detection and quantitation methods exploiting the specificity of antibodies comprise for example immunohistochemistry (in situ). Western blotting combines separation of a mixture of proteins by electrophoresis and specific detection with antibodies. Electrophoresis may be multi-dimensional such as 2D electrophoresis. Usually, polypeptides are separated in 2D electrophoresis by their apparent molecular weight along one dimension and by their isoelectric point along the other direction. Alternatively, protein quantitation methods may involve but are not limited to mass spectrometry or enzyme-linked immunosorbant assay methods.

Accordingly, the present invention relates to the following aspects:

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said status is the expression level of integrin β4, wherein the expression level of integrin β4 is the protein expression level of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4, wherein the expression level of integrin β4 is the protein expression level of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4, wherein the expression level of integrin β4 is the protein expression level of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4, wherein the expression level of integrin β4 is the protein expression level of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4, wherein an increase in said expression level in comparison to the control is indicative of the responsiveness of said cell to the inhibitor, wherein the expression level of integrin β4 is the protein expression level of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4, wherein an increase in said expression level in comparison to the control is indicative of the responsiveness of said cell to the inhibitor, wherein the expression level of integrin β4 is the protein expression level of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4, wherein an increase in said expression level in comparison to the control is indicative of the responsiveness of said cell to the inhibitor, wherein the expression level of integrin β4 is the protein expression level of integrin β4.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said status is the expression level of integrin β4, wherein an increase in said expression level in comparison to the control is indicative of the responsiveness of said cell to the inhibitor and wherein the expression level of integrin β4 is the protein expression level of integrin β4.

Also the use of high throughput screening (HTS) is envisaged in the context of the present invention, in particular the screening methods of cell(s), tissue(s) and/or cell culture(s) for responsiveness/sensitivity to an inhibitor of a kinase of the Src family. Suitable (HTS) approaches are known in the art and a person skilled in the art is readily in the position to adapt such protocols or known HTS approaches to the performance of the methods of the present invention. Such approaches are particularly useful in the screening, identifying and/or validation of potential inhibitors of a kinase of the Src family. Screening-assays are usually performed in liquid phase, wherein for each cell/tissue/cell culture to be tested at least one reaction batch is made. Typical containers to be used are micro titer plates having for example, 384, 1536, or 3456 wells (i.e. multiples of the "original" 96 reaction vessels).

Robotics, data processing and control software, and sensitive detectors, are further commonly used components of a HTS device. Often robot system are used to transport micro titer plates from station to station for addition and mixing of sample(s) and reagent(s), incubating the reagents and final readout (detection). Usually, HTS can be used in the simultaneous preparation, incubation and analysis of many plates.

The assay can be performed in a single reaction (which is usually preferred), may, however, also comprise washing and/or transfer steps. Detection can be performed taking advantage of radioactivity, luminescence or fluorescence, like fluorescence-resonance-energytransfer (FRET) and fluorescence polarisation (FP) and the like. The biological samples described herein can also be used in such a context. In particular cellular assays and in vivo assays can be employed in HTS. Cellular assays may also comprise cellular extracts, i.e. extracts from cells, tissues and the like. However, preferred herein is the use of cell(s) or tissue(s) as biological sample (in particular a sample obtained from a patient/subject suffering or being prone to suffer from cancer), whereas in vivo assays are particularly useful in the validation of potential inhibitors to be used herein. Depending on the results of a first assay, follow up assays can be performed by re-running the experiment to collect further data on a narrowed set (e.g. samples found "positive" in the first assay), confirming and refining observations. HTS is therefore also useful in identifying further inhibitors to be used herein.

The screening of compound libraries with usually several hundred thousands of substances takes usually between days and weeks. An experimental high throughput screen may be supplemented (or even be replaced) by a virtual screen. For example, if the structure of the target molecule (e.g. a kinase of the Src family) is known, methods can be employed, which are known under the term "docking". If the structure of several target-binding molecules is known (e.g. the herein described inhibitor of a kinase of the Src family) methods for Pharmacophor-Modelling can be used aiming at the development of new substances which also bind to the target molecule.

As mentioned, an increased expression level of Integrin β4 as compared to a control indicates responsiveness of a cell or an individual to an inhibitor of a kinase of the Src family, such as dasatinib, bosutinib, saractinib or ponatinib.

As used in context of the methods of the present invention, a non-limiting example of a "control" is preferably a "non-responder" control, for example a sample/cell/tissue obtained from one or more healthy subjects or one or more patients that suffer from a cancer/tumor and are known to be not responsive to an inhibitor of a kinase of the Src family. Another example for a "non-responder" control is a cell line/sample/cell/tissue that shows no response to an inhibitor of a kinase of the Src family in an ex-vivo test. Another non-limiting example of a "control" is an "internal standard", for example purified or synthetically produced proteins and/or peptides or a mixture thereof, where the amount of each protein/peptide is gauged by using the "non-responder" control described above. In particular, this "internal standard" can contain the protein Integrin β4, phosphorylated peptides of Integrin β4 and/or phosphorylated peptides of BAIAP2, GPRC5A, ITPR3, TNKS1BP1, ARHGEF18, IASPP, APG16L, TPD52L2 as described and defined herein. A further non-limiting example of a "control" may be a "healthy" control, for example a sample/cell/tissue obtained from a healthy subject or patient that is not suffering from a cancer/tumor or a cell obtained from such a subject. In accordance with the above, the reference or control status e.g. of integrin β4 is that determined in (a sample of) the corresponding healthy control subject/patient, i.e. it is the "normal" status of e.g. integrin β4. The control may also be a sample/cell/tissue obtained from the individual or patient suspected of suffering from the cancer provided that the sample/cell/tissue does not contain tumor or cancer cells. In a further alternative, the "control" may be a sample/cell/tissue obtained from an individual or patient suffering from the cancer, that has been obtained prior to the development or diagnosis of said cancer.

The herein provided methods (i.e. methods for predicting the responsiveness of a mammalian tumor or cancer cell to an inhibitor of the Src-family by evaluation of the status of ITGB4) may further comprise evaluating the phosphorylation of integrin β4 in said cell or said sample, wherein an increase in said phosphorylation of one or more phosphorylation sites of integrin β4 in comparison to the control is indicative of the responsiveness of said cell or a responsive individual to the inhibitor Accordingly, the present invention also comprises the evaluation/assessment/scrutinization of the phosphorylation status or the phophosignature of ITGB4, either alone or also on combination with the evaluation/assessment/scrutinization of the (expression) level of ITGB4, e.g. the mRNA expression level or the protein expression level.

The term "sample" and as used herein relates, inter alia, to a biological sample, including but not limiting to tissue samples or samples comprising said (tumor or cancer) cell(s) to be tested and/or scrutinized. As used here, the terms "sample" or "sample to be evaluated/measured/tested/scrutinized/assessed" may also comprise tissue from biopsies etc. The term "sample" is preferably an in vitro sample. The definition of "control" or "control samples" was provided herein above and applies, mutatis mutantis, to the embodiments of the invention provided herein.

Accordingly, the present invention relates to the following aspects:

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor and wherein said status is the expression level of integrin β4, said method further comprising evaluating the phosphorylation of integrin β4 in said cell or a sample, for example a biological sample comprising said cell.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor and wherein said status is the expression level of integrin β4, wherein an increase in said expression level in comparison to the control is indicative of the responsiveness of said cell to the inhibitor, further comprising evaluating the phosphorylation of integrin β4 in said cell or a sample comprising said cell.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, and wherein said status is the expression level of integrin β4, said method further comprising evaluating the phosphorylation of integrin β4 in said cell or in a sample comprising said cell.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4, said method further comprising evaluating the phosphorylation of integrin β4 in said cell or in a sample comprising said cell.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4, said method further comprising evaluating the phosphorylation of integrin β4 in said cell or in a sample comprising said cell.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4 and wherein an increase in said expression level in comparison to the control is indicative of the responsiveness of said cell to the inhibitor, said method further comprising evaluating the phosphorylation of integrin β4 in said cell or in a sample comprising said cell.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4 and wherein an increase in said expression level in comparison to the control is indicative of the responsiveness of said cell to the inhibitor, said method further comprising evaluating the phosphorylation of integrin β4 in said cell or in a sample comprising said cell.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4, and wherein an increase in said expression level in comparison to the control is indicative of the responsiveness of said cell to the inhibitor, said method further comprising evaluating the phosphorylation of integrin β4 in said cell or a in sample comprising said cell.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor and wherein said status is the expression level of integrin β4, said method further comprising evaluating the phosphorylation of integrin β4 in said cell or in a sample comprising said cell, wherein an increase in said phosphorylation of one or more phosphorylation sites of integrin β4 in comparison to the control is indicative of the responsiveness of said tumor or cancer cell. Accordingly, in context of this invention a method for predicting the responsiveness of a mammalian tumor or cancer cell of an individual suffering from said tumor or cancer cell is provided. An increase in said phosphorylation of one or more phosphorylation sites of integrin β4 in comparison to the control is indicative of the responsiveness of said cell or tumor to the inhibitor of a kinase of the Src-family. The same applies, mutatis mutandis, to the prediction of the responsiveness of an individual to said inhibitor, whereby in this or other case(s) a sample of said individual is to be evaluated in vitro. This embodiment applies for all the aspects of the invention, as described herein above and herein below. Accordingly, this applies also to the following embodiments, wherein the responsiveness of an individual to the inhibitor(s) of a kinase of the Src-family is to be predicted/assessed and/or scrutinized.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said status is the expression level of integrin β4 and wherein an increase in said expression level in comparison to the control is indicative of the responsiveness of said cell to the inhibitor, said method further comprising evaluating the phosphorylation of integrin β4 in said cell or in a sample comprising said cell, wherein an increase in said phosphorylation of one or more phosphorylation sites of integrin β4 in comparison to the control is (also) indicative of the responsiveness of said cancer cell or said tumor.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4, said method further comprising evaluating the phosphorylation of integrin β4 in said cell or in a sample comprising said cell, wherein an increase in said expression level in comparison to the control is indicative of the responsiveness of said cell to the inhibitor and wherein an increase in said phosphorylation of one or more phosphorylation sites of integrin β4 in comparison to the control is indicative of the responsiveness of said cancer cell or said tumor.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4, said method further comprising evaluating the phosphorylation of integrin β4 in said cell or in a sample comprising said cell, wherein an increase in said expression level in comparison to the control is indicative of the responsiveness of said cell to the inhibitor and wherein an increase in said phosphorylation of one or more phosphorylation sites of integrin β4 in comparison to the control is indicative of the responsiveness of said cancer cell or said tumor.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4, said method further comprising evaluating the phosphorylation of integrin β4 in said cell or in a sample comprising said cell, wherein an increase in said expression level in comparison to the control is indicative of the responsiveness of said cell to the inhibitor and wherein an increase in said phosphorylation of one or more phosphorylation sites of integrin β4 in comparison to the control is indicative of the responsiveness of said cancer cell or said tumor.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4, said method further comprising evaluating the phosphorylation of integrin β4 in said cell or in a sample comprising said cell, wherein an increase in said phosphorylation of one or more phosphorylation sites of integrin β4 in comparison to the control is indicative of the responsiveness of said cancer cell or said tumor.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4, said method further comprising evaluating the phosphorylation of integrin β4 in said cell or in a sample comprising said cell, wherein an increase in said phosphorylation of one or more phosphorylation sites of integrin β4 in comparison to the control is indicative of the responsiveness of said cancer cell or said tumor.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4, said method further comprising evaluating the phosphorylation of integrin β4 in said cell or in a sample comprising said cell, wherein an increase in said phosphorylation of one or more phosphorylation sites of integrin β4 in comparison to the control is indicative of the responsiveness of said cancer cell or said tumor.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4, wherein an increase in said expression level in comparison to the control is indicative of the responsiveness of said cell to the inhibitor, said method further comprising evaluating the phosphorylation of integrin β4 in said cell or in a sample comprising said cell and wherein an increase in said phosphorylation of one or more phosphorylation sites of integrin β4 in comparison to the control is indicative of the responsiveness of said cancer cell or said tumor.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4, wherein an increase in said expression level in comparison to the control is indicative of the responsiveness of said cell to the inhibitor, said method further comprising evaluating the phosphorylation of integrin β4 in said cell or in a sample comprising said cell, wherein an increase in said phosphorylation of one or more phosphorylation sites of integrin β4 in comparison to the control is indicative of the responsiveness of said cancer cell or said tumor.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4, wherein an increase in said expression level in comparison to the control is indicative of the responsiveness of said cell to the inhibitor, said method further comprising evaluating the phosphorylation of integrin β4 in said cell or in a sample comprising said cell, wherein an increase in said phosphorylation of one or more phosphorylation sites of integrin β4 in comparison to the control is indicative of the responsiveness of said cancer cell or said tumor. A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor and wherein said status is the expression level of integrin β4, said method further comprising evaluating the phosphorylation of integrin β4 in said cell or in a sample comprising said cell, wherein the expression level of integrin β4 is the mRNA expression level of integrin β4.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said status is the expression level of integrin β4, wherein an increase in said expression level in comparison to the control is indicative of the responsiveness of said cell to the inhibitor and wherein the expression level of integrin β4 is the mRNA expression level of integrin β4, said method further comprising evaluating the phosphorylation of integrin β4 in said cell or in a sample comprising said cell.

A method for predicting the responsiveness of a mammalian tumor or cancer cell to an inhibitor of a kinase of the Src-family, said method comprising evaluating the status of integrin β4 (ITGB4) in said cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4 and wherein the expression level of integrin β4 is the mRNA expression level of integrin β4, said method further comprising evaluating the phosphorylation of integrin β4 in said cell or in a sample comprising said cell.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4 and wherein the expression level of integrin β4 is the mRNA expression level of integrin β4, said method further comprising evaluating the phosphorylation of integrin β4 in said cell or in a sample comprising said cell.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4 and wherein the expression level of integrin β4 is the mRNA expression level of integrin β4, said method further comprising evaluating the phosphorylation of integrin β4 in said cell or in a sample, comprising said cell.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4 and, wherein the expression level of integrin β4 is the mRNA expression level of integrin β4 and wherein an increase in said expression level in comparison to the control is indicative of the responsiveness of said cell to the inhibitor, said method further comprising evaluating the phosphorylation of integrin β4 in said cell or in a sample comprising said cell.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4 and wherein the expression level of integrin β4 is the mRNA expression level of integrin β4 and wherein an increase in said expression level in comparison to the control is indicative of the responsiveness of said cell to the inhibitor, said method further comprising evaluating the phosphorylation of integrin β4 in said cell or in a sample comprising said cell.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4, wherein the expression level of integrin β4 is the mRNA expression level of integrin β4 and wherein an increase in said expression level in comparison to the control is indicative of the responsiveness of said cell to the inhibitor, said method further comprising evaluating the phosphorylation of integrin β4 in said cell or in a sample comprising said cell.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said status is the expression level of integrin β4 and wherein the expression level of integrin β4 is the mRNA expression level of integrin β4, said method further comprising evaluating the phosphorylation of integrin β4 in said cell or in a sample comprising said cell, wherein an increase in said phosphorylation of one or more phosphorylation sites of integrin β4 in comparison to the control is indicative of the responsiveness of said cell or is indicative of the responsiveness of an individual suffering from said tumor or cancer cells to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said status is the expression level of integrin β4 and wherein the expression level of integrin β4 is the mRNA expression level of integrin β4, wherein an increase in said expression level in comparison to the control is indicative of the responsiveness of said cell to the inhibitor, said method further comprising evaluating the phosphorylation of integrin β4 in said cell or said sample, wherein an increase in said phosphorylation of one or more phosphorylation sites of integrin β4 in comparison to the control is indicative of the responsiveness of said cell to the inhibitor of a kinase of the Src-family and/or wherein an increase in said phosphorylation of one or more phosphorylation sites of integrin β4 in comparison to the control is indicative of the responsiveness of an individual (suffering from said tumor or cancer cells) to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4, wherein the expression level of integrin β4 is the mRNA expression level of integrin β4 and wherein an increase in said expression level in comparison to the control is indicative of the responsiveness of said cell to the inhibitor, said method further comprising evaluating the phosphorylation of integrin β4 in said cell or said sample, wherein an increase in said phosphorylation of one or more phosphorylation sites of integrin β4 in comparison to the control is indicative of the responsiveness of said cell to the inhibitor of a kinase of the Src-family and/or wherein an increase in said phosphorylation of one or more phosphorylation sites of integrin β4 in comparison to the control is indicative of the responsiveness of an individual is indicative of the responsiveness of an individual (suffering from said tumor or cancer cells) to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4, wherein the expression level of integrin β4 is the mRNA expression level of integrin β4 and wherein an increase in said expression level in comparison to the control is indicative of the responsiveness of said cell to the inhibitor, said method further comprising evaluating the phosphorylation of integrin β4 in said cell or said sample, wherein an increase in said phosphorylation of one or more phosphorylation sites of integrin β4 in comparison to the control is indicative of the responsiveness of said cell to the inhibitor of a kinase of the Src-family and/or wherein an increase in said phosphorylation of one or more phosphorylation sites of integrin β4 in comparison to the control is indicative of the responsiveness of an individual (suffering from said tumor or cancer cells) to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4, wherein the expression level of integrin β4 is the mRNA expression level of integrin β4 and wherein an increase in said expression level in comparison to the control is indicative of the responsiveness of said cell to the inhibitor, said method further comprising evaluating the phosphorylation of integrin β4 in said cell or said sample, wherein an increase in said phosphorylation of one or more phosphorylation sites of integrin β4 in comparison to the control is indicative of the responsiveness of said cell to the inhibitor of a kinase of the Src-family and/or wherein an increase in said phosphorylation of one or more phosphorylation sites of integrin β4 in comparison to the control is indicative of the responsiveness of an individual is indicative of the responsiveness of an individual (suffering from said tumor or cancer cells) to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said status is the expression level of integrin β4 and wherein the expression level of integrin β4 is the protein expression level of integrin β4, said method further comprising evaluating the phosphorylation of integrin β4 in said cell or in a sample comprising said cell.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said status is the expression level of integrin β4 wherein the expression level of integrin β4 is the protein expression level of integrin β4 and wherein an increase in said expression level in comparison to the control is indicative of the responsiveness of said cell to the inhibitor, said method further comprising evaluating the phosphorylation of integrin β4 in said cell or in said sample comprising said cell.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4 and wherein the expression level of integrin β4 is the protein expression level of integrin β4, said method further comprising evaluating the phosphorylation of integrin β4 in said cell or in a sample comprising said cell.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4 and wherein the expression level of integrin β4 is the protein expression level of integrin β4, said method further comprising evaluating the phosphorylation of integrin β4 in said cell or in a sample comprising said cell.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4 and wherein the expression level of integrin β4 is the protein expression level of integrin β4, said method further comprising evaluating the phosphorylation of integrin β4 in said cell or in a sample comprising said cell.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4, wherein the expression level of integrin β4 is the protein expression level of integrin β4 and wherein an increase in said expression level in comparison to the control is indicative of the responsiveness of said cell to the inhibitor, said method further comprising evaluating the phosphorylation of integrin β4 in said cell or in a sample comprising said cell.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4, wherein the expression level of integrin β4 is the protein expression level of integrin β4 and wherein an increase in said expression level in comparison to the control is indicative of the responsiveness of said cell to the inhibitor, said method further comprising evaluating the phosphorylation of integrin β4 in said cell or in a sample comprising said cell.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4, wherein the expression level of integrin β4 is the protein expression level of integrin β4 and wherein an increase in said expression level in comparison to the control is indicative of the responsiveness of said cell to the inhibitor, said method further comprising evaluating the phosphorylation of integrin β4 in said cell or in a sample comprising said cell.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4, wherein the expression level of integrin β4 is the protein expression level of integrin β4 and wherein an increase in said expression level in comparison to the control is indicative of the responsiveness of said cell to the inhibitor, said method further comprising evaluating the phosphorylation of integrin β4 in said cell or in a sample comprising said cell.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said status is the expression level of integrin β4 and wherein the expression level of integrin β4 is the protein expression level of integrin β4, said method further comprising evaluating the phosphorylation of integrin β4 in said cell or in a sample comprising said cell, wherein an increase in said phosphorylation of one or more phosphorylation sites of integrin β4 in comparison to the control is (also) indicative of the responsiveness of said cell to the inhibitor of a kinase of the Src-family and/or wherein an increase in said phosphorylation of one or more phosphorylation sites of integrin β4 in comparison to the control is (also) indicative of the responsiveness of an individual is indicative of the responsiveness of an individual (suffering from said tumor or cancer cells) to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said status is the expression level of integrin β4, wherein the expression level of integrin β4 is the protein expression level of integrin β4 and wherein an increase in said expression level in comparison to the control is indicative of the responsiveness of said cell to the inhibitor, said method further comprising evaluating the phosphorylation of integrin β4 in said cell or in a sample comprising said cell, wherein an increase in said phosphorylation of one or more phosphorylation sites of integrin 134 in comparison to the control is (also) indicative of the responsiveness of said cell to the inhibitor of a kinase of the Src-family and/or wherein an increase in said phosphorylation of one or more phosphorylation sites of integrin β4 in comparison to the control is indicative of the responsiveness of an individual (suffering from said tumor or cancer cells) to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said status is the expression level of integrin β4 and wherein the expression level of integrin β4 is the protein expression level of integrin β4, wherein said inhibitor of a kinase of the Src-family is dasatinib or pharmaceutically acceptable salts, solvates, and/or hydrates of dasatinib, said method further comprising evaluating the phosphorylation of integrin β4 in said cell or in a sample comprising said cell, wherein an increase in said phosphorylation of one or more phosphorylation sites of integrin β4 in comparison to the control is (also) indicative of the responsiveness of said cell to the inhibitor of a kinase of the Src-family and/or wherein an increase in said phosphorylation of one or more phosphorylation sites of integrin β4 in comparison to the control is indicative of the responsiveness of an individual (suffering from said tumor or cancer cells) to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said status is the expression level of integrin β4 and wherein the expression level of integrin β4 is the protein expression level of integrin β4, wherein said inhibitor of a kinase of the Src-family is bosutinib (SKI-606) or pharmaceutically acceptable salts, solvates, and/or hydrates of bosutinib (SKI-606), said method further comprising evaluating the phosphorylation of integrin β4 in said cell or in a sample comprising said cell, wherein an increase in said phosphorylation of one or more phosphorylation sites of integrin β4 in comparison to the control is (also) indicative of the responsiveness of said cell to the inhibitor of a kinase of the Src-family and/or wherein an increase in said phosphorylation of one or more phosphorylation sites of integrin β4 in comparison to the control is indicative of the responsiveness of an individual (suffering from said tumor or cancer cells) to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said status is the expression level of integrin β4 and wherein the expression level of integrin β4 is the protein expression level of integrin β4, wherein said inhibitor of a kinase of the Src-family is saracatinib (AZD530) or pharmaceutically acceptable salts, solvates, and/or hydrates of saracatinib (AZD530), said method further comprising evaluating the phosphorylation of integrin β4 in said cell or in a sample comprising said cell, wherein an increase in said phosphorylation of one or more phosphorylation sites of integrin β4 in comparison to the control is (also) indicative of the responsiveness of said cell to the inhibitor of a kinase of the Src-family and/or wherein an increase in said phosphorylation of one or more phosphorylation sites of integrin β4 in comparison to the control is indicative of the responsiveness of an individual is indicative of the responsiveness of an individual (suffering from said tumor or cancer cells) to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4, wherein the expression level of integrin β4 is the protein expression level of integrin β and wherein an increase in said expression level in comparison to the control is indicative of the responsiveness of said cell to the inhibitor, said method further comprising evaluating the phosphorylation of integrin β4 in said cell or in a sample comprising said cell, wherein an increase in said phosphorylation of one or more phosphorylation sites of integrin β4 in comparison to the control is (also) indicative of the responsiveness of said cell to the inhibitor of a kinase of the Src-family and/or wherein an increase in said phosphorylation of one or more phosphorylation sites of integrin β4 in comparison to the control is indicative of the responsiveness of an individual (suffering from said tumor or cancer cells) to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4, wherein the expression level of integrin β4 is the protein expression level of integrin β and wherein an increase in said expression level in comparison to the control is indicative of the responsiveness of said cell to the inhibitor, said method further comprising evaluating the phosphorylation of integrin β4 in said cell or in a sample comprising said cell, wherein an increase in said phosphorylation of one or more phosphorylation sites of integrin β4 in comparison to the control is (also) indicative of the responsiveness of said cell to the inhibitor of a kinase of the Src-family and/or wherein an increase in said phosphorylation of one or more phosphorylation sites of integrin β4 in comparison to the control is indicative of the responsiveness of an individual (suffering from said tumor or cancer cells) to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4, wherein the expression level of integrin β4 is the protein expression level of integrin β and wherein an increase in said expression level in comparison to the control is indicative of the responsiveness of said cell to the inhibitor, said method further comprising evaluating the phosphorylation of integrin β4 in said cell or in a sample comprising said cell, wherein an increase in said phosphorylation of one or more phosphorylation sites of integrin β4 in comparison to the control is (also) indicative of the responsiveness of said cell to the inhibitor of a kinase of the Src-family and/or wherein an increase in said phosphorylation of one or more phosphorylation sites of integrin β4 in comparison to the control is indicative of the responsiveness of an individual is indicative of the responsiveness of an individual (suffering from said tumor or cancer cells) to the inhibitor of a kinase of the Src-family.

As explained above, the phosphorylation status of integrin β4 indicates, independently of the expression level of integrin β4, whether a cell or individual/patient is responsive to an inhibitor of a kinase of the Src family. Accordingly, it is also envisaged herein that the phosphorylation of integrin β4 can be evaluated independently of the expression level of integrin β4. The present invention, therefore, also provides for the assessment/elucidation/scrutinization of the phosphosignature of integrin β4 in the prediction of the responsiveness of a mammalian tumor or cancer cell to an inhibitor of a kinase of the Src-family. This assessment/elucidation/scrutinization of the phosphosignature of integrin β4 may be carried out individually or may be carried out in combination with the assessment/elucidation/scrutinization of the (expression) staus of integrin β4. Said (expression) status may by the (expression) level of integrin β4 mRNA or integrin β4 protein. Ample details are provided herein and the person skilled in the art is readily in a position to carry out the invention as described. In this context it is also of note that when the assessment/elucidation/scrutinization of the phosphosignature integrin β4 is combined with a concomitant integrin β4 assessment/elucidation/scrutinization of the (expression) status integrin β4, said assessment/elucidation/scrutinization may take place on the same (cellular) sample or on different samples. The assessment/elucidation/scrutinization may take place at the same time or on different time points.

Again, when a concomitant assessment/elucidation/scrutinization takes place, the elucidation of the (expression) "status" may be the confirmation of the results obtained when the "phosphosignature" is assessed and, vice versa, the elucidation of the "phosphosignature" may be the confirmation of the (expression) "status".

Therefore, the present invention relates in one embodiment to a method for predicting the responsiveness of a mammalian tumor or cancer cell to an inhibitor of a kinase of the Src-family, said method comprising evaluating the status of integrin β4 (ITGB4) in tumor or cancer cell, wherein said status is indicative of the responsiveness of said cell to the inhibitor, and wherein said status of integrin β4 is the phosphorylation of integrin β4 and an increase in said phosphorylation of one or more phosphorylation sites of integrin β4 in comparison to the control is indicative of the responsiveness of said cell.

In accordance with the above, the present invention relates to a method for predicting the responsiveness of an individual to an inhibitor of a kinase of the Src-family, said method comprising (in vitro) evaluating the status of integrin β4

(ITGB4) in a sample of an individual suffering from, suspected to suffer from or being prone to suffer from cancer, wherein said status is indicative of a responsive individual to the inhibitor, wherein said status of integrin β4 is the phosphorylation of integrin β4 and an increase in said phosphorylation of one or more phosphorylation sites of integrin β4 in comparison to the control is indicative of a responsive individual to the inhibitor.

Accordingly, the present invention relates to the following aspects:

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said status of integrin β4 is the phosphorylation of integrin β4.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status of integrin β4 is the phosphorylation of integrin β4.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status of integrin β4 is the phosphorylation of integrin β4.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status of integrin β4 is the phosphorylation of integrin β4.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said status of integrin β4 is the phosphorylation of integrin β4, wherein an increase in said phosphorylation of one or more phosphorylation sites of integrin β4 in comparison to the control is indicative of the responsiveness of said cell to the inhibitor.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status of integrin β4 is the phosphorylation of integrin β4, wherein an increase in said phosphorylation of one or more phosphorylation sites of integrin β4 in comparison to the control is indicative of the responsiveness of said cell to the inhibitor.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status of integrin β4 is the phosphorylation of integrin β4, wherein an increase in said phosphorylation of one or more phosphorylation sites of integrin β4 in comparison to the control is indicative of the responsiveness of said cell to the inhibitor.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status of integrin β4 is the phosphorylation of integrin β4, wherein an increase in said phosphorylation of one or more phosphorylation sites of integrin β4 in comparison to the control is indicative of the responsiveness of said cell to the inhibitor.

The following explanations on the phosphorylation status (or the "phopsphosignature") of integrin β4 relate to embodiments where the phosphorylation status is evaluated independently of the expression level, the explanations on the phosphorylation status of integrin β4 also relate to embodiments where the phosphorylation status is evaluated in addition to the expression level (or vice versa).

Again, term "control" has been explained herein above in context of the evaluation of the expression level of integrin β4. These explanations and definitions apply, mutatis mutandis, also in context of the determination and evaluation of the phosphorylation status of integrin β4 or of other herein described proteins. In particular, a "control" is a "non-responder" control or an "internal standard" as explained herein above. Such "controls" may also comprise "healthy" controls, for example a sample/cell/tissue obtained from a healthy subject or patient that is not suffering from a cancer/tumor or a cell obtained from such a subject. In accordance with the explanations provided herein above, the reference or control status e.g. of integrin β4 is that determined in (a sample of) the corresponding healthy control subject/patient, i.e. it is the "normal" status of e.g. Integrin β4. The control may also be a sample/cell/tissue obtained from the individual or patient suspected of suffering from the cancer provided that the sample/cell/tissue does not contain tumor or cancer cells. In a further alternative, the "control" may be a sample/cell/tissue obtained from an individual or patient suffering from the cancer, that has been obtained prior to the development or diagnosis of said cancer.

In one embodiment and in context of the evaluation of the "phosphosignature" of integrin β4, the methods of the present invention comprise the evaluation of phosphorylation sites of integrin β4, preferably of one or more of the phosphorylation sites S1518, S1457, T1455 and S1069 of integrin β4 (preferably of the ITGB4 isoform C as, for example, shown in SEQ ID NO: 5). Preferably, all of these sites are evaluated. Preferably an increase in the phosphorylation of said one or more phosphorylation sites in comparison to the control is indicative of the responsiveness of said cell or a responsive individual to the inhibitor.

These phosphorylation sites are also shown in the amino acid sequence of integrin β4 depicted in SEQ ID NO: 5.

In accordance with the above, the present invention relates to the following aspects:

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said status of integrin β4 is the phosphorylation of integrin β4, wherein the phosphorylation site is one or more of the phosphorylation sites S1518, S1457, T1455 and S1069 of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status of integrin β4 is the phosphorylation of integrin β4, wherein the phosphorylation site is one or more of the phosphorylation sites S1518. S1457, T1455 and S1069 of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status of integrin β4 is the phosphorylation of integrin β4, wherein the phosphorylation site is one or more of the phosphorylation sites S1518, S1457, T1455 and S1069 of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status of integrin β4 is the phosphorylation of integrin β4, wherein the phosphorylation site is one or more of the phosphorylation sites S1518, S1457, T1455 and S1069 of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said status of integrin β4 is the phosphorylation of integrin 134, wherein an increase in said phosphorylation of one or more phosphorylation sites of integrin β4 in comparison to the control is indicative of the responsiveness of said cell to the inhibitor, wherein the phosphorylation site is one or more of the phosphorylation sites S1518, S1457, T1455 and S1069 of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status of integrin β4 is the phosphorylation of integrin β4, wherein an increase in said phosphorylation of one or more phosphorylation sites of integrin β4 in comparison to the control is indicative of the responsiveness of said cell to the inhibitor, wherein the phosphorylation site is one or more of the phosphorylation sites S1518, S1457, T1455 and S1069 of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status of integrin β4 is the phosphorylation of integrin β4, wherein an increase in said phosphorylation of one or more phosphorylation sites of integrin β4 in comparison to the control is indicative of the responsiveness of said cell to the inhibitor, wherein the phosphorylation site is one or more of the phosphorylation sites S1518, S1457, T1455 and S1069 of integrin β4.

A method for predicting the responsiveness of a mammalian tumor or cancer cell to an inhibitor of a kinase of the Src-family, said method comprising evaluating the status of integrin β4 (ITGB4) in/of said cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status of integrin β4 is the phosphorylation of integrin β4, wherein an increase in said phosphorylation of one or more phosphorylation sites of integrin β4 in comparison to the control is indicative of the responsiveness of said cell to the inhibitor, wherein the phosphorylation site is one or more of the phosphorylation sites S1518, S1457, T1455 and S1069 of integrin β4.

In the aspects of the present invention relating to the phosphorylation status/the phosphosignature of integrin P34, the phosphorylation site can be one or more of the phosphorylation sites S1518, S1457. T1455 and S1069 of integrin β4. In other words, the phosphorylation site(s) can be as follows (It is to be understood that any of the aspects of the invention described herein can be combined with any of the following aspects):

The phosphorylation site is S1518 of integrin β4.

The phosphorylation site is S1457 of integrin β4.

The phosphorylation site is T1455 of integrin β4.

The phosphorylation site is S1069 of integrin β4.

The phosphorylation site is S1518 and S1457 of integrin β4.

The phosphorylation site is S1518 and T1455 of integrin β4.

The phosphorylation site is S1518 and S1069 of integrin β4.

The phosphorylation site is S1457 and T1455 of integrin β4.

The phosphorylation site is S1457 and S1069 of integrin β4.

The phosphorylation site is T1455 and S1069 of integrin β4.

The phosphorylation site is S1518, S1457 and T 1455 of integrin β4.

The phosphorylation site is S1518, T1455 and S1069 of integrin β4.

The phosphorylation site is S1457, T1455 and S1069 of integrin β4.

The phosphorylation site is S1518, S1457, T1455 and S1069 of integrin β4.

The herein provided methods may further comprise evaluating the phosphorylation of one or more additional phosphorylation sites in said cell or said sample, wherein said phosphorylation site is one or more of the following phosphorylation sites:

a. S509 of BAIAP2 (preferably as shown in SEQ ID NO: 9);

b. S345 of GPRC5A (preferably as shown in SEQ ID NO: 10);

c. S916 of ITPR3 (preferably as shown in SEQ ID NO: 11);

d. S429 of TNKS1BP1 (preferably as shown in SEQ ID NO: 12);

e. S1101 of ARHGEF18 (preferably as shown in SEQ ID NO: 13);

f. S102 of IASPP (preferably as shown in SEQ ID NO: 16);

g. S269 of APG16L (preferably as shown in SEQ ID NO: 17); and/or h. S161 of TPD52L2 (preferably as shown in SEQ ID NO: 20).

An increase in said phosphorylation of one or more phosphorylation sites in comparison to the control is indicative of the responsiveness of said cell or a responsive individual to the inhibitor.

It is envisaged herein that the above phosphorylation sites may also be evaluated independently of the status of Integrin β4 (e.g. phosphorylation status and/or expression level of Integrin β4) and be suitable markers for responsiveness to an inhibitor of a kinase of the Src family.

Accordingly, the present invention relates in one embodiment to a method for predicting the responsiveness of a mammalian tumor or cancer cell to an inhibitor of a kinase of the Src-family as defined herein, said method comprising evaluating the status of one or more of BAIAP2, GPRC5A, ITPR3, TNKS1BP1, ARHGEF18, IASPP, APG16L, TPD52L2, wherein the status is preferably the phosphorylation status and wherein, more preferably, the phosphorylation of one or more of the following phosphorylation sites is evaluated:

a. S509 of BAIAP2 (preferably as shown in SEQ ID NO: 9);

b. S345 of GPRC5A (preferably as shown in SEQ ID NO: 10);

c. S916 of ITPR3 (preferably as shown in SEQ ID NO: 11);

d. S429 of TNKS1BP1 (preferably as shown in SEQ ID NO: 12);

e. S1101 of ARHGEF18 (preferably as shown in SEQ ID NO: 13);

f. S102 of IASPP (preferably as shown in SEQ ID NO: 16);

g. S269 of APG16L (preferably as shown in SEQ ID NO: 17); and/or h. S161 of TPD52L2 (preferably as shown in SEQ ID NO: 20).

Preferably, an increase in said phosphorylation of one or more phosphorylation sites in comparison to the control is indicative of the responsiveness of said cell to the inhibitor.

In accordance with the above, the present invention relates to a method for predicting the responsiveness of an individual to an inhibitor of a kinase of the Src-family, said method comprising evaluating the status of one or more of BAIAP2, GPRC5A, ITPR3, TNKS1BP1, ARHGEF18, IASPP, APG16L, TPD52L2, wherein the status is preferably the phosphorylation status and wherein, more preferably, the phosphorylation of one or more of the following phosphorylation sites is evaluated:

a. S509 of BAIAP2 (preferably as shown in SEQ ID NO: 9);

b. S345 of GPRC5A (preferably as shown in SEQ ID NO: 10);

c. S916 of ITPR3 (preferably as shown in SEQ ID NO: 11);

d. S429 of TNKS1BP1 (preferably as shown in SEQ ID NO: 12);

e. S1101 of ARHGEF18 (preferably as shown in SEQ ID NO: 13);

f. S102 of IASPP (preferably as shown in SEQ ID NO: 16);

g. S269 of APG16L (preferably as shown in SEQ ID NO: 17); and/or h. S161 of TPD52L2 (preferably as shown in SEQ ID NO: 20).

Preferably, an increase in said phosphorylation of one or more phosphorylation sites in comparison to the control is indicative of a responsive individual to the inhibitor.

It is particularly preferred herein that the herein provided methods comprise evaluating the phosphorylation of one or more of the following combination of phosphorylation sites:

a. S1518, S1457, T1455 and S1069 of ITGB4 and S916 of ITPR3;

b. S1518, S1457, T1455 and S1069 of ITGB4 and S429 of TNKS1BP1;

c. S1518, S1457. T1455 and S1069 of ITGB4 and S1101 of ARHGEF18;

d. S1518, S1457, T1455 and S1069 of ITGB4 and S269 of APG16L;

e. S1518, S1457, T1455 and S1069 of ITGB4 and S161 of TPD52L2;

f. S1101 of ARHGEF18 and S345 of GPRC5A g. S1101 of ARHGEF18 and S916 of ITPR3; and/or h. S1101 of ARHGEF18 and S102 of IASPP.

It is also preferred herein that the herein provided methods comprise evaluating the phosphorylation of one or more of the following combination of phosphorylation sites:

a. S1518, S1457, T1455 and S1069 of ITGB4 and S509 of BAIAP2;

b. S1518, S1457, T1455 and S1069 of ITGB4 and S345 of GPRC5A;

c. S1518, S1457, T1455 and S1069 of ITGB4 and S102 of IASPP;

d. S509 of BAIAP2 and S429 of TNKS1BP1;

e. S509 of BAIAP2 and S1101 of ARHGEF18, f. S429 of TNKS1BP1 and S345 of GPRC5A;

g. S429 of TNKS1BP1 and S916 of ITPR3;

h. S161 of TPD52L2 and S916 of ITPR3;

i. S1101 of ARHGEF18 and S429 of TNKS1BP1;

j. S102 of IASPP and S429 of TNKS1BP; 1;

k. S269 of APG16L and S429 of TNKS1BP1;

l. S161 of TPD52L2 and S429 of TNKS1BP1; and/or m. S269 of APG16L and S1101 of ARHGEF18;

The herein provided methods may also comprise evaluating the phosphorylation of one or more of the following combination of phosphorylation sites:

a. S345 of GPRC5A and S509 of BAIAP2;

b. S916 of ITPR3 and S509 of BAIAP2;

c. S269 of APG16L and S509 of BAIAP2;

d. S161 of TPD52L2 and S509 of BAIAP2;

e. S916 of ITPR3 and S345 of GPRC5A;

f. S102 of IASPP and S345 of GPRC5A;

g. S269 of APG16L and S345 of GPRC5A;

h. S161 of TPD52L2 and S345 of GPRC5A;

i. S102 of IASPP and S916 of ITPR3; and/or j. S161 of TPD52L2 and S1101 of ARHGEF18.

Also useful herein is the evaluation of the phosphorylation of one or more of the following combination of phosphorylation sites in context of the herein provided method:

a. S102 of IASPP and S509 of BAIAP2;

b. S269 of APG16L and S916 of ITPR3;

c. S269 of APG16L and S102 of IASPP;

d. S161 of TPD52L2 and S102 of IASPP; and/or e. S161 of TPD52L2 and S269 of APG16L.

It is also envisaged in context of the present invention that in addition or in alternative to the above described phosphorylation sites, the phosphorylation status of fragments of the above phosphorylated polypeptides, splice variants, polypeptides having at least 60% or more homology to the polypeptide, or mutant polypeptides may be evaluated, provided that these polypeptides are phosphorylated at any of the above defined sites or at an equivalent site. Particularly envisaged is the evaluation of phosphorylation sites of isoforms of ITGB4, ARHGEF18, ATG16L1 and/or TPD526L.

Accordingly, the methods of the present invention may comprise evaluating the phosphorylation of one or more of the following phosphorylation sites:

a. S943 of ARHGEF18 isoform2 (preferably as shown in SEQ ID NO: 14);

b. S943 of ARHGEF18 isoform3 (preferably as shown in SEQ ID NO: 15);

c. S269 of ATG16L1 isoform 3 (preferably as shown in SEQ ID NO: 18);

d. S125 of ATG16L1 isoform 4 (preferably as shown in SEQ ID NO: 19); and/or e. S141 of TPD526L isoform 2 (preferably as shown in SEQ ID NO: 21);

Preferably, the methods of the present invention comprise in addition or in the alternative to the remaining herein described phosphorylations sites the evaluation of phosphorylation sites of integrin β4, for example, of isoform4A, preferably of one or more of the phosphorylation sites S1069, T1385, S1387, S1448 of isoform4A (preferably as shown in SEQ ID NO: 6); of isoform4B, preferably of one or more of the phosphorylation sites S1069, T1385, S1387, of isoform4B (preferably as shown in SEQ ID NO: 7); of isoform4D, preferably of one or more of the phosphorylation sites S1069, T1385, S1387, S1448 of isoform4D (preferably as shown in SEQ ID NO: 8). Preferably, an increase in the phosphorylation of said one or more phosphorylation sites in comparison to the control is indicative of the responsiveness of said cell or a responsive individual to the inhibitor.

It is envisaged herein that the phosphorylation sites of proteins other than Integrin β4 may also be evaluated independently of the status of Integrin β4 (e.g. phosphorylation status and/or expression level of Integrin β4) and/or of other phosphorylation sites and be suitable markers for responsiveness to an inhibitor of a kinase of the Src family.

Accordingly, the present invention relates in one embodiment to a method for predicting the responsiveness of a mammalian tumor or cancer cell to an inhibitor of a kinase of the Src-family as defined herein, said method comprising evaluating the status of one or more of ARHGEF18, APG16L, TPD52L2, wherein the status is preferably the phosphorylation status and wherein, more preferably, the phosphorylation of one or more of the following phosphorylation sites is evaluated:

a. S943 of ARHGEF18 isoform2 (preferably as shown in SEQ ID NO: 14);

b. S943 of ARHGEF18 isoform2 (preferably as shown in SEQ ID NO: 15);

c. S269 of ATG16L1 isoform 3 (preferably as shown in SEQ ID NO: 18);

d. S125 of ATG16L1 isoform 4 (preferably as shown in SEQ ID NO: 19); and/or e. S141 of TPD526L isoform 2 (preferably as shown in SEQ ID NO: 21);

Preferably, an increase in the phosphorylation of said one or more phosphorylation sites in comparison to the control is indicative of the responsiveness of said cell to the inhibitor.

In accordance with the above, the present invention relates to a method for predicting the responsiveness of an individual to an inhibitor of a kinase of the Src-family, said method comprising evaluating the status of one or more of ARHGEF18, APG16L, TPD52L2, wherein the status is preferably the phosphorylation status and wherein, more preferably, the phosphorylation of one or more of the following phosphorylation sites is evaluated:

a. S943 of ARHGEF18 isoform2 (preferably as shown in SEQ ID NO: 14);

b. S943 of ARHGEF18 isoform2 (preferably as shown in SEQ ID NO: 15);

c. S269 of ATG16L isoform 3 (preferably as shown in SEQ ID NO: 18);

d. S125 of ATG16L1 isoform 4 (preferably as shown in SEQ ID NO: 19); and/or e. S141 of TPD526L isoform 2 (preferably as shown in SEQ ID NO: 21).

Preferably, an increase in the phosphorylation of said one or more phosphorylation sites in comparison to the control is indicative of a responsive individual to the inhibitor.

It has been found herein that the evaluation of the above combination of phosphorylation sites allows an excellent prediction or assessment whether (a) tumor/cancer cell(s) or (an) individual(s) is (are) responsive to an inhibitor of a kinase of the Src family.

Preferably, the phosphorylation of the phosphorylation site is at least 2.5-fold, preferably at least 5-fold increased, in comparison to the control. As shown in the appended examples, phosphorylation can be determined by routine methods, such as wherein said phosphorylation is detected by immunoassay, IHC, mass spectrometry or intracellular flow cytometry.

In accordance with the above, the present invention relates to the following aspects:

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, said method further comprising evaluating the phosphorylation of one or more phosphorylation sites in said cell or in a sample comprising said cell, wherein said phosphorylation site is one or more of the following phosphorylation sites:

a. S509 of BAIAP2;

b. S345 of GPRC5A;

c. S916 of ITPR3;

d. S429 of TNKS1BP1;

e. S101 of ARHGEF18;

f. S102 of IASPP;

g. S269 of APG16L; and h. S161 of TPD52L2, and wherein an increase in said phosphorylation of one or more of said phosphorylation sites of integrin β4 in comparison to the control is (also) indicative of the responsiveness of said cell to the inhibitor of a kinase of the Src-family and/or wherein an increase in said phosphorylation of one or more phosphorylation sites of integrin β4 in comparison to the control is indicative of the responsiveness of an individual (suffering from said tumor or cancer cells) to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), said method further comprising evaluating the phosphorylation of one or more phosphorylation sites in said cell or in a sample comprising said cell, wherein said phosphorylation site is one or more of the following phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, and wherein an increase in said phosphorylation of one or more of said phosphorylation sites of integrin β4 in comparison to the control is (also) indicative of the responsiveness of said cell to the inhibitor of a kinase of the Src-family and/or wherein an increase in said phosphorylation of one or more phosphorylation sites of integrin β4 in comparison to the control is indicative of the responsiveness of an individual (suffering from said tumor or cancer cells) to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), said method further comprising evaluating the phosphorylation of one or more phosphorylation sites in said cell or in a sample comprising said cell, wherein said phosphorylation site is one or more of the following phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, and wherein an increase in said phosphorylation of one or more of said phosphorylation sites of integrin β4 in comparison to the control is (also) indicative of the responsiveness of said cell to the inhibitor of a kinase of the Src-family and/or wherein an increase in said phosphorylation of one or more phosphorylation sites of integrin β4 in comparison to the control is indicative of the responsiveness of an individual (suffering from said tumor or cancer cells) to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said status is the expression level of integrin β4, said method further comprising evaluating the phosphorylation of one or more phosphorylation sites in said cell or in a sample comprising said cell, wherein said phosphorylation site is one or more of the following phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2.

wherein an increase in said phosphorylation of one or more phosphorylation sites in comparison to the control is indicative of the responsiveness of said cell and/or is indicative of the responsiveness of the assessed individual to the inhibitor of a kinase of the Src-family. The same applies, mutatis mutandis, to the prediction of the responsiveness of an individual to said inhibitor, whereby in this or other case(s) a sample of said individual is to be evaluated in vitro. This embodiment applies for all the corresponding aspects of the invention herein above and herein below.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4, further comprising evaluating the phosphorylation of one or more phosphorylation sites in said cell or in a sample comprising said cell, wherein said phosphorylation site is one or more of the following phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more phosphorylation sites in comparison to the control is indicative of the responsiveness of said cell or is indicative of the responsiveness of the assessed individual to dasatinib or pharmaceutically acceptable salts, solvates, and/or hydrates of dasatinib.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4, further comprising evaluating the phosphorylation of one or more phosphorylation sites in said cell or in a sample comprising said cell, wherein said phosphorylation site is one or more of the following phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more phosphorylation sites in comparison to the control is indicative of the responsiveness of said cell or is indicative of the responsiveness of the assessed individual to bosutinib (SKI-606) or pharmaceutically acceptable salts, solvates, and/or hydrates of bosutinib (SKI-606).

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4, further comprising evaluating the phosphorylation of one or more phosphorylation sites in said cell or in a sample comprising said cell, wherein said phosphorylation site is one or more of the following phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more phosphorylation sites in comparison to the control is indicative of the responsiveness of said cell or is indicative of the responsiveness of the assessed individual to saracatinib (AZD530) or pharmaceutically acceptable salts, solvates, and/or hydrates of saracatinib (AZD530).

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor wherein said status is the expression level of integrin β4 and wherein an increase in said expression level in comparison to the control is indicative of the responsiveness of said cell to the inhibitor, wherein said inhibitor of a kinase of the Src-family is dasatinib or pharmaceutically acceptable salts, solvates, and/or hydrates of dasatinib, said method further comprising evaluating the phosphorylation of one or more phosphorylation sites in said cell or in a sample comprising said cell, wherein said phosphorylation site is one or more of the following phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more phosphorylation sites in comparison to the control is indicative of the responsiveness of said cell or is indicative of the responsiveness of the assessed individual to dasatinib or pharmaceutically acceptable salts, solvates, and/or hydrates of dasatinib.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor wherein said status is the expression level of integrin β4 and wherein an increase in said expression level in comparison to the control is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), said method further comprising evaluating the phosphorylation of one or more phosphorylation sites in said cell or in a sample comprising said cell, wherein said phosphorylation site is one or more of the following (further or additional) phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more (further or additional) phosphorylation sites in comparison to the control is (also) indicative of the responsiveness of said cell or is indicative of the responsiveness of the assessed individual to bosutinib (SKI-606) or pharmaceutically acceptable salts, solvates, and/or hydrates of bosutinib (SKI-606).

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor wherein said status is the expression level of integrin β4 and wherein an increase in said expression level in comparison to the control is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), said method further comprising evaluating the phosphorylation of one or more phosphorylation sites in said cell or in a sample comprising said cell, wherein said phosphorylation site is one or more of the following (further or additional) phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more phosphorylation sites in comparison to the control is (also) indicative of the responsiveness of said cell or is indicative of the responsiveness of the assessed individual to saracatinib (AZD530) or pharmaceutically acceptable salts, solvates, and/or hydrates of saracatinib (AZD530).

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said status is the expression level of integrin β4 and wherein an increase in said expression level in comparison to the control is indicative of the responsiveness of said cell to the inhibitor, said method further comprising evaluating the phosphorylation of one or more phosphorylation sites in said cell or in a sample comprising said cell, wherein said phosphorylation site is one or more of the following phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2.

wherein an increase in said phosphorylation of one or more phosphorylation sites in comparison to the control is indicative of the responsiveness of said cell and/or is indicative of the responsiveness of the assessed individual to the inhibitor of a kinase of the Src-family A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said status of integrin β4 is the phosphorylation of integrin β4, said method further comprising evaluating the phosphorylation of one or more additional phosphorylation sites in said cell or in a sample comprising said cell, wherein said phosphorylation site is one or more of the following (further or additional) phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more (further or additional) phosphorylation sites in comparison to the control is indicative of the responsiveness of said cell and/or is (also) indicative of the responsiveness of the assessed individual to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status of integrin β4 is the phosphorylation of integrin β4, said method further comprising evaluating the phosphorylation of one or more additional phosphorylation sites in said cell or in a sample comprising said cell, wherein said phosphorylation site is one or more of the following (further or additional) phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more (further or additional) phosphorylation sites in comparison to the control is indicative of the responsiveness of said cell and/or is (also) indicative of the responsiveness of the assessed individual to dasatinib or pharmaceutically acceptable salts, solvates, and/or hydrates of dasatinib A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status of integrin β4 is the phosphorylation of integrin β4, said method further comprising evaluating the phosphorylation of one or more additional phosphorylation sites in said cell or in a sample comprising said cell, wherein said phosphorylation site is one or more of the following (further or additional) phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more (further or additional) phosphorylation sites in comparison to the control is indicative of the responsiveness of said cell and/or is (also) indicative of the responsiveness of the assessed individual to bosutinib (SKI-606) or pharmaceutically acceptable salts, solvates, and/or hydrates of bosutinib (SKI-606).

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status of integrin β4 is the phosphorylation of integrin β4, said method further comprising evaluating the phosphorylation of one or more additional phosphorylation sites in said cell or in a sample comprising said cell, wherein said phosphorylation site is one or more of the following (further or additional) phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more (further or additional) phosphorylation sites in comparison to the control is indicative of the responsiveness of said cell and/or is (also) indicative of the responsiveness of the assessed individual to saracatinib (AZD530) or pharmaceutically acceptable salts, solvates, and/or hydrates of saracatinib (AZD530)

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said status of integrin β4 is the phosphorylation of integrin β4, wherein an increase in said phosphorylation of one or more phosphorylation sites of integrin β4 in comparison to the control is indicative of the responsiveness of said cell to the inhibitor, said method comprising the evaluation of the phosphorylation of one or more additional phosphorylation sites in said cell or in a sample comprising said cell, wherein said phosphorylation site is one or more of the following (additional) phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more (additional) phosphorylation sites in comparison to the control is indicative of the responsiveness of said cell and/or is indicative of the responsiveness of the assessed individual to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status of integrin β4 is the phosphorylation of integrin β4 and wherein an increase in said phosphorylation of one or more phosphorylation sites of integrin β4 in comparison to the control is indicative of the responsiveness of said cell to the inhibitor, said method comprising the evaluation of the phosphorylation of one or more additional phosphorylation sites in said cell or in a sample comprising said cell, wherein said phosphorylation site is one or more of the following phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more (further or additional) phosphorylation sites in comparison to the control is indicative of the responsiveness of said cell and/or is (also) indicative of the responsiveness of the assessed individual to dasatinib or pharmaceutically acceptable salts, solvates, and/or hydrates of dasatinib.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status of integrin β4 is the phosphorylation of integrin β4 and wherein an increase in said phosphorylation of one or more phosphorylation sites of integrin β4 in comparison to the control is indicative of the responsiveness of said cell to the inhibitor, said method comprising the evaluation of the phosphorylation of one or more additional phosphorylation sites in said cell or in a sample comprising said cell, wherein said phosphorylation site is one or more of the following (further or additional) phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more (further or additional) phosphorylation sites in comparison to the control is indicative of the responsiveness of said cell and/or is (also) indicative of the responsiveness of the assessed individual to is bosutinib (SKI-606) or pharmaceutically acceptable salts, solvates, and/or hydrates of bosutinib (SKI-606).

A method for predicting the responsiveness of a mammalian tumor or cancer cell to an inhibitor of a kinase of the Src-family, said method comprising evaluating the status of integrin β4 (ITGB4) in said tumor or cancer cell, wherein said status is indicative of the responsiveness of said cell to the inhibitor, wherein said inhibitor of a kinase of the Src-family is saracatinib (AZD530) and pharmaceutically acceptable salts, solvates, and/or hydrates of saracatinib (AZD530), wherein said status of integrin β4 is the phosphorylation of integrin β4 and wherein an increase in said phosphorylation of one or more phosphorylation sites of integrin β4 in comparison to the control is indicative of the responsiveness of said cell to the inhibitor, said method comprising the evaluation of the phosphorylation of one or more additional phosphorylation sites in said cell or in a sample comprising said cell, wherein said phosphorylation site is one or more of the following (further or additional) phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more (further or additional) phosphorylation sites in comparison to the control is indicative of the responsiveness of said cell and/or is (also) indicative of the responsiveness of the assessed individual to is saracatinib (AZD530) and pharmaceutically acceptable salts, solvates, and/or hydrates of saracatinib (AZD530).

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said status is the expression level of integrin β4, said method further comprising evaluating the phosphorylation of integrin β4 in said cell or in a sample comprising said cell, wherein one or more of the following (further or additional) phosphorylation sites is/are evaluated:

a. S509 of BAIAP2;
b. S345 of GPRC5A;

c. S916 of ITPR3;
d. S429 of TNKS1BP1;
e. S1101 of ARHGEF18;
f. S102 of IASPP;
g. S269 of APG16L; and
h. S161 of TPD52L2, and wherein an increase in said phosphorylation of one or more phosphorylation sites in comparison to the control is indicative of the responsiveness of said cell and/or is indicative of the responsiveness of the assessed individual to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said status is the expression level of integrin β4, wherein an increase in said expression level in comparison to the control is indicative of the responsiveness of said cell to the inhibitor, said method further comprising evaluating the phosphorylation of integrin β4 in said cell or in a sample comprising said cell, wherein one or more of the following phosphorylation sites is/are additionally evaluated:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2.

and wherein an increase in said phosphorylation of one or more phosphorylation sites in comparison to the control is (also) indicative of the responsiveness of said cell and/or is indicative of the responsiveness of the assessed individual to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4, said method further comprising evaluating the phosphorylation of integrin β4 in said cell or in a sample comprising said cell, wherein one or more of the following phosphorylation sites is/are evaluated:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more phosphorylation sites in comparison to the control is indicative of the responsiveness of said cell and/or is indicative of the responsiveness of the assessed individual to dasatinib or pharmaceutically acceptable salts, solvates, and/or hydrates of dasatinib.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4, said method further comprising evaluating the phosphorylation of integrin β4 in said cell or in a sample comprising said cell, wherein one or more of the following phosphorylation sites is/are evaluated:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more phosphorylation sites in comparison to the control is indicative of the responsiveness of said cell and/or is indicative of the responsiveness of the assessed individual to bosutinib (SKI-606) or pharmaceutically acceptable salts, solvates, and/or hydrates of bosutinib (SKI-606).

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4, said method further comprising evaluating the phosphorylation of integrin β4 in said cell or in a sample comprising said cell, wherein one or more of the following phosphorylation sites is/are additionally evaluated:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more phosphorylation sites in comparison to the control is (also) indicative of the responsiveness of said cell and/or is indicative of the responsiveness of the assessed individual to saracatinib (AZD530) or pharmaceutically acceptable salts, solvates, and/or hydrates of saracatinib (AZD530)

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4, wherein an increase in said expression level in comparison to the control is indicative of the responsiveness of said cell to the inhibitor, said method further comprising evaluating the phosphorylation of integrin β4 in said cell or in a sample comprising said cell, further comprising evaluating the phosphorylation of one or more additional phosphorylation sites in said cell or in said sample, wherein one or more of the following phosphorylation sites is/are (additionally) evaluated:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more phosphorylation sites in comparison to the control is (also) indicative of the responsiveness of said cell and/or is indicative of the responsiveness of the assessed individual to dasatinib or pharmaceutically acceptable salts, solvates, and/or hydrates of dasatinib.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4, wherein an increase in said expression level in comparison to the control is indicative of the responsiveness of said cell to the inhibitor, said method further comprising evaluating the phosphorylation of integrin β4 in said cell or in a sample comprising said cell, further comprising evaluating the phosphorylation of one or more additional phosphorylation sites in said cell or in said sample, wherein one or more of the following phosphorylation sites is/are (additionally) evaluated:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more phosphorylation sites in comparison to the control is (also) indicative of the responsiveness of said cell and/or is indicative of the responsiveness of the assessed individual to bosutinib (SKI-606) or pharmaceutically acceptable salts, solvates, and/or hydrates of bosutinib (SKI-606).

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4, wherein an increase in said expression level in comparison to the control is indicative of the responsiveness of said cell to the inhibitor, said method further comprising evaluating the phosphorylation of integrin β4 in said cell or in a sample comprising said cell, further comprising evaluating the phosphorylation of one or more additional phosphorylation sites in said cell or in said sample, wherein one or more of the following phosphorylation sites is/are (additionally) evaluated:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more phosphorylation sites in comparison to the control is (also) indicative of the responsiveness of said cell and/or is indicative of the responsiveness of the assessed individual saracatinib (AZD530) or pharmaceutically acceptable salts, solvates, and/or hydrates of saracatinib (AZD530).

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor and wherein said status is the expression level of integrin β4, said method further comprising evaluating the phosphorylation of integrin β4 in said cell or in a sample comprising said cell, wherein an increase in said phosphorylation of one or more phosphorylation sites of integrin β4 in comparison to the control is (also) indicative of the responsiveness of said cell or a responsive individual to the inhibitor, wherein one or more of the following phosphorylation sites is/are (additionally) evaluated:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, and wherein an increase in said phosphorylation of one or more phosphorylation sites in comparison to the control is (also) indicative of the responsiveness of said cell and/or is indicative of the responsiveness of the assessed individual to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said status is the expression level of integrin β4 and wherein an increase in said expression level in comparison to the control is indicative of the responsiveness of said cell to the inhibitor, said method further comprising evaluating the phosphorylation of integrin β4 in said cell or in a sample comprising said cell, wherein an increase in said phosphorylation of one or more phosphorylation sites of integrin β4 in comparison to the control is indicative of the responsiveness of said cell or is indicative of the responsiveness of an individual to the inhibitor, said method comprising the (additional) evaluation of one or more of the following phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, and wherein an increase in said phosphorylation of one or more phosphorylation sites in comparison to the control is (also) indicative of the responsiveness of said cell and/or is indicative of the responsiveness of the assessed individual to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor and wherein said status is the expression level of integrin β4, wherein said inhibitor of a kinase of the Src-family is dasatinib or pharmaceutically acceptable salts, solvates, and/or hydrates of dasatinib, said method further comprising evaluating the phosphorylation of integrin β4 in said cell or said sample, wherein an increase in said phosphorylation of one or more phosphorylation sites of integrin β4 in comparison to the control is indicative of the responsiveness of said cell or a responsive individual to the inhibitor, wherein one or more of the following phosphorylation sites is/are (additionally) evaluated:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, and wherein an increase in said phosphorylation of one or more of these phosphorylation sites in comparison to the control is (also) indicative of the responsiveness of said cell and/or is indicative of the responsiveness of the assessed individual to dasatinib or pharmaceutically acceptable salts, solvates, and/or hydrates of dasatinib.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor and wherein said status is the expression level of integrin β4, wherein said inhibitor of a kinase of the Src-family is bosutinib (SKI-606) or pharmaceutically acceptable salts, solvates, and/or hydrates of bosutinib (SKI-606), said method further comprising evaluating the phosphorylation of integrin β4 in said cell or said sample, wherein an increase in said phosphorylation of one or more phosphorylation sites of integrin β4 in comparison to the control is indicative of the responsiveness of said cell or a responsive individual to the inhibitor, wherein one or more of the following phosphorylation sites is/are (additionally) evaluated:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, and wherein an increase in said phosphorylation of one or more of these phosphorylation sites in comparison to the control is (also) indicative of the responsiveness of said cell and/or is indicative of the responsiveness of the assessed individual to bosutinib (SKI-606) or pharmaceutically acceptable salts, solvates, and/or hydrates of bosutinib (SKI-606).

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor and wherein said status is the expression level of integrin β4, wherein said inhibitor of a kinase of the Src-family is saracatinib (AZD530) or pharmaceutically acceptable salts, solvates, and/or hydrates of saracatinib (AZD530), said method further comprising evaluating the phosphorylation of integrin β4 in said cell or said sample, wherein an increase in said phosphorylation of one or more phosphorylation sites of integrin β4 in comparison to the control is indicative of the responsiveness of said cell or a responsive individual to the inhibitor, wherein one or more of the following phosphorylation sites is/are (additionally) evaluated:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, and wherein an increase in said phosphorylation of one or more of these phosphorylation sites in comparison to the control is (also) indicative of the responsiveness of said cell and/or is indicative of the responsiveness of the assessed individual to saracatinib (AZD530) or pharmaceutically acceptable salts, solvates, and/or hydrates of saracatinib (AZD530).

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor and wherein said status is the expression level of integrin β4, wherein an increase in said expression level in comparison to the control is indicative of the responsiveness of said cell to the inhibitor, wherein said inhibitor of a kinase of the Src-family is dasatinib or pharmaceutically acceptable salts, solvates, and/or hydrates of dasatinib, said method further comprising evaluating the phosphorylation of integrin β4 in said cell or in a sample comprising said cell, wherein an increase in said phosphorylation of one or more phosphorylation sites of integrin β4 in comparison to the control is indicative of the responsiveness of said cell or is indicative of the responsiveness of an individual to the inhibitor, wherein one or more of the following phosphorylation sites is/are (additionally) evaluated:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, and wherein an increase in said phosphorylation of one or more of these phosphorylation sites in comparison to the control is (also) indicative of the responsiveness of said cell and/or is indicative of the responsiveness of the assessed individual to dasatinib or pharmaceutically acceptable salts, solvates, and/or hydrates of dasatinib.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor and wherein said status is the expression level of integrin β4, wherein an increase in said expression level in comparison to the control is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), said method further comprising evaluating the phosphorylation of integrin β4 in said cell or in a sample comprising said cell, wherein an increase in said phosphorylation of one or more phosphorylation sites of integrin β4 in comparison to the control is indicative of the responsiveness of said cell or is indicative of the responsiveness of an individual to the inhibitor, wherein one or more of the following phosphorylation sites is/are (additionally) evaluated:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, and wherein an increase in said phosphorylation of one or more of these phosphorylation sites in comparison to the control is (also) indicative of the responsiveness of said cell and/or is indicative of the responsiveness of the assessed individual to bosutinib (SKI-606) or pharmaceutically acceptable salts, solvates, and/or hydrates of bosutinib (SKI-606).

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor and wherein said status is the expression level of integrin β4, wherein an increase in said expression level in comparison to the control is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), said method further comprising evaluating the phosphorylation of integrin β4 in said cell or in a sample comprising said cell, wherein an increase in said phosphorylation of one or more phosphorylation sites of integrin β4 in comparison to the control is indicative of the responsiveness of said cell or is indicative of the responsiveness of an individual to the inhibitor, wherein one or more of the following phosphorylation sites is/are (additionally) evaluated:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, and wherein an increase in said phosphorylation of one or more of these phosphorylation sites in comparison to the control is (also) indicative of the responsiveness of said cell and/or is indicative of the responsiveness of the assessed individual to saracatinib (AZD530) or pharmaceutically acceptable salts, solvates, and/or hydrates of saracatinib (AZD530).

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said status of integrin β4 is the phosphorylation of integrin β4, wherein the phosphorylation site is one or more of the phosphorylation sites S1518, S1457, T1455 and S1069 of integrin β4, said method further comprising evaluating the phosphorylation of one or more additional phosphorylation sites in said cell or in a sample comprising said cell, wherein said phosphorylation site to be evaluated is one or more of the following phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more phosphorylation sites in comparison to the control is (also) indicative of the responsiveness of said cell or a responsive individual to the inhibitor of a kinase of the Src-family.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status of integrin β4 is the phosphorylation of integrin β4 and wherein the phosphorylation site is one or more of the phosphorylation sites S1518, S1457, T1455 and S1069 of integrin β4, said method further comprising evaluating the phosphorylation of one or more additional phosphorylation sites in said cell or in a sample comprising said cell, wherein said (additional) phosphorylation site is one or more of the following phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said additional phosphorylation of one or more phosphorylation sites in comparison to the control is (also) indicative of the responsiveness of said cell or is also indicative of the responsiveness of an individual to dasatinib or pharmaceutically acceptable salts, solvates, and/or hydrates of dasatinib.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status of integrin β4 is the phosphorylation of integrin β4 and wherein the phosphorylation site is one or more of the phosphorylation sites S1518, S1457, T1455 and S1069 of integrin β4, said method further comprising evaluating the phosphorylation of one or more additional phosphorylation sites in said cell or in a sample comprising said cell, wherein said (additional) phosphorylation site is one or more of the following phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said additional phosphorylation of one or more phosphorylation sites in comparison to the control is (also) indicative of the responsiveness of said cell or is also indicative of the responsiveness of an individual to bosutinib (SKI-606) or pharmaceutically acceptable salts, solvates, and/or hydrates of bosutinib (SKI-606).

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status of integrin β4 is the phosphorylation of integrin β4 and wherein the phosphorylation site is one or more of the phosphorylation sites S1518, S1457, T1455 and S1069 of integrin β4, said method further comprising evaluating the phosphorylation of one or more additional phosphorylation sites in said cell or in a sample comprising said cell, wherein said (additional) phosphorylation site is one or more of the following phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said additional phosphorylation of one or more phosphorylation sites in comparison to the control is (also) indicative of the responsiveness of said cell or is also indicative of the responsiveness of an individual to saracatinib (AZD530) or pharmaceutically acceptable salts, solvates, and/or hydrates of saracatinib (AZD530).

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said status of integrin β4 is the phosphorylation of integrin β4, wherein an increase in said phosphorylation of one or more phosphorylation sites of integrin β4 in comparison to the control is indicative of the responsiveness of said cell to the inhibitor, wherein the phosphorylation site is one or more of the phosphorylation sites S1518, S1457, T1455 and S1069 of integrin β4, said method further comprising evaluating the phosphorylation of one or more additional phosphorylation sites in said cell or in a sample comprising said cell, wherein said additional phosphorylation site is one or more of the following phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of one or more phosphorylation sites in comparison to the control is (also) indicative of the responsiveness of said cell or is (also) indicative of the responsiveness of an individual to the inhibitor. Said inhibitor may be inhibitor of a kinase of the Src-family is dasatinib or pharmaceutically acceptable salts, solvates, and/or hydrates of dasatinib. Said inhibitor may be bosutinib (SKI-606) or pharmaceutically acceptable salts, solvates, and/or hydrates of bosutinib (SKI-606). Said inhibitor may be saracatinib (AZD530) or pharmaceutically acceptable salts, solvates, and/or hydrates of saracatinib (AZD530).

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said status is the expression level of integrin β4 and wherein the expression level of integrin β4 is the mRNA expression level of integrin β4, said method further comprising evaluating the phosphorylation of one or more phosphorylation sites in said cell or a sample comprising said cell, wherein said phosphorylation site is one or more of the following phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, wherein an increase in said phosphorylation of any of these phosphorylation sites in comparison to the control is (also) indicative of the responsiveness of said cell or is (also) indicative of the responsiveness a responsive individual to the inhibitor. Said inhibitor of a kinase of the Src-family may be dasatinib or pharmaceutically acceptable salts, solvates, and/or hydrates of dasatinib. Said inhibitor may be bosutinib (SKI-606) or pharmaceutically acceptable salts, solvates, and/or hydrates of bosutinib (SKI-606). Said inhibitor may be saracatinib (AZD530) or pharmaceutically acceptable salts, solvates, and/or hydrates of saracatinib (AZD530).

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is dasatinib or pharmaceutically acceptable salts, solvates, and/or hydrates of dasatinib, wherein said status is the expression level of integrin β4 and wherein an increase in said expression level in comparison to the control is indicative of the responsiveness of said cell to the inhibitor and wherein the expression level of integrin β4 is the mRNA expression level of integrin β4, said method further comprising evaluating the phosphorylation of one or more phosphorylation sites in said cell or in a sample comprising said cell, wherein said phosphorylation site is one or more of the following (additional) phosphorylation sites:

a. S509 of BAIAP2;
b. S345 of GPRC5A;
c. S916 of ITPR3;
d. S429 of TNKS1BP1;
e. S1101 of ARHGEF18;

f. S102 of IASPP;

g. S269 of APG16L; and h. S161 of TPD52L2.

wherein an increase in said phosphorylation of any of these phosphorylation sites in comparison to the control is (also) indicative of the responsiveness of said cell or is indicative of the responsiveness a responsive individual o dasatinib or pharmaceutically acceptable salts, solvates, and/or hydrates of dasatinib.

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is bosutinib (SKI-606) or pharmaceutically acceptable salts, solvates, and/or hydrates of bosutinib (SKI-606), wherein said status is the expression level of integrin β4 and wherein an increase in said expression level in comparison to the control is indicative of the responsiveness of said cell to the inhibitor and wherein the expression level of integrin β4 is the mRNA expression level of integrin β4, said method further comprising evaluating the phosphorylation of one or more phosphorylation sites in said cell or in a sample comprising said cell, wherein said phosphorylation site is one or more of the following (additional) phosphorylation sites:

a. S509 of BAIAP2;

b. S345 of GPRC5A;

c. S916 of ITPR3;

d. S429 of TNKS1BP1;

e. S1101 of ARHGEF18;

f. S102 of IASPP;

g. S269 of APG16L; and h. S161 of TPD52L2, wherein an increase in said phosphorylation of any of these phosphorylation sites in comparison to the control is (also) indicative of the responsiveness of said cell or is indicative of the responsiveness a responsive individual o the bosutinib (SKI-606) or pharmaceutically acceptable salts, solvates, and/or hydrates of bosutinib (SKI-606).

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said inhibitor of a kinase of the Src-family is saracatinib (AZD530) or pharmaceutically acceptable salts, solvates, and/or hydrates of saracatinib (AZD530), wherein said status is the expression level of integrin β4 and wherein an increase in said expression level in comparison to the control is indicative of the responsiveness of said cell to the inhibitor and wherein the expression level of integrin β4 is the mRNA expression level of integrin β4, said method further comprising evaluating the phosphorylation of one or more phosphorylation sites in said cell or in a sample comprising said cell, wherein said phosphorylation site is one or more of the following phosphorylation sites:

a. S509 of BAIAP2;

b. S345 of GPRC5A;

c. S916 of ITPR3;

d. S429 of TNKS1BP1;

e. S1101 of ARHGEF18;

f. S102 of IASPP;

g. S269 of APG16L; and h. S161 of TPD52L2, wherein an increase in said phosphorylation of any of these phosphorylation sites in comparison to the control is (also) indicative of the responsiveness of said cell or is indicative of the responsiveness a responsive individual o the saracatinib (AZD530) or pharmaceutically acceptable salts, solvates, and/or hydrates of saracatinib (AZD530)

A method for predicting the responsiveness of a mammalian tumor or cancer cell to an inhibitor of a kinase of the Src-family, said method comprising evaluating the status of integrin β4 (ITGB4) in/of said tumor or cancer cell, wherein said status is indicative of the responsiveness of said cell to the inhibitor, wherein said status is the expression level of integrin β4 and wherein the expression level of integrin β4 is the mRNA expression level of integrin β4, wherein an increase in said expression level in comparison to the control is indicative of the responsiveness of said cell to the inhibitor, said method further comprising evaluating the phosphorylation of one or more phosphorylation sites in said cell or said sample, wherein said phosphorylation site is one or more of the following phosphorylation sites:

a. S509 of BAIAP2;0 b. S345 of GPRC5A;

c. S916 of ITPR3;

d. S429 of TNKS1BP1;

e. S1101 of ARHGEF18;

f. S102 of IASPP;

g. S269 of APG16L; and h. S161 of TPD52L2, wherein an increase in said phosphorylation of one or more phosphorylation sites in comparison to the control is (also) indicative of the responsiveness of said cell or is (also) indicative of the responsiveness of an individual to the inhibitor.

Besides the assessment of the expression status (mRNA and/or protein) of integrin β4 (ITGB4) in combination with is one or more of the phosphorylation sites a. S509 of BAIAP2; b. S345 of GPRC5A; c. S916 of ITPR3; d. S429 of TNKS1BP1; e. S1101 of ARHGEF18; f. S102 of IASPP; g. S269 of APG16L; and h. S161 of TPD52L2 for the prediction of the responsiveness to an inhibitor of a kinase of the Src-family. It is also within the gist of this invention that these phosphorylation sites a.) to h.) are also combined in such an assessment with the assessment of the phosphorylation status of integrin β4 (ITGB4)/the phosphosignature of integrin β4 (ITGB4) as disclosed herein.

Accordingly, as non-limiting examples, also the following assessments are within the scope of this invention:

A method for predicting the responsiveness of a mammalian tumor or cancer cell to an inhibitor of a kinase of the Src-family, said method comprising evaluating the expression and/or phosphorylation status of integrin β4 (ITGB4) in/of said tumor or cancer cell, wherein said status is indicative of the responsiveness of said cell to the inhibitor, said method further comprising evaluating the phosphorylation of one or more additional phosphorylation sites in said cell or said sample, wherein said phosphorylation site is one or more of the following phosphorylation sites:

a. S509 of BAIAP2;

b. S345 of GPRC5A;

c. S916 of ITPR3;

d. S429 of TNKS1BP1;

e. S1101 of ARHGEF8;

f. S102 of IASPP;

g. S269 of APG16L; and h. S161 of TPD52L2, wherein an increase in said phosphorylation of one or more phosphorylation sites in comparison to the control is (also) indicative of the responsiveness of said cell or is (also) indicative of the responsiveness an individual to said inhibitor. The expression level of integrin β4 to be assessed may be the mRNA expression level. The expression level of integrin β4 to be assessed may be the protein level. As discussed above, an increase in said expression level in comparison to the control may already be indicative of the responsiveness of said cell to the inhibitor. Also an increased phosphorylation level of integrin β4 as compared to the control may already be indicative of the responsiveness of said cell to the inhibitor. The inhibitor may be dasatinib or pharmaceutically acceptable salts, solvates, and/or hydrates of dasatinib. The inhibitor may be bosutinib (SKI-606) or pharmaceutically acceptable salts, solvates, and/or hydrates of bosutinib (SKI-606). The inhibitor may be saracatinib (AZD530) or pharmaceutically acceptable salts, solvates, and/or hydrates of saracatinib (AZD530).

As is evident from the disclosure herein, the present invention provides also for additional phosphorylation markers which can be used for the determination of responsiveness of a tumor or a cancer cell to Src-inhibitors. Therefore, the present invention also relates to methods for predicting the responsiveness of a mammalian tumor or cancer cell to an inhibitor of a kinase of the Src-family, whereby the phosphorylation status of one or more of the following phosphorylation sites are assessed: a. S509 of BAIAP2; b. S345 of GPRC5A; c. S916 of ITPR3; d. S429 of TNKS1BP1; e. S1101 of ARHGEF18; f. S102 of IASPP; g. S269 of APG16L; and/or h. S161 of TPD52L2, wherein an increase in said phosphorylation phosphorylation site(s) in comparison to the control is indicative of the responsiveness of the tumor or cancer cell to an inhibitor of a kinase of the Src-family. The corresponding proteins as well as the phosphorylation sites are also provided and exemplified herein below and also comprise the individual sequences provided herein.

In accordance with the disclosure provided herein, methods for predicting the responsiveness of a mammalian tumor or cancer cell to an inhibitor of a kinase of the Src-family are provided. These methods may comprise, either alone or in combination,

- The evaluation of the (expression) status of integrin β4 (ITGB4) wherein an increase in said expression level in comparison to the control is indicative of the responsiveness of said cell to the inhibitor of a kinase of the Src-family;
- The evaluation of the phosphorylation status/the phophosignature of integrin β4 (ITGB4) wherein an increase in said phosphorylation of one or more phosphorylation sites of integrin β4 in comparison to the control is indicative of the responsiveness of said cell to the inhibitor of a kinase of the Src-family; and
- The evaluation of (additional) phosphorylation site(s), wherein said phosphorylation site(s) is/are one or more of the following phosphorylation sites: a. S509 of BAIAP2; b. S345 of GPRC5A; c. S916 of ITPR3; d. S429 of TNKS1BP1; e. S1101 of ARHGEF18; f. S102 of IASPP; g. S269 of APG16L; and h. S161 of TPD52L2, wherein an increase in said phosphorylation phosphorylation site(s) in comparison to the control is indicative of the responsiveness of the tumor or cancer cell to an inhibitor of a kinase of the Src-family.

Any of the items of the invention described above can be combined with the following item: The method of any one of the above items, comprising evaluating the phosphorylation of the following combination of phosphorylation sites:

a. S1518, S1457, T1455 and S1069 of ITGB4 and S916 of ITPR3;

b. S1518, S1457, T1455 and S1069 of ITGB4 and S429 of TNKS1BP;

c. S1518, S1457, T1455 and S1069 of ITGB4 and S1101 of ARHGEF18;

d. S1518. S1457, T1455 and S1069 of ITGB4 and S269 of APG16L;

e. S1518, S1457, T1455 and S1069 of ITGB4 and S161 of TPD52L2;

f. S1101 of ARHGEF18 and S345 of GPRC5A;

g. S1101 of ARHGEF18 and S916 of ITPR3; or h. S1101 of ARHGEF18 and S102 of IASPP; or i. any combinations of a. to h.

Any of the items of the invention described above can be combined with the following item: The method of any of one of the above items, wherein said tumor/cancer is a solid tumor, in particular a lung tumor/cancer, such as non small cell lung cancer (NSCLC) or a breast tumor/cancer.

In above aspects of the present invention relating to the evaluation of one or more additional phosphorylation sites, the phosphorylation site can be one or more of the following phosphorylation sites (It is to be understood that any of the items of the invention described above can be combined with any of the following items):

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2, In other words, the phosphorylation site(s) can be as follows a. S509 of BAIAP2; and b. S345 of GPRC5A;
a. S509 of BAIAP2; and c. S916 of ITPR3;
a. S509 of BAIAP2; and d. S429 of TNKS1BP1;
a. S509 of BAIAP2; and e. S1101 of ARHGEF18;
a. S509 of BAIAP2; and f. S102 of IASPP;
a. S509 of BAIAP2; and g. S269 of APG16L;
a. S509 of BAIAP2; and h. S161 of TPD52L2, a. S509 of BAIAP2; b. S345 of GPRC5A and c. S916 of ITPR3;

a. S509 of BAIAP2; b. S345 of GPRC5A; and d. S429 of TNKS1BP1;

a. S509 of BAIAP2; and b. S345 of GPRC5A; and e. S1101 of ARHGEF18;

a. S509 of BAIAP2; and b. S345 of GPRC5A; and f. S102 of IASPP;

a. S509 of BAIAP2; and b. S345 of GPRC5A; and g. S269 of APG16L;

a. S509 of BAIAP2; and b. S345 of GPRC5A; and h. S1161 of TPD52L2, a. S509 of BAIAP2; b. S345 of GPRC5A c. S916 of ITPR3; and d. S429 of TNKS1BP1 ;

a. S509 of BAIAP2; b. S345 of GPRC5A c. S916 of ITPR3; and e. S1101 of ARHGEF18;

a. S509 of BAIAP2; b. S345 of GPRC5A c. S916 of ITPR3; and f. S102 of IASPP;

a. S509 of BAIAP2; b. S345 of GPRC5A c. S916 of ITPR3; and g. S269 of APG16L;

a. S509 of BAIAP2; b. S345 of GPRC5A c. S916 of ITPR3; and h. S161 of TPD52L2, a. S509 of BAIAP2; b. S345 of GPRC5A c. S916 of ITPR3; and d. S429 of TNKS1BP1; and e. S1101 of ARHGEF18;

a. S509 of BAIAP2; b. S345 of GPRC5A c. S916 of ITPR3; and d. S429 of TNKS1BP1; and f. S102 of IASPP;

a. S509 of BAIAP2; b. S345 of GPRC5A c. S916 of ITPR3; and d. S429 of TNKS1BP1; and g. S269 of APG16L;

a. S509 of BAIAP2; b. S345 of GPRC5A c. S916 of ITPR3; and d. S429 of TNKS1BP1; and h. S161 of TPD52L2, a. S509 of BAIAP2; b. S345 of GPRC5A c. S916 of ITPR3; d. S429 of TNKS1BP1; e. S1101 of ARHGEF18; and f. S102 of IASPP;

a. S509 of BAIAP2; b. S345 of GPRC5A c. S916 of ITPR3; and d. S429 of TNKS1BP1; and e. S1101 of ARHGEF18; and g. S269 of APG16L;

a. S509 of BAIAP2; b. S345 of GPRC5A c. S916 of ITPR3; and d. S429 of TNKS1BP1; and e. S1101 of ARHGEF18; and h. S161 of TPD52L2.

a. S509 of BAIAP2; b. S345 of GPRC5A c. S916 of ITPR3; d. S429 of TNKS1BP1; e. S1101 of ARHGEF18; f. S102 of IASPP; and g. S269 of APG16L;

a. S509 of BAIAP2; b. S345 of GPRC5A c. S916 of ITPR3; d. S429 of TNKS1BP1; e. S1101 of ARHGEF18; f. S102 of IASPP; and h. S161 of TPD52L2, a. S509 of BAIAP2; b. S345 of GPRC5A; c. S916 of ITPR3; d. S429 of TNKS1BP1; e. S1101 of ARHGEF18; f. S102 of IASPP; g. S269 of APG16L; and h. S161 of TPD52L2, b. S345 of GPRC5A and c. S916 of ITPR3;

b. S345 of GPRC5A; and d. S429 of TNKS1BP1;

b. S345 of GPRC5A; and e. S1101 of ARHGEF18;

b. S345 of GPRC5A; and f. S102 of IASPP;

b. S345 of GPRC5A; and g. S269 of APG16L;

b. S345 of GPRC5A; and h. S161 of TPD52L2, b. S345 of GPRC5A; c. S916 of ITPR3; and d. S429 of TNKS1BP1;

b. S345 of GPRC5A; c. S916 of ITPR3; and e. S1101 of ARHGEF18;

b. S345 of GPRC5A; c. S916 of ITPR3; and f. S102 of IASPP;

b. S345 of GPRC5A; c. S916 of ITPR3; and g. S269 of APG16L;

b. S345 of GPRC5A; c. S916 of ITPR3; and h. S161 of TPD52L2, b. S345 of GPRC5A; c. S916 of ITPR3; and d. S429 of TNKS1BP1; and e. S1101 of ARHGEF18;

b. S345 of GPRC5A; c. S916 of ITPR3; and d. S429 of TNKS1BP1; and f. S102 of IASPP;

b. S345 of GPRC5A; c. S916 of ITPR3; and d. S429 of TNKS1BP1; and g. S269 of APG16L;

b. S345 of GPRC5A; c. S916 of ITPR3; and d. S429 of TNKS1BP1; and h. S161 of TPD52L2, b. S345 of GPRC5A; c. S916 of ITPR3; d. S429 of TNKS1BP1; e. S1101 of ARHGEF18; and f. S102 of IASPP;

b. S345 of GPRC5A; c. S916 of ITPR3; and d. S429 of TNKS1BP1; and e. S1101 of ARHGEF18; and g. S269 of APG16L;

b. S345 of GPRC5A; c. S916 of ITPR3; and d. S429 of TNKS1BP1; and e. S1101 of ARHGEF18; and h. S161 of TPD52L2, b. S345 of GPRC5A; c. S916 of ITPR3; d. S429 of TNKS1BP1; e. S1101 of ARHGEF18; f. S102 of IASPP; and g. S269 of APG16L;

b. S345 of GPRC5A; c. S916 of ITPR3; d. S429 of TNKS1BP1; e. S1101 of ARHGEF18; f. S102 of IASPP; and h. S161 of TPD52L2, b. S345 of GPRC5A; c. S916 of ITPR3; d. S429 of TNKS1BP1; e. S11101 of ARHGEF18; f. S102 of IASPP; g. S269 of APG16L; and h. S161 of TPD52L2, c. S916 of ITPR3; and d. S429 of TNKS1BP1;

c. S916 of ITPR3; and e. S1101 of ARHGEF18;

c. S916 of ITPR3; and f. S102 of IASPP;

c. S916 of ITPR3; and g. S269 of APG16L;

c. S916 of ITPR3; and h. S161 of TPD52L2, c. S916 of ITPR3; and d. S429 of TNKS1BP1; and e. S1101 of ARHGEF18;

c. S916 of ITPR3; and d. S429 of TNKS1BP1; and f. S102 of IASPP;

c. S916 of ITPR3; and d. S429 of TNKS1BP1; and g. S269 of APG16L;

c. S916 of ITPR3; and d. S429 of TNKS1BP1; and h. S161 of TPD52L2, c. S916 of ITPR3; d. S429 of TNKS1BP1; e. S1101 of ARHGEF18; and f. S102 of IASPP;

c. S916 of ITPR3; and d. S429 of TNKS1BP1; and e. S1101 of ARHGEF18; and g. S269 of APG16L;

c. S916 of ITPR3; and d. S429 of TNKS1BP1; and e. S1101 of ARHGEF18; and h. S161 of TPD52L2, c. S916 of ITPR3; d. S429 of TNKS1BP1; e. S1101 of ARHGEF18; f. S102 of IASPP; and g. S269 of APG16L;

c. S916 of ITPR3; d. S429 of TNKS1BP1; e. S1101 of ARHGEF18; f. S102 of IASPP; and h. S161 of TPD52L2, c. S916 of ITPR3; d. S429 of TNKS1BP; e. S1101 of ARHGEF18; f. S102 of IASPP; g. S269 of APG16L; and h. S161 of TPD52L2, d. S429 of TNKS1BP1; and e. S1101 of ARHGEF18;

d. S429 of TNKS1BP1; and f. S102 of IASPP;

d. S429 of TNKS1BP1; and g. S269 of APG16L;

d. S429 of TNKS1BP1; and h. S161 of TPD52L2, e. S1101 of ARHGEF18; and f. S102 of IASPP;

e. S1101 of ARHGEF18; and g. S269 of APG16L;

e. S1101 of ARHGEF18; and h. S161 of TPD52L2, e. S1101 of ARHGEF18; f. S102 of IASPP; and g. S269 of APG16L;

e. S1101 of ARHGEF18; f. S102 of IASPP; and h. S161 of TPD52L2, e. S1101 of ARHGEF18; f. S102 of IASPP; g. S269 of APG16L; and h. S161 of TPD52L2, f. S102 of IASPP; and g. S269 of APG16L;

f. S102 of IASPP; and h. S161 of TPD52L2.

f. S102 of IASPP; g. S269 of APG16L; and h. S161 of TPD52L2; or g. S269 of APG16L; and h. S161 of TPD52L2, The difference in phosphorylation of a specific site between a sample/cell/tissue etc. and a control as defined herein may be due to a difference in either expression of the corresponding protein, or the degree of phosphorylation of this site, or a combination of both. However, as long as the abundance of a certain phosphorylated peptide consistently differs between responsive and non-responsive cells/samples/tissues etc. the cause for its difference is not important for its use in the predictive biomarker signature.

The meaning of the terms “cell(s)”, “tissue(s)” and “cell culture(s)” is well known in the art and may, for example, be deduced from “The Cell” (Garland Publishing, Inc., third edition). Generally, the term “cell(s) used herein refers to a single cell or a plurality of cells. The term “plurality of cells” means in the context of the present invention a group of cells comprising more than a single cell. Thereby, the cells out of said group of cells may have a similar function. Said cells may be connected cells and/or separate cells. The term “tissue” in the context of the present invention particularly means a group of cells that perform a similar function. The term “cell culture(s)” means in context of the present invention cells as defined herein above which are grown/cultured under controlled conditions. Cell culture(s) comprise in particular cells (derived/obtained) from multicellular eukaryotes, preferably animals, in particular mammals, most particularly humans as defined elsewhere herein. It is to be understood that the term "cell culture(s)" as used herein refers also "tissue culture (s)" and/or "organ culture(s)", an "organ" being a group of tissues which perform the some function. Preferably, the cell(s), tissue(s) or cell culture(s) to be contacted with/exposed to an inhibitor comprise/are derived from or are (a) tumor cell(s). The tumor cells may, for example, be obtained from a biopsy, in particular a biopsy/biopsies from a patient/subject suffering from cancer or, though less preferred a patient/subject being prone to suffer from cancer. It is preferred herein that said subject is a human. The term "mammalian tumor cell(s)" used herein refers to (a) tumor cell(s) which is derived from or is a tumor cell from a mammal, the term mammal being defined herein below. As described herein above in respect of "cell(s)", "tissue(s)" and "cell culture(s)" the "mammalian tumor cells" may be obtained from a sample, like a biopsy, in particular a biopsy/biopsies from a patient/subject/individual suffering from cancer or suspected to suffer from cancer or, though less preferred a patient/subject/individual being prone to suffer from cancer. The term "tumor cell" also relates to "cancer cells". Thus, the method for predicting the responsiveness of a mammalian tumor or cancer cell can be used to predict whether a patient/subject/individual suffering from cancer, suspected to suffer from cancer or being prone to suffer from cancer is responsive to an inhibitor of a kinase of the Src-family.

Generally, said tumor cell or cancer cell may be obtained from any biological source/organism, particularly any biological source/organism, suffering from the above-mentioned cancer.

Preferably, the (tumor) cell(s) or (cancer) cell to be contacted is (are) obtained/derived from an animal. More preferably, said (tumor)/(cancer) cell(s) is (are) derived from a mammal. The meaning of the terms "animal" or "mammal" is well known in the art and can, for example, be deduced from Wehner und Gehring (1995; Thieme Verlag). Non-limiting examples for mammals are even-toed ungulates such as sheep, cattle and pig, odd-toed angulates such as horses as well as carnivors such as cats and dogs. In the context of this invention, it is particularly envisaged that samples are derived from organisms that are economically, agronomically or scientifically important. Scientifically or experimentally important organisms include, but are not limited to, mice, rats, rabbits, guinea pigs and pigs.

The tumor cell(s) may also be obtained from primates which comprise lemurs, monkeys and apes. The meaning of the terms "primate", "lemur", "monkey" and "ape" is known and may, for example, be deduced by an artisan from Wehner und Gehring (1995, Thieme Verlag). As mentioned above, the tumor or cancer cell(s) is (are) most preferably derived from a human being suffering from the above-mentioned cancer. In context of this invention particular useful cells, in particular tumor or cancer cells, are, accordingly, human cells. These cells can be obtained from e.g. biopsies or from biological samples but the term "cell" also relates to in vitro cultured cells.

Preferably, said tumor/cancer/tumor cell/cancer cell is a solid tumor/cancer/tumor cell/cancer cell. In accordance with the above, the cancer/tumor cell is preferably a lung cancer/tumor cell or a breast cancer/tumor cell or said sample comprises a cancer/tumor cell, such as a lung cancer/tumor cell or a breast cancer/tumor cell. In line with the above, said tumor/cancer is preferably a lung tumor/cancer or a breast tumor/cancer.

Further cancers may be selected from the group consisting of adenocarcinoma comprising, for example, colorectal, cervical, prostate, urachus, vagina, esophagus, pancreas, stomach, or throat cancer.

Further cancers may be selected from the group consisting of squamous cell carcinoma, for example, skin, head and neck, esophagus, prostate, vaginal, or bladder cancer.

Further cancers may be selected from the group of cancers of the nervous system, for example glioblastoma, astrocytoma, ependymoma, neuroblastoma, retinoblastoma, meningiomas, granular cell tumors, or nerve sheath tumors.

Yet further cancers may be choroidal melanoma, acoustic neurinoma, ampullary carcinoma, anal carcinoma, basal cell carcinoma, desmoid tumor, bronchial carcinoma, Nut midline carcinoma, corpus cancer, CUP-syndrome (carcinoma of unknown primary), small intestine cancer, small intestinal tumors, ovarian cancer, endometrial carcinoma, epithelial cancer types, Ewing's tumors, gastrointestinal tumors, gastric cancer, gallbladder cancer, gall bladder carcinomas, uterine cancer, cervix, gynecologic tumors, ear, nose tumors, hematologic neoplasias, urethral cancer, skin testis cancer, brain tumors (gliomas), brain metastases, testicle cancer, hypophysis tumor, carcinoids, Kaposi's sarcoma, laryngeal cancer, germ cell tumor, bone cancer, tumors of the ear or nosearea), colon carcinoma, craniopharyngiomas, oral cancer (cancer in the mouth area and on lips), cancer of the central nervous system, liver cancer, liver metastases, eyelid tumor, malignant melanoma, malignant neoplasia, malignant tumors gastrointestinal tract, rectal cancer, medulloblastomas, melanoma, Hodgkin's disease, mycosis fungoides, nasal cancer, neurinoma, kidney cancer, renal cell carcinomas, oligodendroglioma, osteolytic carcinomas and osteoplastic carcinomas, osteosarcomas, ovarial carcinoma, penile cancer, plasmocytoma, prostate cancer, pharyngeal cancer, rectal carcinoma, thyroid carcinoma. Schneeberg disease, spinalioms, thymoma, tube carcinoma, eye tumors, urethral cancer, urologic tumors, urothelial carcinoma, vulva cancer, wart appearance, soft tissue tumors, soft tissue sarcoma, Wilm's tumor, tongue cancer, invasive ductal carcinoma, invasive lobular carcinoma, ductal carcinoma in situ, lobular carcinoma in situ, small-cell lung carcinoma, non-small-cell lung carcinoma, bronchial adenoma, pleuropulmonary blastoma, mesothelioma, brain stem glioma, hypophtalmic glioma, cerebellar astrocytoma, cerebral astrocytoma, neuroectodermal tumours, pineal tumors, sarcoma of the uterus, salivary gland cancers, anal gland adenocarcinomas, mast cell tumors, pelvis tumours, ureter tumours, hereditary papillary renal cancers, sporadic papillary renal cancers, intraocular melanoma, hepatocellular carcinoma (liver cell carcinomas with or without fibrolamellar variant), cholangiocarcinoma (intrahepatic bile duct carcinoma), mixed hepatocellular cholangiocarcinoma, malignant melanoma, Merkel cell skin cancer, non-melanoma skin cancer, hypopharyngeal cancer, nasopharyngeal cancer, oropharyngeal cancer, oral cavity cancer, oral melanoma, malignant fibrous histiocytoma, lymphosarcoma, rhabdomyosarcoma, malignant histiocytosis, fibrosarcoma, hemangiosarcoma, hemangiopericytoma, leiomyosarcoma, canine mammary carcinoma, feline mammary carcinoma, cancer of the central nervous system, colon carcinoma, or tumors of the ear or nose area).

In a further embodiment, the present invention relates to integrin β4 as defined herein for use in detecting an individual responsive to an inhibitor of a kinase of the Src-family as herein disclosed.

Another embodiment of the present invention relates to the use of a nucleic acid or antibody capable of detecting the expression level of integrin β4 for predicting the responsiveness of a cancer or tumor cell or a responsive individual to an inhibitor of a kinase of the Src-family as defined herein. Antibodies to be used in this context are known in the art, like commercially available anti integrin β4 antibodies, such as anti-integrin beta 4 antibody [M126](ab29042, Abcam), CAB005258 (sc-9090, Santa Cruz Biotechnology), NB100-78102 (Novus Biologicals), #4707 (Cell Signaling Technology) or SAB4501588 (Sigma-Aldrich). Preferably, the oligonucleotide(s) is (are) about 15 to 100 nucleotides in length. A person skilled in the art is, based on his general knowledge and the teaching provided herein, easily in the position to identify and/or prepare (a) an oligo- or polynucleotide capable of detecting the expression level of integrin β4 and/or of one or more of the other herein disclosed marker genes. In particular these oligo- or polynucleotides may be used as probe(s) in the detection methods described herein. A skilled person will know, for example, computer programs which may be useful for the identification of corresponding probes to be used herein. For example, the Integrin β4 nucleic acid sequence (SEQ ID NO: 1) may be used in this context for identifying specific probes for detecting the expression level of Integrin β4. Exemplary nucleic acid sequences are available on corresponding databases, such as the NCBI database (www.ncbi.nlm.nih.gov/sites/entrez).

The present invention also relates to a kit useful for carrying out the herein provided methods, the kit comprising a nucleic acid or an antibody capable of detecting the expression level of integrin β4 and/or of one or more of the herein provided marker genes. The kit may comprise antibodies known in the art, like commercially available anti integrin β4 antibodies, such as anti-integrin beta 4 antibody [M126] (ab29042, Abcam), CAB005258 (sc-9090, Santa Cruz Biotechnology), NB100-78102 (Novus Biologicals), #4707 (Cell Signaling Technology), SAB4501588 (Sigma-Aldrich). Also envisaged herein is the use of the herein described kit for carrying out the herein provided methods.

In a preferred embodiment, said kit useful for carrying out the methods and uses described herein comprises oligonucleotides or polynucleotides capable of determining the expression level of integrin β4 and/or of one or more of the herein provided marker genes.

For example, said kit may comprise (a) compound(s) required for specifically determining the expression level of integrin β4 and/or of one or more of the herein provided marker genes. Moreover, the present invention also relates to the use of (a) compound(s) required for specifically determining the expression level of integrin β4 and/or of one or more of the herein provided marker genes as defined herein for the preparation of a kit for carrying out the methods or uses of this invention. On the basis of the teaching of this invention, the skilled person knows which compound(s) is (are) required for specifically determining the expression level of integrin β4 and/or of one or more of the herein provided marker genes. For example, such compound(s) may be (a) “binding molecule(s)”. Particularly, such compound(s) or binding molecule(s) may be (a) (nucleotide) probe(s), (a) primer(s) (pair (s)), (an) antibody(ies) and/or (an) aptamer(s) specific for at least one marker gene as described herein or for a product thereof. In a preferred embodiment, the kit (to be prepared in context) of this invention is a diagnostic kit.

In a particularly preferred embodiment of the present invention, the kit (to be prepared in context) of this invention or the methods and uses of the invention may further comprise or be provided with (an) instruction manual(s). For example, said instruction manual(s) may guide the skilled person (how) to determine the (reference/control) expression level of integrin β4 and/or of one or more of the herein provided marker genes or i.e. (how) to diagnose responsiveness to an inhibitor of a kinase of the Src family. Particularly, said instruction manual(s) may comprise guidance to use or apply the herein provided methods or uses.

The kit (to be prepared in context) of this invention may further comprise substances/chemicals and/or equipment suitable/required for carrying out the methods and uses of this invention. For example, such substances/chemicals and/or equipment are solvents, diluents and/or buffers for stabilizing and/or storing (a) compound(s) required for specifically determining the expression level of integrin β4 and/or of one or more of the herein provided marker genes.

In a further embodiment, the present invention relates to an inhibitor of a kinase of the Src family as defined herein for use in the treatment of cancer in an individual or patient identified by the herein described methods. The present invention also provides a method for the treatment of cancer comprising administering an effective amount of an inhibitor of a kinase of the Src family as defined herein to an individual or subject identified by the herein described methods in need of such a treatment. Preferably, said individual or said subject is a human. In other words, the present invention relates to an inhibitor of a kinase of the Src family as defined herein for use in the treatment of cancer in an individual or patient which is predicted to respond according to the herein described methods. The present invention also provides a method for the treatment of cancer comprising administering an effective amount of an inhibitor of a kinase of the Src family as defined herein to an individual or subject predicted to respond according to the herein described methods in need of such a treatment. Preferably, said individual or said subject is a human.

The inhibitor may be administered as a single anti-tumor agent or in form of a combination therapy. The therapy used in said combination therapy may be chemotherapy or an anti-hormonal therapy. The chemotherapy may be anthracycline/taxane chemotherapy, therapy with an anti-metabolite agents, therapy with an anti-hormonal compound, therapy with an anti-estrogen, therapy with a tyrosine kinase inhibitor, therapy with a raf inhibitor, therapy with a ras inhibitor, therapy with a dual tyrosine kinase inhibitor, therapy with taxol, therapy with taxane, therapy with doxorubicin, therapy with adjuvant (anti-) hormone drugs, and/or therapy with cisplatin and the like. The inhibitor may be administered by any one of a parenteral route, oral route, intravenous route, subcutaneous route, intranasal route or transdermal route. The inhibitor may also be administered in a neoadjuvant or adjuvant setting.

The present invention also relates to the use of an inhibitor of a kinase of the Src family as defined herein for the preparation of a pharmaceutical composition for the treatment of a patient identified by the herein provided methods.

The pharmaceutical composition will be formulated and dosed in a fashion consistent with good medical practice, taking into account the clinical condition of the individual patient, the site of delivery of the pharmaceutical composition, the method of administration, the scheduling of administration, and other factors known to practitioners. The “effective amount” of the pharmaceutical composition for purposes herein is thus determined by such considerations.

The skilled person knows that the effective amount of pharmaceutical composition administered to an individual will, inter alia, depend on the nature of the compound. For example, if said compound is a (poly)peptide or protein the total pharmaceutically effective amount of pharmaceutical composition administered parenterally per dose will be in the range of about 1 μg protein/kg/day to 10 mg protein/kg/day of patient body weight, although, as noted above, this will be subject to therapeutic discretion. More preferably, this dose is at least 0.01 mg protein/kg/day, and most preferably for humans between about 0.01 and 1 mg protein/kg/day. If given continuously, the pharmaceutical composition is typically administered at a dose rate of about 1 μg/kg/hour to about 50 μg/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect. The particular amounts may be determined by conventional tests which are well known to the person skilled in the art.

Pharmaceutical compositions of the invention may be administered orally, rectally, parenterally, intracisternally, intravaginally, intraperitoneally, topically (as by powders, ointments, drops or transdermal patch), bucally, or as an oral or nasal spray.

Pharmaceutical compositions of the invention preferably comprise a pharmaceutically acceptable carrier. By “pharmaceutically acceptable carrier” is meant a non-toxic solid, semisolid or liquid filler, diluent, encapsulating material or formulation auxiliary of any type. The term “parenteral” as used herein refers to modes of administration which include intravenous, intramuscular, intraperitoneal, intrasternal, subcutaneous and intraarticular injection and infusion.

The pharmaceutical composition is also suitably administered by sustained release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133,988). Sustained release pharmaceutical composition also include liposomally entrapped compound. Liposomes containing the pharmaceutical composition are prepared by methods known per se: DE 3,218.121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapy.

For parenteral administration, the pharmaceutical composition is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the components of the pharmaceutical composition uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer’s solution, and dextrose solution. Non aqueous vehicles such as fixed oils and ethyl oleate are also useful herein, as well as liposomes. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The components of the pharmaceutical composition to be used for therapeutic administration should be sterile. Sterility is readily accomplished by filtration through sterile filtration membranes (e.g., 0.2 micron membranes). Therapeutic components of the pharmaceutical composition generally are placed into a container having a sterile access port, for example, an intravenous solution bag or vial having a stopper pierceable by a hypodermic injection needle.

The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic Water-for-Injection.

In certain polypeptides the following novel phosphorylation sites have been identified in context of the present invention: S509 of BAIAP2, T1455 of ITGB4, S1069 of ITGB4. These novel phosphorylated proteins are particularly useful in context of the herein provided methods.

Accordingly, the present invention relates in a further embodiment to a polypeptide selected from the group consisting of (a) a polypeptide comprising an amino acid sequence encoded by a nucleic acid molecule having the nucleic acid sequence as depicted in SEQ ID NO: 1;

(b) a polypeptide having an amino acid sequence as depicted in SEQ ID NO 5;

(c) a polypeptide as defined in (a) or (b) wherein one or more amino acids are deleted, inserted, added or substituted, (d) a polypeptide comprising an amino acid sequence encoded by a nucleic acid molecule encoding a peptide having an amino acid sequence as depicted in SEQ ID NO 5;

(e) a polypeptide comprising an amino acid sequence encoded by a nucleic acid molecule hybridizing under stringent conditions to the complementary strand of nucleic acid molecules as defined in (a) or (d) and encoding a functional ITGB4 or a functional fragment thereof;

(f) a polypeptide having at least 60% homology to the polypeptide of any one of (a) to (e), and being a functional ITGB4 or a functional fragment thereof; and (g) a polypeptide comprising an amino acid sequence encoded by a nucleic acid molecule having a nucleic acid sequence which is degenerate as a result of the genetic code to the nucleic acid sequence of a nucleic acid molecule as defined in (a), (d), (e) and (f), wherein the polypeptide is phosphorylated at the phosphorylation site S1069 and/or the phosphorylation site T1455 as shown in SEQ ID NO: 5 or at an equivalent phosphorylation site. Preferably, the polypeptide is phosphorylated at the phosphorylation site S1069 and/or the phosphorylation site T1455 as shown in SEQ ID NO: 5 or at an equivalent phosphorylation site.

The term "functional ITGB4" refers to a polypeptide having the same or substantially the same activity as a polypeptide shown in SEQ ID NO: 5.

The present invention relates in a further embodiment to a polypeptide selected from the group consisting of (a) a polypeptide comprising an amino acid sequence encoded by a nucleic acid molecule having the nucleic acid sequence as depicted in SEQ ID NO: 3;

(b) a polypeptide having an amino acid sequence as depicted in SEQ ID NO 6;

(c) a polypeptide as defined in (a) or (b) wherein one or more amino acids are deleted, inserted, added or substituted;

(d) a polypeptide comprising an amino acid sequence encoded by a nucleic acid molecule encoding a peptide having an amino acid sequence as depicted in SEQ ID NO 6;

(e) a polypeptide comprising an amino acid sequence encoded by a nucleic acid molecule hybridizing under stringent conditions to the complementary strand of nucleic acid molecules as defined in (a) or (d) and encoding a functional ITGB4 or a functional fragment thereof;

(f) a polypeptide having at least 60% homology to the polypeptide of any one of (a) to (e), and being a functional ITGB4 or a functional fragment thereof; and (g) a polypeptide comprising an amino acid sequence encoded by a nucleic acid molecule having a nucleic acid sequence which is degenerate as a result of the genetic code to the nucleic acid sequence of a nucleic acid molecule as defined in (a), (d), (e) and (f), wherein the polypeptide is phosphorylated at the phosphorylation site S1069 as shown in SEQ ID NO: 6 or at an equivalent phosphorylation site.

The term "functional ITGB4" refers to a polypeptide having the same or substantially the same activity as a polypeptide shown in SEQ ID NO: 6.

The present invention relates in a further embodiment to a polypeptide selected from the group consisting of (a) a polypeptide comprising an amino acid sequence encoded by a nucleic acid molecule having the nucleic acid sequence as depicted in SEQ ID NO: 2;

(b) a polypeptide having an amino acid sequence as depicted in SEQ ID NO 7;

(c) a polypeptide as defined in (a) or (b) wherein one or more amino acids are deleted, inserted, added or substituted;

(d) a polypeptide comprising an amino acid sequence encoded by a nucleic acid molecule encoding a peptide having an amino acid sequence as depicted in SEQ ID NO 7;

(e) a polypeptide comprising an amino acid sequence encoded by a nucleic acid molecule hybridizing under stringent conditions to the complementary strand of nucleic acid molecules as defined in (a) or (d) and encoding a functional ITGB4 or a functional fragment thereof;

(f) a polypeptide having at least 60% homology to the polypeptide of any one of (a) to (e), and being a functional ITGB4 or a functional fragment thereof; and (g) a polypeptide comprising an amino acid sequence encoded by a nucleic acid molecule having a nucleic acid sequence which is degenerate as a result of the genetic code to the nucleic acid sequence of a nucleic acid molecule as defined in (a), (d), (e) and (f), wherein the polypeptide is phosphorylated at the phosphorylation site S1069 as shown in SEQ ID NO: 7 or at an equivalent phosphorylation site.

The term "functional ITGB4" refers to a polypeptide having the same or substantially the same activity as a polypeptide shown in SEQ ID NO: 7.

The amino acid sequence of ITGB4 isoform 4D corresponds to the amino acid sequence of ITGB4 as shown in SEQ ID NO: 5 with the exception that ITGB4 isoform 4D does not comprise amino acids 1370-1439 of SEQ ID NO:5. Further, amino acids 1678-1685 (i.e. CEMAQGGG) of SEQ ID NO. 5 are replaced by a tryptophan (W) in the amino acids sequences of ITGB4 isoform 4D.

Accordingly, the present invention relates in a further embodiment to a polypeptide selected from the group consisting of (a) a polypeptide having an amino acid sequence as depicted in SEQ ID NO 8;

(b) a polypeptide as defined in (a) wherein one or more amino acids are deleted, inserted, added or substituted;

(c) a polypeptide comprising an amino acid sequence encoded by a nucleic acid molecule encoding a peptide having an amino acid sequence as depicted in SEQ ID NO 8;

(d) a polypeptide comprising an amino acid sequence encoded by a nucleic acid molecule hybridizing under stringent conditions to the complementary strand of nucleic acid molecules as defined in (c) and encoding a functional ITGB4 or a functional fragment thereof;

(e) a polypeptide having at least 60% homology to the polypeptide of any one of (a) to (d). and being a functional ITGB4 or a functional fragment thereof; and (f) a polypeptide comprising an amino acid sequence encoded by a nucleic acid molecule having a nucleic acid sequence which is degenerate as a result of the genetic code to the nucleic acid sequence of a nucleic acid molecule as defined in (c), or (d), wherein the polypeptide is phosphorylated at the phosphorylation site S1069 as shown in SEQ ID NO: 8 or at an equivalent phosphorylation site.

The term "functional ITGB4" refers to a polypeptide having the same or substantially the same activity as a polypeptide shown in SEQ ID NO: 8.

The present invention relates in a further embodiment to a polypeptide selected from the group consisting of (a) a polypeptide comprising an amino acid sequence encoded by a nucleic acid molecule having the nucleic acid sequence as depicted in SEQ ID NO: 4;

(b) a polypeptide having an amino acid sequence as depicted in SEQ ID NO 9;

(c) a polypeptide as defined in (a) or (b) wherein one or more amino acids are deleted, inserted, added or substituted;

(d) a polypeptide comprising an amino acid sequence encoded by a nucleic acid molecule encoding a peptide having an amino acid sequence as depicted in SEQ ID NO 9;

(e) a polypeptide comprising an amino acid sequence encoded by a nucleic acid molecule hybridizing under stringent conditions to the complementary strand of nucleic acid molecules as defined in (a) or (d) and encoding a functional ITGB4 or a functional fragment thereof;

(f) a polypeptide having at least 60% homology to the polypeptide of any one of (a) to (e), and being a functional BAIAP2 or a functional fragment thereof; and (g) a polypeptide comprising an amino acid sequence encoded by a nucleic acid molecule having a nucleic acid sequence which is degenerate as a result of the genetic code to the nucleic acid sequence of a nucleic acid molecule as defined in (a), (d), (e) and (f), wherein the polypeptide is phosphorylated at the phosphorylation site S509 as shown in SEQ ID NO: 9 or at an equivalent phosphorylation site.

The term "functional BAIAP2" refers to a polypeptide having the same or substantially the same activity as a polypeptide shown in SEQ ID NO: 9.

The meaning of the term "homologous" and "homology", respectively, particularly with respect to two amino acid sequences to be compared, is also known in the art. These terms are used herein accordingly. For example, the term "homology"/"homologous" is used herein in context of a polypeptide which has a homology, that is to say a sequence identity, of at least 60%, preferably of at least 70%, more preferably of at least 80%, even more preferably of at least 90% and particularly preferred of at least 95%, especially preferred of at least 98% and even more preferred of at least 99% to the, preferably entire, amino acid sequence of as shown in the above described polypeptides, in particular those shown in SEQ ID NO. 5, 6, 7, 8 and 9, respectively. Methods for sequence comparison, particularly amino acid sequence comparison, and hence, determination of homology are well known in the art. For example, the degree of homology can be determined conventionally using known computer programs such as the DNASTAR program with the ClustalW analysis. This program can be obtained from DNASTAR, Inc., 1228 South Park Street, Madison, Wis. 53715 or from DNASTAR, Ltd., Abacus House, West Ealing, London W13 0AS UK (support@dnastar.com) and is accessible at the server of the EMBL outstation.

When using the Clustal analysis method to determine whether a particular sequence is, for instance, 90% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

Hybridization assays for the characterization of orthologs of given nucleic acid sequences are well known in the art; see e.g. Sambrook, Russell "Molecular Cloning, A Laboratory Manual", Cold Spring Harbor Laboratory. N.Y. (2001); Ausubel, "Current Protocols in Molecular Biology", Green Publishing Associates and Wiley Interscience, N.Y. (1989). The term "hybridization" or "hybridizes" as used herein may relate to hybridizations under stringent or non-stringent conditions. If not further specified, the conditions are preferably non-stringent. Said hybridization conditions may be established according to conventional protocols described, e.g., in Sambrook (2001) loc. cit.; Ausubel (1989) loc. cit., or Higgins and Hames (Eds.) "Nucleic acid hybridization, a practical approach" IRL Press Oxford, Washington D.C., (1985). The setting of conditions is well within the skill of the artisan and can be determined according to protocols described in the art. Thus, the detection of only specifically hybridizing sequences will usually require stringent hybridization and washing conditions such as, for example, the highly stringent hybridization conditions of 0.1×SSC. 0.1% SDS at 65° C. or 2×SSC, 60° C., 0.1% SDS. Low stringent hybridization conditions for the detection of homologous or not exactly complementary sequences may, for example, be set at 6×SSC, 1% SDS at 65° C. As is well known, the length of the probe and the composition of the nucleic acid to be determined constitute further parameters of the hybridization conditions.

The phosphorylation status of the above described polypeptides or fragments thereof can be evaluated in accordance with the present invention.

In a further embodiment, the present invention relates to antibodies specifically binding to or specifically recognizing one or more of the herein described and provided phosphorylated polypeptides. Preferably, these antibodies specifically bind to or specifically recognize one or more of the following phosphorylated polypeptides: Integrin β4, BAIAP2, GPRC5A, ITPR3, TNKS1BP1, ARHGEF18, IASPP, APG16L and/or TPD52L2 as described and defined herein. More preferably, the antibodies specifically bind to or specifically recognize phosphorylation sites of Integrin β4, preferably one or more of the phosphorylation sites S1518, S1457, T1455 and S1069 of integrin β4 (preferably of the ITGB4 isoform C as, for example, shown in SEQ ID NO: 5), more preferably T1455 and/or S1069 of integrin β4 (preferably of the ITGB4 isoform C as, for example, shown in SEQ ID NO: 5). Preferably, the antibodies specifically bind to or specifically recognize T1455 and S1069 of integrin β4 (preferably of the ITGB4 isoform C as, for example, shown in SEQ ID NO: 5). It is also preferred herein that the antibodies specifically bind to or specifically recognize all of the above described phosphorylation sites of integrin β4.

Further, the herein provided antibodies may specifically bind to or specifically recognize one or more one or more of the following phosphorylation sites:

a. S509 of BAIAP2 (preferably as shown in SEQ ID NO: 9);

b. S345 of GPRC5A (preferably as shown in SEQ ID NO: 10);

c. S916 of ITPR3 (preferably as shown in SEQ ID NO: 11);

d. S429 of TNKS1BP1 (preferably as shown in SEQ ID NO: 12);

e. S1101 of ARHGEF18 (preferably as shown in SEQ ID NO: 13);

f. S102 of IASPP (preferably as shown in SEQ ID NO: 16);

g. S269 of APG16L (preferably as shown in SEQ ID NO: 17); and/or h. S161 of TPD52L2 (preferably as shown in SEQ ID NO: 20).

Antibodies that specifically bind to or specifically recognize phosphorylated BAIAP2 (preferably as shown in SEQ ID NO: 9), especially the phosphorylation site S509 of BAIAP2 are particularly preferred.

As explained herein above, in addition or in alternative to the above described phosphorylation sites, the phosphorylation status of fragments of the above phosphorylated polypeptides, splice variants, polypeptides having at least 60% or more homology to the polypeptide, or mutant polypeptides may be evaluated, provided that these polypeptides are phosphorylated at any of the above defined sites or at an equivalent site.

Accordingly, the present invention provides antibodies that specifically bind to or specifically recognize such phosphorylated fragments of the above described phosphorylated polypeptides, splice variants, homologous polypeptides, mutant polypeptides, provided that these polypeptides are phosphorylated at any of the above defined sites or at an equivalent site. Particularly preferred herein are antibodies that specifically bind to or specifically recognize phosphorylated isoforms of ITGB4, ARHGEF18, ATG16L1 and/or TPD526L, preferably phosphorylation sites of isoforms of ITGB4, ARHGEF18, ATG16L1 and/or TPD526L.

Accordingly, antibodies are provided that specifically bind to or specifically recognize one or more of the phosphorylated isoforms of ITGB4, such as the main isoform of ITGB4, ITGB4C (preferably as shown in SEQ ID NO: 5), isoform4A (preferably as shown in SEQ ID NO: 6); isoform4B, (preferably as shown in SEQ ID NO: 7); isoform4D, (preferably as shown in SEQ ID NO: 8). Further, it is preferred herein that the antibodies specifically bind to or specifically recognize one or more of the phosphorylation sites of such phosphorylated isoforms, such as of isoform4A, preferably of one or more of the phosphorylation sites S1069, T1385, S1387, S1448 of isoform4A (preferably as shown in SEQ ID NO: 6); of isoform4B, preferably of one or more of the phosphorylation sites S1069, T1385, S1387, of isoform4B (preferably as shown in SEQ ID NO: 7); and/or of isoform4D, preferably of one or more of the phosphorylation sites S1069, T1385, S1387, S1448 of isoform4D (preferably as shown in SEQ ID NO: 8).

Further, antibodies are provided that specifically bind to or specifically recognize one or more of the following phosphorylation sites:

a. S943 of ARHGEF18 isoform2 (preferably as shown in SEQ ID NO: 14);

b. S943 of ARHGEF18 isoform3 (preferably as shown in SEQ ID NO: 15);

c. S269 of ATG16L1 isoform 3 (preferably as shown in SEQ ID NO: 18);

d. S125 of ATG16L1 isoform 4 (preferably as shown in SEQ ID NO: 19); and/or e. S141 of TPD526L isoform 2 (preferably as shown in SEQ ID NO: 21);

The above antibodies can be used in context of the present invention, especially in the evaluation of the phosphorylation status of the herein described and defined phosphorylated polypeptides Integrin β4, BAIAP2, GPRC5A, ITPR3, TNKS1BP1, ARHGEF18, IASPP, APG16L and/or TPD52L2 (as well as of fragments of the above described phosphorylated polypeptides, splice variants, homologous polypeptides, mutant polypeptides and/or isoforms thereof), particularly of the herein disclosed phosphorylation sites of these peptides. All explanations given herein above in context of the evaluation of these peptides apply, mutatis mutandis, to the use of antibodies in this context. It is also envisaged that these antibodies can be used in the evaluation of the protein expression level and/or activity of the herein disclosed polypeptides.

Accordingly, the present invention relates to the use of these antibodies in the methods of the present invention. Therefore, the present invention relates in a further embodiment to the use of the herein above described antibody/antibodies specifically binding to or specifically recognizing one or more of the herein described and provided phosphorylated polypeptides for predicting the responsiveness of a cancer or tumor cell or a responsive individual to an inhibitor of a kinase of the Src-family as defined herein.

The present invention also provides for a kit useful for carrying out the herein disclosed method comprising the above described antibody/antibodies specifically binding to or specifically recognizing one or more of the herein described and provided phosphorylated polypeptides. In a further embodiment, the present invention relates to the use of such a kit in the methods of the present invention. All explanations given herein above in context of kits apply, mutatis mutandis, to kits described in this context.

The herein provided antibodies may also be comprised in a composition, preferably a diagnostic composition. Also a kit comprising such a composition, preferably a diagnostic composition, and corresponding uses of the kit as described above are envisaged in context of the present invention.

The present invention also relates to an antibody/antibodies as defined above or the above composition comprising said antibody/antibodies for the preparation of a diagnostic kit for use in the methods of the present invention, particularly for predicting the responsiveness of a cancer or tumor cell or a responsive individual to an inhibitor of a kinase of the Src-family as defined herein.

The antibody may be a polyclonal antibody, a monoclonal antibody, a full antibody (immunoglobulin), a F(ab)-fragment, a $F(ab)_2$-fragment, a single-chain antibody, a chimeric antibody, a CDR-grafted antibody, a bivalent antibody-construct, a bispecific single chain antibody, a synthetic antibody or a cross-cloned antibody and the like.

Polyclonal or monoclonal antibodies or other antibodies (derived therefrom) can be routinely prepared using, inter alia, standard immunization protocols; see Ed Harlow, David Lane, (December 1988), Antibodies: A Laboratory Manual, Cold Spring Harbor Laboratory; or Ed Harlow, David Lane, (December 1998), Portable Protocols (Using Antibodies): A Laboratory Manual $2^{nd}$ edition, Cold Spring Harbor Laboratory.

For example, immunization may involve the intraperitoneal or subcutaneous administration of the phosphorylated protein/polypeptide (and/or fragments, isoforms, homologues and so on) as defined herein to a mammal (e.g. rodents such as mice, rats, hamsters and the like). A phosphorylated protein/polypeptide may be used. Preferably, fragments of the phosphorylated protein/polypeptide are used, wherein the fragment preferably bears the phosphorylated site as defined herein and preferably at least four of the amino acids of the phosphorylated polypeptide adjacent to each side of the phosphosite. For example, the following fragment of the phosphorylated ITGB4 (preferably ITGB4 shown in amino acids 1065-1073 of SEQ ID NO: 5) may be used: QEVDSLLRG. The phosphosite S1069 is indicated in bold letters.

More preferably, the fragment bears the phosphorylated site as defined herein and preferably at least five, six, seven, eight, nine, ten, eleven, twelve, thirteen, fourteen, fifteen or sixteen of the amino acids of the phosphorylated polypeptide adjacent to each side of the phosphosite. Corresponding phosphopeptides may be prepared by enzymatic phosphorylation or by chemical synthesis.

Methods for the preparation and screening of antibodies that specifically bind to or specifically recognize phosphorylated polypeptides or phosphorylation sites are known in the art. Such standardized methods are, for example, described in Methods Mol. Biol. 2011; 717: 3-43 (Chapter 1) which provides an Overview of the Generation, Validation, and Application of Phosphosite-Specific Antibodies. Chapter 4 of said textbook describes an optimized protocol to make phosphospecific antibodies: see Methods Mol. Biol. 2011:717:69-88. A further protocol to be used in the preparation of phosphorspecific antibodies is disclosed in Goto and Inagaki (2007), Nature Protocols 2, 2574-2581. For example, antibodies recognizing the protein that is phosphorylated at the specific amino acid of interest (the phosphorylation site) may be affinity purified. ELISA is commonly used for screening sera and/or assaying affinity column fractions. Western Blots can be used to demonstrate that the antibody can detect the actual protein of interest and to evaluate whether the antibody only recognizes the protein of interest, or if it cross-reacts with other proteins.

A person skilled in the art is in the position to apply and to adapt the teaching of these documents for the generation and validation of antibodies specifically binding to or specifically recognizing the phosphorylated polypeptides as defined herein in context of the present invention.

The present invention is further described by reference to the following non-limiting figures and examples.

The Figures show:

FIG. 1. The general workflow of phospho-biomarker classification.

First, a predictive phospho-signature is identified based on phospho-profiles of sensitive and resistant cell lines using the cross validation approach (described in detail in the text). Once this signature has been identified, it can be applied to new samples to predict the response of the donor to the respective drug.

Figure 2:
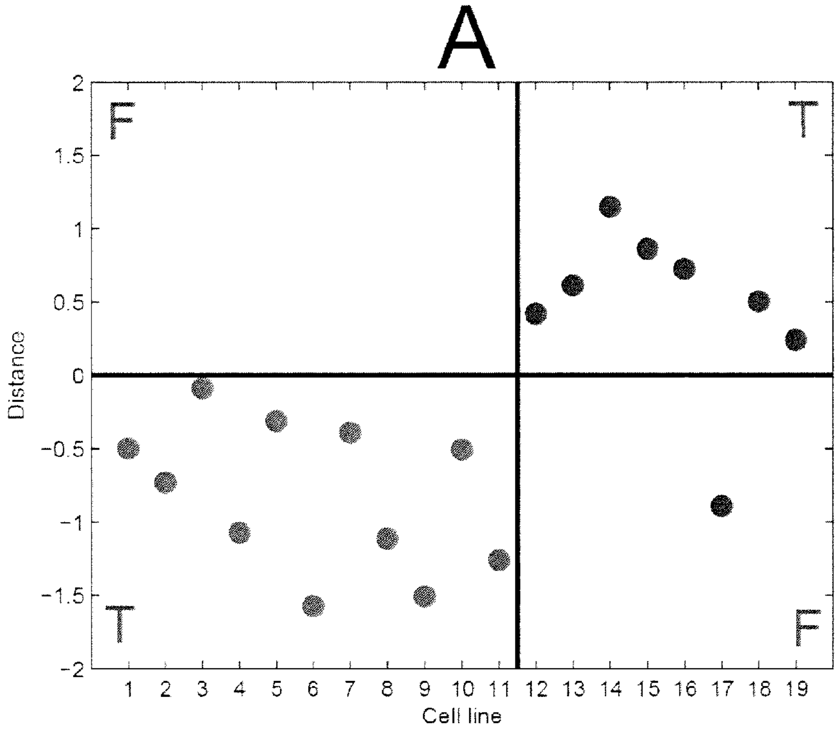
Figure 2:
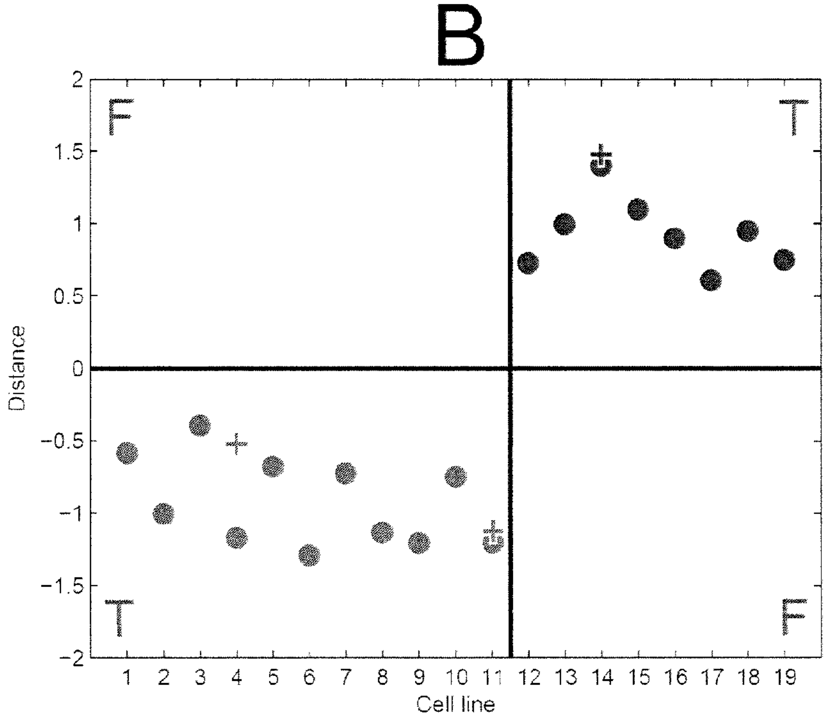
Figure 2:
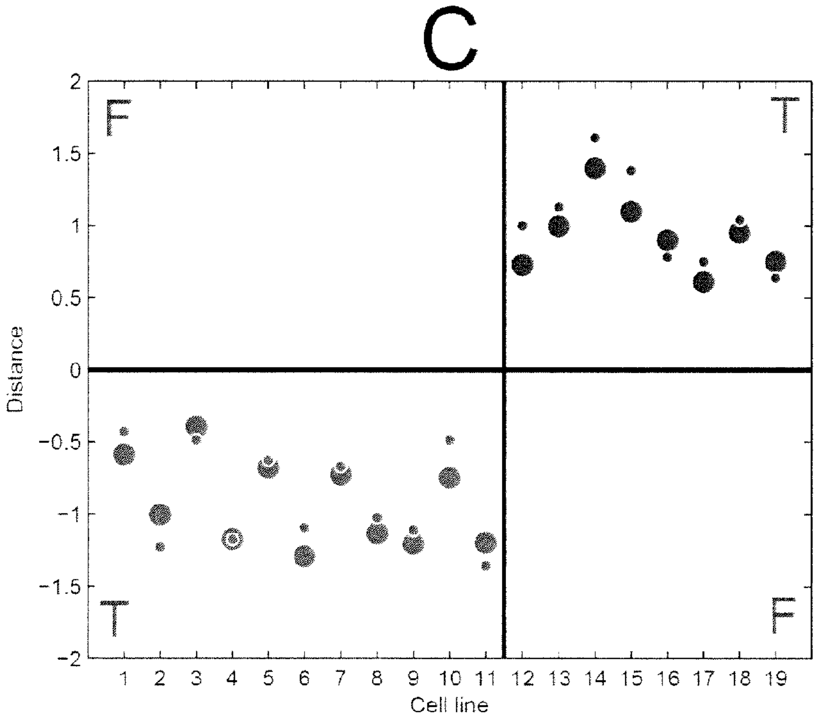
Figure 2:
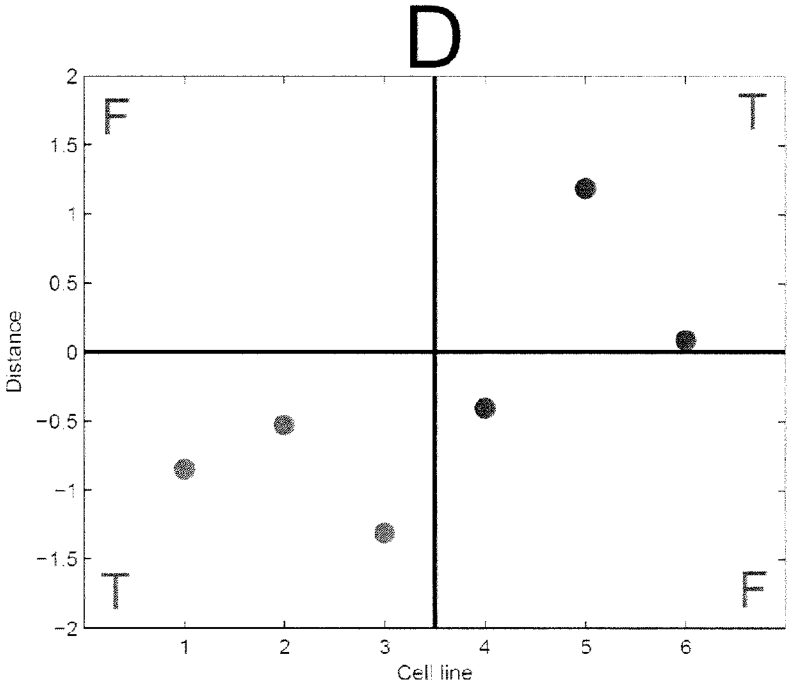

FIG. 2. Classification results represented by distance to the respective Support vector machine (SVM)'s separating hyperplane.

Blue circles represent sensitive cell lines, red ones resistant cells. The cell lines in A, B and C are: 1 LouNH91, 2 H1648, 3 HCC827, 4 H322M, 5 H2030, 6 HCC2279, 7 HCC366, 8 HCC4006, 9 H1666, 10 PC9, 111 H2009, 12 H460, 13 Calu6, 14 H2077, 15 H1395, 16 H2172, 17 HCC78, 18 H 157, 19 H520; in D: 1 BT-20, 2 MDA-MB-231, 3 HCC1937, 4 MDA-MB-468, 5 BT-549, 6 MCF7. Sensitive cell lines are predicted correctly if they get assigned a negative value; resistant ones are correct if they are assigned a positive value. (A) The results of the prediction quality assessment. (B) Prediction results of the final predictor when applied to the same date as used for training (circles) along with the results for the label switch experiments (crosses). (C) Prediction results of the final predictor when applied to the same data as used for training (circles), along with the results for the same data when normalized by the selected set of ribosomal proteins (dots). (D) Prediction results of the final predictor when applied to the breast cancer samples.

Figure 3:
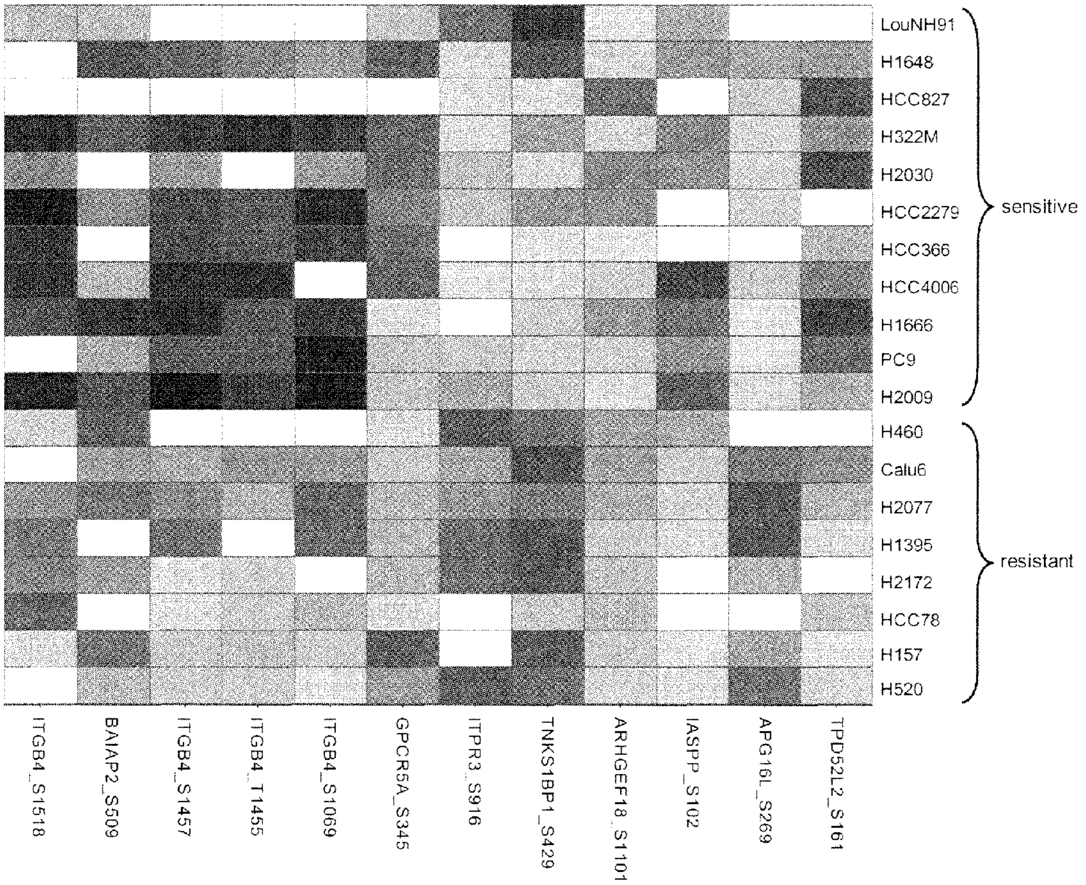

FIG. 3. Heat map of the final 12 selected phosphorylation sites.

Rows are the 19 cell lines that were used to identify the phospho-signature (the upper 11 are sensitive, the lower 8 resistant), columns are the phosphosites ordered by their importance ranks (left is the best). Red indicates up-, blue down-regulation, grey no regulation. Missing values are coloured white.

Figure 4:
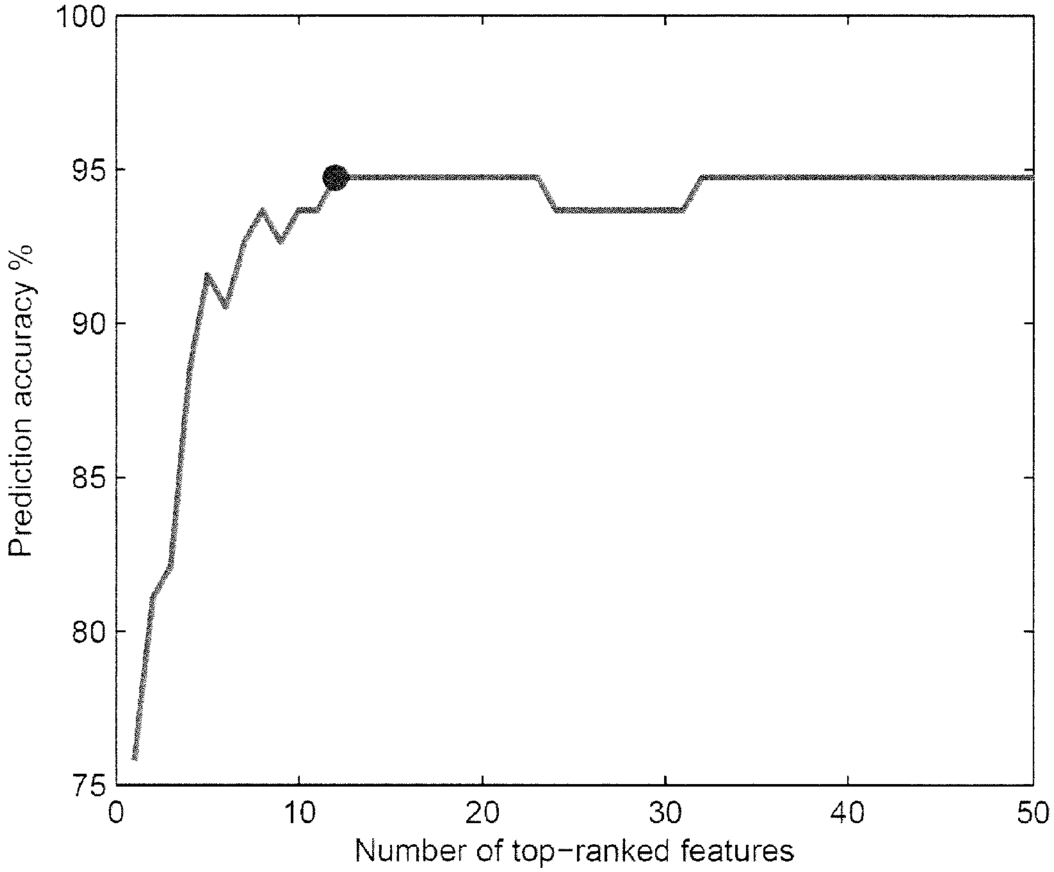

FIG. 4. Prediction accuracy.

The plot shows the prediction accuracy depending on the number of top-ranked features incorporated into the phospho-signature. While the accuracy increases with the first few features, it reaches its maximum at 12 features (red dot), where it saturates (with some fluctuation).

Figure 5:
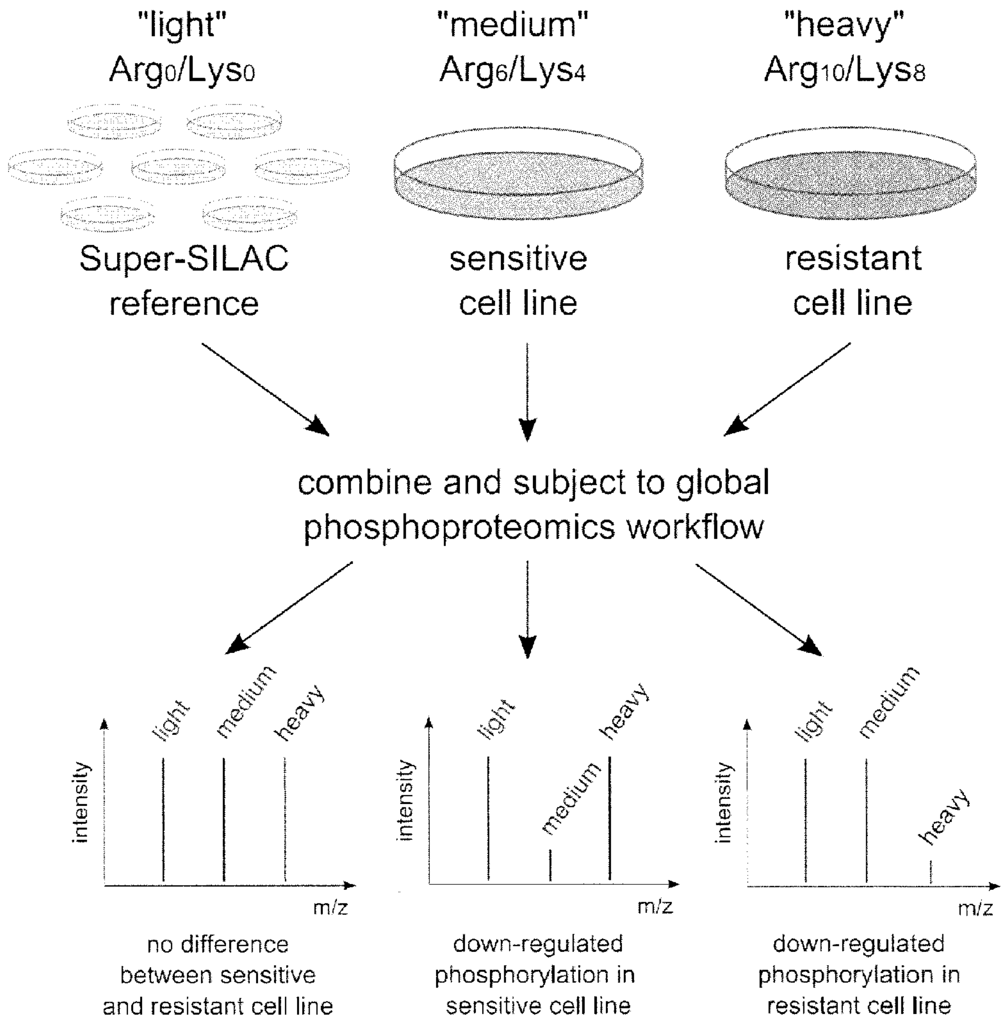

FIG. 5. SILAC labelling diagram.

The scheme illustrates how isotopic labelling enables relative quantification of phosphorylation amounts via a spike-in reference.

Figure 6:
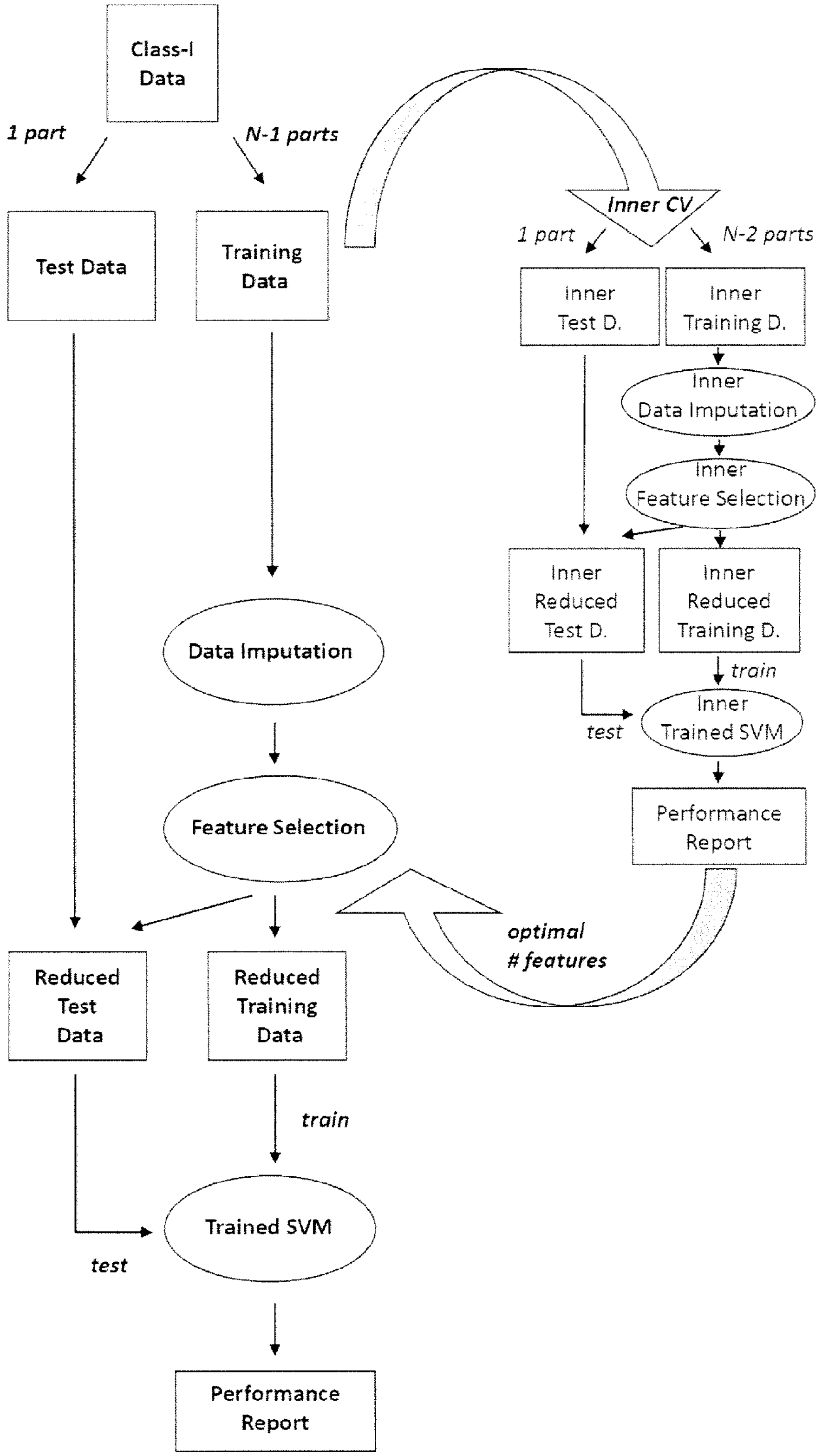

FIG. 6. Workflow diagram for prediction quality assessment.

Two cross validation loops are applied to estimate the prediction accuracy: in the inner CV loop the optimal number of features is determined. This number is then used in the feature selection process in the outer CV loop. Subsequently, an SVM is trained and tested with the respective data sets. The prediction results in each outer CV loop are combined and the prediction accuracy is calculated.

Figure 7:
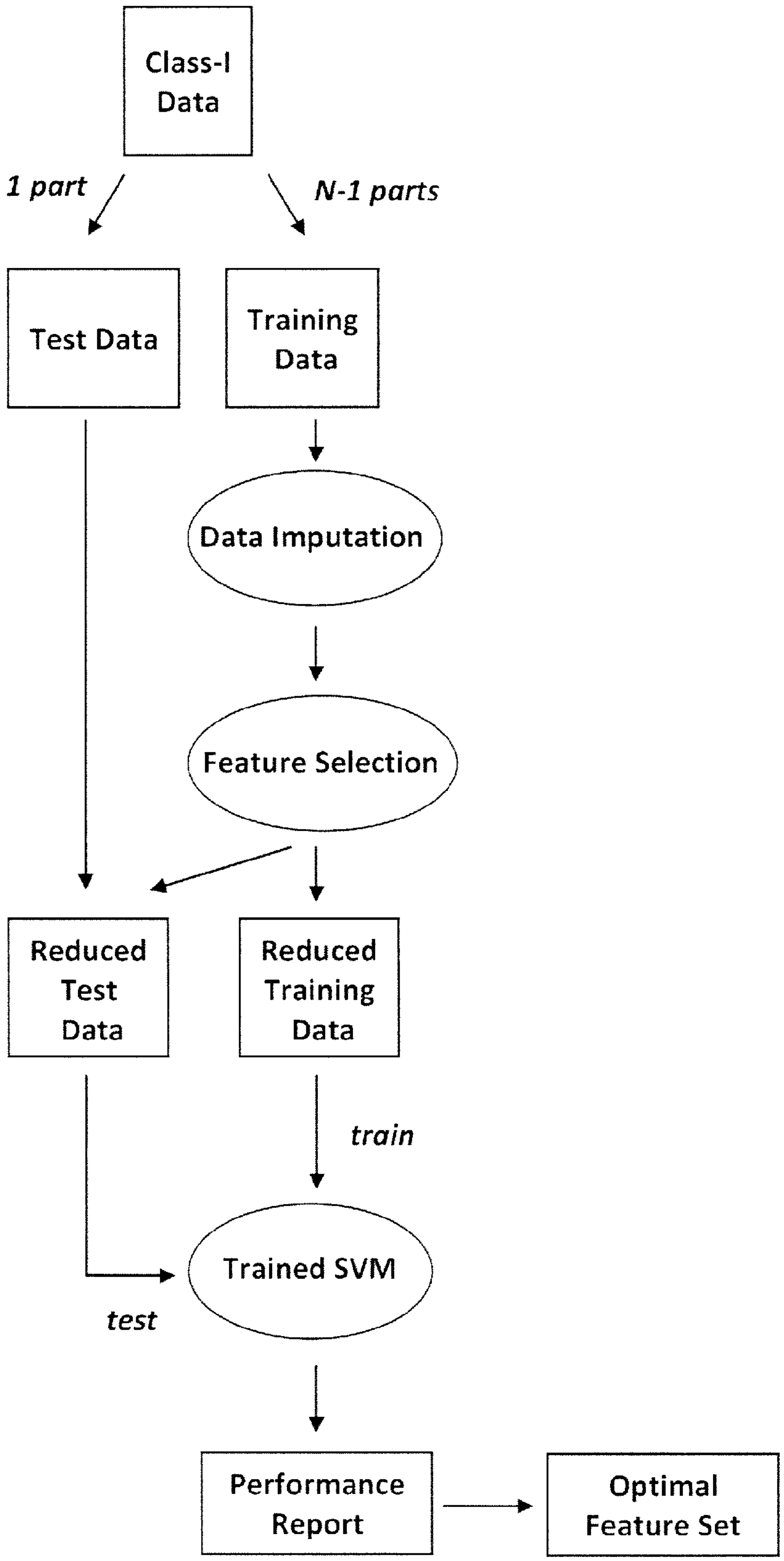

FIG. 7. Workflow diagram for finding the final phospho-signature.

The workflow corresponds to one inner CV loop in FIG. 6 resulting in the optimal set of features, which is then used to train the final SVM predictor.

Figure 8:
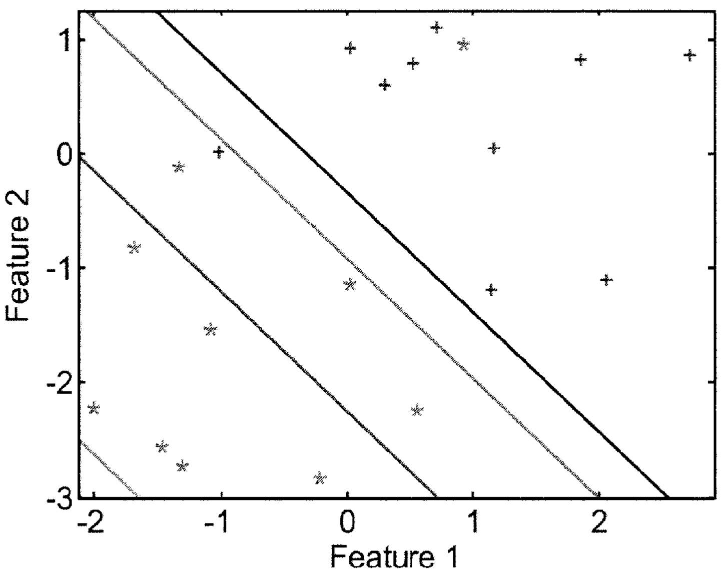

FIG. 8. Cost matrix example

The example shows how the introduction of cost matrices influences the support vector classification. The figure shows a classification example that aims at separating red stars from blue plusses. Each class contains 10 samples with two features. The values of both features were sampled from normal distributions (N(1,1) and N(−1,1) for plusses and stars, respectively). The black line represents the separating hyperplane of the SVM classification with linear kernel (parameter C=1), when no explicit cost matrix is applied (i.e. the cost of misclassifying a star is the same as the cost for misclassifying a plus). One can clearly see that the data is not linearly separable, which leads to one misclassified plus and one misclassified star. The red line shows the hyperplane when the cost for the false classification of stars is twice as high as the cost for star misclassification. As a result, the separating hyperplane is shifted towards the cloud of red stars, but the classification result is still the same. By increasing the cost factor of plus misclassification to ten times the cost of star misclassification, the hyperplane (blue line) is shifted further and all plusses are classified correctly. However, instead of one falsely predicted star there are now four. Finally, when using a cost factor of 200 (see purple line), all samples would be classified as plusses leading to ten wrongly predicted stars.

Figure 9:
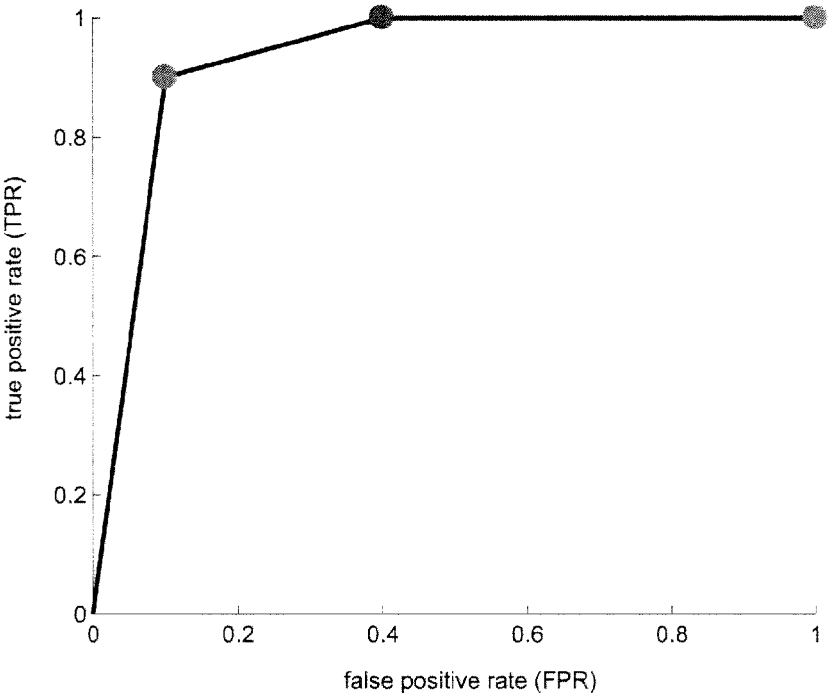

FIG. 9. Receiver operating characteristic (ROC) example

This shifting of the hyperplane can be used to calculate the receiver operating characteristic (ROC) curve and the area under it. A ROC curve based on the four different cost matrices above would look like FIG. 9 (assuming that the plusses are the positives and the stars the negatives in the ROC statistics). The point at (1.0|1.0) corresponds to the purple hyperplane, where all plusses are classified correctly and all stars wrongly; the point at (0.4|1.0) to the blue discrimination line, where all plusses are classified correctly and 4 stars are falsely predicted as positives; the point at (0.1|0.9) to both the red and black hyperplane, where 9 plusses are classified correctly and one star wrongly as positive; and finally one more point at (0|0) that is not depicted in FIG. 8 but represents the extreme when all samples are assumed to be negatives (stars), which can be considered the opposite of the purple discrimination line. Finally, the area under the curve can be computed, which is 0.93 in this example.

Figures 10, 11:
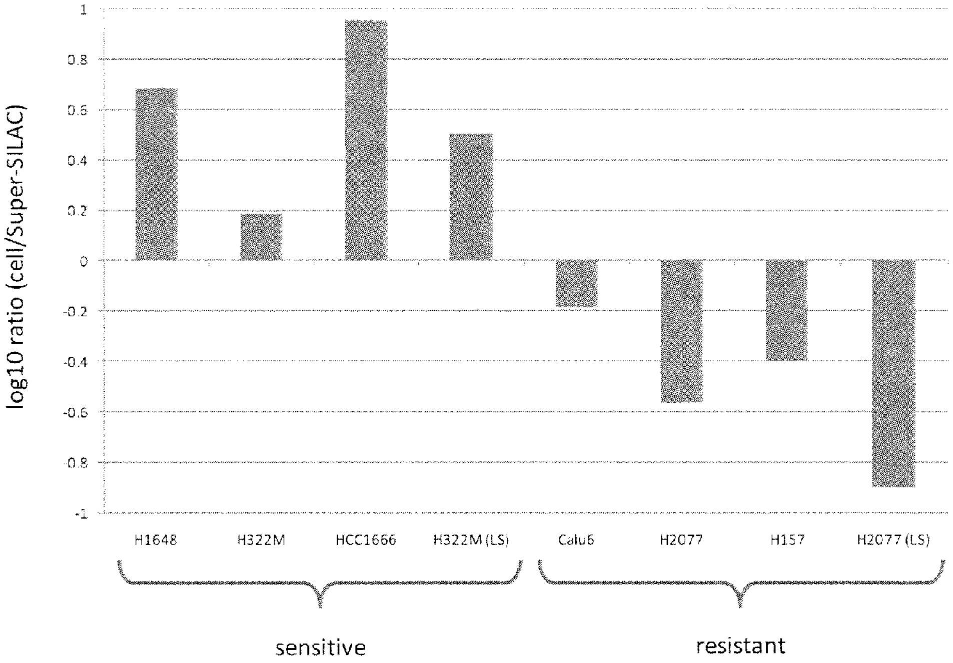

FIG. 10. Protein expression of ITGB4

The protein expression of ITGB4 with respect to the Super-SILAC standard differs strongly between sensitive and resistant cell lines. ITGB4 is up-regulated in all four sensitive cell line data points, and down-regulated in all four resistant ones. Cell lines data points labeled with (LS) were part of a label switch experiment.

FIG. 11. Prediction accuracy of feature pairs

The half matrix displays the prediction accuracy for all pairs of features from the phospho-signature. Surprisingly, some pairs could achieve the maximum prediction accuracy of 19/19 correct predictions.

Figure 12:
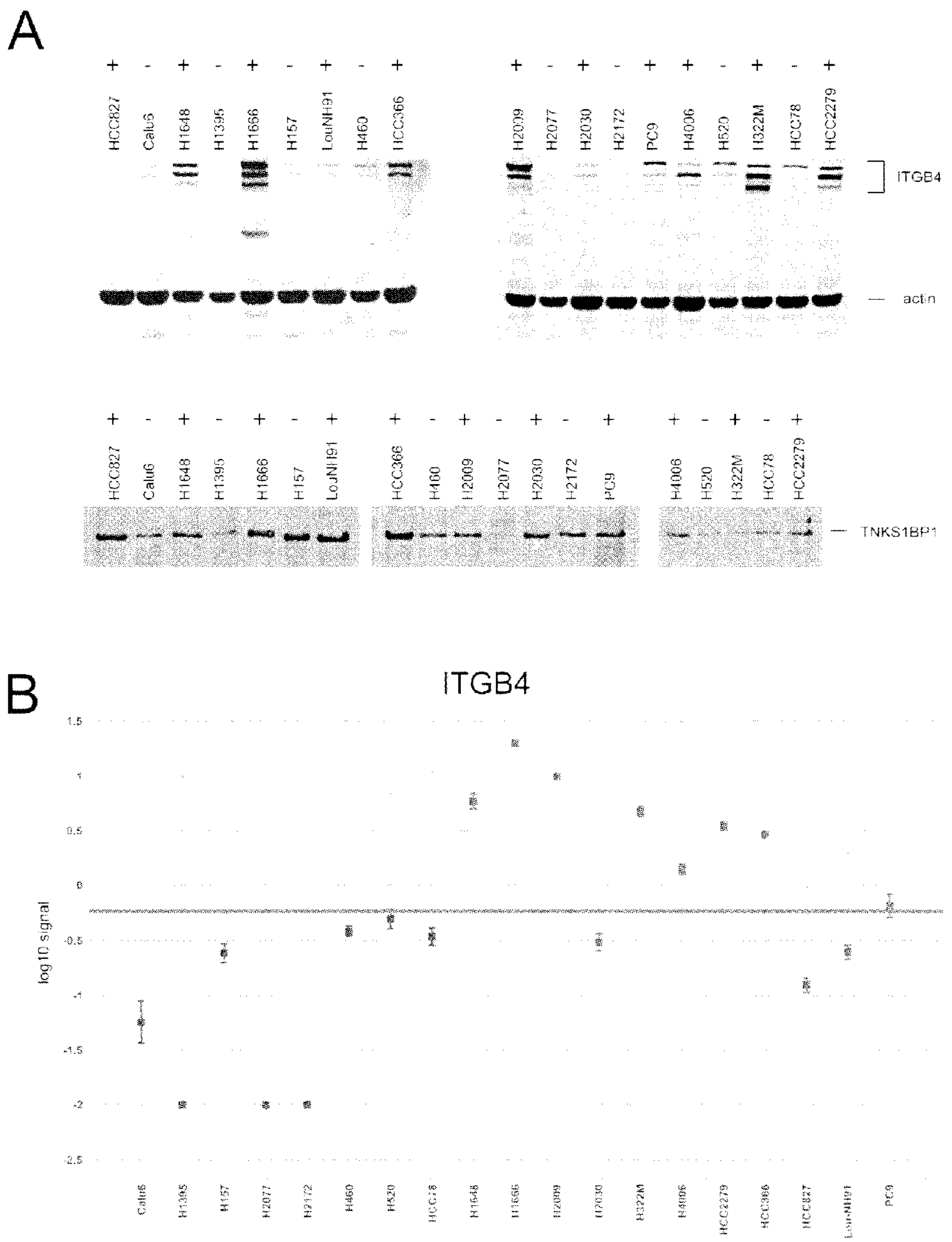
Figure 12:
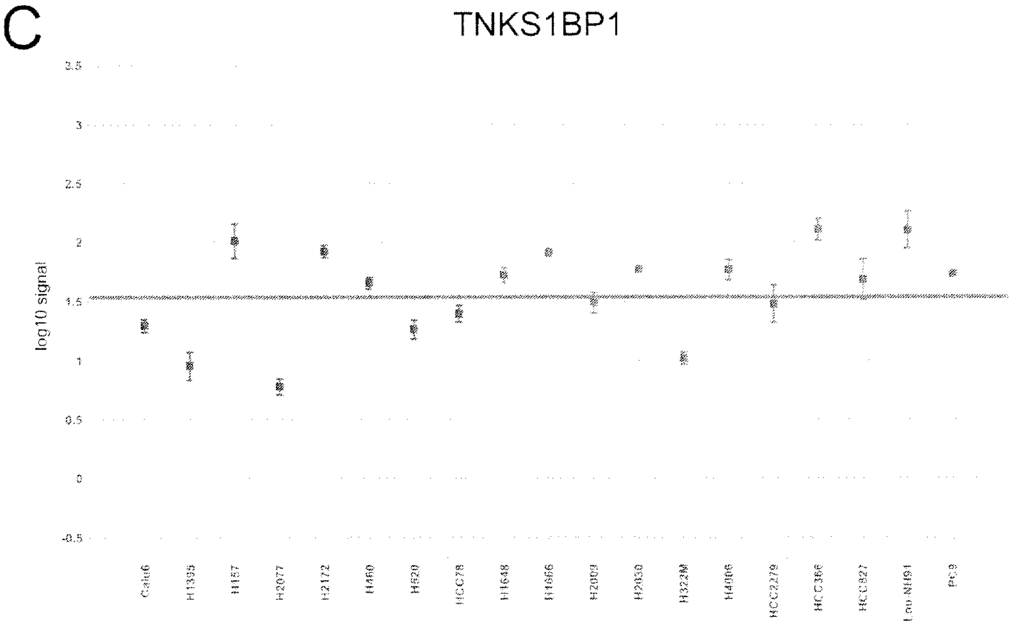

FIG. 12. Western blots of ITGB 4 and TNKS1BP1 in NSCLC cell lines.

A: Western blot images for one replicate. The top (bottom) panel shows Western blots for ITGB4 (TNKS1BP1). The sensitivity to dasatinib treatment is noted by +/− above the cell line labels. B: Quantitative readout for ITGB4 in resistant (left) and sensitive (right) cell lines. The error bars represent the standard error across three replicates. The green horizontal line represents the average of the class medians. C: Quantitative readout for TNKS1BP1.

The present invention is additionally described by way of the following illustrative non-limiting examples that provide a better understanding of the present invention and of its many advantages. Unless otherwise indicated, established methods of recombinant gene technology were used as described, for example, in Sambrook, Russell "Molecular Cloning, A Laboratory Manual", Cold Spring Harbor Laboratory, N.Y. (2001).

The following non-limiting Examples illustrate the invention.

EXAMPLE 1

Phospho-Signature Predicts Dasatinib Response in Non-Small Cell Lung Cancer

Materials and Methods

Cell Lines

Based on the $GI_{50}$ values of dasatinib on a panel of 84 NSCLC cell lines reported in Supplemental Table 5 of Sos, Michel et al., 2009, 13 cell lines with low and 13 with high $GI_{50}$ values were selected (cf. Table 2). These 26 cell lines were obtained from the LGC Standards (Wesel, Germany), from the DSMZ—Deutsche Sammlung von Mikroorganismen und Zellkulturen (Braunschweig, Germany), and Roman Thomas' group at the Max Planck Institute for Neurological Research (Cologne, Germany).

The six breast cancer cell lines were obtained from the LGC Standards (see Table 2).

Cell Culture

All cell lines were cultivated in RPMI1640, 10% foetal bovine serum, 2 mM glutamine, 1 mM sodium pyruvate and penicillin/streptomycin (PAA, Cölbe, Germany). Cells were routinely monitored for mycoplasma infection using the MycoAlert reagents (Lonza, Cologne, Germany).

Metabolic labelling of the cell lines was performed using SILAC (stable isotope labelling with amino acids in cell culture). Cells were cultivated in media containing SILAC-RPMI (PAA) and dialysed FBS (Invitrogen, Darmstadt, Germany). L-lysine and L-arginine were replaced by normal L-lysine (Lys-0) and L-arginine (Arg-0), or medium isotope-labelled L-$D_4{}^{14}N_2$-lysine (Lys-4) and L-${}^{13}C_6{}^{14}N_4$-arginine (Arg-6), or heavy isotope-labelled L-${}^{13}C_6{}^{15}N$-lysine (Lys-8) and L-${}^{13}C_6{}^{15}N_4$-arginine (Arg-10). Isotope-labelled amino acids were purchased from Cambridge Isotope Laboratories (Andover, Mass., USA). Cells were cultivated for a minimum of six doubling times to obtain an incorporation efficiency for the labelled amino acids of at least 95%. Subconfluent cultures of the cell lines were harvested, washed with PBS and lysed in lysis buffer (50 mM Tris pH 8.2, 75 mM NaCl, 8 M urea, 10 mM sodium pyrophosphate, 10 mM NaF, 10 mM 3-glycerophosphate, 2.5 mM sodium orthovanadate, phosphatase inhibitor cocktails 2 and 3 (Sigma, Taufkirchen, Germany), and protease inhibitor cocktail Complete (Roche, Mannheim, Germany).

Determination of Cellular Growth Inhibition

Sensitivity of the cell lines for dasatinib was determined by measuring the cellular ATP content after 96 hours of treatment using the CellTiter Glo chemiluminescent viability assay (Promega, Mannheim, Germany). Cells were cultivated in 96-well plates (Greiner, Frickenhausen, Germany) in the presence of dasatinib (LC Laboratories, Woburn, Mass., USA) within a concentration range between 3 nM and 30 μM.

The raw data from the chemiluminometer (FLUOstar OPTIMA, BMG Labtech, Offenburg, Germany) was used to determine the $GI_{50}$ value. First, the background was determined by calculating the median value of the plate's border wells, which contained only growth media. This value was then subtracted from each inner well. Since two experiments were conducted on one 96-well plate with 10 compound concentrations each (0(DMSO), 3 nM, 10 nM, 30 nM, 100 nM, 300 nM, 1 M, 3 μM, 10 μM, 30 μM), three data points per concentration and experiment were available. Ratios representing the percentage of growth inhibition were calculated by dividing each data point coming from a concentration >0 by the median of the DMSO values. A logistic regression was performed to fit a curve to those ratios and compute the $GI_{50}$ value.

Classification into Sensitive/Resistant

The calculated $GI_{50}$ values of the 26 selected cell lines were compared with the values reported in (Sos, Michel et al., 2009). Although the correlation between the two sets was strong (Pearson correlation=0.50, p=0.009 on logged $GI_{50}$s), a few cell lines showed inconsistent behaviour. By setting the threshold to discriminate between sensitive and resistant cells to a $GI_{50}$ value of 1 μM, seven cell lines were classified inconsistently (5 were resistant in the reference paper, but sensitive in this study, 2 vice versa). Consequently, these cell lines were excluded from the workflow that aims at finding a predictive phospho-signature.

Reference Cell Line Pool

16 NSCLC cell lines were selected as a reference pool: A549, Calu6, H1395, H1437, H1755, H2030, H2052, H2172. H28, H460, HCC827 (obtained from LGC Standards), LCLC103H. LouNH91 (obtained from DSMZ), H322M, HCC2279, HCC2429 (obtained from MPI for Neurological Research). The selected cell lines were grown in SILAC media supplemented with the natural 'light' forms of arginine and lysine. The labelled cells of each cell line were lysed, pooled, aliquoted, and stored at −80° C. In total, 40 aliquots with 12 mg of protein each were generated.

Phosphoproteomics Workflow

Responsive and non-responsive cell lines were grown in medium or heavy SILAC media and after washing the cells twice with ice-cold PBS the cell cultures were lysed directly on the plates by the addition of ice-cold lysis buffer (8 M urea. 50 mM Tris pH 8.2, 5 mM EDTA, 5 mM EGTA, SIGMA HALT Phosphatase Inhibitor Mix, ROCHE Complete Protease Inhibitor Mix). After sonication cell debris was sedimented by centrifugation and the protein concentration was determined by Bradford assays. Equal protein amounts of the reference cell culture mix and a medium and heavy labelled cell line, (7 mg protein each) were mixed as depicted in FIG. 5 and subsequently subjected to reduction (20 mM DTT. 30 min 37° C.) and alkylation (50 mM iodoacetamide, 30 min RT) prior to proteolytic cleavage. Then 80 μg of LysC (Wako) was added for 4 h followed by a 4-times dilution with 50 mM Tris pH 8.2. Proteolytic cleavage was continued by the addition of 120 μg of trypsin (Promega) overnight. The peptide mixtures were acidified by addition of TFA to a final concentration of 0.5% and subsequently desalted via C18 SephPack columns (Waters). Peptides were eluted with 50% ACN and dried under vacuum. For a first separation of phosphorylated and non-phosphorylated peptides, the dried peptide powder was reconstituted in 1 ml SCX buffer A (5 mM $K_2HPO_4$, pH 2.7, 30% ACN) and loaded onto a polysulphoethyl column (9.4×250 mm, PolyLC) using an ÄKTA Purifier chromatography system equipped with a fraction collector. The peptides were separated by a linear gradient to 25% SCX buffer B (buffer A supplemented with 500 mM KCl) over 40 min at flow rate of 3 ml/min. Twenty fractions (12 ml each) were collected across the gradient.

Prior to IMAC enrichment the solvent of the SCX-fractions was removed by lyophilisation. Dried peptides were reconstituted in 1 ml of 0.1% TFA and desalted by using C18 reversed phase cartridges (Waters). The bound peptides were eluted with 50% ACN, 0.5% HOAc and the peptides were lyophilized again. Dried peptides were reconstituted in 40% ACN, 25 mM formic acid and phosphopeptides were captured using PhosSelect (Sigma) according to the manufacture's instructions. Eluted phosphopeptides were subjected to mass spectrometric analysis.

Mass spectrometric analysis was carried out by on-line nanoLC-MS/MS. The sample was loaded directly by an Agilent 1200 nanoflow system (Agilent Technologies) on a 15 cm fused silica emitter (New Objective) packed in-house with reversed phase material (Reprusil-Pur C18-AQ, 3 μm, Dr. Maisch GmbH) at a flow of 500 nl/min. The bound peptides were eluted by a gradient from 2% to 40% of solvent B (80% ACN, 0.5% HOAc) at a flow of 200 nl/min and sprayed directly into a LTQ-Orbitrap XL or LTQ-Orbitrap Discovery mass spectrometer (Thermo Fischer Scientific) at a spray voltage of 2 kV applying a nanoelectrospray ion source (ProxeonBiosystems). The mass spectrometer was operated in the positive ion mode and a data dependent switch between MS and MS/MS acquisition. To improve mass accuracy in the MS mode, the lock-mass option was enabled. Full scans were acquired in the orbitrap at a resolution R=60.000 (Orbitrap XL) or 30,000 (Orbitrap Discovery) and a target value of 1,000,000 ions. The five most intense ions detected in the MS were selected for collision induced dissociation in the LTQ at a target value of 5000. The resulting fragmentation spectra were also recorded in the linear ion trap. To improve complete dissociation of phophopeptides, the multi-stage activation option was enabled applying additional dissociation energy on potential neutral loss fragments (precursor minus 98, 49 and 32.7 Thompson). Ions that were once selected for data dependent acquisition were 90 sec dynamically excluded for further fragmentation.

Recent advances in mass spectrometry, methods for enriching phosphorylated proteins or peptides, and computer algorithms for analysing proteomics data have enabled the application of mass spectrometry-based proteomics to monitor phosphorylation events in a global and unbiased manner. These methods have become sufficiently sensitive and robust to localize and quantify the phosphorylation sites within a peptide sequence (Olsen. Blagoev et al., 2006; Macek, Mann et al., 2009; Schaab, 2011). Phosphorylation events are important in signal transduction, where signals caused by external stimuli are transmitted from the cell membrane to the nucleus. Aberrations in these signal transduction pathways are particularly important for understanding the mechanisms of certain diseases, such as cancer, inflammation and diabetes (Blume-Jensen and Hunter, 2001; Kaminska, 2005).

MaxQuant Analysis

The raw mass spectral data was processed using the MaxQuant software (version 1.1.1.25) (Cox and Mann, 2008), applying the Mascot search engine (version 2.2.0) for peptide and protein identification. A concatenated forward and reversed human UNIPROT database (version: 57.12) was used comprising 221.564 database entries. The minimal peptide length was set to 6 amino acids, trypsin was selected as proteolytic enzyme and maximally 3 missed cleavage sites were allowed. Carbamidomethylation of cysteines was selected as fixed modification, whereas methionine oxidation, N-terminal protein acetylation and phosphorylation of serine, threonine and tyrosine residues were considered as variable modifications. As MaxQuant automatically extracts isotopic SILAC peptide triplets, the corresponding isotopic forms of lysine and arginine were automatically selected. The maximal mass deviation of precursor and fragment masses was set to 20 ppm and 0.5 Da before internal mass recalibration by MaxQuant. A false discovery rate (FDR) of 0.01 was selected for proteins and peptides and a posterior error probability (PEP) below or equal to 0.1 for each MS/MS spectrum was required.

Identification and Evaluation of Phospho-Signature

Pre-Processing

Data from MaxQuant's PhosphoSTY table are the data source for identifying a predictive phospho-signature. Each entry in this table describes one specific phosphosite along with information about its localisation, confidence and regulation. The regulation of a phosphosite is provided as ratio of the site's abundance between each cell line and the super-SILAC standard. MaxQuant already provides normalized ratios, which are used in this study. There are two coefficients that account for the reliability of identification and localization of a phosphosites, i.e. Localization Probability and Score Diff. Sites that satisfy the constraints Localization Probability>=0.75 and Score Diff>=5 were considered to be sufficiently reliable (Class I sites). Furthermore, sites that are flagged as Reverse or Contaminant hits were also excluded. All phosphosites that fulfil both requirements (Class I, no Contaminant/Reverse) were subjected to further analysis.

Cross Validation

To find a predictive phospho-signature, leave-one-out cross validation (LOOCV) was applied. The data set containing N objects was split into two parts, one containing data of one object, and the other containing the data of the remaining N−1 objects. The larger part was then used for training a predictor (training set) and the smaller one for testing this predictor (test set). By alternating the objects that made up the training set, each object was used once for testing. Each of the N cross validation steps included missing data imputation, feature selection, predictor training and predictor testing.

A phosphosite was only considered as a potential feature if it had training data values in at least two thirds of the experiments in each class (e.g. if the training set contained data from 10 sensitive and 8 insensitive cell lines, at least 7 and 6 training data points had to be present, respectively).

Data Imputation

For each phosphosite and class the mean and standard deviation was computed and the missing values were filled by sampling from the resulting normal distribution. This procedure was only applied to the training data, since the test data should be handled as if the class association was unknown. Nevertheless, test data can also contain missing values. If so, the mean of the corresponding two group means was imputed, which is an unbiased way of replacing the missing value that does not involve information about the test sample's class association. Geometrically speaking, the imputed test sample value is located exactly halfway between the two class means, which should minimize its influence on the prediction process.

Feature Selection

In this study, a simple Wilcoxon rank-sum test in combination with the ensemble feature selection method (Abeel. Helleputte et al., 2010) was used. Since the Wilcoxon test often delivers identical p-values (due to its rank-based nature), ties were broken by preferring features that have a larger difference in their two classes' medians. The main idea of the ensemble method is that robust features should still rank among the best if the dataset is slightly modified. For this purpose, different samplings of the training data were generated by drawing (with replacement) 50 different bootstrap samples, applying the Wilcoxon rank-sum test to these samples, and thus generating a diverse set of feature rankings. The ranks of each feature were then averaged across all bootstrap runs and sorted in descending order according to this meta-ranking. Subsequently, the k best features were used to train and test the predictor. By varying k and assessing the prediction accuracy and area under the receiver operator curve (AUROC), one can find the optimal number of features.

Support Vector Machine Training

Once a set of features has been selected, and the training and test data have been modified to include only those features (i.e. 'reduced' sets), the SVM with linear kernel can be trained. Besides the kernel function, an SVM has a cost parameter C, which controls the trade-off between margin maximization and training error minimization, if the hyper plane cannot perfectly separate the two classes. The default value of C=1 was used throughout the analysis. First, the SVM was trained with the training data. Subsequently, the class association of the test data was predicted with the trained SVM. The result of this prediction is the probability of the test sample belonging to either of the two classes (the closer the test data is to the decision boundary, the less confident the prediction is). The class prediction with the larger probability was then taken and compared to the actual class association. In this way, correct predictions were counted across all cross validation steps.

Area Under the Receiver Operating Characteristic Curve

To calculate the area under the receiver operating characteristic curve (AUROC), the separating hyperplane of a trained SVM was shifted by introducing cost matrices. For example, by shifting the hyperplane towards the group of sensitive training samples, it becomes more likely for a test sample to be classified as resistant. Ultimately, this shifting leads to the extreme that every test sample is classified as resistant, which means that all resistant test samples have been classified correctly (true negative rate=1 and false positive rate=0, given that the resistant ones are the negatives) and all sensitive test samples wrongly (true positive rate=0). The exact opposite is true if the separating hyperplane is shifted towards the resistant group. Thus, by applying different cost values, one can control the degree of shifting, calculate the respective true positive rates and false positive rates, and compute the resulting area under the curve by means of the trapezoidal rule (see FIG. 8 and FIG. 9 for an example).

Random Seeds

For the imputation of missing values, a random number generator is needed to sample values from a normal distribution. Different seeds of the random generator will produce different imputation data. To avoid a bias of the data towards the seeding, the entire cross validation procedure was repeated five times using different random number generator seeds. The prediction accuracies, AUROC values and global feature rankings for different numbers of selected features (k) were averaged over the five CV runs and used for the final selection of the phospho-signature.

Data Normalization

Among the fraction of non-phosphorylated peptides, 15 peptides had values in at least two thirds of the experiments and a standard deviation <0.1 (log 10 scale). Eight of them were from ribosomal proteins, which are expected to be constantly expressed. Thus, for each experiment the median of the corresponding eight ratios was computed and used as an alternative normalization approach (by subtracting the median from each phosphosite's non-MaxQuant-normalized logarithmic ratio).

Final Predictor Construction

When selecting the final set of phosphosites (phospho-signature) to be used for the prediction of future samples, the optimal number of features was determined in a CV loop. This is essentially the same as the inner loop in the quality assessment process (see also FIG. 7). Therefore, after running the cross validation process five times with different random number generator seeds, we obtained the following results: A 200×5 prediction result matrix (200 being the rows, 5 the columns) containing the number of correct CV predictions for k=1 . . . 200 selected features (i.e. k best ranking in each CV step) across the 5 random seeds; a 200×5 AUROC matrix containing the corresponding area under the ROC curve values; and a 25,073×19×5 rank matrix holding the rank of each feature in each CV step across the 5 random seed runs (features that were not subjected to imputation/feature selection due to too many missing values received the rank maxRank+1, where maxRank is the number of features that were subjected to imputation/feature selection).

The primary criterion for selecting the best subset of features was the number of correct predictions. For this purpose the values in the prediction matrix and AUROC matrix were row-averaged, leading to a vector of 200 average correct predictions and area under the curve values. Within this vector the indices (numbers of features) that lead to the best number of correct predictions were determined. Among those the one index that had the highest AUROC value was selected as best performing feature number, which was twelve.

Next, the final feature rank was determined by averaging first over the third and subsequently over the second dimension of the rank matrix. The resulting vector of length 25,073 containing the average rank of each feature was sorted in ascending order and the 12 top-ranked were selected. These were the phosphosites described in Table 1.

The twelve selected final features were then used to train the final predictor. However, since these features also contained missing values, imputation had to be performed first. In principle, the imputation procedure was the same as described above, but this time the sampling from normal distributions was omitted, rather the mean of each feature and class was taken directly as imputation value. The reason for this is that the original sampling should reflect the variance within each feature and class, which is crucial for the quality of a feature. Since the best features had already been selected at this stage, the sampling was dispensable. Finally, a SVM based on the predictive 12-site phospho-signature (again with linear kernel and C=1) was trained and can now be applied to the classification of new samples.

Details on SVM Prediction

The decision function of the SVM classification is given by:

$$f(\bar{x}) = \mathrm{sgn}\left(\sum_{i=1}^{m} y_i \alpha_i k(\bar{x}_i, \bar{x}) + b\right). \quad (1)$$

where m is the number of training samples (cell lines), $y_i$ the class label of the $i^{th}$ training sample (−1 or 1 for sensitive and resistant cell lines, respectively), $\alpha_i$ the respective Lagrange multiplier, $\bar{x}_i$ a vector of length f (f being the number of selected features) holding the ratios of the $i^{th}$ training sample, $\bar{x}$ a vector of length f holding the ratios of the test sample, and b the bias (i.e. the translation of the hyperplane with respect to the origin). $k(\bar{x}_i,\bar{x})$ is called a kernel, i.e. a function that characterizes the similarity of two vectors. Equation (1) can be rewritten as:

$$f(\bar{x}) = \mathrm{sgn}(k(\bar{w},\bar{x}) + b), \quad (2)$$

with the weight vector $\bar{w}$, whose elements represent the importance (influence) of the corresponding features, defined as $$\overline{w} = \sum_{i=1}^{m} \alpha_i y_i \overline{x}_i.$$

In the case of the linear SVM, the kernel function is defined as the dot product of the two vectors, which leads to the linear decision function:

$$f(\overline{x}) = \text{sgn}\left(\sum_{j=1}^{f} w_j x_j + b\right). \quad (3)$$

So far, changes in the phosphorylation level were represented by ratios, which can be expressed as=S−$S_{ref}$, where S is the signal of the phosphosite in the corresponding cell line and $S_{ref}$ the signal of the site in the reference cell line pool. Here, the signal is defined as log intensity of the corresponding phosphosite. For data produced by other methods such as multiple reaction monitor ing or ELISA, where the quantitative data are represented by intensities, one can still make predictions with the proposed phospho-signature, but the decision function (Equation 2) has to be modified to:

$$f(\overline{S}) = \text{sgn}(k(\overline{w}, \overline{S}) + \underbrace{b - k(\overline{w}, \overline{S}_{ref})}_{\tilde{b}}). \quad (4)$$

Note, that only the bias term has to be modified while the weight vector $\overline{w}$ stays the same. In geometrical terms, the orientation of the hyperplane does not change, but is translated to the new position. In the case of the linear SVM the decision function thus changes to:

$$f(\overline{S}) = \text{sgn}\left(\sum_{j=1}^{f} w_j S_j + \tilde{b}\right). \quad (5)$$

Results

Sensitivity to Dasatinib was Confirmed

Based on the half-maximum growth inhibitory concentration ($GI_{50}$) of dasatinib reported previously (Sos. Michel et al., 2009), 13 sensitive and 13 resistant NSCLC cell lines were pre-selected. For these 26 cell lines we repeated viability assays to verify the reported $GI_{50}$ values. Depending on the $GI_{50}$ the cell lines were assigned to sensitive ($GI_{50}$<1 μM) and resistant ($GI_{50}$>1 μM) classes. For 19 of 26 cell lines the assignment was consistent. For 7 cell lines the assignment based on the sensitivity determined here differed from that reported previously (Sos, Michel et al., 2009). These cell lines were therefore excluded from the training set (see Table 2 for $GI_{50}$ values). The remaining 19 cell lines (11 sensitive and 8 resistant) were used to identify a predictive phospho-signature.

A Predictive Phospho-Signature was Identified

To quantitatively compare the analysed cell lines, we isotopically labelled sensitive and resistant NSCLC cell lines by stable isotope labelling by amino acid in cell culture (SILAC; Ong, Blagoev et al., 2002). The sensitive cell lines were grown in SILAC media supplemented with the medium forms of arginine and lysine ($Arg^6/Lys^4$), whereas the resistant cell lines were grown in heavy media ($Arg^{10}/Lys^8$, see Table 3 for experimental pairing scheme). A Super-SILAC reference (Geiger. Cox et al., 2010) was generated by mixing protein lysates of 16 randomly selected cell lines in unlabelled (light, $Arg^0/Lys^0$) media. The Super-SILAC reference serves as a spike-in standard, enabling accurate cross-sample comparison (see FIG. 5). The resulting 13 triply-SILAC-labeled samples were subjected to a global, quantitative phosphoproteomics workflow using strong cation exchange chromatography (SCX) and immobilised metal ion affinity chromatography (IMAC) followed by liquid chromatography-tandem mass spectrometry (LC-MS/MS) analysis (see Materials and Methods for details). In total, 37,747 phosphosites were identified in the 26 profiled cell lines. 88% of all quantifications had a cell line to Super-SILAC ratio <4-fold, which allowed for accurate quantification of phosphorylation changes between cell lines. From the 37,747 identified phosphorylation sites, 25,073 were determined as class-I sites, i.e. sites that could be identified with high localization confidence (Olsen, Blagoev et al., 2006). Only these sites were used in the following analyses.

Following the general workflow for detecting phospho-signatures (FIG. 1), starting with the training set (19 valid cell lines), a predictive phospho-signature is identified and its accuracy is estimated by cross validation (CV). Feature selection is applied within each CV loop, to reduce dimensionality of the data and thus avoid overfitting the resulting predictor. We used a Wilcoxon rank-sum test combined with the ensemble method (Abeel, Helleputte et al., 2010) for selecting the phosphosites used for the signatures. The number of phosphosites is optimized in an inner leave-one-out cross-validation loop. The phosphosites were used to train a support-vector machine (SVM) with linear kernel, which was chosen as the predictor, since it offers state-of-the-art prediction quality and has been successfully applied several times to biological data (e.g. see Ramaswamy, Tamayo et al., 2001; Hutter, Schaab et al. 2004; Thuerigen, Schneeweiss et al. 2006). SVMs separate two classes by a hyper plane, such that the margin between the classes becomes as wide as possible (e.g. Schölkopf and Smola, 2002). SVMs are already capable of handling high-dimensional data well, but their performances can still be enhanced when applying feature selection techniques. The standard version uses a linear kernel, resulting in linearly separated classes. Alternatively, other kernels can be used, which leads to mapping the input data to a higher-dimensional feature space, resulting in a non-linear separation in the input space. However, linear SVM was found to be sufficient for the kind of data as studied herein The final phospho-signature has twelve phosphosites (Table 1) located on nine different proteins. All of them showed higher phosphorylation abundance in the sensitive cell lines.

The Phospho-Signature has High Sensitivity and Specificity

The general idea of cross validation (CV) analysis is to split a data set into N parts and use N−1 parts to train a predictor, and the remaining one part to test its performance. By alternating the N subsets, each part is used once for testing. In our analysis we used N=19, i.e. 18 cell lines for training and one cell line for testing in each cross-validation step (leave-one-out CV or LOOCV). It has been shown that CV, including LOOCV, estimates the true prediction performance accurately and shows a low bias (Molinaro, Simon et al., 2005). Since not all phosphosites discriminate well between sensitive and resistant cell lines, feature selection is applied in each CV step, which selects a defined subset of predictive phosphosites. First the features are ranked according to their discriminative power, and then the optimal number of top-ranking features is determined by an inner parameter optimization cross validation. In this inner CV procedure, different numbers of top-ranking features (k=1 . . . 200) are used, and their respective performance is assessed. The smallest number of features leading to the best prediction quality in the inner CV loop is then applied to the feature selection in the outer cross validation loop (see also FIG. 6). Subsequently, a predictor is trained on the reduced training data (reduced in the sense of containing only features that passed the feature selection criteria) and tested with the reduced test data. It is important to note, that the test sample has neither be used for optimizing the number of features nor for selecting the features within CV. Otherwise, the prediction accuracy would be overestimated.

Since missing data are very common in MS-based shotgun proteomics, and many machine learning techniques (SVMs among them) cannot handle them, they were replaced by values that were randomly sampled from the respective empirical distributions (data imputation). As a consequence, the entire assessment was carried out five times with different seeds for the random number generator used for imputation, leading to five distinct prediction results. The five results were strikingly similar (as can be expected from a robust set of features), i.e. four times only one cell line was misclassified (HCC78), and once two were falsely classified (HCC78 and HCC827), which leads to a prediction accuracy of 94% and an area under the receiver operating characteristic curve (AUROC) of 0.92 (FIG. 2A). Each circle in FIG. 2A shows the averaged predicted outcome of this cell line when all other cell lines were used as training data. A sensitive cell line is predicted correctly if the SVM predictor assigns it a negative value; vice versa for a resistant cell line. The larger the distance to the separating hyperplane (i.e. the distance from 0 in the plot), the more confident the prediction is. It can be clearly seen that 18 of 19 cell lines were predicted correctly in cross validation, if the average distance is taken as classification criterion.

For the final predictor, the workflow was carried out with only one CV loop, corresponding to the inner loop during the prediction quality assessment (see FIG. 7). This resulted in identifying a predictive phospho-signature containing 12 phosphosites. Interestingly, the average number of selected features within the inner parameter optimization loop during the prediction quality assessment was also ~12, which further supported the robustness of the selected phosphosites. The sites are listed in Table 1 sorted by their global feature ranks (best first), and depicted as a heat map in FIG. 3 (see also Table 4 for more data). With an increasing number of features the prediction accuracy also increased, until it saturated at 12 features (see FIG. 4). Additional features could not improve the prediction accuracy.

In addition, the prediction quality assessment workflow was carried out using randomized class labels to investigate whether a predictive signature could be found for arbitrary class assignment. Strikingly, the prediction accuracy was only 51% (AUROC=0.53), which is almost exactly what one would expect if predicting the classes by chance. These results further strengthen the specificity of the deduced phospho-signature.

The Phospho-Signature is Robust

A good feature and consequently a good set of features should be robust to small variations in data. Only when slight changes in the data composition still lead to correct predictions, is the biomarker reliably applicable to samples not used for training. Therefore, robustness already plays a crucial role in the process of feature selection. First, a robust feature is chosen frequently by the feature selection method across all cross validation steps. Second, within each cross validation step, slight variations in the training data should also result in the constant selection of robust features.

To find such robust phosphosites, we applied an ensemble method (Abeel, Helleputte et al. 2010): in each CV step, various bootstrap samples are created from the original training data, i.e. if the training set consists of 10 sensitive and 8 resistant cell lines, one randomly draws 10 and 8 times with replacement from the respective set. This is performed various times (i.e. 50 times in this study), resulting in 50 differently sampled training sets. On each of these sampled training sets, feature ranking is applied and the phosphosites' achieved ranks are averaged. The final ranking will then be based on this "meta" rank.

The average of these meta ranks across all CV iterations for the signature's 12 features along with the number of times each of them was ranked under the first 12 positions are listed in Table 1. The best features turned out to be very stable, e.g. the top four have an average rank smaller than 6 and were among the 12 best in more than 90% of all iterations. The importance of these features is also indicated by their high weight in the SVM. Overall, 7 features are among the 12 best in more than two thirds of the iterations, and only 2 in less than one third. To ensure that the SILAC labelling procedure of cell lines has no effect on the results, label switch experiments were performed, where originally medium-labelled cell lines were now labelled with heavy amino acids and vice versa. The classification results of the final predictor applied to these experiments are depicted in FIG. 2B. For two of the three label switched samples, the prediction is virtually identical to the original data (red circles and crosses on position 4 and 11, and red circle and cross on position 14; FIG. 2B). In the case of the blue circle on position 4, the difference is somewhat larger, but the corresponding label switch experiment still classifies it correctly.

Since phosphosites in this study are detected in a global and unbiased way, we applied the global normalization strategy provided by the MaxQuant software during the discovery phase. However, when the phospho-signature is applied in the clinic, a method that specifically measures the phosphosites of the signature in a robust and cheap way is more likely to be used (see "Details on SVM prediction" in the Materials and Methods section of Example 1 for how SVM prediction can be adapted to use data from other methods). Such targeted methods could be either based on phospho-specific antibodies (e.g. ELISA based assays) or targeted mass spectrometry methods such as multiple reaction monitor ing (MRM). Since a global normalisation strategy is not applicable to targeted methods, it is necessary to develop an alternative. We focused on non-modified peptides that showed a very low variance across all cell lines' regulation data (regardless of whether the cell line was sensitive or resistant). Although the phosphoproteomic workflow is designed to specifically enrich for phosphorylated peptides, a significant fraction of non-phosphorylated peptides is still present. In this study, a normalization factor based on a set of unmodified ribosomal proteins exhibiting low variance across all cell lines proved useful (see Table 5 for normalization data). The classification results of the ribosomal protein normalized data are depicted in FIG. 2C, which shows that the prediction quality is essentially as good as for the globally normalized data the predictor was trained on.

The Phospho-Signature was Validated in Breast Cancer Cells

To test whether the phospho-signature is also applicable to other cancer types, we selected 3 sensitive and 3 resistant breast cancer cell lines described previously (Huang, Reeves et al., 2007). Again, $GI_{50}$ values were also determined in-house and compared to the values reported in the publication.

This time, all data were consistent (cf. Table 2) and the 6 breast cancer cell lines were subjected to our global phosphoproteomics workflow (see Table 4 for data). Subsequently, the cell lines were classified with the SVM predictor trained on the set of NCSLC cell lines. Strikingly, 5 of the 6 breast cancer cell lines could be classified correctly (FIG. 2D); only one resistant sample was wrongly predicted to be sensitive (MDA-MB-468). These findings indicate that the proposed phospho-signature is also predictive for dasatinib sensitivity in other cancer types.

TABLE 1

Phosphorylation sites of the final phospho-signature (sequences disclosed as SEQ ID NOS 22-33, respectively, in order of appearance)

| Uniprot id | Gene name | Site | Modified sequence* | Avg rank† | Median diff‡ | #Rank ≤ 12§ | ¶SV weight | All Uniprot ids‖ | **Known site |
|---|---|---|---|---|---|---|---|---|---|
| P16144 | ITGB4 | S1518 | DYSTLTSVS(p)SHDSR | 2.716 | 1.544 | 18 | −0.386 | P16144; P16144-2; P16144-4 | yes |
| Q9UQB8-5 | BAIAP2 | S509 | (p)SMSSADVEVARF | 3.611 | 1.197 | 18 | −0.311 | Q9UQB8-5 | NO |
| P161144 | ITGB4 | S1457 | MDFAFPGSTN(p)SLHR | 4.337 | 0.992 | 19 | −0.155 | P16144; P16144-2; P16144-3; P16144-4 | yes |
| P161144 | ITGB4 | T1455 | MDFAFPGS(p)TNSLHR | 5.716 | 0.937 | 18 | −0.275 | P16144; P16144-2; P16144-3; P16144-4 | NO |
| P161144 | ITGB4 | S1069 | LLELQEVD(p)SLLRGR | 7.937 | 1.236 | 13 | −0.076 | P16144; P16144-2; P16144-3; P16144-4 | ††yes |
| Q8NFJ5 | GPCR5A | S345 | AHAWP(p)SPYKDYEVK | 9.632 | 0.872 | 16 | −0.174 | Q8NFJ5 | yes |
| Q14573 | ITPR3 | S916 | (p)SIQGVGHMMSTMVLSR | 14.168 | 0.782 | 8 | −0.205 | Q14573 | yes |
| Q9C0C2 | TNKS1BP1 | S429 | RF(p)SEGVLQSPSQDQEK | 15.032 | 0.968 | 1 | −0.159 | Q9C0C2 | yes |
| Q6ZSZ5 | ARHGEF18 | S1101 | (p)SLSPILPGR | 16.874 | 0.419 | 0 | −0.188 | Q6ZSZ5; Q6ZSZ5-2; Q6ZSZ5-3 | yes |
| Q8WUF5 | IASPP | S102 | SE(p)SAPTLHPYSPLSPK | 17.516 | 0.528 | 7 | −0.145 | Q8WUF5 | yes |
| Q676U5 | APG16L | S269 | RL(p)SQPAGGLLDSITNIF GR | 18.190 | 0.725 | 13 | −0.240 | Q676U5; Q676U5-3; Q676U5-4; | yes |
| O43399 | TPD52L2 | S161 | KLGDMRN(p)SATFK | 18.274 | 0.563 | 8 | −0.155 | O43399; O43399-2 | yes |

*the sequence of the peptide on which the phosphosite was detected; (p) indicates that the subsequent amino acid was phosphorylated
†average rank of the feature across all cross validation steps
‡median difference of log10 ratios between sensitive and resistant classes
§the number of times the feature was among the 12 best across all CV steps
¶the importance of the feature in the SVM predictor (lhe larger the absolute weight, the more important)
‖all reviewed Uniprot accession numbers from which the corresponding phosphopeptide could originate
**according to PhosphoSitePlus (www.phosphosite.org) accessed on 6th Aug. 2011
††detected in mouse only

TABLE 2

Cell line information

| Cell line | Indication | Origin | Supplier number | GI50 literature* | GI50 this paper | Class | Valid† | TP53 mutation‡ | TP53 status |
|---|---|---|---|---|---|---|---|---|---|
| Calu6 | NSCLC | ATCC | HTB-56 | 22.54 | 2.8 | − | YES | c.586C>T: Arg−>STOP | MUT |
| H1395 | NSCLC | ATCC | CRL-5868 | 31.12 | 4.7 | − | YES | WT | WT |
| H1568 | NSCLC | ATCC | CRL-5876 | 0.8975 | 5.44 | + | no | — | — |
| H157 | NSCLC | MPI§ | — | 10.54 | 2.63 | − | YES | c.892G>T: Glu−>STOP | MUT |
| H1648 | NSCLC | ATCC | CRL-5882 | 0.0593 | 0.079 | + | YES | c.102_103ins1: Leu−>? | MUT |
| H1666 | NSCLC | ATCC | CRL-5885 | 0.175 | 0.076 | + | YES | WT | WT |
| H2009 | NSCLC | ATCC | CRL-5911 | 0.7465 | 0.085 | + | YES | c.818G>T: Arg−>Leu | MUT |
| H2030 | NSCLC | ATCC | CRL-5914 | 0.1183 | 0.022 | + | YES | c.785G>T: Gly−>Val | MUT |
| H2077 | NSCLC | MPI | — | 10.07 | 4.75 | − | YES | — | — |
| H2172 | NSCLC | ATCC | CRL-5930 | 16.71 | 5.85 | − | YES | — | — |
| H2887 | NSCLC | MPI | — | 11.3 | 0.176 | − | no | — | — |
| H322 | NSCLC | MPI | — | 0.2588 | 2.1 | + | no | c.743G>T: Arg−>Leu | MUT |
| H460 | NSCLC | ATCC | HTB-177 | 24.16 | 3.9 | − | YES | WT | WT |
| HCC827 | NSCLC | ATCC | CRL-2868 | 0.1456 | 0.033 | + | YES | — | — |
| H520 | NSCLC | ATCC | HTB-182 | 11.56 | 1.43 | − | YES | c.438G>A: Trp−>STOP | MUT |
| H647 | NSCLC | ATCC | CRL-5834 | 12.39 | 0.016 | − | no | c.782 + 1G>T: [intron!] | MUT |
| HCC1359 | NSCLC | MPI | — | 11.3 | 0.52 | − | no | c.388C>T: Leu−>Phe | MUT |
| LCLC103H | NSCLC | DSMZ | ACC 384 | 13.9 | 0.08 | − | no | c.646G>T: Val−>Leu | MUT |
| LouNH91 | NSCLC | DSMZ | ACC 393 | 0.113 | 0.068 | + | YES | — | — |

TABLE 2-continued

| Cell line information | | | | | | | | | |
|---|---|---|---|---|---|---|---|---|---|
| Cell line | Indication | Origin | Supplier number | GI50 literature* | GI50 this paper | Class | Valid† | TP53 mutation‡ | TP53 status |
| HCC366 | NSCLC | DSMZ | ACC 492 | 0.482 | 0.017 | + | YES | — | — |
| HCC4006 | NSCLC | ATCC | CRL-2871 | 0.8376 | 0.95 | + | YES | — | — |
| HCC78 | NSCLC | DSMZ | ACC 563 | 13.9 | 17.05 | − | YES | — | — |
| H322M | NSCLC | MPI | — | 0.0819 | 0.311 | + | YES | c.743G>T: Arg−>Leu | MUT |
| HOP62 | NSCLC | MPI | — | 12.76 | 0.014 | − | no | c.633_634ins36: Phe−>? | MUT |
| HCC2279 | NSCLC | MPI | — | 0.139 | 0.045 | + | YES | c.701A>G: Tyr−>Cys | MUT |
| PC9 | NSCLC | MPI | — | 0.4603 | 0.02 | + | YES | c.743G>A: Arg−>Gln | MUT |
| BT-20 | Breast c. | ATCC | HTB-19 | 0.1652 | 0.497 | + | YES | c.394A>C: Lys−>Gln | MUT |
| BT-549 | Breast c. | ATCC | HTB-122 | 9.0576 | 1.71 | − | YES | c.747G>C: Arg−>Ser | MUT |
| MDA-MB-468 | Breast c. | ATCC | HTB-132 | 7.1258 | 2.8 | − | YES | c.818G>A: Arg−>His | MUT |
| MDA-MB-231 | Breast c. | ATCC | HTB-26 | 0.0095 | 0.036 | + | YES | c.839G>A: Arg−>Lys | MUT |
| MCF7 | Breast c. | ATCC | HTB-22 | >9.524 | 3.27 | − | YES | WT | WT |
| HCC1937 | Breast c. | ATCC | CRL-2336 | 0.07 | 0.082 | + | YES | c.916C>T: Arg−>STOP | MUT |

*NSCLC data from Sos, et al. (2009), breast cancer data from Huang, et al. (2007)

†whether the GI50 values from the literature and this paper agree

‡according to the IARC TP53 database [Petitjean, et al. (2007)] version R15

§Max Planck Institute for Neurological Research (Cologne, Germany)

TABLE 3

| Mass spectrometric pairing scheme | | | | | |
|---|---|---|---|---|---|
| Exp. number | Group medium | Group heavy | Cell line light | Cell line medium | Cell line heavy |
| 1 | + | − | CELLMIX | LouNH91 | H460 |
| 2 | + | − | CELLMIX | H1648 | Calu6 |
| 3 | + | − | CELLMIX | HCC827 | LCLC103H |
| 4 | + | − | CELLMIX | H322M | H2077 |
| 5 | + | − | CELLMIX | H2030 | H1395 |
| 6 | + | − | CELLMIX | HCC2279 | H2172 |
| 7 | + | − | CELLMIX | H1568 | H647 |
| 8 | + | − | CELLMIX | H322 | HOP62 |
| 9 | + | − | CELLMIX | HCC366 | HCC78 |
| 10 | + | − | CELLMIX | HCC4006 | HCC1359 |
| 11 | + | − | CELLMIX | H1666 | H157 |

TABLE 3-continued

| Mass spectrometric pairing scheme | | | | | |
|---|---|---|---|---|---|
| Exp. number | Group medium | Group heavy | Cell line light | Cell line medium | Cell line heavy |
| 12 | + | − | CELLMIX | PC9 | H520 |
| 13 | + | − | CELLMIX | H2009 | H2887 |
| 14* | − | + | CELLMIX | H2077 | H322M |
| 15† | − | + | CELLMIX | H2887 | H2009 |
| 16 | + | − | CELLMIX | BT-20 | MDA-MB-468 |
| 17 | − | + | CELLMIX | BT-549 | MDA-MB231 |
| 18 | + | − | CELLMIX | HCC1937 | MCF7 |

*label switch of experiment 4

†label switch of experiment 13

TABLE 4

| Log10 ratios of cell lines versus SuperSILAC mix | | | | | | | | | |
|---|---|---|---|---|---|---|---|---|---|
| Cell line | Indication | Class | ITGB4 S1518 | BAIAP2 S509 | ITGB4 S1457 | ITGB4 T1455 | ITGB4 S1069 | GPCR5A S345 | ITPR3 S916 |
| LouNH91 | NSCLC | + | 0.265 | 0.239 | | | | 0.192 | 0.560 |
| H1648 | NSCLC | + | | 0.735 | 0.643 | 0.507 | 0.412 | 0.644 | −0.103 |
| HCC827 | NSCLC | + | | | | | | | 0.033 |
| H322M | NSCLC | + | 0.926 | 0.645 | 0.819 | 0.909 | 0.852 | 0.588 | −0.070 |
| H2030 | NSCLC | + | 0.463 | | 0.377 | | 0.383 | 0.567 | −0.305 |
| HCC2279 | NSCLC | + | 1.012 | 0.442 | 0.758 | 0.656 | 0.943 | 0.484 | 0.194 |
| HCC366 | NSCLC | + | 0.896 | | 0.746 | 0.655 | 0.818 | 0.562 | |
| HCC4006 | NSCLC | + | 0.890 | 0.261 | 0.900 | 0.903 | | 0.603 | −0.034 |
| H1666 | NSCLC | + | 0.717 | 0.865 | 0.913 | 0.690 | 0.865 | 0.032 | |
| PC9 | NSCLC | + | | 0.296 | 0.644 | 0.644 | 1.101 | 0.173 | 0.160 |
| H2009 | NSCLC | + | 0.962 | 0.685 | 0.996 | 0.820 | 1.466 | 0.172 | −0.456 |
| H460 | NSCLC | − | −0.142 | −0.866 | | | | −0.073 | −1.025 |
| Calu6 | NSCLC | − | | −0.477 | −0.421 | −0.554 | −0.544 | −0.223 | −0.479 |
| H2077 | NSCLC | − | −0.597 | −0.757 | −0.609 | −0.410 | −0.892 | −0.349 | −0.579 |
| H1395 | NSCLC | − | −0.765 | | −0.787 | | −0.857 | −0.353 | −0.792 |
| H2172 | NSCLC | − | −0.705 | −0.549 | 0.042 | −0.174 | | −0.350 | −0.839 |
| HCC78 | NSCLC | − | −0.936 | | −0.049 | −0.218 | 0.257 | −0.071 | |
| H157 | NSCLC | − | −0.109 | −0.797 | −0.233 | −0.310 | −0.211 | −0.971 | |
| H520 | NSCLC | − | | −0.348 | −0.189 | −0.189 | 0.029 | −0.552 | −0.986 |
| BT-20 | Breast c. | + | | 0.585 | 0.457 | 0.575 | 0.478 | 0.135 | 0.083 |
| MDA-MB-231 | Breast c. | + | 0.580 | | 0.403 | 0.432 | 0.738 | 0.243 | 0.547 |
| HCC1937 | Breast c. | + | 0.495 | 0.555 | 0.723 | 0.685 | 0.834 | −0.487 | 0.648 |
| MDA-MB-468 | Breast c. | − | | −0.163 | 0.160 | 0.290 | −0.055 | −0.181 | −0.147 |
| BT-549 | Breast c. | − | −0.934 | | −1.239 | −1.428 | −0.622 | −0.296 | −0.642 |
| MCF7 | Breast c. | − | −0.471 | 0.305 | −0.181 | −0.114 | −0.795 | 0.127 | −0.059 |

TABLE 4-continued

Log10 ratios of cell lines versus SuperSILAC mix

| Cell line | Indication | Class | TNKS1BP1 S429 | ARHGEF18 S1101 | IASPP S102 | APG16L S269 | TPD52L2 S161 |
|---|---|---|---|---|---|---|---|
| LouNH91 | NSCLC | + | 0.840 | −0.042 | 0.312 | | |
| H1648 | NSCLC | + | 0.693 | 0.074 | 0.402 | 0.345 | 0.393 |
| HCC827 | NSCLC | + | 0.032 | 0.558 | | −0.194 | 0.734 |
| H322M | NSCLC | + | −0.479 | 0.085 | 0.456 | −0.118 | 0.399 |
| H2030 | NSCLC | + | 0.070 | 0.439 | 0.421 | 0.089 | 0.746 |
| HCC2279 | NSCLC | + | 0.396 | 0.422 | | 0.124 | |
| HCC366 | NSCLC | + | 0.011 | −0.008 | | | 0.259 |
| HCC4006 | NSCLC | + | 0.044 | 0.121 | 0.799 | −0.235 | 0.461 |
| H1666 | NSCLC | + | 0.130 | 0.386 | 0.529 | −0.008 | 0.810 |
| PC9 | NSCLC | + | −0.132 | 0.123 | 0.399 | −0.021 | 0.580 |
| H2009 | NSCLC | + | 0.138 | 0.047 | 0.605 | −0.082 | 0.279 |
| H460 | NSCLC | − | −0.736 | −0.484 | −0.429 | | |
| Calu6 | NSCLC | − | −0.998 | −0.467 | −0.188 | −0.716 | −0.597 |
| H2077 | NSCLC | − | −0.692 | −0.411 | −0.139 | −1.069 | −0.367 |
| H1395 | NSCLC | − | −1.086 | −0.211 | 0.058 | −1.077 | −0.077 |
| H2172 | NSCLC | − | −0.998 | −0.263 | | −0.381 | |
| HCC78 | NSCLC | − | −0.239 | −0.334 | | | 0.192 |
| H157 | NSCLC | − | −0.990 | −0.226 | −0.040 | −0.478 | 0.017 |
| H520 | NSCLC | − | −0.807 | −0.129 | 0.051 | −0.776 | −0.127 |
| BT-20 | Breast c. | + | 0.295 | | 0.668 | −0.008 | 0.911 |
| MDA-MB-231 | Breast c. | + | −0.114 | | | −0.188 | −0.431 |
| HCC1937 | Breast c. | + | 0.807 | 0.092 | 0.098 | 0.569 | 1.252 |
| MDA-MB-468 | Breast c. | − | 0.747 | | 0.316 | 0.327 | 0.634 |
| BT-549 | Breast c. | − | 0.153 | | | −0.009 | −0.494 |
| MCF7 | Breast c. | − | 0.231 | −0.531 | 0.177 | 0.049 | 0.586 |

TABLE 5

Log10 ratios (cell line versus SuperSILAC) of the eight non-modified ribosomal peptides used for the alternative normalisation (sequences disclosed as SEQ ID NOS 34-41, respectively, in order of appearance)

| | Peptide Seq. | | | | |
|---|---|---|---|---|---|
| | FNADEFEDMVAEK | FTPGTFTNQIQAAFREPR | HGSLGFLPR | HMYHSLYLK | ILDSVGIEADDDRLNK |
| | Name | | | | |
| Uniprot Id | RPL10 P27635 | RPSA P08865 | RPL3 P39023 | RPL19 P84098 | RPLP2 P05387 |
| LouNH1 | 0.247 | 0.243 | 0.273 | | 0.080 |
| H1648 | 0.282 | 0.238 | 0.220 | | 0.320 |
| HCC827 | 0.182 | 0.146 | | | 0.056 |
| H322M | | | 0.277 | 0.306 | 0.177 |
| H2030 | | 0.196 | 0.264 | 0.308 | 0.181 |
| HCC2279 | 0.270 | 0.063 | 0.219 | 0.154 | 0.307 |
| HCC366 | 0.238 | 0.158 | 0.140 | 0.148 | 0.295 |
| HCC4006 | | | | | 0.301 |
| H1666 | 0.095 | 0.121 | 0.138 | 0.149 | 0.151 |
| PC9 | 0.208 | 0.143 | 0.228 | 0.257 | 0.218 |
| H2009 | 0.087 | 0.174 | 0.103 | 0.096 | 0.223 |
| H460 | 0.426 | 0.417 | 0.471 | | 0.252 |
| Calu6 | 0.340 | 0.278 | 0.303 | | 0.397 |
| H2077 | | | 0.445 | 0.456 | 0.409 |
| H1395 | | 0.068 | 0.241 | 0.344 | 0.264 |
| H2172 | 0.214 | 0.198 | 0.173 | 0.182 | 0.302 |
| HCC7 | 0.203 | 0.167 | 0.243 | 0.280 | 0.240 |
| H157 | 0.200 | 0.189 | 0.145 | 0.211 | 0.210 |
| H520 | 0.149 | 0.198 | 0.205 | 0.250 | 0.221 |

| | Peptide Seq. | | |
|---|---|---|---|
| | NIEDVIAQGIGK | TIAECLADELINAAK | VCTLAIIDPGDSDIIR |
| | Name | | |
| Uniprot Id | RPLP2 P05387 | RPS5 P46782 | RPL30 P62888 |
| LouNH1 | 0.157 | 0.255 | 0.161 |
| H1648 | 0.257 | 0.255 | 0.287 |
| HCC827 | 0.147 | 0.180 | 0.130 |
| H322M | | | |
| H2030 | 0.250 | | |

TABLE 5-continued

| Log10 ratios (cell line versus SuperSILAC) of the eight non-modified ribosomal peptides used for the alternative normalisation (sequences disclosed as SEQ ID NOS 34-41, respectively, in order of appearance) | | | |
|---|---|---|---|
| HCC2279 | 0.232 | 0.132 | 0.218 |
| HCC366 | 0.221 | 0.220 | 0.259 |
| HCC4006 | 0.161 | | |
| H1666 | 0.125 | 0.112 | 0.147 |
| PC9 | 0.272 | 0.276 | 0.282 |
| H2009 | 0.021 | | |
| H460 | 0.353 | 0.461 | 0.361 |
| Calu6 | 0.383 | 0.330 | 0.339 |
| H2077 | | | |
| H1395 | 0.249 | | |
| H2172 | 0.238 | 0.194 | 0.149 |
| HCC7 | 0.228 | 0.211 | 0.193 |
| H157 | 0.100 | 0.129 | 0.111 |
| H520 | 0.217 | 0.225 | 0.192 |

EXAMPLE 2

ITGB4 Expression Predicts Dasatinib Response in Non-Small Cell Lung Cancer

Methods

Additional ITGB4 Protein Expression Analysis

Data from MaxQuant's ProteinGroups table are used to assess the difference in protein expression between sensitive and resistant cell lines. Each entry in this table describes one specific protein (or protein group if the detected peptides can originate from multiple proteins) along with information about its regulation. The regulation of a protein is provided as ratio of the protein's abundance between each cell line and the super-SILAC standard. This ratio is calculated from the ratios of the protein's non-modified peptides. MaxQuant already provides normalized ratios, which are used in this study. ITGB4 formed a protein group without any other protein (i.e. it was identified unambiguously) and had 8 cell line-to-Super-SILAC ratios present (4 in sensitive cells and 4 in resistant cells).

Results

ITGB4 Protein Expression Analysis

Based on the herein provided results it was investigated whether the difference in phosphorylation on ITGB4, the predominant protein in the phospho-signature, might be due to a difference in protein expression. To answer this question, one has to analyse data generated from non-modified (i.e. non-phosphorylated) peptides. Although the phosphoproteomic workflow is designed to specifically enrich for phosphorylated peptides, a significant fraction of non-phosphorylated peptides was also detected. For 6 of the 19 valid cell lines, quantitative data of non-modified peptides were available. Additionally, one label switch experiment pair also produced non-phosphorylated data, resulting in a total number of 8 available cell line data points. Strikingly, all 4 sensitive cell line data points were up-regulated with respect to the Super-SILAC reference (median≈4-fold) and all 4 resistant down-regulated (median≈3-fold) leading to a median fold change of ~12 between sensitive and resistant cells (see FIG. 10). When omitting the label switch experiment (since the cells in this experiment are redundant), the corresponding values are median up-regulation ~5-fold, median down-regulation ~2.5-fold, median fold change ~12.

These results indicate that the measured differences on ITGB4 between sensitive and resistant cell lines on the phosphoproteome level are in fact due to a difference on the protein expression level. Furthermore, the protein expression of ITGB4 alone perfectly separates sensitive from resistant cells on the available data (see FIG. 10) and might thus be applicable as a single-protein marker for dasatinib sensitivity.

EXAMPLE 3

Additional Signature Subset Analysis

Methods

Additional Signature Subset Analysis

The analysis was performed as depicted in FIG. 7 and described hereinbut without the feature selection step. The entire cross-validation workflow was carried out five times to avoid a bias towards the random number generator seeds used for data imputation (see also Materials and Methods in the paper) and the averaged prediction accuracy values were used.

Results

Signature Subset Analysis

To analyse whether already a subset of the proposed signature of 12 phosphorylation sites is predictive, we calculated the performance of each possible combination of the 12 features by means of leave-one-out cross validation. Here, the cross validation was performed without feature selection, since the set of features is given. The four phosphorylation sites of ITGB4 were used as one block of features, reducing the set under investigation to 9 entities. Thus, the total number of investigated feature combinations was $2^9-1=511$. It turned out that different combinations of feature pairs can already achieve the maximum accuracy of 19 out of 19 correct predictions (see FIG. 11). In total, 8 feature pairs lead to the best prediction (ITGB4+ITPR3. ITGB4+TNKS1BP1, ITGB4+ARHGEF18, ITGB4+APG16L, ITGB4+TPD52L2, ARHGEF18+GPRC5A, ARHGEF18+ITPR3, ARHGEF18+IASPP). All combinations of three or more features that correctly predict 19 out of 19 cell lines include at least one of these 8 pairs.

EXAMPLE 4

Protein Expression of ITGB4 in NSCLC Cell Lines Confirms that its Expression can be Used to Predict Responsiveness to an Inhibitor of a Kinase of the Src Family Methods For protein detection in human lung cancer cell lines, exponentially growing cells from 15 cm dishes were used. After cell lysis 80 μg of total protein was separated on 4-12% Bis-Tris NuPAGE gels (Invitrogen) for the detection of integrin β4 or on 7.5% Tris-Glycine gels (Biorad Mini PROTEAN) for the detection of tankyrase 1-binding protein (TNKS1BP1). Proteins were transferred overnight to 0.2 μm nitrocellulose membranes and probed with the appropriate antibodies in LI-COR Odyssey blocking buffer. All primary antibodies were used in 1:1000 dilutions:anti-integrin beta 4 antibody [M126](ab29042, Abcam); anti-TNKS1BP1 (SAB4503414; Sigma Aldrich); anti-actin (1-19) (sc-1616-R. Santa Cruz Biotech). Actin served as a loading control. Following primary antibody incubation, membranes were probed with IRDye 800CW conjugated goat anti-mouse IgG (H+L9 (LI-COR #926-32210), dilution 1:15000 for the detection of integrin β4; or IRDye 800 conjugated Affinity Purified Anti-Rabbit IgG, (611-732-127; Rockland), dilution 1:20000, for the detection of TNKS1BP1 and actin; or DyLight 800 conjugated affinity purified anti-rabbit IgG (H+L) (611-145-122; Rockland), dilution 1:50000 for the detection of actin. Signals were detected at 800 nm using the LI-COR Odyssey infrared system.

Results

Integrin β4 Expression can be Used as a Marker for Responsiveness to an Inhibitor of a Kinase of the Src Family Four of the highest ranked predictive phospho-sites reside on the protein Integrin β4 (ITGB4). Since we did enrich for phosphorylated peptides and did not measure the abundance of the non-phosphorylated peptides or the total protein, it is principally impossible to distinguish between differences in the phosphorylation degree and differences in the expression of the corresponding protein. However, in case of ITGB4 it is likely that the differences in the phosphorylation of the four sites are caused by differences in the abundance of the protein itself. To prove that the expression of this protein is indeed different in the two classes of the NSCLC cell lines, we performed quantitative western blots using antibodies against the total protein of ITGB4 and 182 kDa tankyrase-1-binding protein (TNKS1BP1). We selected TNKS1BP1 as one of the eight proteins, for which only one phosphosite was identified as predictive feature. Whereas TNKS1BP1 is present in almost all cell lines and its expression shows no correlation with the sensitivity of the cell line to dasatinib, ITGB4 can be detected in 8 sensitive cell lines, but only in 2 resistant cell lines (s. FIG. 12A). This is confirmed by quantitative analysis of three replicate experiments (s. FIGS. 12B and C). The background-corrected signals of ITGB4 correlate with the phosphorylation degree measured by mass spectrometry (Pearson correlation 0.88, $p=2\times10^{-6}$). The signals of most resistant cell lines are low, while strong signals can be determined in the sensitive cell lines. This clearly shows that expression of ITGB4 is also predictive and that it can be used as alternative or additional marker to its phosphorylation status. Indeed, if choosing the average of the median signals in each group as classification threshold, all resistant and 8 sensitive cell lines would be correctly classified, whereas 3 sensitive cell lines would be falsely classified as resistant. Nevertheless, the prediction accuracy of ITGB4 expression (84%) is not as high as the accuracy of the full phospho-signature (94%). In contrast, the signals for total TNKS1BP1 expression do not correlate with sensitivity, although its phosphorylation is predictive.

ITGB4 is Expressed in Subpopulation of Lung and Breast Cancer Tissues.

We demonstrated that a signature of 12 phosphorylation sites and the expression of ITGB4 are predictive in NSCLC and breast cancer cell lines. In order to show that ITGB4 is expressed in cancer tissues, we examined immunohistochemistry images of several cancer tissue slices. The Human Protein Atlas systematically analyses the human proteome in cell lines, normal tissues and cancer tissues using antibodies. In particular, it contains a number of immunohistochemistry images of cancer tissues stained with an antibody (CAB005258) against total protein of ITGB4. Five lung cancer samples (42%) are negative, whereas seven samples show weak to strong expression of ITGB4. Similarly, six breast cancer samples (50%) are negative, whereas six samples show weak expression. Thus, it is expected that many patients having ITGB4 expressing tumors will profit from the herein provided methods for determining responsiveness to an inhibitor of a kinase of the Src family.

In summary, we showed that the expression of ITGB4 correlates with its phosphorylation status. Therefore, we confirmed that both ITGB4 expression and ITGB4 phosphorylation are useful for predicting the responsiveness to an inhibitor of a kinase of the Src-family. The marker is measurable by immunohistochemistry in clinical tissue samples and it is present in a sub-population of approximately 50% of the investigated cancer tissues.

The difference in phosphorylation of a specific site between two cell lines may be due to a difference in either expression of the corresponding protein, or the degree of phosphorylation of this site, or a combination of both. As long as the abundance of a certain phosphorylated peptide consistently differs between sensitive and resistant cell lines, the cause for its difference is not important for its use as a predictive biomarker. In case of ITGB4, we could indeed show that its protein expression is also predictive. In contrast, the protein expression of TNKS1BP1 does not differentiate between sensitive and resistant cell lines. Accordingly, we demonstrated that the expression of ITGB4 correlates with its phosphorylation status and can, hence, be considered as marker for its phosphorylation status. The ITGB4 expression is measurable by immunohistochemistry in clinical tissue samples and it is present in a sub-population of approximately 50% of the investigated cancer tissues.

EXAMPLE 5

Phospho-Signature Predicts Responsiveness to Inhibitors of Kinases of the Src Family Dasatinib, Saracatinib, and Bosutinib Methods Responsiveness of the cell lines for the src family kinase inhibitors dasatinib, saracatinib and bosutinib was determined by measuring the cellular ATP content after 96 hours of treatment using the CellTiter Glo chemiluminescent viability assay (Promega. Mannheim, Germany). Cells were cultivated in 96-well plates (Greiner, Frickenhausen. Germany) in the presence of inhibitors (LC Laboratories, Woburn, Mass., USA) within a concentration range between 3 nM and 30 μM.

The raw data from the chemiluminometer (FLUOstar OPTIMA. BMG Labtech, Offenburg, Germany) was used to determine the $GI_{50}$ value. First, the background was determined by calculating the median value of the plate's border wells, which contained only growth media. This value was then subtracted from each inner well. Since two experiments were conducted on one 96-well plate with 10 compound concentrations each (0(DMSO), 3 nM, 10 nM. 30 nM, 100 nM, 300 nM, 1 μM, 3 μM, 10 μM, 30 μM), three data points per concentration and experiment were available. Ratios representing the percentage of growth inhibition were calculated by dividing each data point coming from a concentration >0 by the median of the DMSO values. A logistic regression was performed to fit a curve to those ratios and compute the $GI_{50}$ value.

For each inhibitor, the average of the class medians of the log-transformed $GI_{50}$ values was used as threshold discriminating between sensitive and resistant cells. This resulted in a threshold of 1 μM for dasatinib, 3.5 μM for saracatinib, and 1.5 μM for bosutinib. Cell lines with $GI_{50}$ values below (above) these thresholds were classified as sensitive (resistant) for the corresponding inhibitor.

Results

We demonstrated that the phospho-signature can predict sensitivity to treatment with dasatinib in various NSCLC and breast cancer cell lines. As one of the main targets of dasatinib is the Src kinase, we believe that the signature can predict sensitivity not only to dasatinib but also for other src family kinase inhibitors. This is confirmed by the herein provided data in relation to saracitinib (AZD0530, AstraZeneca) and bosutinib (SKI-606, Pfizer). We tested our panel of 19 NSCLC cell lines against these two additional src family kinase inhibitors.

Table 6 shows the obtained $GI_{50}$ values of the three therapeutic agents together with the classification into sensitive (or responsive) and resistant across all cell lines. Cell lines that are sensitive/responsive to dasatinib treatment are likely to be sensitive to saracatinib and bosutinib and vice versa. Additionally, the prediction obtained by use of the herein provided phospho-signature is shown. As we have shown above, the predicted sensitivity/responsiveness perfectly agrees with the here determined dasatinib sensitivity/responsiveness. For Saracatinib one sensitive and one resistant cell line was misclassified. Similarly, for bosutinib two sensitive and one resistant cell line was misclassified. Thus the obtained classification accuracy is 89.5% for saracatinib and 84.2% for bosutinib. The same phospho-signature (and likewise the expression level of ITGB4) can therefore predict sensitivity/responsiveness not only for dasatinib, but also for saracatinib and bosutinib.

TABLE 6

Sensitivity/responsiveness of cell lines to treatment with the three src family kinase inhibitors dasatinib, saracatinib and bosutinib. The cell lines were classified as sensitive/responsive if the $GI_{50}$ value is below a certain threshold (see Methods, +: sensitive; −: resistant). The sensitivity predicted by the phospho-signature is shown in the last column.

| | $GI_{50}$ [μM] | | | Sensitivity | | | |
|---|---|---|---|---|---|---|---|
| Cell Line | Dasatinib | Saracatinib | Bosutinib | Dasatinib | Saracatinib | Bosutinib | Prediction |
| Calu-6 | 2.800 | 30.000 | 2.130 | − | − | − | − |
| H1395 | 4.700 | 31.700 | 4.720 | − | − | − | − |
| H157 | 2.630 | 13.900 | 1.810 | − | − | − | − |
| H2077 | 4.750 | 14.800 | 3.790 | − | − | − | − |
| H2172 | 5.850 | 28.500 | 2.590 | − | − | − | − |
| H460 | 3.900 | 12.100 | 1.370 | − | − | + | − |
| H520 | 1.430 | 4.560 | 2.640 | − | − | − | − |
| HCC78 | 17.050 | 0.267 | 3.040 | − | + | − | − |
| H1648 | 0.079 | 1.510 | 3.720 | + | + | − | + |
| H1666 | 0.076 | 2.200 | 1.080 | + | + | + | + |
| H2009 | 0.085 | 4.310 | 2.330 | + | − | − | + |
| H2030 | 0.022 | 0.443 | 0.896 | + | + | + | + |
| PC9 | 0.020 | 0.147 | 0.234 | + | + | + | + |
| HCC827 | 0.033 | 0.722 | 0.141 | + | + | + | + |
| LouNH91 | 0.068 | 1.180 | 0.186 | + | + | + | + |
| HCC366 | 0.017 | 1.240 | 1.270 | + | + | + | + |
| HCC4006 | 0.950 | 0.132 | 0.120 | + | + | + | + |
| H322M | 0.311 | 0.876 | 0.528 | + | + | + | + |
| HCC2279 | 0.045 | 0.660 | 3.250 | + | + | − | + |

EXAMPLE 6

Target Profiles of Src Family Kinase Inhibitors

Methods

KinAffinity™ Target Profiling

For in vitro association experiments $4\times10^8$ PC9 cells were lysed in buffer containing 20 mM HEPES pH 7.5, 400 mM NaCl. 0.25% Triton X-100, 1 mM DTT, 1.5 mM $MgCl_2$, 0.5 mM $ZnCl_2$, 0.5 mM EDTA, 0.5 mM EGTA, 1600 U/ml Benzonase plus additives (10 μg/ml aprotinin, 10 μg/ml leupeptin, 1 mM PMSF, 1 mM $Na_3VO_4$, 10 mM NaF). After centrifugation the supernatant was adjusted to 1 M NaCl, filtered through a 0.45 μm celluloseacetate filter and subjected to KinAffinity™ beads representing several different broad-spectrum kinase inhibitors immobilized on Sepharose beads. For each in vitro association experiment 750 μl cell extract (4 mg/ml) were incubated with 30 μl KinAffinity™ beads for 2.5 h at 4° C. The incubation procedure was essentially performed as described in Sharma et al. (2009) with the addition that KinAffinity™ beads representing five different compound densities were incubated with cell extract to determine binding curves for each identified protein kinase. For competition experiments, cell extracts were incubated with different concentrations of the inhibitor to be profiled (30 nM, 100 nM, 300 nM, 3 μM, 30 μM) for 30 min prior to the addition of KinAffinity™ beads. Alternatively, the inhibitor (3 nM, 30 nM, 100 nM, 300 nM, 3 μM) and KinAffinity™ beads were added simultaneously to the cell extract. In all in vitro association experiments the subsequent washing and elution steps including the separation of proteins by electrophoresis and the in-gel digest with trypsin were performed as described in Sharma et al. (2009) with the exception that 1 slice was cut out of the gel. The extracted peptides were derivatized for quantitative mass spectrometry using the TMT 6-plex reagent according to the manufactures instructions and were subsequently combined for mass spectrometric analysis.

Mass Spectrometry and Data Analysis

Mass spectrometric analysis of the labeled and combined peptide fractions was carried out by on-line nanoLC-MS/MS. The samples were loaded directly by an Agilent 1200 nanoflow system (Agilent Technologies) on a 15 cm fused silica emitter (New Objective) packed in-house with reversed phase material (Reprusil-Pur C18-AQ, 3 μm, Dr. Maisch GmbH) at a flow of 500 mL/min. The bound peptides were eluted by a gradient from 2% to 40% solvent B (80% ACN, 0.5% HOAc) at a flow of 200 mL/min and sprayed directly into an LTQ-Orbitrap XL mass spectrometer (Thermo Fischer Scientific) at a spray voltage of 2 kV applying a nano electrospray ion source (ProxeonBiosystems). The mass spectrometer was operated in the positive ion mode and a data dependent switch between MS and MS/MS acquisition. To improve mass accuracy in the MS mode the lock-mass option was enabled. Full scans were acquired in the orbitrap at a resolution R=60 000 and a target value of 1 000 000 charges. The six most intense ions were selected for pulsed Q dissociation in the LTQ (Bantscheff et al. 2008). The resulting fragmentation spectra were also recorded in the linear ion trap.

The acquired mass spectra were processed using the MaxQuant software package (version 1.0.13.12) (Cox and Mann 2008), applying the Mascot search engine (version 2.2.0) for peptide and protein identification. A concatenated forward and reversed Swissprot database (version: 57.11) including a set of the most commonly observed protein contaminations was used comprising 69906 database entries. Regarding the search parameters, the minimal peptide length was set to 6 amino acids, trypsin was selected as proteolytic enzyme and maximally 2 missed cleavage sites were allowed. Carbamidomethylation of cysteins was selected as fixed modification whereas methionine oxidation, N-terminal protein acetylation and TMT modification lysines and peptide N-termi were considered as variable modifications. The maximal mass deviation of precursor and fragment masses was set to 7 ppm and 0.5 Da. A false discovery rate (FDR) of 0.01 was selected for proteins and peptides and a posterior error propability (PEP) below or equal to 0.1 for each MS/MS spectrum was required. The intensities of the TMT reporter ions were read from the msm files. For each protein group identified by MaxQuant the MS/MS spectra corresponding to razor peptides of this protein group were collected, and the reporter ion intensities were averaged over all MS/MS spectra. Finally the sigmoid model y=1−a/(1+(x/b)^c) was fitted to the binding values for each protein group. Similarly the model y=a/(1+(x/b)^c) was fitted to the competition values. Using the Cheng-Prusoff equation the dissociation constant for the compound was derived from the obtained model parameters for each protein group (Cheng and Prusoff 1973).

Results

We used the KinAffinity target profiling to identify the targets binding to the src family kinase inhibitors dasatinib, saracatinib, bosutinib, and ponatinib in the NSCLC cell line PC9. The profiling experiments revealed not only the identity of the kinases binding to the inhibitors but also the corresponding affinity ($k_D$). In general, the set of targeted kinases and the corresponding affinity values are rather similar between the four tested inhibitors (Tab. 1). In particular, all four inhibitors have low $k_D$-values against src family kinases Src, Fyn, and Yes. Dasatinib and saracatinib show rather specific target profiles including mostly kinases of the tyrosine kinase, the tyrosine kinase-like, and the homologs of yeast sterile kinases. In contrast, bosutinib shows a broader profile binding many additional kinases, such as casein kinases and protein kinases C. Ponatinib, on the other hand, targets the inhibitor of nuclear factor κ-B subunits β and γ (IKBKB and IKBKG) with high affinity ($k_D$=13 and 65 nM, respectively). Both kinases are not bound by any of the other three inhibitors. IKBK inhibition suppresses growth of cancer cells in vitro and in vivo (e.g. Olsen et al. Int. J. Cancer 111 (2004) 198). We therefore hypothesize, that because of these additional molecular targets ponatinib is able to inhibit cell proliferation of additional cell lines, which are sensitive against treatment with the other three inhibitors.

TABLE 7

| | KD_free [μM] | | | |
|---|---|---|---|---|
| Gene Names | Dasatinib | Bosutinib | Saracatinib | Ponatinib |
| AAK1/FLJ45252 | | **2.081** | | |
| AXL | | 3.385 | | |
| BMPR2 | | | 16.760 | |
| CCNC | | | | 2.688 |
| CDC42BPB | | **0.596** | | |
| CDK13 | | | | >19.221 |
| CDK16 | | | | 0.625 |
| CDK17 | | | | 0.800 |
| CDK18 | | | | **0.356** |
| CDK8; CDK19 | | | | 17.143 |
| CHUK | | | | **0.065** |
| CSK | 0.004 | **0.295** | 0.093 | **0.050** |
| CSNK1A1 | | **1.726** | 9.345 | |
| CSNK1D | | **0.182** | 8.684 | |
| CSNK1E | 13.114 | **0.105** | 1.850 | |
| DCK | | | | 3.353 |
| DDR1 | 0.026 | 7.103 | 0.427 | **0.034** |
| EGFR | | **0.457** | 2.105 | |
| EPHA1 | 0.008 | | 0.072 | 0.499 |
| EPHA2 | **0.003** | **1.155** | 0.108 | **0.030** |
| EPHB2 | **0.001** | 11.837 | 0.272 | 0.812 |
| EPHB4 | | 6.751 | 0.363 | 1.746 |
| EPHB6 | | | 1.103 | 12.381 |
| FER | 4.771 | **0.168** | 3.471 | **0.358** |
| FRK | 0.007 | **2.164** | | |
| FYN | **0.003** | **0.569** | **0.023** | **0.030** |
| GAK | 0.070 | **0.031** | 0.054 | 2.059 |
| IKBKB | | | | **0.013** |
| IKBKG | | | | **0.044** |
| ILK | 0.175 | 4.049 | | |
| JAK1 | | | | 1.138 |
| LIMK1 | | | 7.211 | **0.250** |
| LIMK2 | 0.289 | | | >16.036 |
| LYN | **0.001** | **0.175** | **0.015** | **0.006** |
| MAP2K1 | 1.301 | **0.060** | 1.226 | |
| MAP2K2 | 1.344 | | 2.307 | |
| MAP3K1 | 0.944 | **0.040** | >16.153 | **0.196** |
| MAP3K2 | 0.716 | **0.806** | | 3.421 |
| MAP3K11 | | 5.439 | | |
| MAP4K3 | 1.547 | **0.060** | >12.804 | 2.972 |
| MAP4K4 | 7.744 | **0.072** | 5.887 | 0.784 |
| MAPK9 | | | | 4.002 |
| MAPK13 | | | | 6.022 |
| MAPK14 | 0.091 | >16.124 | 0.332 | **0.025** |
| MARK2 | | >16.104 | | |
| MARK3 | | 7.192 | | |
| MELK | | | | 2.711 |
| MET | | 5.559 | 6.659 | |
| MLTK | 0.078 | 11.533 | 0.750 | **0.024** |
| NEK2 | | **1.225** | | |
| PAK4 | | 3.395 | | |
| PKN1 | 17.608 | 8.995 | | |
| PRKAA1 | | | | 5.577 |
| PRKAB1 | | | | 7.170 |
| PRKAB2 | | | | 7.727 |
| PRKACA | | **0.894** | | 5.618 |
| PRKACB | | **1.896** | | 12.261 |
| PRKACG | | | | 6.913 |
| PRKAG1 | | | | 6.753 |
| PRKCD | | 2.507 | | |
| PRKD2 | | 4.309 | | |
| PRKD3 | | >10.152 | | |
| PTK2 | | **0.493** | | |
| PTK2B | | **0.619** | 11.449 | **0.180** |
| PTK6 | 0.009 | | 0.030 | |
| RIPK2 | 0.006 | | **0.001** | **0.036** |
| RPS6KA1 | | | 14.081 | |
| SIK2 | 0.011 | **0.172** | 0.301 | |
| SIK3 | 0.408 | 3.048 | 3.043 | |
| SLK | 7.761 | **0.252** | 3.424 | 5.054 |
| SRC | **0.0004** | **0.288** | **0.002** | **0.039** |
| STK3 | | **2.738** | | 1.543 |
| STK4 | | **1.514** | | 2.023 |
| TEC | 0.029 | | 4.610 | |
| TNK1 | | | >5.464 | **0.015** |
| TYK2 | 5.447 | | | |
| ULK3 | | | >7.051 | >7.051 |
| YES1 | **0.001** | **1.199** | **0.011** | **0.070** |

Tab 7: Kinase profiles of four src inhibitors. $K_D$-values that are in the range of the corresponding $K_D$-value for src (i.e. below 4 nM for dasatinib, 3 μM for bosutinib, 20 nM for saracatinib, and 400 nM for ponatinib) are written in bold.

Dasatinib and saracatinib show rather specific target profiles including mostly kinases of the tyrosine kinase, the tyrosine kinase-like, and the homologs of yeast sterile kinases. In contrast, bosutinib shows a broader profile binding many additional kinases, such as casein kinases and protein kinases C. In accordance with the above, Dasatinib and saracitinib can be seen as examples of selective inhibitors of a kinase of the Src family (i.e. inhibitors which specifically target a kinase of the Src family), while bosutinib is an example of an inhibitor of a kinase of the Src family with a broad spectrum of targets.

The present invention refers to the following nucleotide and amino acid sequences:

The sequences provided herein are available in the Uniprot or NCBI database and can be retrieved from http://www.uniprot.org/ and www.ncbi.nlm.nih.gov/sites/entrez?db=gene, respectively. Theses sequences also relate to annotated and modified sequences. The present invention also provides techniques and methods wherein homologous sequences, and variants of the concise sequences provided herein are used. Preferably, such "variants" are genetic variants.

Nucleotide sequence encoding *homo sapiens* Integrin beta4 (ITGB4) transcript variant 1 (corresponds to Uniprot id P16144).
>gi|54607034:188-5656 *Homo sapiens* integrin, beta 4 (ITGB4), transcript variant 1, mRNA
SEQ ID No. 1:

```
ATGGCAGGGCCACGCCCCAGCCCATGGGCCAGGCTGCTCCTGGCAGCCTTGATCAGCGTCAGCCTCTCTG
GGACCTTGGCAAACCGCTGCAAGAAGGCCCCAGTGAAGAGCTGCACGGAGTGTGTCCGTGTGGATAAGGA
CTGCGCCTACTGCACAGACGAGATGTTCAGGGACCGGCGCTGCAACACCCAGGCGGAGCTGCTGGCCGCG
GGCTGCCAGCGGGAGAGCATCGTGGTCATGGAGAGCAGCTTCCAAATCACAGAGGAGACCCAGATTGACA
CCACCCTGCGGCGCAGCCAGATGTCCCCCCAAGGCCTGCGGGTCCGTCTGCGGCCCGGTGAGGAGCGGCA
TTTTGAGCTGGAGGTGTTTGAGCCACTGGAGAGCCCCGTGGACCTGTACATCCTCATGGACTTCTCCAAC
TCCATGTCCGATGATCTGGACAACCTCAAGAAGATGGGGCAGAACCTGGCTCGGGTCCTGAGCCAGCTCA
CCAGCGACTACACTATTGGATTTGGCAAGTTTGTGGACAAAGTCAGCGTCCCGCAGACGGACATGAGGCC
TGAGAAGCTGAAGGAGCCCTGGCCCAACAGTGACCCCCCCTTCTCCTTCAAGAACGTCATCAGCCTGACA
GAAGATGTGGATGAGTTCCGGAATAAACTGCAGGGAGAGCGGATCTCAGGCAACCTGGATGCTCCTGAGG
GCGGCTTCGATGCCATCCTGCAGACAGCTGTGTGCACGAGGGACATTGGCTGGCGCCCGGACAGCACCCA
CCTGCTGGTCTTCTCCACCGAGTCAGCCTTCCACTATGAGGCTGATGGCGCCAACGTGCTGGCTGGCATC
ATGAGCCGCAACGATGAACGGTGCCACCTGGACACCACGGGCACCTACACCCAGTACAGGACACAGGACT
ACCCGTCGGTGCCCACCCTGGTGCGCCTGCTCGCCAAGCACAACATCATCCCCATCTTTGCTGTCACCAA
CTACTCCTATAGCTACTACGAGAAGCTTCACACCTATTTCCCTGTCTCCTCACTGGGGGTGCTGCAGGAG
GACTCGTCCAACATCGTGGAGCTGCTGGAGGAGGCCTTCAATCGGATCCGCTCCAACCTGGACATCCGGG
CCCTAGACAGCCCCCGAGGCCTTCGGACAGAGGTCACCTCCAAGATGTTCCAGAAGACGAGGACTGGGTC
CTTTCACATCCGGCGGGGGGAAGTGGGTATATACCAGGTGCAGCTGCGGGCCCTTGAGCACGTGGATGGG
ACGCACGTGTGCCAGCTGCCGGAGGACCAGAAGGGCAACATCCATCTGAAACCTTCCTTCTCCGACGGCC
TCAAGATGGACGCGGGCATCATCTGTGATGTGTGCACCTGCGAGCTGCAAAAAGAGGTGCGGTCAGCTCG
CTGCAGCTTCAACGGAGACTTCGTGTGCGGACAGTGTGTGTGCAGCGAGGGCTGGAGTGGCCAGACCTGC
AACTGCTCCACCGGCTCTCTGAGTGACATTCAGCCCTGCCTGCGGGAGGGCGAGGACAAGCCGTGCTCCG
GCCGTGGGGAGTGCCAGTGCGGGCACTGTGTGTGCTACGGCGAAGGCCGCTACGAGGGTCAGTTCTGCGA
GTATGACAACTTCCAGTGTCCCCGCACTTCCGGGTTCCTCTGCAATGACCGAGGACGCTGCTCCATGGGC
CAGTGTGTGTGTGAGCCTGGTTGGACAGGCCCAAGCTGTGACTGTCCCCTCAGCAATGCCACCTGCATCG
ACAGCAATGGGGGCATCTGTAATGGACGTGGCCACTGTGAGTGTGGCCGCTGCCACTGCCACCAGCAGTC
GCTCTACACGGACACCATCTGCGAGATCAACTACTCGGCGATCCACCCGGGCCTCTGCGAGGACCTACGC
TCCTGCGTGCAGTGCCAGGCGTGGGGCACCGGCGAGAAGAAGGGGCGCACGTGTGAGGAATGCAACTTCA
AGGTCAAGATGGTGGACGAGCTTAAGAGAGCCGAGGAGGTGGTGGTGCGCTGCTCCTTCCGGGACGAGGA
TGACGACTGCACCTACAGCTACACCATGGAAGGTGACGGCGCCCCTGGGCCCAACAGCACTGTCCTGGTG
CACAAGAAGAAGGACTGCCCTCCGGGCTCCTTCTGGTGGCTCATCCCCCTGCTCCTCCTCCTCCTGCCGC
TCCTGGCCCTGCTACTGCTGCTATGCTGGAAGTACTGTGCCTGCTGCAAGGCCTGCCTGGCACTTCTCCC
GTGCTGCAACCGAGGTCACATGGTGGGCTTTAAGGAAGACCACTACATGCTGCGGGAGAACCTGATGGCC
TCTGACCACTTGGACACGCCCATGCTGCGCAGCGGGAACCTCAAGGGCCGTGACGTGGTCCGCTGGAAGG
TCACCAACAACATGCAGCGGCCTGGCTTTGCCACTCATGCCGCCAGCATCAACCCCACAGAGCTGGTGCC
CTACGGGCTGTCCTTGCGCCTGGCCCGCCTTTGCACCGAGAACCTGCTGAAGCCTGACACTCGGGAGTGC
GCCCAGCTGCGCCAGGAGGTGGAGGAGAACCTGAACGAGGTCTACAGGCAGATCTCCGGTGTACACAAGC
TCCAGCAGACCAAGTTCCGGCAGCAGCCCAATGCCGGGAAAAAGCAAGACCACACCATTGTGGACACAGT
GCTGATGGCGCCCCGCTCGGCCAAGCCGGCCCTGCTGAAGCTTACAGAGAAGCAGGTGGAACAGAGGGCC
TTCCACGACCTCAAGGTGGCCCCCGGCTACTACACCCTTACTGCAGACCAGGACGCCCGGGGCATGGTGG
AGTTCCAGGAGGGCGTGGAGCTGGTGGACGTACGGGTGCCCCTCTTTATCCGGCCTGAGGATGACGACGA
GAAGCAGCTGCTGGTGGAGGCCATCGACGTGCCCGCAGGCACTGCCACCCTCGGCCGCCGCCTGGTAAAC
ATCACCATCATCAAGGAGCAAGCCAGAGACGTGGTGTCGTTTGAGCAGCCTGAGTTCTCGGTCAGCCGCG
GGGACCAGGTGGCCCGCATCCCTGTCATCCGGCGTGTCCTGGACGGCGGGAAGTCCCAGGTCTCCTACCG
CACACAGGATGGCACCGCGCAGGGCAACCGGGACTACATCCCCGTGGAGGGTGAGCTGCTGTTCCAGCCT
GGGGAGGCCTGGAAAGAGCTGCAGGTGAAGCTCCTGGAGCTGCAAGAAGTTGACTCCCTCCTGCGGGGCC
GCCAGGTCCGCCGTTTCCACGTCCAGCTCAGCAACCCTAAGTTTGGGGCCCACCTGGGCCAGCCCCACTC
CACCACCATCATCATCAGGGACCCAGATGAACTGGACCGGAGCTTCACGAGTCAGATGTTGTCATCACAG
CCACCCCCTCACGGCGACCTGGGCGCCCCGCAGAACCCCAATGCTAAGGCCGCTGGGTCCAGGAAGATCC
ATTTCAACTGGCTGCCCCCTTCTGGCAAGCCAATGGGGTACAGGGTAAAGTACTGGATTCAGGGTGACTC
CGAATCCGAAGCCCACCTGCTCGACAGCAAGGTGCCCTCAGTGGAGCTCACCAACCTGTACCCGTATTGC
GACTATGAGATGAAGGTGTGCGCCTACGGGGCTCAGGGCGAGGGACCCTACAGCTCCCTGGTGTCCTGCC
GCACCCACCAGGAAGTGCCCAGCGAGCCAGGGCGTCTGGCCTTCAATGTCGTCTCCTCCACGGTGACCCA
GCTGAGCTGGGCTGAGCCGGCTGAGACCAACGGTGAGATCACAGCCTACGAGGTCTGCTATGGCCTGGTC
AACGATGACAACCGACCTATTGGGCCCATGAAGAAAGTGCTGGTTGACAACCCTAAGAACCGGATGCTGC
TTATTGAGAACCTTCGGGAGTCCCAGCCCTACCGCTACACGGTGAAGGCGCGCAACGGGGCCGGCTGGGG
GCCTGAGCGGGAGGCCATCATCAACCTGGCCACCCAGCTCAAGAGGCCCATGTCCATCCCCATCATCCCT
GACATCCCTATCGTGGACGCCCAGAGCGGGGAGGACTACGACAGCTTCCTTATGTACAGCGATGACGTTC
TACGCTCTCCATCGGGCAGCCAGAGGCCCAGCGTCTCCGATGACACTGGCTGCGGCTGGAAGTTCGAGCC
CCTGCTGGGGGAGGAGCTGGACCTGCGGCGCGTCACGTGGCGGCTGCCCCCGGAGCTCATCCCGCGCCTG
TCGGCCAGCAGCGGGCGCTCCTCCGACGCCGAGGCGCCCCACGGGCCCCCGGACGACGGCGGCGCGGGCG
GGAAGGGCGGCAGCCTGCCCCGCAGTGCGACACCCGGGCCCCCCGGAGAGCACCTGGTGAATGGCCGGAT
GGACTTTGCCTTCCCGGGCAGCACCAACTCCCTGCACAGGATGACCACGACCAGTGCTGCTGCCTATGGC
ACCCACCTGAGCCCACACGTGCCCCACCGCGTGCTAAGCACATCCTCCACCCTCACACGGGACTACAACT
CACTGACCCGCTCAGAACACTCACACTCGACCACACTGCCCAGGGACTACTCCACCCTCACCTCCGTCTC
CTCCCACGACTCTCGCCTGACTGCTGGTGTGCCCGACACGCCCACCCGCCTGGTGTTCTCTGCCCTGGGG
CCCACATCTCTCAGAGTGAGCTGGCAGGAGCCGCGGTGCGAGCGGCCGCTGCAGGGCTACAGTGTGGAGT
```

-continued

ACCAGCTGCTGAACGGCGGTGAGCTGCATCGGCTCAACATCCCCAACCCTGCCCAGACCTCGGTGGTGGT
GGAAGACCTCCTGCCCAACCACTCCTACGTGTTCCGCGTGCGGGCCCAGAGCCAGGAAGGCTGGGGCCGA
GAGCGTGAGGGTGTCATCACCATTGAATCCCAGGTGCACCCGCAGAGCCCACTGTGTCCCCTGCCAGGCT
CCGCCTTCACTTTGAGCACTCCCAGTGCCCCAGGCCCGCTGGTGTTCACTGCCCTGAGCCCAGACTCGCT
GCAGCTGAGCTGGGAGCGGCCACGGAGGCCCAATGGGGATATCGTCGGCTACCTGGTGACCTGTGAGATG
GCCCAAGGAGGAGGGCCAGCCACCGCATTCCGGGTGGATGGAGACAGCCCCGAGAGCCGGCTGACCGTGC
CGGGCCTCAGCGAGAACGTGCCCTACAAGTTCAAGGTGCAGGCCAGGACCACTGAGGGCTTCGGGCCAGA
GCGCGAGGGCATCATCACCATAGAGTCCCAGGATGGAGGACCCTTCCCGCAGCTGGGCAGCCGTGCCGGG
CTCTTCCAGCACCCGCTGCAAAGCGAGTACAGCAGCATCACCACCACCCACACCAGCGCCACCGAGCCCT
TCCTAGTGGATGGGCTGACCCTGGGGGCCCAGCACCTGGAGGCAGGCGGCTCCCTCACCCGGCATGTGAC
CCAGGAGTTTGTGAGCCGGACACTGACCACCAGCGGAACCCTTAGCACCCACATGGACCAACAGTTCTTC
CAAACTTGA

Nucleotide sequence encoding *homo sapiens* Integrin beta4 (ITGB4) transcript variant 2 (corresponds to Uniprot id P16144-3).
>gi|54607026:9-5426 *Homo sapiens* integrin, beta 4 (ITGB4), transcript variant 2, mRNA
SEQ ID No. 2:
ATGGCAGGGCCACGCCCCAGCCCATGGGCCAGGCTGCTGCTGGCAGCCTTGATCAGCGTCAGCCTCTCTG
GGACCTTGGCAAACCGCTGCAAGAAGGCCCCAGTGAAGAGCTGCACGGAGTGTGTCCGTGTGGATAAGGA
CTGCGCCTACTGCACAGACGAGATGTTCAGGGACCGGCGCTGCAACACCCAGGCGGAGCTGCTGGCCGCG
GGCTGCCAGCGGGAGAGCATCGTGGTCATGGAGAGCAGGTTCCAAATCACAGAGGAGACCCAGATTGACA
CCACCCTGCGGCGCAGCCAGATGTCCCCCCAAGGCCTGGGGGTCCGTCTGCGGCCCGGTGAGGAGCGGCA
TTTTGAGCTGGAGGTGTTTGAGCCACTGGAGAGCCCCGTGGACCTGTACATCCTCATGGACTTCTCCAAC
TCCATGTCCGATGATCTGGACAACCTCAAGAAGATGGGGCAGAACCTGGCTCGGGTCCTGAGCCAGCTCA
CCAGCGACTACACTATTGGATTTGGCAAGTTTGTGGACAAAGTCAGCGTCCCGCAGACGGACATGAGGCC
TGAGAAGCTGAAGGAGCCCTGGCCCAACAGTGACCCCCCCTTCTCCTTCAAGAACGTCATCAGCCTGACA
GAAGATGTGGATGAGTTCCGGAATAAACTGCAGGGAGAGCGGATCTCAGGCAACCTGGATGCTCCTGAGG
GCGGCTTCGATGCCATCCTGCAGACAGCTGTGTGCACGAGGGACATTGGCTGGCGCCCGGACAGCACCCA
CCTGCTGGTCTTCTCCACCGAGTCAGCCTTCCACTATGAGGCTGATGGCGCCAACGTGCTGGCTGGCATC
ATGAGCCGCAACGATGAACGGTGCCACCTGGACACCACGGGCACCTACACCCAGTACAGGACACAGGACT
CTACTCCTATAGCTACTACGAGAAGCTTCACACCTATTTCCCTGTCTCCTCACTGGGGGTGCTGCAGGAG
GACTCGTCCAACATCGTGGAGCTGCTGGAGGAGGCCTTCAATCGGATCCGCTCCAACCTGGACATCCGGG
CCCTAGACAGCCCCCGAGGCCTTCGGACAGAGGTCACCTCCAAGATGTTCCAGAAGACGAGGACTGGGTC
CTTTCACATCCGGCGGGGGGAAGTGGGTATATACCAGGTGCAGCTGCGGGCCCTTGAGCACGTGGATGGG
ACGCACGTGTGCCAGCTGCCGGAGGACCAGAAGGGCAAGATCCATCTGAAACCTTCCTTCTCCGACGGCC
TCAAGATGGACGCGGGCATCATCTGTGATGTGTGCACCTGCGAGCTGCAAAAAGAGGTGCGGTCAGCTCG
CTGCAGCTTCAACGGAGACTTCGTGTGCGGACAGTGTGTGTGCAGCGAGGGCTGGAGTGGCCAGACCTGC
AACTGCTCCACCGGCTCTCTGAGTGACATTCAGCCCTGCCTGCGGGAGGGCGAGGACAAGCCGTGCTCCG
GCCGTGGGGAGTGCCAGTGCGGGCACTGTGTGTGCTACGGCGAAGGCCGCTACGAGGGTCAGTTCTGCGA
GTATGACAACTTCCAGTGTCCCCGCACTTCCGGGTTCCTCTGCAATGACCGAGGACGCTGCTCCATGGGC
CAGTGTGTGTGTGAGCCTGGTTGGACAGGCCCAAGCTGTGACTGTCCCCTCAGCAATGCCACCTGCATCG
ACAGCAATGGGGGCATCTGTAATGGACGTGGCCACTGTGAGTGTGGCCGCTGCCACTGCCACCAGCAGTC
GCTCTACACGGACACCATCTGCGAGATCAACTACTCGGCGATCCACCCGGGCCTCTGCGAGGACCTACGC
TCCTGCGTGCAGTGCCAGGCGTGGGGCACCGGCGAGAAGAAGGGGCGCACGTGTGAGGAATGCAACTTCA
AGGTCAAGATGGTGGACGAGCTTAAGAGAGCCGAGGAGGTGGTGGTGCGCTGCTCCTTCCGGGACGAGGA
TGACGACTGCACCTACAGCTACACCATGGAAGGTGACGGCGCCCCTGGGCCCAACAGCACTGTCCTGGTG
CACAAGAAGAAGGACTGCCCTCCGGGCTCCTTCTGGTGGCTCATCCCCCTGCTCCTCCTCCTCCTGCCGC
TCCTGGCCCTGCTACTGCTGCTATGCTGGAAGTACTGTGCCTGCTGCAAGGCCTGCCTGGCACTTCTCCC
GTGCTGCAACCGAGGTCACATGGTGGGCTTTAAGGAAGACCACTACATGCTGCGGGAGAACCTGATGGCC
TCTGACCACTTGGACACGCCCATGCTGCGCAGCGGGAACCTCAAGGGCCGTGACGTGGTCCGCTGGAAGG
TCACCAACAACATGCAGCGGCCTGGCTTTGCCACTCATGCCGCCAGCATCAACCCCACAGAGCTGGTGCC
CTACGGGCTGTCCTTGCGCCTGGCCCGCCTTTGCACCGAGAACCTGCTGAAGCCTGACACTCGGGAGTGC
GCCCAGCTGCGCCAGGAGGTGGAGGAGAACCTGAACGAGGTCTACAGGCAGATCTCCGGTGTACACAAGC
TCCAGCAGACCAAGTTCCGGCAGCAGCCCAATGCCGGGAAAAAGCAAGACCACACCATTGTGGACACAGT
GCTGATGGCGCCCCGCTCGGCCAAGCCGGCCCTGCTGAAGCTTACAGAGAAGCAGGTGGAACAGAGGGCC
TTCCACGACCTCAAGGTGGCCCCCGGCTACTACACCCTGACTGCAGACCAGGACGCCCGGGGCATGGTGG
AGTTCCAGGAGGGCGTGGAGCTGGTGGACGTACGGGTGCCCCTCTTTATCCGGCCTGAGGATGACGACGA
GAAGCAGCTGCTGGTGGAGGCCATCGACGTGCCCGCAGGCACTGCCACCCTCGGCCGCCGCCTGGTAAAC
ATCACCATCATCAAGGAGCAAGCCAGAGACGTGGTGTCCTTTGAGCAGCCTGAGTTCTCGGTCAGCCGCG
GGGACCAGGTGGCCCGCATCCCTGTCATCCGGCGTGTCCTGGACGGCGGGAAGTCCCAGGTCTCCTACCG
CACACAGGATGGCACCGCGCAGGGCAACCGGGACTACATCCCCGTGGAGGGTGAGCTGCTGTTCCAGCCT
GGGGAGGCCTGGAAAGAGCTGCAGGTGAAGCTCCTGGAGCTGCAAGAAGTTGACTCCCTCCTGCGGGGCC
GCCAGGTCCGCCGTTTCCACGTCCAGCTCAGCAACCCTAAGTTTGGGGCCCACCTGGGCCAGCCCCACTC
CACCACCATCATCATCAGGGACCCAGATGAACTGGACCGGAGCTTCACGAGTCAGATGTTGTCATCACAG
CCACCCCCTCACGGCGACCTGGGCGCCCCGCAGAACCCCAATGCTAAGGCCGCTGGGTCCAGGAAGATCC
ATTTCAACTGGCTGCCCCCTTCTGGCAAGCCAATGGGGTACAGGGTAAAGTACTGGATTCAGGGTGACTC
CGAATCCGAAGCCCACCTGCTCGACAGCAAGGTGCCCTCAGTGGAGCTCACCAACCTGTACCCGTATTGC
GACTATGAGATGAAGGTGTGCGCCTACGGGGCTCAGGGCGAGGGACCCTACAGCTCCCTGGTGTCCTGCC
GCACCCACCAGGAAGTGCCCAGCGAGCCAGGGCGTCTGGCCTTCAATGTCGTCTCCTCCACGGTGACCCA
GCTGAGCTGGGCTGAGCCGGCTGAGACCAACGGTGAGATCACAGCCTACGAGGTCTGCTATGGCCTGGTC
AACGATGACAACCGACCTATTGGGCCCATGAAGAAAGTGCTGGTTGACAACCCTAAGAACCGGATGCTGC
TTATTGAGAACCTTCGGGAGTCCCAGCCCTACCGCTACACGGTGAAGGCGCGCAACGGGGCCGGCTGGGG
GCCTGAGCGGGAGGCCATCATCAACCTGGCCACCCAGCCCAAGAGGCCCATGTCCATCCCCATCATCCCT
GACATCCCTATCGTGGACGCCCAGAGCGGGGAGGACTACGACAGCTTCCTTATGTACAGCGATGACGTTC
TACGCTCTCCATCGGGCAGCCAGAGGCCCAGCGTCTCCGATGACACTGAGCACCTGGTGAATGGCCGGAT
GGACTTTGCCTTCCCGGGCAGCACCAACTCCCTGCACAGGATGACCACGACCAGTGCTGCTGCCTATGGC
ACCCACCTGAGCCCACACGTGCCCCACCGCGTGCTAAGCACATCCTCCACCCTCACACGGGACTACAACT
CACTGACCCGCTCAGAACACTCACACTCGACCACACTGCCCAGGGACTACTCCACCCTCACCTCCGTCTC -continued CTCCCACGGCCTCCCTCCCATCTGGGAACACGGGAGGAGCAGGCTTCCGCTGTCCTGGGCCCTGGGGTCC
CGGAGTCGGGCTCAGATGAAAGGGTTCCCCCTTCCAGGGGCCCACGAGACTCTATAATCCTGGCTGGGA
GGCCAGCAGCGCCCTCCTGGGGCCCAGACTCTCGCCTGACTGCTGGTGTGCCCGACACGCCCACCCGCCT
GGTGTTCTCTGCCCTGGGGCCCACATCTCTCAGAGTGAGCTGGCAGGAGCCGCGGTGCGAGCGGCCGCTG
CAGGGCTACAGTGTGGAGTACCAGCTGCTGAACGGCGGTGAGCTGCATCGGCTCAACATCCCCAACCCTG
CCCAGACCTCGGTGGTGGTGGAAGACCTCCTGCCCAACCACTCCTACGTGTTCCGCGTGCGGGCCCAGAG
CCAGGAAGGCTGGGGCCGAGAGCGTGAGGGTGTCATCACCATTGAATCCCAGGTGCACCCGCAGAGCCCA
CTGTGTCCCCTGCCAGGCTCCGCCTTCACTTTGAGCACTCCCAGTGCCCCAGGCCCGCTGGTGTTCACTG
CCCTGAGCCCAGACTCGCTGCAGCTGAGCTGGGAGCGGCCACGGAGGCCCAATGGGGATATCGTCGGCTA
CCTGGTGACCTGTGAGATGGCCCAAGGAGGAGGGCCAGCCACCGCATTCCGGGTGGATGGAGACAGCCCC
GAGAGCCGGCTGACCGTGCCGGGCCTCAGCGAGAACGTGCCCTACAAGTTCAAGGTGCAGGCCAGGACCA
CTGAGGGCTTCGGGCCAGAGCGCGAGGGCATCATCACCATAGAGTCCCAGGATGGAGGACCCTTCCCGCA
GCTGGGCAGCCGTGCCGGGCTCTTCCAGCACCCGCTGCAAAGCGAGTACAGCAGCATCACCACCACCCAC
ACCAGCGCCACCGAGCCCTTCCTAGTGGATGGGCTGACGCTGGGGGCCCAGCACCTGGAGGCAGGCGGCT
CCCTCACCCGGCATGTGACCCAGGAGTTTGTGAGCCGGACACTGACCACCAGCGGAACCCTTAGCACCCA
CATGGACCAACAGTTCTTCCAAACTTGA Nucleotide sequence encoding *homo sapiens* Integrin beta4 (ITGB4)
transcript variant 3 (corresponds to Uniprot id P16144-2).
>gi|54607032:188-5446 *Homo sapiens* integrin, beta 4 (ITGB4),
transcript variant 3, mRNA
SEQ ID No. 3:
ATGGCAGGGCCACGCCCCAGCCCATGGGCCAGGCTGCTCCTGGCAGCCTTGATCAGCGTCAGCCTCTCTG
GGACCTTGGCAAACCGCTGCAAGAAGGCCCCAGTGAAGAGCTGCACGGAGTGTGTCCGTGTGGATAAGGA
CTGCGCCTACTGCACAGACGAGATGTTCAGGGACCGGCGCTGCAACACCCAGGCGGAGCTGCTGGCCGCG
GGCTGCCAGCGGGAGAGCATCGTGGTCATGGAGAGCAGTCTCCAAATCACAGAGGAGACCCAGATTGACA
CCACCCTGCGGCGCAGCCAGATGTCCCCCCAAGGCCTGGGGGTCCGTCTGCGGCCCGGTGAGGAGCGGCA
TTTTGAGCTGGAGGTGTTTGAGCCACTGGAGAGCCCCGTGGACCTGTACATCCTCATGGACTTCTCCAAC
TCCATGTCCGATGATCTGGACAACCTCAAGAAGATGGGGCAGAACCTGGCTCGGGTCCTGAGCCAGCTCA
CCAGCGACTACACTATTGGATTTGGCAAGTTTGTGGACAAAGTCAGCGTCCCGCAGACGGACATGAGGCC
TGAGAAGCTGAAGGAGCCCTGGCCCAACAGTGACCCCCCCTTCTCCTTCAAGAACGTCATCAGCCTGACA
GAAGATGTGGATGAGTTCCGGAATAAACTGCAGGGAGAGCGGATCTCAGGCAACCTGGATGCTCCTGAGG
GCGGCTTCGATGCCATCCTGCAGACAGCTGTGTGCACGAGGGACATTGGCTGGCGCCCGGACAGCACCCA
CCTGCTGGTCTTCTCCACCGAGTCAGCCTTCCACTATGAGGCTGATGGCGCCAACGTGCTGGCTGGCATC
ATGAGCCGCAACGATGAACGGTGCCACCTGGACACCACGGGCACCTACACCCAGTACAGGACACAGGACT
ACCCGTCGGTGCCCACCCTGGTGCGCCTGCTCGCCAAGCACAACATCATCCCCATCTTTGCTGTCACCAA
CTACTCCTATAGCTACTACGAGAAGCTTCACACCTATTTCCCTGTCTCCTCACTGGGGGTGCTGCAGGAG
GACTCGTCCAACATCGTGGAGCTGCTGGAGGAGGCCTTCAATCGGATCCGCTCCAACCTGGACATCCGGG
CCCTAGACAGCCCCCGAGGCCTTCGGACAGAGGTCACCTCCAAGATGTTCCAGAAGACGAGGACTGGGTC
CTTTCACATCCGGCGGGGGGAAGTGGGTATATACCAGGTGCAGCTGCGGGCCCTTGAGCACGTGGATGGG
ACGCACGTGTGCCAGCTGCCGGAGGACCAGAAGGGCAAGATCCATCTGAAACCTTCCTTCTCCGACGGCC
TCAAGATGGACGCGGGCATCATCTGTGATGTGTGCACCTGCGAGCTGCAAAAAGAGGTGCGGTCAGCTCG
CTGCAGCTTCAACGGAGACTTCGTGTGCGGACAGTGTGTGTGCAGCGAGGGCTGCAGTGGCCAGACCTGC
AACTGCTCCACCGGCTCTCTGAGTGACATTCAGCCCTGCCTGCGGGAGGGCGAGGACAAGCCGTGCTCCG
GCCGTGGGGAGTGCCAGTGCGGGCACTGTGTGTGCTACGGCGAAGGCCGCTACGAGGGTCAGTTCTGCGA
GTATGACAACTTCCAGTGTCCCCGCACTTCCGGGTTCCTCTGCAATGACCGAGGACGCTGCTCCATGGGC
CAGTGTGTGTGTGAGCCTGGTTGGACAGGCCCAAGCTGTGACTGTCCCCTCAGCAATGCCACCTGCATCG
ACAGCAATGGGGGCATCTGTAATGGACGTGGCCACTGTGAGTGTGGCCGCTGCCACTGCCACCAGCAGTC
GCTCTACACGGACACCATCTGCGAGATCAACTACTCGGCGATCCACCCGGGCCTCTGCGAGGACCTACGC
TCCTGCGTGCAGTGCCAGGCGTGGGGCACCGGCGAGAAGAAGGGGCGCACGTGTGAGGAATGCAACTTCA
AGGTCAAGATGGTGGACGAGCTTAAGAGAGCCGAGGAGGTGGTGGTGCGCTGCTCCTTCCGGGACGAGGA
TGACGACTGCACCTACAGCTACACCATGGAAGGTGACGGCGCCCCTGGGCCCAACAGCACTGTCCTGGTG
CACAAGAAGAAGGACTGCCCTCCGGGCTCCTTCTGGTGGCTCATCCCCCTGCTCCTCCTCCTGCCGC
TCCTGGCCCTGCTACTGCTGCTATGCTGGAAGTACTGTGCCTGCTGCAAGGCCTGCCTGGCACTTCTCCC
GTGCTGCAACCGAGGTCACATGGTGGGCTTTAAGGAAGACCACTACATGCTGCGGGAGAACCTGATGGCC
TCTGACCACTTGGACACGCCCATGCTGCGCAGCGGGAACCTCAAGGGCCGTGACGTGGTCCGCTGGAAGG
TCACCAACAACATGCAGCGGCCTGGCTTTGCCACTCATGCCGCCAGCATCAACCCCACAGAGCTGGTGCC
CTACGGGCTGTCCTTGCGCCTGGCCCGCCTTTGCACCGAGAACCTGCTGAAGCCTGACACTCGGGAGTGC
GCCCAGCTGCGCCAGGAGGTGGAGGAGAACCTGAACGAGGTCTACAGGCAGATCTCCGGTGTACACAAGC
TCCAGCAGACCAAGTTCCGGCAGCAGCCCAATGCCGGGAAAAAGCAAGACCACACCATTGTGGACACAGT
GCTGATGGCGCCCCGCTCGGCCAAGCCGGCCCTGCTGAAGCTTACAGAGAAGCAGGTGGAACAGAGGGCC
TTCCACGACCTCAAGGTGGCCCCCGGCTACTACACCCTCACTGCAGACCAGGACGCCCGGGGCATGGTGG
AGTTCCAGGAGGGCGTGGAGCTGGTGGACGTACGGGTGCCCCTCTTTATCCGGCCTGAGGATGACGACGA
GAAGCAGCTGCTGGTGGAGGCCATCGACGTGCCCGCAGGCACTGCCACCCTCGGCCGCCGCCTGGTAAAC
ATCACCATCATCAAGGAGCAAGCCAGAGACGTGGTGTCCTTTGAGCAGCCTGAGTTCTCGGTCAGCCGCG
GGGACCAGGTGGCCCGCATCCCTGTCATCCGGCGTGTCCTGGACGGCGGGAAGTCCCAGGTCTCCTACCG
CACACAGGATGGCACCGCGCAGGGCAACCGGGACTACATCCCCGTGGAGGGTGAGCTGCTGTTCCAGCCT
GGGGAGGCCTGGAAAGAGCTGCAGGTGAAGCTCCTGGAGCTGCAAGAAGTTGACTCCCTCCTGCGGGGCC
GCCAGGTCCGCCGTTTCCACGTCCAGCTCAGCAACCCTAAGTTTGGGGCCCACCTGGGCCAGCCCCACTC
CACCACCATCATCATCAGGGACCCAGATGAACTGGACCGGAGCTTCACGAGTCAGATGTTGTCATCACAG
CCACCCCCTCACGGCGACCTGGGCGCCCCGCAGAACCCCAATGCTAAGGCCGCTGGGTCCAGGAAGATCC
ATTTCAACTGGCTGCCCCCTTCTGGCAAGCCAATGGGGTACAGGGTAAAGTACTGGATTCAGGGTGACTC
CGAATCCGAAGCCCACCTGCTCGACAGCAAGGTGCCCTCAGTGGAGCTCACCAACCTGTACCCGTATTGC
GACTATGAGATGAAGGTGTGCGCCTACGGGGCTCAGGGCGAGGGACCCTACAGCTCCCTGGTGTCCTGCC
GCACCCACCAGGAAGTGCCCAGCGAGCCAGGGCGTCTGGCCTTCAATGTCGTCTCCTCCACGGTGACCCA
GCTGAGCTGGGCTGAGCCGGCTGAGACCAACGGTGAGATCACAGCCTACGAGGTCTGCTATGGCCTGGTC
AACGATGACAACCGACCTATTGGGCCCATGAAGAAAGTGCTGGTTGACAACCCTAAGAACCGGATGCTGC
TTATTGAGAACCTTCGGGAGTCCCAGCCCTACCGCTACACGGTGAAGGCGCGCAACGGGGCCGGCTGGGG
GCCTGAGCGGGAGGCCATCATCAACCTGGCCACCCAGCCCAAGAGGCCCATGTCCATCCCCATCATCCCT -continued GACATCCCTATCGTGGACGCCCAGAGCGGGGAGGACTACGACAGCTTCCTTATGTACAGCGATGACGTTC
TACGCTCTCCATCGGGCAGCCAGAGGCCCAGCGTCTCCGATGACACTGAGCACCTGGTGAATGGCCGGAT
GGACTTTGCCTTCCCGGGCAGCACCAACTCCCTGCACAGGATGACCACGACCAGTGCTGCTGCCTATGGC
ACCCACCTGAGCCCACACGTGCCCCACCGCGTGCTAAGCACATCCTCCACCCTCACACGGGACTACAACT
CACTGACCCGCTCAGAACACTCACACTCGACCACACTGCCCAGGGACTACTCCACCCTCACCTCCGTCTC
CTCCCACGACTCTCGCCTGACTGCTGGTGTGCCCGACACGCCCACCCGCCTGGTGTTCTCTGCCCTGGGG
CCCACATCTCTCAGAGTGAGCTGGCAGGAGCCGCGGTGCGAGCGGCCGCTGCAGGGCTACAGTGTGGAGT
ACCAGCTGCTGAACGGCGGTGAGCTGCATCGGCTCAACATCCCCAACCCTGCCCAGACCTCGGTGGTGGT
GGAAGACCTCCTGCCCAACCACTCCTACGTGTTCCGCGTGCGGGCCCAGAGCCAGGAAGGCTGGGGCCGA
GAGCGTGAGGGTGTCATCACCATTGAATCCCAGGTGCACCCGCAGAGCCCACTGTGTCCCCTGCCAGGCT
CCGCCTTCACTTTGAGCACTCCCAGTGCCCCAGGCCCGCTGGTGTTCACTGCCCTGAGCCCAGACTCGCT
GCAGCTGAGCTGGGAGCGGCCACGGAGGCCCAATGGGGATATCGTCGGCTACCTGGTGACCTGTGAGATG
GCCCAAGGAGGAGGGCCAGCCACCGCATTCCGGCTGGATGGAGACAGCCCCGAGAGCCGGCTGACCGTGC
CGGGCCTCAGCGAGAACGTGCCCTACAAGTTCAAGGTGCAGGCCAGGACCACTGAGGGCTTCGGGCCAGA
GCGCGAGGGCATCATCACCATAGAGTCCCAGGATGGAGGACCCTTCCCGCAGCTGGGCAGCCGTGCCGGG
CTCTTCCAGCACCCGCTGCAAAGCGAGTACAGCAGCATCACCACCACCCACACCAGCGCCACCGAGCCCT
TCCTAGTGGATGGGCTGACCCTGGGGGCCCAGCACCTGGAGGCAGGCGGCTCCCTCACCCGGCATGTGAC
CCAGGAGTTTGTGAGCCGGACACTGACCACCAGCGGAACCCTTAGCACCCACATGGACCAACAGTTCTTC
CAAACTTGA Nucleotide sequence encoding *homo sapiens* Brain-specific angiogenesis inhibitor 1-associated protein 2 (BAIAP2) transcript variant 3 (corresponds to Uniprot id Q9UQB8-5).
>gi|222080098:109-1671 *Homo sapiens* BAI1-associated protein 2 (BAIAP2), transcript variant 3, mRNA
SEQ ID No. 4:
ATGTCTCTGTCTCGCTCAGAGGAGATGCACCGGCTCACGGAAAATGTCTATAAGACCATCATGGAGCAGT
TCAACCCTAGCCTCCGGAACTTCATCGCCATGGGGAAGAATTACGAGAAGGCACTGGCAGGTGTGACGTA
TGCAGCCAAAGGCTACTTTGACGCCCTGGTGAAGATGGGGGAGCTGGCCAGCGAGAGCCAGGGCTCCAAA
GAACTCGGAGACGTTCTCTTCCAGATGGCTGAAGTCCACAGGCAGATCCAGAATCAGCTGGAAGAAATGC
TGAAGTCTTTTCACAACGAGCTGCTTACGCAGCTGGAGCAGAAGGTGGAGCTGGACTCCAGGTATCTGAG
TGCTGCGCTGAAGAAATACCAGACTGAGCAAAGGAGCAAAGGCGACGCCCTGGACAAGTGTCAGGCTGAG
CTGAAGAAGCTTCGGAAGAAGAGCCAGGGCAGCAAGAATCCTCAGAAGTACTCGGACAAGGAGCTGCAGT
ACATCGACGCCATCAGCAACAAGCAGGGCGAGCTGGAGAATTACGTGTCCGACGGCTACAAGACCGCACT
GACAGAGGAGCGCAGGCGCTTCTGCTTCCTGGTGGAGAAGCAGTGCGCCGTGGCCAAGAACTCCGCGGCC
TACCACTCCAAGGGCAAGGAGCTGCTGGCGCAGAAGCTGCCGCTGTGGCAACAGGCCTGTGCCGACCCCA
GCAAGATCCCGGAGCGCGCGGTGCAGCTCATGCAGCAGGTGGCCAGCAACGGCGCCACCCTCCCCAGCGC
CCTGTCGGCCTCCAAGTCCAACCTGGTCATTTCCGACCCCATTCCGGGGGCCAAGCCCCTGCCGGTGCCC
CCCGAGCTGGCACCGTTCGTGGGGCGGATGTCTGCCCAGGAGAGCACACCCATCATGAACGGCGTCACAG
GCCCGGATGGCGAGGACTACAGCCCGTGGGCTGACCGCAAGGCTGCCCAGCCCAAATCCCTGTCTCCTCC
GCAGTCTCAGAGCAAGCTCAGCGACTCCTACTCCAACACACTCCCCGTGCGCAAGAGCGTGACCCCAAAA
AACAGCTATGCCACCACCGAGAACAAGACTCTGCCTCGCTCGAGCTCCATGGCAGCCGGCCTGGAGCGCA
ATGGCCGTATGCGGGTGAAGGCCATCTTCTCCCACGCTGCTGGGGACAACAGCACCCTCCTGAGCTTCAA
GGAGGGTGACCTCATTACCCTGCTGGTGCCTGAGGCCCGCGATGGCTGGCACTACGGAGAGAGTGAGAAG
ACCAAGATGCGGGGCTGGTTTCCCTTCTCCTACACCCGGGTCTTGGACAGCGATGGCAGTGACAGGCTGC
ACATGAGCCTGCAGCAAGGGAAGAGCAGCAGCACGGGCAACCTCCTGGACAAGGACGACCTGGCCATCCC
ACCCCCCGATTACGGCGCCGCCTCCCGGGCCTTCCCCGCCCAGACGGCCAGCGGCTTCAAGCAGAGGCCC
TACAGTGTGGCCGTGCCCGCCTTCTCCCAGGGCCTGGATGACTATGGAGCGCGGTCCATGAGCAGCGCCG
ATGTGGAAGTGGCCAGATTCTGA Amino acid sequence of *homo sapiens* Integrin beta4 (ITGB4) isoform 4C; the phosphorylation sites S1069, T1455, S1457 and S1518 are indicated in bold letters.
>sp|P16144 ITB4_HUMAN Integrin beta-4 OS = *Homo sapiens* GN = ITGB4 PE = 1 SV = 5
SEQ ID No. 5:

```
        10         20         30         40         50         60
MAGPRPSPWA RLLLAALISV SLSGTLANRC KKAPVKSCTE CVRVDKDCAY CTDEMFRDRR
        70         80         90        100        110        120
CNTQAELLAA GCQRESIVVM ESSFQITEET QIDTTLRRSQ MSPQGLRVRL RPGEERHFEL
       130        140        150        160        170        180
EVFEPLESPV DLYILMDFSN SMSDDLDNLK KHGQNLARVL SQLTSDYTIG FGKFVDKVSV
       190        200        210        220        230        240
PQTDMRPEKL KEPWPNSDPP FSFKNVISLT EDVDEFRNKL QGERISGNLD APEGGFDAIL
       250        260        270        280        290        300
QTAVCTRDIG WRPDSTHLLV FSTESAFHYE ADGANVLAGI MSRNDERCHL DTTGTYTQYR
       310        320        330        340        350        360
TQDYPSVPTL VRLLAKKNII PIFAVTNYSY SYYEKLHTYF PVSSLGVLQE DSSNIVELLE
       370        380        390        400        410        420
EAFNRIRSNL DIRALDSPRG LRTEVTSKMF QKTRTGSFHI RRGEVGIYQV QLRALEHVDG
       430        440        450        460        470        480
THVCQLPEDQ KGNIKLKPSF SDGLKMDAGI ICDVCTCELQ KEVRSARCSF NGDFVCGQCV
       490        500        510        520        530        540
CSEGWSGQTC NCSTGSLSDI QPCLREGEDK PCSGRGECQC GHCVCYGEGR YEGQFCEYDN
       550        560        570        580        590        600
FQCPRTSGFL CNDRGRCSMG QCVCEPGWTG PSCDCPLSNA TCIDSNGGIC NGRGHCECGR
       610        620        630        640        650        660
CHCHQQSLYT DTICEINYSA IHPGLCEDLR SCVQCQAWGT GEKKGRTCEE CNFKVKMVDE
       670        680        690        700        710        720
```

-continued

LKRAEEVVVR CSFRDEDDDC TYSYTMEGDG APGPNSTVLV HKKKDCPPGS FWWLIPLLLL
730 740 750 760 770 780
LLPLLALLLL LCWKYCACCK ACLALLPCCN RGHMVGFKED HYMLRENLMA SDHLDTPMLR
790 800 810 820 830 840
SGNLKGRDVV RWKVTNNMQR PGFATHAASI NPTELVPYGL SLRLARLCTE NLLKPDTREC
850 660 870 8B0 890 900
AQLRQEVEEN LNEVYRQISG VHKLQQTKFR QQPNAGKKQD HTIVDTVLMA PRSAKPALLK
910 920 930 940 950 960
LTEKQVEQRA FHDLKVAPGY YTLTADQDAR GMVEFQEGVE LVDVRVPLFI RPEDDDEKQL
970 980 990 1000 1010 1020
LVEAIDVPAG TATLGRRLVN ITIIKEQARD VVSFEQPEFS VSRGDQVARI PVIRRVLDGG
1030 1040 1050 1060 1070 1080
KSQVSYRTQD GTAQGNRDYI PVEGELLFQP GEAWKELQVK LLELQEVDSL LRGRQVRRFH
1090 1100 1110 1120 1130 1140
VQLSNPKFGA HLGQPHSTTI IIRDPDELDR SFTSQMLSSQ PFPHGDLGAP QNPNAKAAGS
1150 1160 1170 1160 1190 1200
RKIHFNWLPP SGKPMGYRVK YWIQGDSESE AHLLDSKVPS VELTNLYPYC DYEMKVCAYG
1210 1220 1230 1240 1250 1260
AQGEGPYSSL VSCRTHQEVP SEPGRLAFNV VSSTVTQLSW AEPAETNGEI TAYEVCYGLV
1270 1280 1290 1300 1310 1320
NDDNRPIGPM KKVLVDNPKN RMLLIENLRE SQPYRYTVKA RNGAGWGPER EAIINLATQP
1330 1340 1350 1360 1370 1380
KRPMSIPIIP DIPIVDAQSG EDYDSFLMYS DDVLRSPSGS QRPSVSDDTG CGWKFEPLLG
1390 1400 1410 1420 1430 1440
EELDLRRVTW RLPPELIPRL SASSGRSSDA EAPHGPPDDG GAGGKGGSLP RSATPGPPGE
1450 1460 1470 1480 1490 1500
HLVNGRMDFA FPGSTNSLHR MTTTSAAAYG THLSPHVPHR VLSTSSTLTR DYNSLTPSEH
1510 1520 1530 1540 1550 1560
SHSTTLPRDY STLTSVSSHD SRLTAGVPDT PTRLVFSALG PTSLRVSWQE PRCERPLQGY
1570 1580 1590 1600 1610 1620
SVEYQLLNGG ELHRLNIPNP AQTSVVVEDL LPNHSYVFRV RAQSQEGWGR EREGVITIES
1630 1640 1650 1660 1670 1680
QVHPQSPLCP LPGSAFTLST PSAPGPLVFT ALSPDSLQLS WERPRRPNGD IVGYLVTCEM
1690 1700 1710 1720 1730 1740
AQGGGPATAF RVDGDSPESR LTVPGLSENV PYKFKVQART TEGFGPEREG IITIESQDGG
1750 1760 1770 1780 1790 1800
PFPQLGSRAG LFQHPLQSEY SSITTTHTSA TEPFLVDGLT LGAQHLEAGG SLTRHVTQEF
1810 1820
VSRTLTTSGT LSTHMDQQFF QT

Amino acid sequence of *homo sapiens* Integrin beta4 (ITGB4) isoform 4A; the phosphorylation sites S1069, T1385, S1387 and S1448 are indicated in bold letters.
>sp|P16144-2|ITB4_HUMAN Isoform Beta-4A of Integrin beta-4 OS = *Homo sapiens* GN = ITGB4
SEQ ID No. 6:
10 20 30 40 50 60
MAGPRPSPWA RLLLAALISV SLSGTLANRC KKAPVKSCTE CVRVDKDCAY CTDEMFRDRR
70 80 90 100 110 120
CNTQAELLAA GCQRESIVVM ESSFQITEET QIDTTLRRSQ MSPQGLRVRL RPGEERHFEL
130 140 150 160 170 180
EVFEPLESPV DLYILMDFSN SMSDDLDNLK KMGQNLARVL SQLTSDYTIG FGKFVDKVSV
190 200 210 220 230 240
PQTDMRPEKL KEPWPNSDPP FSFKNVISLT EDVDEFRNKL QGERISGNLD APEGGFDAIL
250 260 270 260 290 300
QTAVCTRDIG WRPDSTHLLV FSTESAFHYE ADGANVLAGI MSRNDERCHL DTTGTYTQYR
310 320 330 340 350 360
TQDYPSVPTL VRLLAKHNII PIFAVTNYSY SYYEKLHTYF PVSSLGVLQE DSSNIVELLE
370 380 390 400 410 420
EAFNRIRSNL DIRALDSPRG LRTEVTSKMF QKTRTGSFHI RRGEVGIYQV QLRALEHVDG
430 440 450 460 470 480
THVCQLPEDQ KGNIHLKPSF SDGLKMDAGI ICDVCTCELQ KEVRSARCSF NGDFVCGQCV
490 500 510 520 530 540
CSEGWSGQTC NCSTGSLSDI QPCLREGEDK PCSGRGECQC GHCVCYGEGR YEGQFCEYDN
550 560 570 580 590 600
FQCPRTSGFL CNDRGRCSMG QCVCEPGWTG PSCDCPLSNA TCIDSNGGIC NGRGHCECGR
610 620 630 640 650 660
CKCHQQSLYT DTICEINYSA IHPGLCEDLR SCVQCQAWGT GEKKGRTCEE CNFKVKMVDE
670 680 690 700 710 720
LKRAEEVVVR CSFRDEDDDC TYSYTMEGDG APGPNSTVLV HKKKDCPPGS FWWLIPLLLL
730 740 750 760 770 780
LLPLLALLLL LCWKYCACCK ACLALLPCCN RGHMVGFKED HYKLRENLMA SDHLDTPMLR
790 800 610 820 830 840
SGNLKGRDVV RWKVTNNMQR PGFATHAASI NPTELVPYGL SLRLARLCTE NLLKPDTREC
850 860 870 880 890 900
AQLRQEVEEN LNEVYRQISG VHKLQQTKFR QQPNAGKKQD HTIVDTVLMA PRSAKPALLK
910 S20 930 940 950 960

-continued

```
LTEKQVEQRA FHDLKVAPGY YTLTADQDAR GMVEFQEGVE LVDVRVPLFI RPEDDDEKQL
       970        980        990       1000       1010       1020
LVEAIDVPAG TATLGRRLVN ITIIKEQARD VVSFEQPEFS VSRGDQVARI PVIRRVLDGG
      1030       1040       1050       1060       1070       1080
KSQVSYRTQD GTAQGNRDYI PVEGELLFQP GEAWKELQVK LLELQEVDSL LRGRQVRRFH
      1090       1100       1110       1120       1130       1140
VQLSNPKFGA HLGQPHSTTI IIRDPDELDR SFTSQMLSSQ PPPHGDLGAP QNPNAKAAGS
      1150       1160       1170       1180       1190       1200
RKIHFNWLPP SGKPMGYRVK YWIQGDSESE AHLLDSKVPS VELTNLYPYC DYEMKVCAYG
      1210       1220       1230       1240       1250       1260
AQGEGPYSSL VSCRTHQEVP SEPGRLAFNV VSSTVTQLSW AEPAETNGEI TAYEVCYGLV
      1270       1260       1290       1300       1310       1320
NDDNRPIGPM KKVLVDNPKN RMLLIENLRE SQPYRYTVKA RNGAGWGPER EAIINLATQP
      1330       1340       1350       1360       1370       1380
KRPMSIPIIP DIPIVDAQSG EDYDSFLMYS DDVLRSPSGS QRPSVSDDTE HLVNGRMDFA
      1390       1400       1410       1420       1430       1440
FPGSTNSLHR MTTTSAAAYG THLSPHVPKR VLSTSSTLTR DYNSLTRSEH SHSTTLPRDY
      1450       1460       1470       1480       1490       1500
STLTSVSSHD SRLTAGVPDT PTRLVFSALG PTSLRVSWQE PRCERPLQGY SVEYQLLNGG
      1510       1520       1530       1540       1550       1560
ELHRLNIPNP AQTSVVVEDL LPNHSYVFRV RAQSQEGWGR EREGVITIES QVHPQSPLCP
      1570       1580       1590       1600       1610       1620
LPGSAFTLST PSAPGPLVFT ALSPDSLQLS WERPRRPNGD IVGYLVTCEM AQGGGPATAF
      1630       1640       1650       1660       1670       1680
RVDGDSPESR LTVPGLSENV PYKFKVQART TEGFGPEREG IITIESQDGG PFPQLGSRAG
      1690       1700       1710       1720       1730       1740
LFQHPLQSEY SSITTTHTSA TEPFLVDGLT LGAQHLEAGG SLTRHVTQEF VSRTLTTSGT
      1750
LSTHMDQQFF QT
```

Amino acid sequence of *homo sapiens* Integrin beta4 (ITGB4) isoform 4B; the phosphorylation sites S1069, T1385 and S1387 are indicated in bold letters.

>sp|P16144-3|ITB4_HUMAN Isoform Beta-4B of Integrin beta-4 OS = *Homo sapiens* GN = ITGB4

SEQ ID No. 7:

```
        10         20         30         40         50         60
MAGPRPSPWA RLLLAALISV SLSGTLANRC KKAPVKSCTE CVRVDKDCAY CTDEMFRDRR
        70         80         90        100        110        120
CNTQAELLAA GCQRESIVVM ESSFQITEET QIDTTLRRSQ MSPQGLRVRL RPGEERHFEL
       130        140        150        160        170        180
EVFEPLESPV DLYILMDFSN SMSDDLDNLK KMGQNLARVL SQLTSDYTIG FGKFVDKVSV
       190        200        210        220        230        240
PQTDMRPEKL KEPWPNSDPP FSFKNVISLT EDVDEFRNKL QGERISGNLD APEGGFDAIL
       250        260        270        280        290        300
QTAVCTRDIG WRPDSTHLLV FSTESAFHYE ADGANVLAGI MSRHDERCHL DTTGTYTQYR
       310        320        330        340        350        360
TQDYPSVPTL VRLLAKHNII PIFAVTNYSY SYYEKLHTYF PVSSLGVLQE DSSNIVELLE
       370        380        390        400        410        420
EAFNRIRSNL DIRALDSPRG LRTEVTSKMF QKTRTGSFHI RRGEVGIYQV QLRALEHVDG
       430        440        450        460        470        480
THVCQLPEDQ KGNIHLKPSF SDGLKMDAGI ICDVCTCELQ KEVRSARCSF NGDFVCGQCV
       490        500        510        520        530        540
CSEGWSGQTC NCSTGSLSDI QPCLREGEDK PCSGRGECQC GHCVCYGEGR YEGQFCEYDN
       550        560        570        580        590        600
FQCPRTSGFL CNDRGRCSMG QCVCEPGWTG PSCDCPLSNA TCIDSNGGIC NGRGHCECGR
       610        620        630        640        650        660
CHCHQQSLYT DTICEINYSA IHPGLCEDLR SCVQCQAWGT GEKKGRTCEE CNFKVKMVDE
       670        680        690        700        710        720
LKRAEEVVVR CSFRDEDDDC TYSYTMEGDG APGPNSTVLV HKKKDCPPGS FWWLIPLLLL
       730        740        750        760        770        780
LLPLLALLLL LCWKYCACCK ACLALLPCCN RGHMVGFKED HYMLRENLMA SDHLDTPMLR
       790        800        810        820        830        840
SGNLKGRDVV RWKVTNNMQR PGFATHAASI NPTELVPYGL SLRLARLCTE NLLKPDTREC
       850        860        870        880        890        900
AQLRQEVEEN LNEVYRQISG VHKLQQTKFR QQPNAGKKQD HTIVDTVLMA PRSAKPALLK
       910        920        930        940        950        960
LTEKQVEQRA FHDLKVAPGY YTLTADQDAR GMVEFQEGVE LVDVRVPLFI RPEDDDEKQL
       970        980        990       1000       1010       1020
LVEAIDVPAG TATLGRRLVN ITIIKEQARD VVSFEQPEFS VSRGDQVARI PVIRRVLDGG
      1030       1040       1050       1060       1070       1060
KSQVSYRTQD GTAQGNRDYI PVEGELLFQP GEAWKELQVK LLELQEVDSL LRGRQVRRFH
      1090       1100       1110       1120       1130       1140
VQLSNPKFGA HLGQPHSTTI IIRDPDELDR SFTSQMLSSQ PPPHGDLGAP QNPNAKAAGS
      1150       1160       1170       1180       1190       1200
RKIHFNWLPP SGKPMGYRVK YWIQGDSESE AHLLDSKVPS VELTNLYPYC DYEMKVCAYG
      1210       1220       1230       1240       1250       1260
```

-continued

AQGEGPYSSL VSCRTHQEVP SEPGRLAFNV VSSTVTQLSW AEPAETNGEI TAYEVCYGLV
1270 1280 1290 1300 1310 1320
NDDNRPIGPM KKVLVDNPKN RMLLIENLRE SQPYRYTVKA RNGAGWGPER EAIINLATQP
1330 1340 1350 1360 1370 1380
KRPMSIPIIP DIPIVDAQSG EDYDSFLMYS DDVLRSPSGS QRPSVSDDTE HLVNGRMDFA
1390 1400 1410 1420 1430 1440
FPGSTNSLHR KTTTSAAAYG THLSPHVPHR VLSTSSTLTR DYNSLTRSEH SHSTTLPRDY
1450 1460 1470 1480 1490 1500
STLTSVSSHG LPPIWEHGRS RLPLSWALGS RSRAQMKGFP PSRGPRDSII LAGRPAAPSW
1510 1520 1530 1540 1550 1560
GPDSRLTAGV PDTPTRLVFS ALGPTSLRVS WQEPRCERPL QGYSVEYQLL NGGELHRLNI
1570 1580 1590 1600 1610 1620
PNPAQTSVVV EDLLPNHSYV FRVRAQSQEG WGREREGVIT IESQVHPQSP LCPLPGSAFT
1630 1640 1650 1660 1670 1680
LSTPSAPGPL VFTALSPDSL QLSWERPRRP NGDIVGYLVT CEMAQGGGPA TAFRVDGDSP
1690 1700 1710 1720 1730 1740
ESRLTVPGLS ENVPYKFKVQ ARTTEGFGPE REGIITIESQ DGGPFPQLGS RAGLFQHPLQ
1750 1760 1770 1780 1790 1800
SEYSSITTTH TSATEPFLVD GLTLGAQHLE AGGSLTRHVT QEFVSRTLTT SGTLSTHMDQ

QFFQT

Amino acid sequence of *homo sapiens* Integrin beta4 (ITGB4) isoform 4D; the phosphorylation sites S1069, T1385, S1387 and S1448 are indicated in bold letters.

>sp|P16I44-4|ITB4_HUMAN Isoform Beta-4D of Integrin beta-4 OS = *Homo sapiens* GN = ITGB4

SEQ ID No. 8:

10 20 30 40 50 60
MAGPRPSPWA RLLLAALISV SLSGTLANRC KKAPVKSCTE CVRVDKDCAY CTDEMFRDRR
70 80 90 100 110 120
CNTQAELLAA GCQRESIVVM ESSFQITEET QIDTTLRRSQ MSPQGLRVRL RPGEERHFEL
130 140 150 160 170 180
EVFEPLESPV DLYILMDFSN SMSDDLDNLK KMGQNLARVL SQLTSDYTIG FGKFVDKVSV
190 200 210 220 230 240
PQTDMRPEKL KEPWPNSDPP FSFKNVISLT EDVDEFRNKL QGERISGNLD APEGGFDAIL
250 260 270 280 290 300
QTAVCTRDIG WRPDSTHLLV FSTESAFHYE ADGANVLAGI MSRNDERCHL DTTGTYTQYR
310 320 330 340 350 360
TQDYPSVPTL VRLLAKKNII PIFAVTNYSY SYYEKLHTYF PVSSLGVLQE DSSNIVELLE
370 380 390 400 410 420
EAFNRIRSNL DIRALDSPRG LRTEVTSKMF QKTRTGSFHI RRGEVGIYQV QLRALEHVDG
430 440 450 460 470 480
THVCQLPEDQ KGNIHLKPSF SDSLKMDAGI ICDVCTCELQ KEVRSARCSF NGDFVCGQCV
490 500 510 520 530 540
CSEGWSGQTC NCSTGSLSDI QPCLREGEDK PCSGRGECQC GHCVCYGEGR YEGQFCEYDN
550 560 570 580 590 600
FQCPRTSGFL CNDRGRCSMG QCVCEPGWTG PSCDCPLSNA TCIDSNGGIC NGRGHCECGR
610 620 630 640 650 660
CHCHQQSLYT DTICEINYSA IHPGLCEDLR SCVQCQAWGT GEKKGRTCEE CNFKVKMVDE
670 680 690 700 710 720
LKRAEEVVVR CSFRDEDDDC TYSYTMEGDG APGPNSTVLV HKKKDCPPGS FWWLIPLLLL
730 740 750 760 770 780
LLPLLALLLL LCWKYCACCK ACLALLPCCN RGHMVGFKED HYMLRENLMA SDHLDTPMLR
790 800 810 820 830 840
SGNLKGRDVV RWKVTNNMQR PGFATHAASI NPTELVPYGL SLRLARLCTE NLLKPDTREC
850 860 870 880 890 900
AQLRQEVEEN LNEVYRQISG VHKLQQTKFR QQPNAGKKQD HTIVDTVLMA PRSAKPALLK
910 920 930 940 950 960
LTEKQVEQRA FHDLKVAPGY YTLTADQDAR GMVEFQEGVE LVDVRVPLFI RPEDDDEKQL
970 980 990 1000 1010 1020
LVEAIDVPAG TATLGRRLVN ITIIKEQARD VVSFEQPEFS VSRGDQVARI PVIRRVLDGG
1030 1040 1050 1060 1070 1080
KSQVSYRTQD GTAQGNRDYI PVEGELLFQP GEAWKELQVK LLELQEVDSL LRGRQVRRFH
1090 1100 1110 1120 1130 1140
VQLSNPKFGA HLGQPHSTTI IIRDPDELDR SFTSQMLSSQ PPPHGDLGAP QNPNAKAAGS
1150 1160 1170 1180 1190 1200
RKIHFNWLPP SGKPMGYRVK YWIQGDSESE AHLLDSKVPS VELTNLYPYC DYEMKVCAYG
1210 1220 1230 1240 1250 1260
AQGEGPYSSL VSCRTHQEVP SEPGRLAFNV VSSTVTQLSW AEPAETNGEI TAYEVCYGLV
1270 1280 1290 1300 1310 1320
NDDNRPIGPM KKVLVDNPKN RMLLIENLRE SQPYRYTVKA RNGAGWGPER EAIINLATQP
1330 1340 1350 1360 1370 1380

-continued

```
KRPMSIPIIP DIPIVDAQSG EDYDSFLMYS DDVLRSPSGS QRPSVSDDTE HLVNGRMDFA
      1390       1400       1410       1420       1430       1440
FPGSTNSLHR MTTTSAAAYG THLSPHVPHR VLSTSSTLTR DYNSLTRSEH SHSTTLPRDY
      1450       1460       1470       1480       1490       1500
STLTSVSSHD SRLTAGVPDT PTRLVFSALG PTSLRVSWQE PRCERFLQGY SVEYQLLNGG
      1510       1520       1530       1540       1550       1560
ELHRLNIPNP AQTSVVVEDL LPNHSYVFRV RAQSQEGWGR EREGVITIES QVHPQSPLCP
      1570       1580       1590       1600       1610       1620
LPGSAFTLST PSAPGPLVFT ALSPDSLQLS WERPRRPNGD IVGYLVTWPA TAFRVDGDSP
      1630       1640       1650       1660       1670       1680
ESRLTVPGLS ENVPYKFKVQ ARTTEGFGPE REGIITIESQ DGGPFPQLGS RAGLFQHPLQ
      1690       1700       1710       1720       1730       1740
SEYSSITTTH TSATEPFLVD GLTLGAQHLE AGGSLTRHVT QEFVSRTLTT SGTLSTHMDQ

QFFQT
```

Amino acid sequence of *homo sapiens* Brain-specific angiogenesis inhibitor 1-associated protein 2 (BAIAP2) isoform 5; the phosphorylation site S509 is indicated in bold letters.
>sp|Q9UQB8-5|BAIP2_HUMAN Isoform 5 of Brain-specific angiogenesis inhibitor 1-associated protein 2 OS = *Homo sapiens* GN = BAIAP2
SEQ ID No. 9:

```
        10         20         30         40         50         60
MSLSRSEEMH RLTENVYKTI MEQFNPSLRN FIAMGKNYEK ALAGVTYAAK GYFDALVKMG
        70         80         90        100        110        120
ELASESQGSK ELGDVLFQMA EVHRQIQNQL EEMLKSFHNE LLTQLEQKVE LDSRYLSAAL
       130        140        150        160        170        180
KKYQTEQRSK GDALDKCQAE LKKLRKKSQG SKNPQKYSDK ELQYIDAISN KQGELENYVS
       190        200        210        220        230        240
DGYKTALTEE RRRFCFLVEK QCAVAKNSAA YHSKGKELLA QKLPLWQQAC ADPSKIPERA
       250        260        270        280        290        300
VQLMQQVASN GATLPSALSA SKSNLVISDP IPGAKPLPVP PELAPFVGRM SAQESTPIMN
       310        320        330        340        350        360
GVTGPDGEDY SPWADRKAAQ PKSLSPPQSQ SKLSDSYSNT LPVRKSVTPK NSYATTENKT
       370        380        390        400        410        420
LPRSSSMAAG LERNGRMRVK AIFSHAAGDN STLLSFKEGD LITLLVPEAR DGWHYGESEK
       430        440        450        460        470        480
TKMRGWFPFS YTRVLDSDGS DRLHMSLQQG KSSSTGNLLD KDDLAIPPPD YGAASRAFPA
       490        500        510        520
QTASGFKQRF YSVAVPAFSQ GLDDYGARSM SSADVEVARF
```

Amino acid sequence of *homo sapiens* Retinoic acid-induced protein 3 (GPRC5A); the phosphorylation site S345 is indicated in bold letters.
>sp|Q8NFJ5|RAI3_HUMAN Retinoic acid-induced protein 3 OS = *Homo sapiens* GN = GPRC5A PE = 1 SV = 2
SEQ ID No. 10:

```
        10         20         30         40         50         60
MATTVPDGCR NGLKSKYYRL CDKAEAWGIV LETVATAGVV TSVAFKLTLP ILVCKVQDSN
        70         80         90        100        110        120
RRKMLFTQFL FLLGVLGIFG LTFAFIIGLD GSTGPTRFFL FGILFSICFS CLLAHAVSLT
       130        140        150        160        170        180
KLVRGRKPLS LLVILSLAVG FSLVQDVIAI EYIVLTMNRT NVNVFSELSA PRRNEDFVLL
       190        200        210        220        230        240
LTYVLFLMAL TFLMSSFTFC GSFTGWKRHG AHIYLTMLLS IAIWVAWITL LMLPDFDRRW
       250        260        270        280        290        300
DDTILSSALA ANGWVFLLAY VSPEFWLLTK QRNPMDYPVE DAFCKPQLVK KSYGVENRAY
       310        320        330        340        350
SQEEITQGFE ETGDTLYAPY STHFQLQNQP PQKEFSIPRA HAWPSPYKDY EVKKEGS
```

Amino acid sequence of *homo sapiens* Inositol 1,4,5-trisphosphate receptor type 3 (ITPR3); the phosphorylation site S916 is indicated in bold letters.
>sp|Q14573|ITPR3_HUMAN Inositol 1,4,5-trisphosphate receptor type 3 OS = *Homo sapiens* GN = ITPR3 PE = 1 SV = 2
SEQ ID No. 11:

```
        10         20         30         40         50         60
MSEMSSFLHI GDIVSLYAEG SVNGFISTLG LVDDRCVVEP AAGDLDNPPK KFRDCLFKVC
        70         80         90        100        110        120
PMNRYSAQKQ YWKAKQTKQD KEKIADVVLL QKLQHAAQME QKQNDTENKK VHGDVVKYGS
       130        140        150        160        170        180
VIQLLHMKSN KYLTVNKRLP ALLEKNAMRV TLDATGNEGS WLFIQPFMKL RSNGDNVVVG
       190        200        210        220        230        240
DKVILNPVNA GQPLHASNYE LSDNAGCKEV NSVNCNTSWK INLFMQFRDH LEEVLKGGDV
       250        260        270        280        290        300
VRLFHAEQEK FLTCDEYKGK LQVFLRTTLR QSATSATSSN ALWEVEVVHH DPCRGGAGHW
       310        320        330        340        350        360
NGLYRFKHLA TGNYLAAEEN PSYKGDASDP KAAGMGAQGR TGRRNAGEKI KYCLVAVFKG
       370        380        390        400        410        420
```

-continued

```
NDIASLFELD PTTLQKTDSF VPRNSYVRLR HLCTNTWIQS TNVPIDIEEE RPIRLMLGTC
       430        440        450        460        470        480
PTKEDKEAFA IVSVPVSEIR DLDFANDASS MLASAVEKLN EGFISQNDRR FVIQLLEDLV
       490        500        510        520        530        540
FFVSDVPNNG QNVLDIMVTK PNRERQKLMR EQNILKQVFG ILKAPFREKG GEGPLVRLEE
       550        560        570        580        590        600
LSDQKNAPYQ HKFRLCYRVL RHSQEDYRKN QEHIAKQFGM MQSQIGYDIL AEDTITALLH
       610        620        630        640        650        660
NNRKLLEKHI TKTEVETFVS LVRKNREPRF LDYLSDLCVS NHIAIPVTQE LICKCVLDPK
       670        680        690        700        710        720
NSDILIRTEL RPVKEMAQSH EYLSIEYSEE EVWLTWTDKN NEHHEKSVRQ LAQEARAGNA
       730        740        750        760        770        780
HDENVLSYYR YQLKLFARMC LDRQYLAIDE ISQQLGVDLI FLCMADEMLP FDLRASFCHL
       790        800        810        820        830        840
MLHVHVDRDP QELVTPVKFA RLWTEIPTAI TIKDYDSNLN ASRDDKKNKF ANTMEFVEDY
       850        860        870        880        890        900
LNNVVSEAVP FANEEKNKLT FEVVSLAHNL IYFGFYSFSE LLRLTRTLLG IIDCVQGPPA
       910        920        930        940        950        960
MLQAYEDPGG KKVRRSIQGV GHMMSTMVLS RKQSVFSAPS LSAGASAAEP LDRSKFEENE
       970        980        990       1000       1010       1020
DIVVMETKLK ILEILQFILN VRLDYRISYL LSVFKKEFVE VFPMQDSGAD GTAPAFDSTT
      1030       1040       1050       1060       1070       1080
ANMNLDRIGE QAEAMFGVGK TSSMLEVLCE GGRMFLRVLI HLTMHDYAPL VSGALQLLFK
      1090       1100       1110       1120       1130       1140
HFSQRQEAMH TFKQVQLLIS AQDVENYKVI KSELDRLRTM VEKSELWVDK KGSGKGEEVE
      1150       1160       1170       1180       1190       1200
AGAAKDKKER PTDEEGFLHP PGEKSSENYQ IVKGILERLN KMCGVGEQMR KKQQRLLKNM
      1210       1220       1230       1240       1250       1260
DAHKVMLDLL QIPYDKGDAK MMEILRYTHQ FLQKFCAGNP GNQALLHKHL HLFLTPGLLE
      1270       1280       1290       1300       1310       1320
AETMQHIFLN NYQLCSEISE PVLQHFVKLL ATHGRHVQYL DFLHTVIKAE GKYVKKCQDM
      1330       1340       1350       1360       1370       1380
IMTELTNAGD DVVVFYNDKA SLAHLLDMMK AARDGVEDHS PLMYHISLVD LLAACAEGKN
      1390       1400       1410       1420       1430       1440
VYTEIKCTSL LPLEDVVSVV THEDCITEVK MAYVNFVNHC YVDTEVEMKE IYTSNHIWTL
      1450       1460       1470       1480       1490       1500
FENFTLDMAR VCSKREKRVA DPTLEKYVLS VVLDTINAFF SSPFSENSTS LQTHQTIVVQ
      1510       1520       1530       1540       1550       1560
LLQSTTRLLE CPWLQQQHKG SVEACIRTLA MVAKGRAILL PMDLDAHISS MLSSGASCAA
      1570       1580       1590       1600       1610       1620
AAQRNASSYK ATTRAFPRVT PTANQWDYKN IIEKLQDIIT ALEERLKPLV QAELSVLVDV
      1630       1640       1650       1660       1670       1680
LHWFELLFLE GSEAYQRCES GGFLSKLIQH TKDLMESEEK LCIKVIRTLQ QMLLKKTKYG
      1690       1700       1710       1720       1730       1740
DRGNQLRKML LQNYLQNRKS TSRGDLPDPI GTGLDPDWSA IAATQCRLDK EGATKLVCDL
      1750       1760       1770       1780       1790       1800
ITSTKNEKIF QESIGLAIHL LDGGNTEIQK SFHNLMMSDK KSERFFKVLH DRMKRAQQET
      1810       1820       1830       1840       1850       1860
KSTVAVNMND LGSQPHEDRE PVDPTTKGRV ASFSIPGSSS RYSLGPSLRR GHEVSERVQS
      1870       1880       1890       1900       1910       1920
SEMGTSVLIM QPILRFLQLL CENHNRDLQN FLRCQNNKTN YNLVCETLQF LDIMCGSTTG
      1930       1940       1950       1960       1970       1980
GLGLLGLYIN EDNVGLVIQT LETLTEYCQG PCHENQTCIV TKESNGIDII TALILNDISP
      1990       2000       2010       2020       2030       2040
LCKYRMDLVL QLKDNASKLL LALMESRHDS ENAERILISL RPQELVDVIK KAYLQEEERE
      2050       2060       2070       2080       2090       2100
NSEVSPREVG HNIYILALQL SRHNKQLQHL LKPVKRIQEE EAEGISSMLS LNNKQLSQML
      2110       2120       2130       2140       2150       2160
KSSAPAQEEE EDFLAYYENH TSQIEIVRQD RSMEQIVFPV PGICQFLTEE TKHRLFTTTE
      2170       2180       2190       2200       2210       2220
QDEQGSKVSD FFDQSSFLHN EMEWQRKLRS MPLIYWFSRR MTLWGSISFN LAVFINIIIA
      2230       2240       2250       2260       2270       2280
FFYPYMEGAS TGVLDSPLIS LLFWILICFS IAALFTKRYS IRPLIVALIL RSIYYLGIGP
      2290       2300       2310       2320       2330       2340
TLNILGALNL TNKIVFVVSF VGNRGTFIRG YKAMVMDMEF LYHVGYILTS VLGLFAHELF
      2350       2360       2370       2380       2390       2400
YSILLFDLIY REETLFNVIK SVTRNGRSIL LTALLALILV YLFSIVGFLF LKDDFILEVD
      2410       2420       2430       2440       2450       2460
RLPNNHSTAS PLGMPHGAAA FVDTCSGDKM DCVSGLSVPE VLEEDRELDS TERACDTLLM
      2470       2480       2490       2500       2510       2520
CIVTVMNHGL RNGGGVGDIL RKPSKDESLF PARVVYDLLF FFIVIIIVLN LIFGVIIDTF
      2530       2540       2550       2560       2570       2580
ADLRSEKQKK EEILKTTCFI CGLERDKFDN KTVSFEEHIK LEHNMWNYLY FIVLVRVKNK
      2590       2600       2610       2620       2630       2640
TDYTGPESYV AQMIKNKNLD WFPRMRAMSL VSNEGEGEQN EIRILQDKLN STMKLVSHLT
      2650       2660       2670
AQLNELKEQM TEQRKRRQRL GFVDVQNCIS R
```

-continued

Amino acid sequence of *homo sapiens* 182 kDa tankyrase-1-binding protein (TNKS1BP1): the phosphorylation site S429 is indicated in bold letters.
>sp|Q9C0C2|TB182_HUMAN 182 kDa tankyrase-1-binding protein OS = *Homo sapiens* GN = TNKS1BP1 PE = 1 SV = 4
SEQ ID No. 12:

```
        10         20         30         40         50         60
MKVSTLRESS AMASPLPREM EEELVPTGSE PGDTRAKPPV KPKPRALPAK PALPAKPSLL
        70         80         90        100        110        120
VPVGPRPPRG PLAELPSARK MNMLAGPQPY GGSKRPLPFA PRPAVEASTG GEATQETGKE
       130        140        150        160        170        180
EAGKEEPPPL TPPARCAAPG GVRKAPAPFR PASERFAATT VEEILAKMEQ PRKEVLASPD
       190        200        210        220        230        240
RLWGSRLTFN HDGSSRYGPR TYGTTTAPRD EDGSTLFRGW SQEGPVKSPA ECREEHSKTP
       250        260        270        280        290        300
EERSLPSDLA FNGDLAKAAS SELPADISKP WIPSSPAPSS ENGGPASPGL PAEASGSGPG
       310        320        330        340        350        360
SPHLHPPDKS SPCHSQLLEA QTPEASQASP CPAVTPSAPS AALPDEGSRH TPSPGLPAEG
       370        380        390        400        410        420
APEAPRPSSP PPEVLEPHSL DQPPATSPRP LIEVGELLDL TRTFPSGGEE EAKGDAHLRP
       430        440        450        460        470        480
TSLVQRRFSE GVLQSPSQDQ EKLGGSLAAL PQGQGSQLAL DRPFGAESNW SLSQSFEWTF
       490        500        510        520        530        540
PTRPSGLGVW RLDSPPPSPI TEASEAAEAA EAGNLAVSSR EEGVSQQGQG AGSAPSGSGS
       550        560        570        580        590        600
SWVQGDDPSM SLTQKGDGES QPQFPAVPLE PLPTTEGTPG LPLQQAEERY ESQEPLAGQE
       610        620        630        640        650        660
SPLPLATREA ALPILEPVLG QEQPAAPDQP CVLFADAPEP GQALPVEEEA VTLARAETTQ
       670        680        690        700        710        720
ARTEAQDLCR ASPEPPGPES SSRWLDDLLA SPPPSGGGAR RGAGAELKDT QSPSTCSEGL
       730        740        750        760        770        780
LGWSQKDLQS EFGITGDPQP SSFSPSSWCQ GASQDYGLGG ASPRGDPGLG ERDWTSKYGQ
       790        800        810        820        830        840
GAGEGSTREW ASRCGIGQEE MEASSSQDQS KVSAPGVLTA QDRVVGKPAQ LGTQRSQEAD
       850        860        870        880        890        900
VQDWEFRKRD SQGTYSSRDA ELQDQEFGKR DSLGTYSSRD VSLGDWEFGK RDSLGAYASQ
       910        920        930        940        950        960
DANEQGQDLG KRDHHGRYSS QDADEQDWEF QKRDVSLGTY GSRAAEPQEQ EFGKSAWIRD
       970        980        990       1000       1010       1020
YSSGGSSRTL DAQDRSFGTR PLSSGFSPEE AQQQDEEFEK KIPSVEDSLG EGSRDAGRPG
      1030       1040       1050       1060       1070       1080
ERGSGGLFSP STAHVPDGAL GQRDQSSWQN SDASQEVGGH QERQQAGAQG PGSADLEDGE
      1090       1100       1110       1120       1130       1140
MGKRGWVGEF SLSVGPQREA AFSPGQQDWS RDFCIEASER SYQFGIIGND RVSGAGFSPS
      1150       1160       1170       1180       1190       1200
SKMEGGHFVP PGKTTAGSVD WTDQLGLRNL EVSSCVGSGG SSEARESAVG QMGWSGGLSL
      1210       1220       1230       1240       1250       1260
RDMNLTGCLE SGGSEEPGGI GVGEKDWTSD VNVKSKDLAE VGEGGGHSQA RESGVGQTDW
      1270       1280       1290       1300       1310       1320
SGVEAGEFLK SRERGVGQAD WTPDLGLRNM APGAVCSPGE SKELGVGQMD WGNNLGLRDL
      1330       1340       1350       1360       1370       1380
EVTCDPDSGG SQGLRGCGVG QMDWTQDLAP QNVELFGAPS EAREHGVGGV SQCPEPGLRH
      1390       1400       1410       1420       1430       1440
NGSLSPGLEA RDPLEARELG VGETSGPETQ GEDYSSSSLE PHPADPGMET GEALSFGASP
      1450       1460       1470       1480       1490       1500
GRCPARPPPS GSQGLLEEML AASSSKAVAR RESAASGLGG LLEEEGAGAG AAQEEVLEPG
      1510       1520       1530       1540       1550       1560
RDSPPSWRPQ PDGEASQTED VDGTWGSSAA RWSDQGPAQT SRRPSQGPPA RSPSQDFSFI
      1570       1580       1590       1600       1610       1620
EDTEILDSAM YRSRANLGRK RGHRAPVIRP GGTLGLSEAA DSDAHLFQDS TEPRASRVPS
      1630       1640       1650       1660       1670       1680
SDEEVVEEPQ SRRTRMSLGT KGLKVNLFPG LSPSALKAKL RPRNRSAEEG ELAESKSSQK
      1690       1700       1710       1720
ESAVQRSKSC KVPGLGKPLT LPPKPEKSSG SEGSSPNWLQ ALKLKKKKV
```

Amino acid sequence of *homo sapiens* Rho guanine nucleotide exchange factor 18 (ARHGEF18) isoform 1; the phosphorylation site S1101 is indicated in bold letters.
>sp|Q6ZSZ5|ARHGI_HUMAN Rho guanine nucleotide exchange factor 18 OS = *Homo sapiens* GN = ARHGEF18 PE = 1 SV = 3
SEQ ID No. 13:

```
        10         20         30         40         50         60
MVTVGTNILP SRPAASANTA REDAALFSRR IPPRHKNGAA QPGAAPGPGA PGANMGNAHS
        70         80         90        100        110        120
KSGDRHSALP GRPELSFYGS FPRKWSENVF LDNELLTSKI LSVLRPQSER GFRAGDLRYP
       130        140        150        160        170        160
THFLSTNSVL ASVTASLKEH PRGTLLSDGS PALSRNVGMT VSQKGGPQPT PSPAGPGTQL
       190        200        210        220        230        240
```

-continued

```
GPITGEMDEA DSAFLKFKQT ADDSLSLTSP NTESIFVEDP YTASLRSEIE SDGHEFEAES
       250        260        270        280        290        300
WSLAVDAAYA KKQKREVVKR QDVLYELMQT EVHHVRTLKI MLKVYSRALQ EELQFSSKAI
       310        320        330        340        350        360
GRLFPCADDL LETKSHFLAR LKERRQESLE EGSDRNYVIQ KIGDLLVQQF SGENGERMKE
       370        380        390        400        410        420
KYGVFCSGHN EAVSHYKLLL QQNKKFQNLI KKIGNFSIVR RLGVQECILL VTQRITKYPV
       430        440        450        460        470        480
LVERIIQNTE AGTEDYEDLT QALNLIKDII SQVDAKVSEC EKGQRLREIA GKMDLKSSSK
       490        500        510        520        530        540
LKNGLTFRKE DMLQRQLHLE GMLCWKTTSG RLKDILAILL TDVLLLLQEK DQKYVFASVD
       550        560        570        580        590        600
SKPPVISLQK LIVREVANEE KAMFLISASL QGPEMYEIYT SSKEDRNAWM AHIQRAVESC
       610        620        630        640        650        660
PDEEEGPFSL PEEERKVVEA RATRLRDFQE RLSMKDQLIA QSLLEKQQIY LEMAEMGGLE
       670        680        690        700        710        720
DLPQPRGLFR GGDPSETLQG ELILKSAMSE IEGIQSLICR QLGSANGQAE DGGSSTGPPR
       730        740        750        760        770        780
RAETFAGYDC TNSPTKNGSF KKKVSSTDPR PRDWRGPPNS PDLKLSDSDI PGSSEESPQV
       790        800        810        820        830        840
VEAPGTESDP RLPTVLESEL VQRIQTLSQL LLNLQAVIAH QDSYVETQRA AIQEREKQFR
       850        860        870        880        890        900
LQSTRGNLLL EQERQRNFEK QREERAALEK LQSQLRHEQQ RWERERQWQH QELERAGARL
       910        920        930        940        950        960
QEREGEARQL RERLEQERAE LERQRQAYQH DLERLREAQR AVERERERLE LLRRLKKQNT
       970        980        990       1000       1010       1020
APGALPPDTL AEAQPPSHPP SFNGEGLEGP RVSMLPSGVG PEYAERPEVA RRDSAPTENR
      1030       1040       1050       1060       1070       1080
LAKSDVPIQL LSATNQFQRQ AAVQQQIPTK LAASTKGGKD KGGKSRGSQR WESSASFDLK
      1090       1100       1110       1120       1130       1140
QQLLLNKLMG KDESTSRNRR SLSPILPGRH SPAPPPDPGF PAPSPPPADS PSEGFSLKAG
      1150       1160       1170
GTALLPGPPA PSPLPATPLS AKEDASKEDV IFF
```

Amino acid sequence of *homo sapiens* Rho guanine nucleotide exchange factor 18 (ARHGEF18) isoform 2; the phosphorylation site S943 is indicated in bold letters.
>sp|Q6ZSZ5-2|ARHGI_HUMAN Isoform 2 of Rho guanine nucleotide exchange factor 18 OS = *Homo sapiens* GN = ARHGEF18
SEQ ID No. 14:

```
        10         20         30         40         50         60
MTVSQKGGPQ PTFSPAGPGT QLGPITGEMD EADSAFLKFK QTADDSLSLT SPNTESIFVE
        70         80         90        100        110        120
DPYTASLRSE IESDGHEFEA ESWSLAVDAA YAKKQKREVV KRQDVLYELM QTEVHHVRTL
       130        140        150        160        170        180
KIMLKVYSRA LQEELQFSSK AIGRLFPCAD DLLETHSHFL ARLKERRQES LEEGSDRNYV
       190        200        210        220        230        240
IQKIGDLLVQ QFSGENGERM KEKYGVFCSG HNEAVSHYKL LLQQNKKFQN LIKKIGNFSI
       250        260        270        280        290        300
VRRLGVQECI LLVTQRITKY PVLVERIIQN TEAGTEDYED LTQALNLIKD IISQVDAKVS
       310        320        330        340        350        360
ECEKGQRLRE IAGKMDLKSS SKLKNGLTFR KEDMLQRQLH LEGMLCWKTT SGRLKDILAI
       370        380        390        400        410        420
LLTDVLLLLQ EKDQKYVFAS VDSKPPVISL QKLIVREVAN EEKAMFLISA SLQGPEMYEI
       430        440        450        460        470        480
YTSSKEDRNA WMAHIQRAVE SCFDEEEGPF SLPEEERKVV EARATRLRDF QERLSMKDQL
       490        500        510        520        530        540
IAQSLLEKQQ IYLEMAEMGG LEDLPQPRGL FRGGDPSETL QGELILKSAM SEIEGIQSLI
       550        560        570        580        590        600
CRQLGSANGQ AEDGGSSTGP PRRAETFAGY DCTNSPTKNG SFKKKVSSTD PRPRDWRGPP
       610        620        630        640        650        660
NSPDLKLSDS DIPGSSEESP QVVEAPGTES DPRLPTVLES ELVQRIQTLS QLLLNLQAVI
       670        680        690        700        710        720
AHQDSYVETQ RAAIQEREKQ FRLQSTRGNL LLEQERQRNF EKQREERAAL EKLQSQLRHE
       730        740        750        760        770        780
QQRWERERQW QHQELERAGA RLQEREGEAR QLRERLEQER AELERQRQAY QHDLERLREA
       790        800        810        820        830        840
QRAVERERER LELLRRLKKQ NTAPGALPPD TLAEAQPPSH PPSFNGEGLE GPRVSMLPSG
       850        860        870        880        890        900
VGPEYAERPE VARRDSAPTE NRLAKSDVPI QLLSATNQFQ RQAAVQQQIP TKLAASTKGG
       910        920        930        940        950        960
KDKGGKSRGS QRWESSASFD LKQQLLLNKL MGKDESTSRN RRSLSPILPG RHSPAPPPDP
       970        980        990       1000       1010
GFPAPSPPPA DSFSEGFSLK AGGTALLPGP PAPSPLPATP LSAKEDASKE DVIFF
```

Amino acid sequence of *homo sapiens* Rho guanine nucleotide exchange factor 18 (ARHGEF18) isoform 3; the phosphorylation site S943 is indicated in bold letters.
>sp|Q6ZSZ5-3|ARHGI_HUMAN Isoform 3 of Rho guanine nucleotide exchange factor 18 OS = Homo sapiens GN = ARHGEF18
SEQ ID No. 15:

```
        10         20         30         40         50         60
MTVSQKGGPQ PTPSPAGPGT QLGPITGEMD EADSAFLKFK QTADDSLSLT SPNTESIFVE
        70         80         90        100        110        120
DPYTASLRSE IESDGHEFEA ESWSLAVDAA YAKKQKREVV KRQDVLYELM QTEVHHVRTL
       130        140        150        160        170        180
KIMLKVYSRA LQEELQFSSK AIGRLFPCAD DLLETHSHFL ARLKERRQES LEEGSDRNYV
       190        200        210        220        230        240
IQKIGDLLVQ QFSGENGERM KEKYGVFCSG HNEAVSHYKL LLQQNKKFQN LIKKIGNFSI
       250        260        270        280        290        300
VRRLGVQECI LLVTQRITKY PVLVERIIQN TEAGTEDYED LTQALNLIKD IISQVDAKVS
       310        320        330        340        350        360
ECEKGQRLRE IAGKMDLKSS SKLKNGLTFR KEDMLQRQLH LEGMLCWKTT SGRLKDILAI
       370        380        390        400        410        420
LLTDVLLLLQ EKDQKYVFAS VDSKPPVISL QKLIVREVAN EEKAMFLISA SLQGPEMYEI
       430        440        450        460        470        480
YTSSKEDRNA WMAHIQRAVE SCPDEEEGPF SLPEEERKVV EARATRLRDF QERLSMKDQL
       490        500        510        520        530        540
IAQSLLEKQQ IYLEMAEMGG LEDLPQPRGL FRGGDPSETL QGELILKSAM SEIEGIQSLI
       550        560        570        580        590        600
CRQLGSANGQ AEDGGSSTGP PRRAETFAGY DCTNSPTKNG SFKKKVSSTD PRPRDWRGPP
       610        620        630        640        650        660
NSPDLKLSDS DIPGSSEESP QVVEAPGTES DPRLPTVLES ELVQRIQTLS QLLLNLQAVI
       670        680        690        700        710        720
AHQDSYVETQ RAAIQEREKQ FRLQSTRGNL LLEQERQRNF EKQREERAAL EKLQSQLREL
       730        740        750        760        770        780
QQRWERERQW QHQELERAGA RLQEREGEAR QLRERLEQER AELERQRQAY QHDLERLREA
       790        800        810        820        830        840
QRAVERERER LELLRRLKKQ NTAPGALPPD TLAEAQPPSH PPSFNGEGLE GPRVSMLPSG
       850        860        870        880        890        900
VGPEYAERPE VARRDSAPTE NRLAKSDVPI QLLSATNQFQ RQAAVQQQIP TKLAASTKGG
       910        920        930        940        950        960
KDKGGKSRGS QRWESSASFD LKQQLLLNKL MGKDESTSRN RR**S**LSPILPG RHSPAPPPDF
       970        980        990       1000       1010       1020
GFPAPSPPPA DSPSEGFSLK AGGTALLPGP PAPSPLPARW RRQHLSPESG RIHFPNRAPR
      1030
RFTMNLRVRE
```

Amino acid sequence of *homo sapiens* RelA-associated inhibitor (PPP1R13L); this protein is also called inhibitor of ASPP protein (1ASPP); these terms can be used interchangeably herein without dererring from the gist of the present invention. The phosphorylation site S102 is indicated in bold letters.
>sp|Q8WUF5|IASPP_HUMAN RelA-associated inhibitor OS = Homo sapiens GN = PPP1R13L PE = 1 SV = 4
SEQ ID No. 16:

```
        10         20         30         40         50         60
MDSEAFCSAR DFLDMNFQSL AMKHMDLKQM ELDTAAAKVD ELTKQLESLW SDSPAPPGPQ
        70         80         90        100        110        120
AGPPSRPPRY SSSSIPEPFG SRGSPRKAAT DGADTPFGRS E**S**APTLHPYS PLSPKGRPSS
       130        140        150        160        170        180
PRTPYLQPD AYGSLDRATS PRPRAFDGAG SSLGRAPSPR PGPGPLRQQG PPTPFDFLGR
       190        200        210        220        230        240
AGSPRGSPLA EGPQAFFPER GPSPRPPATA YDAPASAFGS SLLGSGGSAF APPLRAQDDL
       250        260        270        260        290        300
TLRRRPPKAW NESDLDVAYE KKPSQTASYE RLDVFARPAS PSLQLLPWRE SSLDGLGGTG
       310        320        330        340        350        360
KDNLTSATLP RNYKVSPLAS DRRSDAGSYR RSLGSAGPSG TLPRSWQPVS RIPMPPSSPQ
       370        380        390        400        410        420
PRGAPRQRPI PLSMIFKLQN AFWEHGASRA MLPGSPLFTR APPPKLQPQP QPQPQPQSQP
       430        440        450        460        470        480
QPQLPPQPQT QPQTPTPAPQ HPQQTWPPVN EGPPKPPTEL EPEPEIEGLL TPVLEAGDVD
       490        500        510        520        530        540
EGPVARPLSP TRLQPALPPE AQSVPELEEV ARVLAEIPRP LKRRGSMEQA PAVALPPTHK
       550        560        570        580        590        600
KQYQQIISRL FHRHGGPGPG GPEPELSPIT EGSEARAGPP APAPPAPIPP PAPSQSSPPE
       610        620        630        640        650        660
QPQSMEMRSV LRKAGSPRKA RRARLNPLVL LLDAALTGEL EVVQQAVKEM NDPSQPNEEG
       670        680        690        700        710        720
ITALHNAICG ANYSIVDFLI TAGANVNSPD SHGWTPLHCA ASCNDTVICM ALVQHGAAIF
       730        740        750        760        770        780
ATTLSDGATA FEKCDPYREG YADCATYLAD VEQSMGLMNS GAVYALWDYS AEFGDELSFR
       790        800        810        820
EGESVTVLRR DGPEETDWWW AALHGQEGYV PRNYFGLFPR VKPQRSKV
```

-continued

Amino acid sequence of *homo sapiens* Autophagy-related protein 16-1 (ATG16L1) isoform 1the phosphorylation site S269 is indicated in bold letters.
>sp|Q676U5|A16L1_HUMAN Autophagy-related protein 16-1 OS = *Homo sapiens* GN = ATG16L1 PE = 1 SV = 2
SEQ ID No. 17:

10 20 30 40 50 60
MSSGLRAADF PRWKRHISEQ LRRRDRLQRQ AFEEIILQYN KLLEKSDLHS VLAQKLQAEK
70 60 90 100 110 120
HDVPNRHEIS PGHDGTWNDN QLQEMAQLRI KHQEELTELH KKRGELAQLV IDLNNQMQRK
130 140 150 160 170 180
DREMQMNEAK IAECLQTISD LETECLDLRT KLCDLERANQ TLKDEYDALQ ITFTALEGKL
190 200 210 220 230 240
RKTTEENQEL VTRWMAEKAQ EANRLNAENE KDSRRRQARL QKELAEAAKE PLPVEQDDDI
250 260 270 280 290 300
EVIVDETSDH TEETSPVRAI SRAATKRLSQ PAGGLLDSIT NIFGRRSVSS FPVPQDNVDT
310 320 330 340 350 360
HPGSGKEVRV PATALCVFDA HDGEVNAVQF SFGSRLLATG GMDRRVKLWE VFGEKCEFKG
370 380 390 400 410 420
SLSGSNAGIT SIEFDSAGSY LLAASNDFAS RIWTVDDYRL RHTLTGHSGK VLSAKFLLDN
430 440 450 460 470 480
ARIVSGSHDR TLKLWDLRSK VCIKTVFAGS SCNDIVCTEQ CVMSGHFDKK IRFWDIRSES
490 500 510 520 530 540
IVREMELLGK ITALDLNPER TELLSCSRDD LLKVIDLRTN AIKQTFSAPG FKCGSDWTRV
550 560 570 580 590 600
VFSPDGSYVA AGSAEGSLYI WSVLTGKVEK VLSKQHSSSI NAVAWSPSGS HVVSVDKGCK

AVLWAQY

Amino acid sequence of *homo sapiens* Autophagy-related protein 16-1 (ATG16L1) isoform 3; the phosphorylation site S269 is indicated in bold letters.
>sp|Q676U5-3|A16L1_HUMAN Isoform 3 of Autophagy-related protein 16-1 OS = *Homo sapiens* GN = ATG16L1
SEQ ID No. 18:

10 20 30 40 50 60
MSSGLRAADF PRWKRHISEQ LRRRDRLQRQ AFEEIILQYN KLLEKSDLHS VLAQKLQAEK
70 80 90 100 110 120
HDVPNRHEIS PGHDGTWNDN QLQEMAQLRI KHQEELTELH KKRGELAQLV IDLNNQMQRK
130 140 150 160 170 180
DREMQMNEAK IAECLQTISD LETECLDLRT KLCDLERANQ TLKDEYDALQ ITFTALEGKL
190 200 210 220 230 240
RKTTEENQEL VTRWMAEKAQ EANRLNAENE KDSRRRQARL QKELAEAAKE PLPVEQDDDI
250 260 270 280 290 300
EVIVDETSDH TEETSPVRAI SRAATKRLSQ PAGGLLDSIT NIFGRRSVSS FPVPQDNVDT
310 320 330 340 350 360
HPGSGKEVRV PATALCVFDA HDGEVNAVQF SFGSRLLATG GMDRRVKLWE VFGEKCEFKG
370 380 390 400 410 420
SLSGSNAGIT SIEFDSAGSY LLAASNDFAS RIWTVDDYRL RHTLTGHSGK VLSAKFLLDN
430 440 450 460 470
ARIVSGSHDR TLKLWDLRSK VCEEIQSLCL CICLDVSVEV CVCTSEPAFM

Amino acid sequence of *homo sapiens* Autophagy-related protein 16-1 (ATG16L1) isoform 4; the phosphorylation site S125 is indicated in bold letters.
>sp|Q676U5-4|A16L1_HUMAN Isoform 4 of Autophagy-related protein 16-1 OS = *Homo sapiens* GN = ATG16L1
SEQ ID No. 19:

10 20 30 40 50 60
MSSGLRAADF PRWKRHISEQ LRRRDRLQRQ AFEEIILQYN KLLEKSDLHS VIAQKLQAEK
70 80 90 100 110 120
HDVPNRHEIR RRQARLQKEL AEAAKEPLPV EQDDDIEVIV DETSDHTEET SPVRAISRAA
130 140 150 160 170 180
TKRLSQPAGG LLDSITNIFG RRSVSSFPVP QDNVDTHPGS GKEVRVPATA LCVFDAHDGE
190 200 210 220 230 240
VNAVQFSRGI TSIEFDSAGS YLLAASNDFA SRIWTVDDYR LRHTLTGHSG KVLSAKFLLD
250 260 270 280 290 300
NARIVSGSHD RTLKLWDLRS KVCIKTVFAG SSCNDIVCTE QCVMSGHFDK KIRFWDIRSE
310 320 330 340 350 360
SIVREMELLG KITALDLNPE RTELLSCSRD DLLKVIDLRT NAIKQTFSAP GFKCGSDWTR
370 380 390 400 410 420
VVFSPDGSYV AAGSAEGSLY IWSVLTGKVE KVLSKQHSSS INAVAWSPSG SHVVSVDKGC

KAVLWAQY

-continued

Amino acid sequence of *homo sapiens* Tumor protein D54 (TPD52L2) isoform 1; the phosphorylation site S161 is indicated in bold letters.
>sp|O43399|TPD54_HUMAN Tumor protein D54 OS = *Homo sapiens* GN = TPD52L2 PE = 1 SV = 2
SEQ ID No. 20:

```
        10         20         30         40         50         60
MDSAGQDINL NSPNKGLLSD SMTDVPVDTG VAARTPAVEG LTEAEEEELR AELTKVEEEI
        70         80         90        100        110        120
VTLRQVLAAK ERHCGELKRR LGLSTLGELK QNLSRSWHDV QVSSAYVKTS EKLGEWNEKV
       130        140        150        160        170        180
TQSDLYKKTQ ETLSQAGQKT SAALSTVGSA ISRKLGDMRN SATFKSFEDR VGTIKSKVVG
       190        200
DRZNGSDNLP SSAGSGDKPL SDPAPF
```

Amino acid sequence of *homo sapiens* Tumor protein D54 (TPD52L2) isoform 2; the phosphorylation site S141 is indicated in bold letters.
>sp|O43399-2|TPD54_HUMAN Isoform 2 of Tumor protein D54 OS = *Homo sapiens* GN = TPD52L2
SEQ ID No. 21:

```
        10         20         30         40         50         60
MDSAGQDINL NSPNKGLLSD SMTDVPVDTG VAARTPAVEG LTEAEEEELR AELTKVEEEI
        70         80         90        100        110        120
VTLRQVLAAK ERHCGELKRR LGLSTLGELK QNLSRSWHDV QVSSAYKKTQ ETLSQAGQKT
       130        140        150        160        170        180
SAALSTVGSA ISRKLGDMRN SATFKSFEDR VGTIKSKVVG DRENGSDNLP SSAGSGDKPL

SDPAPF
```

REFERENCES

1. Talpaz M, et al.; N. Engl. J. Med. 354 (24): 2531-41.
2. Karaman M W, et al.; Nat. Biotechnol. 2008; 26(1):127-32.
3. Golas et al. Cancer Res. 2003; 63(2): 375-81.
4 Remsing et al.; Leukemia. 2009; 23(3): 477-85.
5 Bantscheff et al. Nat. Biotechnol. 2007; 25(9): 1035-44.
6 Hennequin et al; J Med. Chem. 2006; 49(22): 6465-88.
7 Green T P et al.; Mol. Oncol. 2009.
8 Huang W S, et al.; J Med. Chem. 2010; 53(12): 4701-19.
9 O'Hare T, et al.; Cancer Cell. 2009; 16(5): 401-12.
10 Kimura S, et al.; Blood. 2005; 106(12): 3948-54.
11 Rix U, et al.; Leukemia. 2010 24(1): 44-50.
12. Ali N. et al.; J Pharmacol Sci. 2005 98(2): 130-41.
13. Rivat C, et al.; FASEB J. 2003; 17(12): 1721-3.
14. Missbach M, et al.; Bioorg Med Chem. Lett. 2000; 10(9): 945-9.
15. Susa M, et al. in: Fabbro D. McCormick F, editors. "Methods in molecular biology 290—Protein Tyrosine Kinases From Inhibitors to Useful Drugs" Totowa, N.J.: Humana Press Inc.; 2005.
16. Summy et al.; Mol Cancer Ther. 2005; 4(12): 1900-11.
17. Azam M, et al.; Proc Natl Acad Sci USA. 2006; 103(24): 9244-9.
18. Blake R A, et al.; Mol Cell Biol. 2000; 20(23): 9018-27.

All references cited herein are fully incorporated by reference. Having now fully described the invention, it will be understood by a person skilled in the art that the invention may be practiced within a wide and equivalent range of conditions, parameters and the like, without affecting the spirit or scope of the invention or any embodiment thereof.

The invention claimed is:

1. A method for the treatment of cancer comprising:

administering an effective amount of an inhibitor of a kinase of the Src family to a subject in need of such a treatment, wherein the subject in need of such treatment is identified by evaluating phosphorylation of integrin β4 (ITGB4) at one or more phosphorylation sites selected from S1518, S1457, T1455 and S1069 of ITGB4 in a sample of a subject suspected to suffer from cancer, suffering from cancer or being prone to suffer from cancer, and wherein an increase in phosphorylation of one or more phosphorylation sites compared to a control indicates responsiveness of the subject to the inhibitor of a kinase of the Src family.

2. The method of claim 1, wherein said inhibitor of a kinase of the Src-family is selected from the group consisting of dasatinib, bosutinib and saracatinib and pharmaceutically acceptable salts, solvates, and/or hydrates of these inhibitors.

3. The method of claim 1, wherein the subject in need of such treatment is identified by further evaluating the phosphorylation of one or more additional phosphorylation sites in said sample.

4. The method of claim 3, wherein said one or more additional phosphorylation site is one or more of the following phosphorylation sites:

a. S509 of BAIAP2;
b. S345 of GPRC5A;
c. S916 of ITPR3;
d. S429 of TNKS1BP1;
e. S1101 of ARHGEF18;
f. S102 of IASPP;
g. S269 of APG16L; and
h. S161 of TPD52L2.

5. The method of claim 4, wherein an increase in said phosphorylation of one or more of the phosphorylation sites a.) to h.) in comparison to the control is indicative of the responsiveness of the subject to the inhibitor of a kinase of the Src family.

6. The method of claim 1, wherein the subject in need of such treatment is identified by evaluating the phosphorylation of the following combination of phosphorylation sites:

a. S1518, S1457, T1455 and S1069 of ITGB4 and S916 of ITPR3;
b. S1518, S1457, T1455 and S1069 of ITGB4 and S429 of TNKS1BP1;
c. S1518, S1457, T1455 and S1069 of ITGB4 and S1101 of ARHGEF18;
d. S1518, S1457, T1455 and S1069 of ITGB4 and S269 of APG16L;
e. S1518, S1457, T1455 and S1069 of ITGB4 and S161 of TPD52L2;
f. S1518, S1457, T1455 and/or S1069 of ITGB4 and S1101 of ARHGEF18 and S345 of GPRC5A;
g. S1518, S1457, T1455 and/or S1069 of ITGB4 and S1101 of ARHGEF18 and S916 of ITPR3; and/or
h. S1518, S1457, T1455 and/or S1069 of ITGB4 and S1101 of ARHGEF18 and S102 of IASPP.

7. The method of claim 1, wherein the phosphorylation of the phosphorylation site is at least 2.5-fold increased, in comparison to the control.

8. The method of claim 1, wherein said phosphorylation is detected by immunoassay, IHC, mass spectrometry or intracellular flow cytometry.

9. The method of claim 1, wherein said cancer is a lung cancer or a breast cancer.

10. The method of claim 9, wherein said cancer is non small cell lung cancer (NSCLC).

11. The method of claim 9, wherein said cancer is breast cancer.

12. The method of claim 1, wherein said cancer is a solid tumor.

13. The method of claim 1, wherein said subject is a human.

14. The method of claim 1, wherein said inhibitor is administered as a single anti-tumor agent.

15. The method of claim 1, wherein said inhibitor is administered in a form of a combination therapy.

16. The method of claim 15, wherein the combination therapy comprises chemotherapy or anti-hormonal therapy.

17. The method of claim 16, wherein said chemotherapy or anti-hormonal therapy is selected from the group consisting of anthracycline/taxane chemotherapy, therapy with one or more anti-metabolite agents, therapy with an anti-hormonal compound, therapy with an anti-estrogen, therapy with a tyrosine kinase inhibitor, therapy with a raf inhibitor, therapy with a ras inhibitor, therapy with a dual tyrosine kinase inhibitor, therapy with taxol, therapy with taxane, therapy with doxorubicin, therapy with adjuvant (anti-) hormone drugs, and therapy with cisplatin.

18. The method o f claim 1, wherein said inhibitor is administered by any one of a parenteral route, oral route, intravenous route, subcutaneous route, intranasal route or transdermal route.

19. The method of claim 1, wherein said inhibitor is to be administered in a neoadjuvant or adjuvant setting.

20. The method of claim 1, wherein the phosphorylation of the phosphorylation site is at least 5-fold in comparison to the control.

* * * * *

SEQUENCE LISTING

```
<160> NUMBER OF SEQ ID NOS: 41

<210> SEQ ID NO 1
<211> LENGTH: 5469
<212> TYPE: DNA
<213> ORGANISM: Homo sapiens

<400> SEQUENCE: 1

atggcagggc cacgccccag cccatgggcc aggctgctcc tggcagcctt gatcagcgtc      60

agcctctctg ggaccttggc aaaccgctgc aagaaggccc cagtgaagag ctgcacggag     120

tgtgtccgtg tggataagga ctgcgcctac tgcacagacg agatgttcag ggaccggcgc     180

tgcaacaccc aggcggagct gctggccgcg ggctgccagc gggagagcat cgtggtcatg     240

gagagcagct tccaaatcac agaggagacc cagattgaca ccaccctgcg gcgcagccag     300

atgtcccccc aaggcctgcg ggtccgtctg cggcccggtg aggagcggca ttttgagctg     360

gaggtgtttg agccactgga gagccccgtg gacctgtaca tcctcatgga cttctccaac     420

tccatgtccg atgatctgga caacctcaag aagatggggc agaacctggc tcgggtcctg     480
```

-continued

```
agccagctca ccagcgacta cactattgga tttggcaagt ttgtggacaa agtcagcgtc    540
ccgcagacgg acatgaggcc tgagaagctg aaggagccct ggcccaacag tgaccccccc    600
ttctccttca agaacgtcat cagcctgaca gaagatgtgg atgagttccg gaataaactg    660
cagggagagc ggatctcagg caacctggat gctcctgagg gcggcttcga tgccatcctg    720
cagacagctg tgtgcacgag ggacattggc tggcgcccgg acagcaccca cctgctggtc    780
ttctccaccg agtcagcctt ccactatgag gctgatggcg ccaacgtgct ggctggcatc    840
atgagccgca acgatgaacg gtgccacctg gacaccacgg gcacctacac ccagtacagg    900
acacaggact acccgtcggt gcccaccctg gtgcgcctgc tcgccaagca caacatcatc    960
cccatctttg ctgtcaccaa ctactcctat agctactacg agaagcttca cacctatttc   1020
cctgtctcct cactgggggt gctgcaggag gactcgtcca acatcgtgga gctgctggag   1080
gaggccttca atcggatccg ctccaacctg gacatccggg ccctagacag cccccgaggc   1140
cttcggacag aggtcacctc caagatgttc cagaagacga ggactgggtc ctttcacatc   1200
cggcgggggg aagtgggtat ataccaggtg cagctgcggg cccttgagca cgtggatggg   1260
acgcacgtgt gccagctgcc ggaggaccag aagggcaaca tccatctgaa accttccttc   1320
tccgacggcc tcaagatgga cgcgggcatc atctgtgatg tgtgcacctg cgagctgcaa   1380
aaagaggtgc ggtcagctcg ctgcagcttc aacggagact tcgtgtgcgg acagtgtgtg   1440
tgcagcgagg gctggagtgg ccagacctgc aactgctcca ccggctctct gagtgacatt   1500
cagccctgcc tgcgggaggg cgaggacaag ccgtgctccg gccgtgggga gtgccagtgc   1560
gggcactgtg tgtgctacgg cgaaggccgc tacgagggtc agttctgcga gtatgacaac   1620
ttccagtgtc cccgcacttc cgggttcctc tgcaatgacc gaggacgctg ctccatgggc   1680
cagtgtgtgt gtgagcctgg ttggacaggc ccaagctgtg actgtcccct cagcaatgcc   1740
acctgcatcg acagcaatgg gggcatctgt aatggacgtg gccactgtga gtgtggccgc   1800
tgccactgcc accagcagtc gctctacacg gacaccatct gcgagatcaa ctactcggcg   1860
atccacccgg gcctctgcga ggacctacgc tcctgcgtgc agtgccaggc gtggggcacc   1920
ggcgagaaga aggggcgcac gtgtgaggaa tgcaacttca aggtcaagat ggtggacgag   1980
cttaagagag ccgaggaggt ggtggtgcgc tgctccttcc gggacgagga tgacgactgc   2040
acctacagct acaccatgga aggtgacggc gcccctgggc ccaacagcac tgtcctggtg   2100
cacaagaaga aggactgccc tccgggctcc ttctggtggc tcatccccct gctcctcctc   2160
ctcctgccgc tcctggccct gctactgctg ctatgctgga agtactgtgc ctgctgcaag   2220
gcctgcctgg cacttctccc gtgctgcaac cgaggtcaca tggtgggctt taaggaagac   2280
cactacatgc tgcgggagaa cctgatggcc tctgaccact tggacacgcc catgctgcgc   2340
agcgggaacc tcaagggccg tgacgtggtc cgctggaagg tcaccaacaa catgcagcgg   2400
cctggctttg ccactcatgc cgccagcatc aaccccacag agctggtgcc ctacgggctg   2460
tccttgcgcc tggcccgcct ttgcaccgag aacctgctga agcctgacac tcgggagtgc   2520
gcccagctgc gccaggaggt ggaggagaac ctgaacgagg tctacaggca gatctccggt   2580
gtacacaagc tccagcagac caagttccgg cagcagccca atgccgggaa aaagcaagac   2640
cacaccattg tggacacagt gctgatggcg ccccgctcgg ccaagccggc cctgctgaag   2700
cttacagaga agcaggtgga acagagggcc ttccacgacc tcaaggtggc ccccggctac   2760
tacaccctca ctgcagacca ggacgcccgg ggcatggtgg agttccagga gggcgtggag   2820
```

-continued ctggtggacg tacgggtgcc cctctttatc cggcctgagg atgacgacga gaagcagctg 2880
ctggtggagg ccatcgacgt gcccgcaggc actgccaccc tcggccgccg cctggtaaac 2940
atcaccatca tcaaggagca agccagagac gtggtgtcct ttgagcagcc tgagttctcg 3000
gtcagccgcg gggaccaggt ggcccgcatc cctgtcatcc ggcgtgtcct ggacggcggg 3060
aagtcccagg tctcctaccg cacacaggat ggcaccgcgc agggcaaccg ggactacatc 3120
cccgtggagg gtgagctgct gttccagcct ggggaggcct ggaaagagct gcaggtgaag 3180
ctcctggagc tgcaagaagt tgactccctc ctgcggggcc gccaggtccg ccgtttccac 3240
gtccagctca gcaaccctaa gtttggggcc cacctgggcc agccccactc caccaccatc 3300
atcatcaggg acccagatga actggaccgg agcttcacga gtcagatgtt gtcatcacag 3360
ccaccccctc acggcgacct gggcgccccg cagaacccca atgctaaggc cgctgggtcc 3420
aggaagatcc atttcaactg gctgccccct tctggcaagc caatggggta cagggtaaag 3480
tactggattc agggtgactc cgaatccgaa gcccacctgc tcgacagcaa ggtgccctca 3540
gtggagctca ccaacctgta cccgtattgc gactatgaga tgaaggtgtg cgcctacggg 3600
gctcagggcg agggacccta cagctccctg gtgtcctgcc gcacccacca ggaagtgccc 3660
agcgagccag ggcgtctggc cttcaatgtc gtctcctcca cggtgaccca gctgagctgg 3720
gctgagccgg ctgagaccaa cggtgagatc acagcctacg aggtctgcta tggcctggtc 3780
aacgatgaca accgacctat tggccccatg aagaaagtgc tggttgacaa ccctaagaac 3840
cggatgctgc ttattgagaa ccttcgggag tcccagccct accgctacac ggtgaaggcg 3900
cgcaacgggg ccggctgggg gcctgagcgg gaggccatca tcaacctggc cacccagccc 3960
aagaggccca tgtccatccc catcatccct gacatcccta tcgtggacgc ccagagcggg 4020
gaggactacg acagcttcct tatgtacagc gatgacgttc tacgctctcc atcgggcagc 4080
cagaggccca gcgtctccga tgacactggc tgcggctgga agttcgagcc cctgctgggg 4140
gaggagctgg acctgcggcg cgtcacgtgg cggctgcccc cggagctcat cccgcgcctg 4200
tcggccagca gcgggcgctc ctccgacgcc gaggcgcccc acgggccccc ggacgacggc 4260
ggcgcgggcg ggaagggcgg cagcctgccc cgcagtgcga cacccgggcc ccccggagag 4320
cacctggtga atggccggat ggactttgcc ttcccgggca gcaccaactc cctgcacagg 4380
atgaccacga ccagtgctgc tgcctatggc acccacctga gcccacacgt gccccaccgc 4440
gtgctaagca catcctccac cctcacacgg gactacaact cactgacccg ctcagaacac 4500
tcacactcga ccacactgcc cagggactac tccaccctca cctccgtctc ctcccacgac 4560
tctcgcctga ctgctggtgt gcccgacacg cccacccgcc tggtgttctc tgccctgggg 4620
cccacatctc tcagagtgag ctggcaggag ccgcggtgcg agcggccgct gcagggctac 4680
agtgtggagt accagctgct gaacggcggt gagctgcatc ggctcaacat ccccaaccct 4740
gcccagacct cggtggtggt ggaagacctc ctgcccaacc actcctacgt gttccgcgtg 4800
cgggcccaga gccaggaagg ctggggccga gagcgtgagg gtgtcatcac cattgaatcc 4860
caggtgcacc cgcagagccc actgtgtccc ctgccaggct ccgccttcac tttgagcact 4920
cccagtgccc caggcccgct ggtgttcact gccctgagcc cagactcgct gcagctgagc 4980
tgggagcggc cacggaggcc caatggggat atcgtcggct acctggtgac ctgtgagatg 5040
gcccaaggag gagggccagc caccgcattc cgggtggatg gagacagccc cgagagccgg 5100
ctgaccgtgc cgggcctcag cgagaacgtg ccctacaagt tcaaggtgca ggccaggacc 5160
actgagggct tcgggccaga gcgcgagggc atcatcacca tagagtccca ggatggagga 5220

```
cccttcccgc agctgggcag ccgtgccggg ctcttccagc acccgctgca aagcgagtac   5280

agcagcatca ccaccaccca caccagcgcc accgagccct tcctagtgga tgggctgacc   5340

ctgggggccc agcacctgga ggcaggcggc tccctcaccc ggcatgtgac ccaggagttt   5400

gtgagccgga cactgaccac cagcggaacc cttagcaccc acatggacca acagttcttc   5460

caaacttga                                                           5469


<210> SEQ ID NO 2
<211> LENGTH: 5418
<212> TYPE: DNA
<213> ORGANISM: Homo sapiens

<400> SEQUENCE: 2

atggcagggc cacgccccag cccatgggcc aggctgctcc tggcagcctt gatcagcgtc     60

agcctctctg ggaccttggc aaaccgctgc aagaaggccc cagtgaagag ctgcacggag    120

tgtgtccgtg tggataagga ctgcgcctac tgcacagacg agatgttcag ggaccggcgc    180

tgcaacaccc aggcggagct gctggccgcg ggctgccagc gggagagcat cgtggtcatg    240

gagagcagct tccaaatcac agaggagacc cagattgaca ccaccctgcg gcgcagccag    300

atgtcccccc aaggcctgcg ggtccgtctg cggcccggtg aggagcggca ttttgagctg    360

gaggtgtttg agccactgga gagccccgtg gacctgtaca tcctcatgga cttctccaac    420

tccatgtccg atgatctgga caacctcaag aagatggggc agaacctggc tcgggtcctg    480

agccagctca ccagcgacta cactattgga tttggcaagt ttgtggacaa agtcagcgtc    540

ccgcagacgg acatgaggcc tgagaagctg aaggagccct ggcccaacag tgaccccccc    600

ttctccttca agaacgtcat cagcctgaca gaagatgtgg atgagttccg gaataaactg    660

cagggagagc ggatctcagg caacctggat gctcctgagg gcggcttcga tgccatcctg    720

cagacagctg tgtgcacgag ggacattggc tggcgcccgg acagcaccca cctgctggtc    780

ttctccaccg agtcagcctt ccactatgag gctgatggcg ccaacgtgct ggctggcatc    840

atgagccgca acgatgaacg gtgccacctg gacaccacgg gcacctacac ccagtacagg    900

acacaggact acccgtcggt gcccaccctg gtgcgcctgc tcgccaagca caacatcatc    960

cccatctttg ctgtcaccaa ctactcctat agctactacg agaagcttca cacctatttc   1020

cctgtctcct cactgggggt gctgcaggag gactcgtcca acatcgtgga gctgctggag   1080

gaggccttca atcggatccg ctccaacctg gacatccggg ccctagacag cccccgaggc   1140

cttcggacag aggtcacctc caagatgttc cagaagacga ggactgggtc ctttcacatc   1200

cggcgggggg aagtgggtat ataccaggtg cagctgcggg cccttgagca cgtggatggg   1260

acgcacgtgt gccagctgcc ggaggaccag aagggcaaca tccatctgaa accttccttc   1320

tccgacggcc tcaagatgga cgcgggcatc atctgtgatg tgtgcacctg cgagctgcaa   1380

aaagaggtgc ggtcagctcg ctgcagcttc aacggagact tcgtgtgcgg acagtgtgtg   1440

tgcagcgagg gctggagtgg ccagacctgc aactgctcca ccggctctct gagtgacatt   1500

cagccctgcc tgcgggaggg cgaggacaag ccgtgctccg gccgtgggga gtgccagtgc   1560

gggcactgtg tgtgctacgg cgaaggccgc tacgagggtc agttctgcga gtatgacaac   1620

ttccagtgtc cccgcacttc cgggttcctc tgcaatgacc gaggacgctg ctccatgggc   1680

cagtgtgtgt gtgagcctgg ttggacaggc ccaagctgtg actgtcccct cagcaatgcc   1740

acctgcatcg acagcaatgg gggcatctgt aatggacgtg gccactgtga gtgtggccgc   1800
```

-continued

```
tgccactgcc accagcagtc gctctacacg gacaccatct gcgagatcaa ctactcggcg   1860
atccacccgg gcctctgcga ggacctacgc tcctgcgtgc agtgccaggc gtggggcacc   1920
ggcgagaaga aggggcgcac gtgtgaggaa tgcaacttca aggtcaagat ggtggacgag   1980
cttaagagag ccgaggaggt ggtggtgcgc tgctccttcc gggacgagga tgacgactgc   2040
acctacagct acaccatgga aggtgacggc gcccctgggc ccaacagcac tgtcctggtg   2100
cacaagaaga aggactgccc tccgggctcc ttctggtggc tcatccccct gctcctcctc   2160
ctcctgccgc tcctggccct gctactgctg ctatgctgga agtactgtgc ctgctgcaag   2220
gcctgcctgg cacttctccc gtgctgcaac cgaggtcaca tggtgggctt taaggaagac   2280
cactacatgc tgcgggagaa cctgatggcc tctgaccact tggacacgcc catgctgcgc   2340
agcgggaacc tcaagggccg tgacgtggtc cgctggaagg tcaccaacaa catgcagcgg   2400
cctggctttg ccactcatgc cgccagcatc aaccccacag agctggtgcc ctacgggctg   2460
tccttgcgcc tggcccgcct ttgcaccgag aacctgctga agcctgacac tcgggagtgc   2520
gcccagctgc gccaggaggt ggaggagaac ctgaacgagg tctacaggca gatctccggt   2580
gtacacaagc tccagcagac caagttccgg cagcagccca atgccgggaa aaagcaagac   2640
cacaccattg tggacacagt gctgatggcg ccccgctcgg ccaagccggc cctgctgaag   2700
cttacagaga agcaggtgga acagagggcc ttccacgacc tcaaggtggc ccccggctac   2760
tacaccctca ctgcagacca ggacgcccgg ggcatggtgg agttccagga gggcgtggag   2820
ctggtggacg tacgggtgcc cctctttatc cggcctgagg atgacgacga gaagcagctg   2880
ctggtggagg ccatcgacgt gcccgcaggc actgccaccc tcggccgccg cctggtaaac   2940
atcaccatca tcaaggagca agccagagac gtggtgtcct ttgagcagcc tgagttctcg   3000
gtcagccgcg gggaccaggt ggcccgcatc cctgtcatcc ggcgtgtcct ggacggcggg   3060
aagtcccagg tctcctaccg cacacaggat ggcaccgcgc agggcaaccg ggactacatc   3120
cccgtggagg gtgagctgct gttccagcct ggggaggcct ggaaagagct gcaggtgaag   3180
ctcctggagc tgcaagaagt tgactccctc ctgcggggcc gccaggtccg ccgtttccac   3240
gtccagctca gcaaccctaa gtttggggcc cacctgggcc agccccactc caccaccatc   3300
atcatcaggg acccagatga actggaccgg agcttcacga gtcagatgtt gtcatcacag   3360
ccacccccctc acggcgacct gggcgccccg cagaacccca atgctaaggc cgctgggtcc   3420
aggaagatcc atttcaactg gctgccccct tctggcaagc caatggggta cagggtaaag   3480
tactggattc agggtgactc cgaatccgaa gcccacctgc tcgacagcaa ggtgccctca   3540
gtggagctca ccaacctgta cccgtattgc gactatgaga tgaaggtgtg cgcctacggg   3600
gctcagggcg agggaccta cagctccctg gtgtcctgcc gcacccacca ggaagtgccc   3660
agcgagccag ggcgtctggc cttcaatgtc gtctcctcca cggtgaccca gctgagctgg   3720
gctgagccgg ctgagaccaa cggtgagatc acagcctacg aggtctgcta tggcctggtc   3780
aacgatgaca accgacctat tgggcccatg aagaaagtgc tggttgacaa ccctaagaac   3840
cggatgctgc ttattgagaa ccttcgggag tcccagccct accgctacac ggtgaaggcg   3900
cgcaacgggg ccggctgggg gcctgagcgg gaggccatca tcaacctggc cacccagccc   3960
aagaggccca tgtccatccc catcatccct gacatcccta tcgtggacgc ccagagcggg   4020
gaggactacg acagcttcct tatgtacagc gatgacgttc tacgctctcc atcgggcagc   4080
cagaggccca gcgtctccga tgacactgag cacctggtga atggccggat ggactttgcc   4140
ttcccgggca gcaccaactc cctgcacagg atgaccacga ccagtgctgc tgcctatggc   4200
```

```
acccacctga gcccacacgt gccccaccgc gtgctaagca catcctccac cctcacacgg   4260

gactacaact cactgacccg ctcagaacac tcacactcga ccacactgcc cagggactac   4320

tccaccctca cctccgtctc ctcccacggc ctccctccca tctgggaaca cgggaggagc   4380

aggcttccgc tgtcctgggc cctggggtcc cggagtcggg ctcagatgaa agggttcccc   4440

ccttccaggg gcccacgaga ctctataatc ctggctggga ggccagcagc gccctcctgg   4500

ggcccagact ctcgcctgac tgctggtgtg cccgacacgc ccacccgcct ggtgttctct   4560

gccctggggc ccacatctct cagagtgagc tggcaggagc cgcggtgcga gcggccgctg   4620

cagggctaca gtgtggagta ccagctgctg aacggcggtg agctgcatcg gctcaacatc   4680

cccaaccctg cccagacctc ggtggtggtg gaagacctcc tgcccaacca ctcctacgtg   4740

ttccgcgtgc gggcccagag ccaggaaggc tggggccgag agcgtgaggg tgtcatcacc   4800

attgaatccc aggtgcaccc gcagagccca ctgtgtcccc tgccaggctc cgccttcact   4860

ttgagcactc ccagtgcccc aggcccgctg gtgttcactg ccctgagccc agactcgctg   4920

cagctgagct gggagcggcc acggaggccc aatggggata tcgtcggcta cctggtgacc   4980

tgtgagatgg cccaaggagg agggccagcc accgcattcc gggtggatgg agacagcccc   5040

gagagccggc tgaccgtgcc gggcctcagc gagaacgtgc cctacaagtt caaggtgcag   5100

gccaggacca ctgagggctt cgggccagag cgcgagggca tcatcaccat agagtcccag   5160

gatggaggac ccttcccgca gctgggcagc cgtgccgggc tcttccagca cccgctgcaa   5220

agcgagtaca gcagcatcac caccacccac accagcgcca ccgagccctt cctagtggat   5280

gggctgaccc tgggggccca gcacctggag gcaggcggct ccctcacccg gcatgtgacc   5340

caggagtttg tgagccggac actgaccacc agcggaaccc ttagcaccca catggaccaa   5400

cagttcttcc aaacttga                                                 5418
```

```
<210> SEQ ID NO 3
<211> LENGTH: 5259
<212> TYPE: DNA
<213> ORGANISM: Homo sapiens

<400> SEQUENCE: 3

atggcagggc cacgccccag cccatgggcc aggctgctcc tggcagcctt gatcagcgtc     60

agcctctctg ggaccttggc aaaccgctgc aagaaggccc cagtgaagag ctgcacggag    120

tgtgtccgtg tggataagga ctgcgcctac tgcacagacg agatgttcag ggaccggcgc    180

tgcaacaccc aggcggagct gctggccgcg ggctgccagc gggagagcat cgtggtcatg    240

gagagcagct tccaaatcac agaggagacc cagattgaca ccaccctgcg gcgcagccag    300

atgtcccccc aaggcctgcg ggtccgtctg cggcccggtg aggagcggca ttttgagctg    360

gaggtgtttg agccactgga gagccccgtg gacctgtaca tcctcatgga cttctccaac    420

tccatgtccg atgatctgga caacctcaag aagatggggc agaacctggc tcgggtcctg    480

agccagctca ccagcgacta cactattgga tttggcaagt ttgtggacaa agtcagcgtc    540

ccgcagacgg acatgaggcc tgagaagctg aaggagccct ggcccaacag tgacccccc    600

ttctccttca agaacgtcat cagcctgaca gaagatgtgg atgagttccg gaataaactg    660

cagggagagc ggatctcagg caacctggat gctcctgagg gcggcttcga tgccatcctg    720

cagacagctg tgtgcacgag ggacattggc tggcgcccgg acagcaccca cctgctggtc    780

ttctccaccg agtcagcctt ccactatgag gctgatggcg ccaacgtgct ggctggcatc    840
```

-continued

```
atgagccgca acgatgaacg gtgccacctg gacaccacgg gcacctacac ccagtacagg    900
acacaggact acccgtcggt gcccaccctg gtgcgcctgc tcgccaagca caacatcatc    960
cccatctttg ctgtcaccaa ctactcctat agctactacg agaagcttca cacctatttc   1020
cctgtctcct cactgggggt gctgcaggag gactcgtcca acatcgtgga gctgctggag   1080
gaggccttca atcggatccg ctccaacctg gacatccggg ccctagacag cccccgaggc   1140
cttcggacag aggtcacctc caagatgttc cagaagacga ggactgggtc ctttcacatc   1200
cggcgggggg aagtgggtat ataccaggtg cagctgcggg cccttgagca cgtggatggg   1260
acgcacgtgt gccagctgcc ggaggaccag aagggcaaca tccatctgaa accttccttc   1320
tccgacggcc tcaagatgga cgcgggcatc atctgtgatg tgtgcacctg cgagctgcaa   1380
aaagaggtgc ggtcagctcg ctgcagcttc aacggagact tcgtgtgcgg acagtgtgtg   1440
tgcagcgagg gctggagtgg ccagacctgc aactgctcca ccggctctct gagtgacatt   1500
cagccctgcc tgcgggaggg cgaggacaag ccgtgctccg gccgtgggga gtgccagtgc   1560
gggcactgtg tgtgctacgg cgaaggccgc tacgagggtc agttctgcga gtatgacaac   1620
ttccagtgtc cccgcacttc cgggttcctc tgcaatgacc gaggacgctg ctccatgggc   1680
cagtgtgtgt gtgagcctgg ttggacaggc ccaagctgtg actgtcccct cagcaatgcc   1740
acctgcatcg acagcaatgg gggcatctgt aatggacgtg gccactgtga gtgtggccgc   1800
tgccactgcc accagcagtc gctctacacg gacaccatct gcgagatcaa ctactcggcg   1860
atccacccgg gcctctgcga ggacctacgc tcctgcgtgc agtgccaggc gtggggcacc   1920
ggcgagaaga aggggcgcac gtgtgaggaa tgcaacttca aggtcaagat ggtggacgag   1980
cttaagagag ccgaggaggt ggtggtgcgc tgctccttcc gggacgagga tgacgactgc   2040
acctacagct acaccatgga aggtgacggc gcccctgggc ccaacagcac tgtcctggtg   2100
cacaagaaga aggactgccc tccgggctcc ttctggtggc tcatccccct gctcctcctc   2160
ctcctgccgc tcctggccct gctactgctg ctatgctgga agtactgtgc ctgctgcaag   2220
gcctgcctgg cacttctccc gtgctgcaac cgaggtcaca tggtgggctt taaggaagac   2280
cactacatgc tgcgggagaa cctgatggcc tctgaccact tggacacgcc catgctgcgc   2340
agcgggaacc tcaagggccg tgacgtggtc cgctggaagg tcaccaacaa catgcagcgg   2400
cctggctttg ccactcatgc cgccagcatc aaccccacag agctggtgcc ctacgggctg   2460
tccttgcgcc tggcccgcct ttgcaccgag aacctgctga agcctgacac tcgggagtgc   2520
gcccagctgc gccaggaggt ggaggagaac ctgaacgagg tctacaggca gatctccggt   2580
gtacacaagc tccagcagac caagttccgg cagcagccca atgccgggaa aaagcaagac   2640
cacaccattg tggacacagt gctgatggcg ccccgctcgg ccaagccggc cctgctgaag   2700
cttacagaga agcaggtgga acagagggcc ttccacgacc tcaaggtggc ccccggctac   2760
tacaccctca ctgcagacca ggacgcccgg ggcatggtgg agttccagga gggcgtggag   2820
ctggtggacg tacgggtgcc cctctttatc cggcctgagg atgacgacga gaagcagctg   2880
ctggtggagg ccatcgacgt gcccgcaggc actgccaccc tcggccgccg cctggtaaac   2940
atcaccatca tcaaggagca agccagagac gtggtgtcct ttgagcagcc tgagttctcg   3000
gtcagccgcg gggaccaggt ggcccgcatc cctgtcatcc ggcgtgtcct ggacggcggg   3060
aagtcccagg tctcctaccg cacacaggat ggcaccgcgc agggcaaccg ggactacatc   3120
cccgtggagg gtgagctgct gttccagcct ggggaggcct ggaaagagct gcaggtgaag   3180
ctcctggagc tgcaagaagt tgactccctc ctgcggggcc gccaggtccg ccgtttccac   3240
```

```
gtccagctca gcaaccctaa gtttggggcc cacctgggcc agccccactc caccaccatc   3300

atcatcaggg acccagatga actggaccgg agcttcacga gtcagatgtt gtcatcacag   3360

ccacccccctc acggcgacct gggcgccccg cagaacccca atgctaaggc cgctgggtcc   3420

aggaagatcc atttcaactg gctgcccccct tctggcaagc caatggggta cagggtaaag   3480

tactggattc agggtgactc cgaatccgaa gcccacctgc tcgacagcaa ggtgccctca   3540

gtggagctca ccaacctgta cccgtattgc gactatgaga tgaaggtgtg cgcctacggg   3600

gctcagggcg agggaccccta cagctccctg gtgtcctgcc gcacccacca ggaagtgccc   3660

agcgagccag ggcgtctggc cttcaatgtc gtctcctcca cggtgaccca gctgagctgg   3720

gctgagccgg ctgagaccaa cggtgagatc acagcctacg aggtctgcta tggcctggtc   3780

aacgatgaca accgacctat tgggcccatg aagaaagtgc tggttgacaa ccctaagaac   3840

cggatgctgc ttattgagaa ccttcgggag tcccagccct accgctacac ggtgaaggcg   3900

cgcaacgggg ccggctgggg gcctgagcgg gaggccatca tcaacctggc cacccagccc   3960

aagaggccca tgtccatccc catcatccct gacatcccta tcgtggacgc ccagagcggg   4020

gaggactacg acagcttcct tatgtacagc gatgacgttc tacgctctcc atcgggcagc   4080

cagaggccca gcgtctccga tgacactgag cacctggtga atggccggat ggactttgcc   4140

ttcccgggca gcaccaactc cctgcacagg atgaccacga ccagtgctgc tgcctatggc   4200

acccacctga gcccacacgt gccccaccgc gtgctaagca catcctccac cctcacacgg   4260

gactacaact cactgacccg ctcagaacac tcacactcga ccacactgcc cagggactac   4320

tccaccctca cctccgtctc ctcccacgac tctcgcctga ctgctggtgt gcccgacacg   4380

cccacccgcc tggtgttctc tgccctgggg cccacatctc tcagagtgag ctggcaggag   4440

ccgcggtgcg agcggccgct gcagggctac agtgtggagt accagctgct gaacggcggt   4500

gagctgcatc ggctcaacat ccccaaccct gcccagacct cggtggtggt ggaagacctc   4560

ctgcccaacc actcctacgt gttccgcgtg cgggcccaga gccaggaagg ctggggccga   4620

gagcgtgagg gtgtcatcac cattgaatcc caggtgcacc cgcagagccc actgtgtccc   4680

ctgccaggct ccgccttcac tttgagcact cccagtgccc caggcccgct ggtgttcact   4740

gccctgagcc cagactcgct gcagctgagc tgggagcggc cacggaggcc caatggggat   4800

atcgtcggct acctggtgac ctgtgagatg gcccaaggag gagggccagc caccgcattc   4860

cgggtggatg gagacagccc cgagagccgg ctgaccgtgc cgggcctcag cgagaacgtg   4920

ccctacaagt tcaaggtgca ggccaggacc actgagggct tcgggccaga gcgcgagggc   4980

atcatcacca tagagtccca ggatggagga cccttcccgc agctgggcag ccgtgccggg   5040

ctcttccagc acccgctgca aagcgagtac agcagcatca ccaccaccca caccagcgcc   5100

accgagccct tcctagtgga tgggctgacc ctgggggccc agcacctgga ggcaggcggc   5160

tccctcaccc ggcatgtgac ccaggagttt gtgagccgga cactgaccac cagcggaacc   5220

cttagcaccc acatggacca acagttcttc caaacttga                           5259
```

<210> SEQ ID NO 4
<211> LENGTH: 1563
<212> TYPE: DNA
<213> ORGANISM: Homo sapiens

<400> SEQUENCE: 4

```
atgtctctgt ctcgctcaga ggagatgcac cggctcacgg aaaatgtcta taagaccatc     60
```

-continued

```
atggagcagt tcaaccctag cctccggaac ttcatcgcca tggggaagaa ttacgagaag    120

gcactggcag gtgtgacgta tgcagccaaa ggctactttg acgccctggt gaagatgggg    180

gagctggcca gcgagagcca gggctccaaa gaactcggag acgttctctt ccagatggct    240

gaagtccaca ggcagatcca gaatcagctg gaagaaatgc tgaagtcttt tcacaacgag    300

ctgcttacgc agctggagca gaaggtggag ctggactcca ggtatctgag tgctgcgctg    360

aagaaatacc agactgagca aaggagcaaa ggcgacgccc tggacaagtg tcaggctgag    420

ctgaagaagc ttcggaagaa gagccagggc agcaagaatc ctcagaagta ctcggacaag    480

gagctgcagt acatcgacgc catcagcaac aagcagggcg agctggagaa ttacgtgtcc    540

gacggctaca agaccgcact gacagaggag cgcaggcgct tctgcttcct ggtggagaag    600

cagtgcgccg tggccaagaa ctccgcggcc taccactcca agggcaagga gctgctggcg    660

cagaagctgc cgctgtggca acaggcctgt gccgacccca gcaagatccc ggagcgcgcg    720

gtgcagctca tgcagcaggt ggccagcaac ggcgccaccc tccccagcgc cctgtcggcc    780

tccaagtcca acctggtcat ttccgacccc attccggggg ccaagcccct gccggtgccc    840

cccgagctgg caccgttcgt ggggcggatg tctgcccagg agagcacacc catcatgaac    900

ggcgtcacag gcccggatgg cgaggactac agcccgtggg ctgaccgcaa ggctgcccag    960

cccaaatccc tgtctcctcc gcagtctcag agcaagctca gcgactccta ctccaacaca   1020

ctccccgtgc gcaagagcgt gaccccaaaa aacagctatg ccaccaccga gaacaagact   1080

ctgcctcgct cgagctccat ggcagccggc ctggagcgca atggccgtat gcgggtgaag   1140

gccatcttct cccacgctgc tggggacaac agcaccctcc tgagcttcaa ggagggtgac   1200

ctcattaccc tgctggtgcc tgaggcccgc gatggctggc actacggaga gagtgagaag   1260

accaagatgc ggggctggtt tcccttctcc tacacccggg tcttggacag cgatggcagt   1320

gacaggctgc acatgagcct gcagcaaggg aagagcagca gcacgggcaa cctcctggac   1380

aaggacgacc tggccatccc acccccgat tacggcgccg cctcccgggc cttccccgcc   1440

cagacggcca gcggcttcaa gcagaggccc tacagtgtgg ccgtgcccgc cttctcccag   1500

ggcctggatg actatggagc gcggtccatg agcagcgccg atgtggaagt ggccagattc   1560

tga                                                                  1563
```

<210> SEQ ID NO 5
<211> LENGTH: 1822
<212> TYPE: PRT
<213> ORGANISM: Homo sapiens
<220> FEATURE:
<221> NAME/KEY: misc_feature
<222> LOCATION: (1069)..(1069)
<223> OTHER INFORMATION: Phosphorylation site
<220> FEATURE:
<221> NAME/KEY: misc_feature
<222> LOCATION: (1455)..(1455)
<223> OTHER INFORMATION: Phosphorylation site
<220> FEATURE:
<221> NAME/KEY: misc_feature
<222> LOCATION: (1457)..(1457)
<223> OTHER INFORMATION: Phosphorylation site
<220> FEATURE:
<221> NAME/KEY: misc_feature
<222> LOCATION: (1518)..(1518)
<223> OTHER INFORMATION: Phosphorylation site

<400> SEQUENCE: 5

```
Met Ala Gly Pro Arg Pro Ser Pro Trp Ala Arg Leu Leu Leu Ala Ala
1               5                   10                  15
```

```
Leu Ile Ser Val Ser Leu Ser Gly Thr Leu Ala Asn Arg Cys Lys Lys
            20                  25                  30

Ala Pro Val Lys Ser Cys Thr Glu Cys Val Arg Val Asp Lys Asp Cys
        35                  40                  45

Ala Tyr Cys Thr Asp Glu Met Phe Arg Asp Arg Arg Cys Asn Thr Gln
    50                  55                  60

Ala Glu Leu Leu Ala Ala Gly Cys Gln Arg Glu Ser Ile Val Val Met
65                  70                  75                  80

Glu Ser Ser Phe Gln Ile Thr Glu Glu Thr Gln Ile Asp Thr Thr Leu
                85                  90                  95

Arg Arg Ser Gln Met Ser Pro Gln Gly Leu Arg Val Arg Leu Arg Pro
            100                 105                 110

Gly Glu Glu Arg His Phe Glu Leu Glu Val Phe Glu Pro Leu Glu Ser
        115                 120                 125

Pro Val Asp Leu Tyr Ile Leu Met Asp Phe Ser Asn Ser Met Ser Asp
    130                 135                 140

Asp Leu Asp Asn Leu Lys Lys Met Gly Gln Asn Leu Ala Arg Val Leu
145                 150                 155                 160

Ser Gln Leu Thr Ser Asp Tyr Thr Ile Gly Phe Gly Lys Phe Val Asp
                165                 170                 175

Lys Val Ser Val Pro Gln Thr Asp Met Arg Pro Glu Lys Leu Lys Glu
            180                 185                 190

Pro Trp Pro Asn Ser Asp Pro Pro Phe Ser Phe Lys Asn Val Ile Ser
        195                 200                 205

Leu Thr Glu Asp Val Asp Glu Phe Arg Asn Lys Leu Gln Gly Glu Arg
    210                 215                 220

Ile Ser Gly Asn Leu Asp Ala Pro Glu Gly Gly Phe Asp Ala Ile Leu
225                 230                 235                 240

Gln Thr Ala Val Cys Thr Arg Asp Ile Gly Trp Arg Pro Asp Ser Thr
                245                 250                 255

His Leu Leu Val Phe Ser Thr Glu Ser Ala Phe His Tyr Glu Ala Asp
            260                 265                 270

Gly Ala Asn Val Leu Ala Gly Ile Met Ser Arg Asn Asp Glu Arg Cys
        275                 280                 285

His Leu Asp Thr Thr Gly Thr Tyr Thr Gln Tyr Arg Thr Gln Asp Tyr
    290                 295                 300

Pro Ser Val Pro Thr Leu Val Arg Leu Leu Ala Lys His Asn Ile Ile
305                 310                 315                 320

Pro Ile Phe Ala Val Thr Asn Tyr Ser Tyr Ser Tyr Tyr Glu Lys Leu
                325                 330                 335

His Thr Tyr Phe Pro Val Ser Ser Leu Gly Val Leu Gln Glu Asp Ser
            340                 345                 350

Ser Asn Ile Val Glu Leu Leu Glu Glu Ala Phe Asn Arg Ile Arg Ser
        355                 360                 365

Asn Leu Asp Ile Arg Ala Leu Asp Ser Pro Arg Gly Leu Arg Thr Glu
    370                 375                 380

Val Thr Ser Lys Met Phe Gln Lys Thr Arg Thr Gly Ser Phe His Ile
385                 390                 395                 400

Arg Arg Gly Glu Val Gly Ile Tyr Gln Val Gln Leu Arg Ala Leu Glu
                405                 410                 415

His Val Asp Gly Thr His Val Cys Gln Leu Pro Glu Asp Gln Lys Gly
            420                 425                 430

Asn Ile His Leu Lys Pro Ser Phe Ser Asp Gly Leu Lys Met Asp Ala
```

```
        435                 440                 445

Gly Ile Ile Cys Asp Val Cys Thr Cys Glu Leu Gln Lys Glu Val Arg
    450                 455                 460

Ser Ala Arg Cys Ser Phe Asn Gly Asp Phe Val Cys Gly Gln Cys Val
465                 470                 475                 480

Cys Ser Glu Gly Trp Ser Gly Gln Thr Cys Asn Cys Ser Thr Gly Ser
                485                 490                 495

Leu Ser Asp Ile Gln Pro Cys Leu Arg Glu Gly Glu Asp Lys Pro Cys
            500                 505                 510

Ser Gly Arg Gly Glu Cys Gln Cys Gly His Cys Val Cys Tyr Gly Glu
        515                 520                 525

Gly Arg Tyr Glu Gly Gln Phe Cys Glu Tyr Asp Asn Phe Gln Cys Pro
    530                 535                 540

Arg Thr Ser Gly Phe Leu Cys Asn Asp Arg Gly Arg Cys Ser Met Gly
545                 550                 555                 560

Gln Cys Val Cys Glu Pro Gly Trp Thr Gly Pro Ser Cys Asp Cys Pro
                565                 570                 575

Leu Ser Asn Ala Thr Cys Ile Asp Ser Asn Gly Gly Ile Cys Asn Gly
            580                 585                 590

Arg Gly His Cys Glu Cys Gly Arg Cys His Cys His Gln Gln Ser Leu
        595                 600                 605

Tyr Thr Asp Thr Ile Cys Glu Ile Asn Tyr Ser Ala Ile His Pro Gly
    610                 615                 620

Leu Cys Glu Asp Leu Arg Ser Cys Val Gln Cys Gln Ala Trp Gly Thr
625                 630                 635                 640

Gly Glu Lys Lys Gly Arg Thr Cys Glu Glu Cys Asn Phe Lys Val Lys
                645                 650                 655

Met Val Asp Glu Leu Lys Arg Ala Glu Glu Val Val Val Arg Cys Ser
            660                 665                 670

Phe Arg Asp Glu Asp Asp Asp Cys Thr Tyr Ser Tyr Thr Met Glu Gly
        675                 680                 685

Asp Gly Ala Pro Gly Pro Asn Ser Thr Val Leu Val His Lys Lys Lys
    690                 695                 700

Asp Cys Pro Pro Gly Ser Phe Trp Trp Leu Ile Pro Leu Leu Leu Leu
705                 710                 715                 720

Leu Leu Pro Leu Leu Ala Leu Leu Leu Leu Leu Cys Trp Lys Tyr Cys
                725                 730                 735

Ala Cys Cys Lys Ala Cys Leu Ala Leu Leu Pro Cys Cys Asn Arg Gly
            740                 745                 750

His Met Val Gly Phe Lys Glu Asp His Tyr Met Leu Arg Glu Asn Leu
        755                 760                 765

Met Ala Ser Asp His Leu Asp Thr Pro Met Leu Arg Ser Gly Asn Leu
    770                 775                 780

Lys Gly Arg Asp Val Val Arg Trp Lys Val Thr Asn Asn Met Gln Arg
785                 790                 795                 800

Pro Gly Phe Ala Thr His Ala Ala Ser Ile Asn Pro Thr Glu Leu Val
                805                 810                 815

Pro Tyr Gly Leu Ser Leu Arg Leu Ala Arg Leu Cys Thr Glu Asn Leu
            820                 825                 830

Leu Lys Pro Asp Thr Arg Glu Cys Ala Gln Leu Arg Gln Glu Val Glu
        835                 840                 845

Glu Asn Leu Asn Glu Val Tyr Arg Gln Ile Ser Gly Val His Lys Leu
    850                 855                 860
```

-continued

```
Gln Gln Thr Lys Phe Arg Gln Gln Pro Asn Ala Gly Lys Lys Gln Asp
865                 870                 875                 880

His Thr Ile Val Asp Thr Val Leu Met Ala Pro Arg Ser Ala Lys Pro
                885                 890                 895

Ala Leu Leu Lys Leu Thr Glu Lys Gln Val Glu Gln Arg Ala Phe His
            900                 905                 910

Asp Leu Lys Val Ala Pro Gly Tyr Tyr Thr Leu Thr Ala Asp Gln Asp
        915                 920                 925

Ala Arg Gly Met Val Glu Phe Gln Glu Gly Val Glu Leu Val Asp Val
    930                 935                 940

Arg Val Pro Leu Phe Ile Arg Pro Glu Asp Asp Asp Glu Lys Gln Leu
945                 950                 955                 960

Leu Val Glu Ala Ile Asp Val Pro Ala Gly Thr Ala Thr Leu Gly Arg
                965                 970                 975

Arg Leu Val Asn Ile Thr Ile Ile Lys Glu Gln Ala Arg Asp Val Val
            980                 985                 990

Ser Phe Glu Gln Pro Glu Phe Ser  Val Ser Arg Gly Asp  Gln Val Ala
        995                 1000                1005

Arg Ile  Pro Val Ile Arg Arg  Val Leu Asp Gly Gly  Lys Ser Gln
    1010                1015                1020

Val Ser  Tyr Arg Thr Gln Asp  Gly Thr Ala Gln Gly  Asn Arg Asp
    1025                1030                1035

Tyr Ile  Pro Val Glu Gly Glu  Leu Leu Phe Gln Pro  Gly Glu Ala
    1040                1045                1050

Trp Lys  Glu Leu Gln Val Lys  Leu Leu Glu Leu Gln  Glu Val Asp
    1055                1060                1065

Ser Leu  Leu Arg Gly Arg Gln  Val Arg Arg Phe His  Val Gln Leu
    1070                1075                1080

Ser Asn  Pro Lys Phe Gly Ala  His Leu Gly Gln Pro  His Ser Thr
    1085                1090                1095

Thr Ile  Ile Ile Arg Asp Pro  Asp Glu Leu Asp Arg  Ser Phe Thr
    1100                1105                1110

Ser Gln  Met Leu Ser Ser Gln  Pro Pro Pro His Gly  Asp Leu Gly
    1115                1120                1125

Ala Pro  Gln Asn Pro Asn Ala  Lys Ala Ala Gly Ser  Arg Lys Ile
    1130                1135                1140

His Phe  Asn Trp Leu Pro Pro  Ser Gly Lys Pro Met  Gly Tyr Arg
    1145                1150                1155

Val Lys  Tyr Trp Ile Gln Gly  Asp Ser Glu Ser Glu  Ala His Leu
    1160                1165                1170

Leu Asp  Ser Lys Val Pro Ser  Val Glu Leu Thr Asn  Leu Tyr Pro
    1175                1180                1185

Tyr Cys  Asp Tyr Glu Met Lys  Val Cys Ala Tyr Gly  Ala Gln Gly
    1190                1195                1200

Glu Gly  Pro Tyr Ser Ser Leu  Val Ser Cys Arg Thr  His Gln Glu
    1205                1210                1215

Val Pro  Ser Glu Pro Gly Arg  Leu Ala Phe Asn Val  Val Ser Ser
    1220                1225                1230

Thr Val  Thr Gln Leu Ser Trp  Ala Glu Pro Ala Glu  Thr Asn Gly
    1235                1240                1245

Glu Ile  Thr Ala Tyr Glu Val  Cys Tyr Gly Leu Val  Asn Asp Asp
    1250                1255                1260
```

```
Asn Arg Pro Ile Gly Pro Met Lys Lys Val Leu Val Asp Asn Pro
    1265                1270                1275

Lys Asn Arg Met Leu Leu Ile Glu Asn Leu Arg Glu Ser Gln Pro
    1280                1285                1290

Tyr Arg Tyr Thr Val Lys Ala Arg Asn Gly Ala Gly Trp Gly Pro
    1295                1300                1305

Glu Arg Glu Ala Ile Ile Asn Leu Ala Thr Gln Pro Lys Arg Pro
    1310                1315                1320

Met Ser Ile Pro Ile Ile Pro Asp Ile Pro Ile Val Asp Ala Gln
    1325                1330                1335

Ser Gly Glu Asp Tyr Asp Ser Phe Leu Met Tyr Ser Asp Asp Val
    1340                1345                1350

Leu Arg Ser Pro Ser Gly Ser Gln Arg Pro Ser Val Ser Asp Asp
    1355                1360                1365

Thr Gly Cys Gly Trp Lys Phe Glu Pro Leu Leu Gly Glu Glu Leu
    1370                1375                1380

Asp Leu Arg Arg Val Thr Trp Arg Leu Pro Pro Glu Leu Ile Pro
    1385                1390                1395

Arg Leu Ser Ala Ser Ser Gly Arg Ser Ser Asp Ala Glu Ala Pro
    1400                1405                1410

His Gly Pro Pro Asp Asp Gly Gly Ala Gly Gly Lys Gly Gly Ser
    1415                1420                1425

Leu Pro Arg Ser Ala Thr Pro Gly Pro Pro Gly Glu His Leu Val
    1430                1435                1440

Asn Gly Arg Met Asp Phe Ala Phe Pro Gly Ser Thr Asn Ser Leu
    1445                1450                1455

His Arg Met Thr Thr Thr Ser Ala Ala Ala Tyr Gly Thr His Leu
    1460                1465                1470

Ser Pro His Val Pro His Arg Val Leu Ser Thr Ser Ser Thr Leu
    1475                1480                1485

Thr Arg Asp Tyr Asn Ser Leu Thr Arg Ser Glu His Ser His Ser
    1490                1495                1500

Thr Thr Leu Pro Arg Asp Tyr Ser Thr Leu Thr Ser Val Ser Ser
    1505                1510                1515

His Asp Ser Arg Leu Thr Ala Gly Val Pro Asp Thr Pro Thr Arg
    1520                1525                1530

Leu Val Phe Ser Ala Leu Gly Pro Thr Ser Leu Arg Val Ser Trp
    1535                1540                1545

Gln Glu Pro Arg Cys Glu Arg Pro Leu Gln Gly Tyr Ser Val Glu
    1550                1555                1560

Tyr Gln Leu Leu Asn Gly Gly Glu Leu His Arg Leu Asn Ile Pro
    1565                1570                1575

Asn Pro Ala Gln Thr Ser Val Val Val Glu Asp Leu Leu Pro Asn
    1580                1585                1590

His Ser Tyr Val Phe Arg Val Arg Ala Gln Ser Gln Glu Gly Trp
    1595                1600                1605

Gly Arg Glu Arg Glu Gly Val Ile Thr Ile Glu Ser Gln Val His
    1610                1615                1620

Pro Gln Ser Pro Leu Cys Pro Leu Pro Gly Ser Ala Phe Thr Leu
    1625                1630                1635

Ser Thr Pro Ser Ala Pro Gly Pro Leu Val Phe Thr Ala Leu Ser
    1640                1645                1650

Pro Asp Ser Leu Gln Leu Ser Trp Glu Arg Pro Arg Arg Pro Asn
```

```
    1655                1660                1665

Gly Asp  Ile Val Gly Tyr Leu  Val Thr Cys Glu Met  Ala Gln Gly
    1670                1675                1680

Gly Gly  Pro Ala Thr Ala Phe  Arg Val Asp Gly Asp  Ser Pro Glu
    1685                1690                1695

Ser Arg  Leu Thr Val Pro Gly  Leu Ser Glu Asn Val  Pro Tyr Lys
    1700                1705                1710

Phe Lys  Val Gln Ala Arg Thr  Thr Glu Gly Phe Gly  Pro Glu Arg
    1715                1720                1725

Glu Gly  Ile Ile Thr Ile Glu  Ser Gln Asp Gly Gly  Pro Phe Pro
    1730                1735                1740

Gln Leu  Gly Ser Arg Ala Gly  Leu Phe Gln His Pro  Leu Gln Ser
    1745                1750                1755

Glu Tyr  Ser Ser Ile Thr Thr  Thr His Thr Ser Ala  Thr Glu Pro
    1760                1765                1770

Phe Leu  Val Asp Gly Leu Thr  Leu Gly Ala Gln His  Leu Glu Ala
    1775                1780                1785

Gly Gly  Ser Leu Thr Arg His  Val Thr Gln Glu Phe  Val Ser Arg
    1790                1795                1800

Thr Leu  Thr Thr Ser Gly Thr  Leu Ser Thr His Met  Asp Gln Gln
    1805                1810                1815

Phe Phe  Gln Thr
    1820


<210> SEQ ID NO 6
<211> LENGTH: 1752
<212> TYPE: PRT
<213> ORGANISM: Homo sapiens
<220> FEATURE:
<221> NAME/KEY: misc_feature
<222> LOCATION: (1069)..(1069)
<223> OTHER INFORMATION: Phosphorylation site
<220> FEATURE:
<221> NAME/KEY: misc_feature
<222> LOCATION: (1385)..(1385)
<223> OTHER INFORMATION: Phosphorylation site
<220> FEATURE:
<221> NAME/KEY: misc_feature
<222> LOCATION: (1387)..(1387)
<223> OTHER INFORMATION: Phosphorylation site
<220> FEATURE:
<221> NAME/KEY: misc_feature
<222> LOCATION: (1448)..(1448)
<223> OTHER INFORMATION: Phosphorylation site

<400> SEQUENCE: 6

Met Ala Gly Pro Arg Pro Ser Pro Trp Ala Arg Leu Leu Leu Ala Ala
1               5                   10                  15

Leu Ile Ser Val Ser Leu Ser Gly Thr Leu Ala Asn Arg Cys Lys Lys
            20                  25                  30

Ala Pro Val Lys Ser Cys Thr Glu Cys Val Arg Val Asp Lys Asp Cys
        35                  40                  45

Ala Tyr Cys Thr Asp Glu Met Phe Arg Asp Arg Arg Cys Asn Thr Gln
    50                  55                  60

Ala Glu Leu Leu Ala Ala Gly Cys Gln Arg Glu Ser Ile Val Val Met
65                  70                  75                  80

Glu Ser Ser Phe Gln Ile Thr Glu Glu Thr Gln Ile Asp Thr Thr Leu
                85                  90                  95

Arg Arg Ser Gln Met Ser Pro Gln Gly Leu Arg Val Arg Leu Arg Pro
            100                 105                 110
```

-continued

```
Gly Glu Glu Arg His Phe Glu Leu Glu Val Phe Glu Pro Leu Glu Ser
        115                 120                 125

Pro Val Asp Leu Tyr Ile Leu Met Asp Phe Ser Asn Ser Met Ser Asp
    130                 135                 140

Asp Leu Asp Asn Leu Lys Lys Met Gly Gln Asn Leu Ala Arg Val Leu
145                 150                 155                 160

Ser Gln Leu Thr Ser Asp Tyr Thr Ile Gly Phe Gly Lys Phe Val Asp
                165                 170                 175

Lys Val Ser Val Pro Gln Thr Asp Met Arg Pro Glu Lys Leu Lys Glu
            180                 185                 190

Pro Trp Pro Asn Ser Asp Pro Pro Phe Ser Phe Lys Asn Val Ile Ser
        195                 200                 205

Leu Thr Glu Asp Val Asp Glu Phe Arg Asn Lys Leu Gln Gly Glu Arg
    210                 215                 220

Ile Ser Gly Asn Leu Asp Ala Pro Glu Gly Gly Phe Asp Ala Ile Leu
225                 230                 235                 240

Gln Thr Ala Val Cys Thr Arg Asp Ile Gly Trp Arg Pro Asp Ser Thr
                245                 250                 255

His Leu Leu Val Phe Ser Thr Glu Ser Ala Phe His Tyr Glu Ala Asp
            260                 265                 270

Gly Ala Asn Val Leu Ala Gly Ile Met Ser Arg Asn Asp Glu Arg Cys
        275                 280                 285

His Leu Asp Thr Thr Gly Thr Tyr Thr Gln Tyr Arg Thr Gln Asp Tyr
    290                 295                 300

Pro Ser Val Pro Thr Leu Val Arg Leu Leu Ala Lys His Asn Ile Ile
305                 310                 315                 320

Pro Ile Phe Ala Val Thr Asn Tyr Ser Tyr Ser Tyr Tyr Glu Lys Leu
                325                 330                 335

His Thr Tyr Phe Pro Val Ser Ser Leu Gly Val Leu Gln Glu Asp Ser
            340                 345                 350

Ser Asn Ile Val Glu Leu Leu Glu Glu Ala Phe Asn Arg Ile Arg Ser
        355                 360                 365

Asn Leu Asp Ile Arg Ala Leu Asp Ser Pro Arg Gly Leu Arg Thr Glu
    370                 375                 380

Val Thr Ser Lys Met Phe Gln Lys Thr Arg Thr Gly Ser Phe His Ile
385                 390                 395                 400

Arg Arg Gly Glu Val Gly Ile Tyr Gln Val Gln Leu Arg Ala Leu Glu
                405                 410                 415

His Val Asp Gly Thr His Val Cys Gln Leu Pro Glu Asp Gln Lys Gly
            420                 425                 430

Asn Ile His Leu Lys Pro Ser Phe Ser Asp Gly Leu Lys Met Asp Ala
        435                 440                 445

Gly Ile Ile Cys Asp Val Cys Thr Cys Glu Leu Gln Lys Glu Val Arg
    450                 455                 460

Ser Ala Arg Cys Ser Phe Asn Gly Asp Phe Val Cys Gly Gln Cys Val
465                 470                 475                 480

Cys Ser Glu Gly Trp Ser Gly Gln Thr Cys Asn Cys Ser Thr Gly Ser
                485                 490                 495

Leu Ser Asp Ile Gln Pro Cys Leu Arg Glu Gly Glu Asp Lys Pro Cys
            500                 505                 510

Ser Gly Arg Gly Glu Cys Gln Cys Gly His Cys Val Cys Tyr Gly Glu
        515                 520                 525
```

```
Gly Arg Tyr Glu Gly Gln Phe Cys Glu Tyr Asp Asn Phe Gln Cys Pro
    530                 535                 540

Arg Thr Ser Gly Phe Leu Cys Asn Asp Arg Gly Arg Cys Ser Met Gly
545                 550                 555                 560

Gln Cys Val Cys Glu Pro Gly Trp Thr Gly Pro Ser Cys Asp Cys Pro
                565                 570                 575

Leu Ser Asn Ala Thr Cys Ile Asp Ser Asn Gly Gly Ile Cys Asn Gly
            580                 585                 590

Arg Gly His Cys Glu Cys Gly Arg Cys His Cys His Gln Gln Ser Leu
        595                 600                 605

Tyr Thr Asp Thr Ile Cys Glu Ile Asn Tyr Ser Ala Ile His Pro Gly
    610                 615                 620

Leu Cys Glu Asp Leu Arg Ser Cys Val Gln Cys Gln Ala Trp Gly Thr
625                 630                 635                 640

Gly Glu Lys Lys Gly Arg Thr Cys Glu Glu Cys Asn Phe Lys Val Lys
                645                 650                 655

Met Val Asp Glu Leu Lys Arg Ala Glu Glu Val Val Val Arg Cys Ser
            660                 665                 670

Phe Arg Asp Glu Asp Asp Asp Cys Thr Tyr Ser Tyr Thr Met Glu Gly
        675                 680                 685

Asp Gly Ala Pro Gly Pro Asn Ser Thr Val Leu Val His Lys Lys Lys
    690                 695                 700

Asp Cys Pro Pro Gly Ser Phe Trp Trp Leu Ile Pro Leu Leu Leu Leu
705                 710                 715                 720

Leu Leu Pro Leu Leu Ala Leu Leu Leu Leu Leu Cys Trp Lys Tyr Cys
                725                 730                 735

Ala Cys Cys Lys Ala Cys Leu Ala Leu Leu Pro Cys Cys Asn Arg Gly
            740                 745                 750

His Met Val Gly Phe Lys Glu Asp His Tyr Met Leu Arg Glu Asn Leu
        755                 760                 765

Met Ala Ser Asp His Leu Asp Thr Pro Met Leu Arg Ser Gly Asn Leu
    770                 775                 780

Lys Gly Arg Asp Val Val Arg Trp Lys Val Thr Asn Asn Met Gln Arg
785                 790                 795                 800

Pro Gly Phe Ala Thr His Ala Ala Ser Ile Asn Pro Thr Glu Leu Val
                805                 810                 815

Pro Tyr Gly Leu Ser Leu Arg Leu Ala Arg Leu Cys Thr Glu Asn Leu
            820                 825                 830

Leu Lys Pro Asp Thr Arg Glu Cys Ala Gln Leu Arg Gln Glu Val Glu
        835                 840                 845

Glu Asn Leu Asn Glu Val Tyr Arg Gln Ile Ser Gly Val His Lys Leu
    850                 855                 860

Gln Gln Thr Lys Phe Arg Gln Gln Pro Asn Ala Gly Lys Lys Gln Asp
865                 870                 875                 880

His Thr Ile Val Asp Thr Val Leu Met Ala Pro Arg Ser Ala Lys Pro
                885                 890                 895

Ala Leu Leu Lys Leu Thr Glu Lys Gln Val Glu Gln Arg Ala Phe His
            900                 905                 910

Asp Leu Lys Val Ala Pro Gly Tyr Tyr Thr Leu Thr Ala Asp Gln Asp
        915                 920                 925

Ala Arg Gly Met Val Glu Phe Gln Glu Gly Val Glu Leu Val Asp Val
    930                 935                 940

Arg Val Pro Leu Phe Ile Arg Pro Glu Asp Asp Asp Glu Lys Gln Leu
```

-continued

```
945                 950                 955                 960

Leu Val Glu Ala Ile Asp Val Pro Ala Gly Thr Ala Thr Leu Gly Arg
                965                 970                 975

Arg Leu Val Asn Ile Thr Ile Ile Lys Glu Gln Ala Arg Asp Val Val
            980                 985                 990

Ser Phe Glu Gln Pro Glu Phe Ser  Val Ser Arg Gly Asp  Gln Val Ala
        995                 1000                1005

Arg Ile  Pro Val Ile Arg Arg  Val Leu Asp Gly Gly  Lys Ser Gln
    1010                 1015                1020

Val Ser  Tyr Arg Thr Gln Asp  Gly Thr Ala Gln Gly  Asn Arg Asp
    1025                 1030                1035

Tyr Ile  Pro Val Glu Gly Glu  Leu Leu Phe Gln Pro  Gly Glu Ala
    1040                 1045                1050

Trp Lys  Glu Leu Gln Val Lys  Leu Leu Glu Leu Gln  Glu Val Asp
    1055                 1060                1065

Ser Leu  Leu Arg Gly Arg Gln  Val Arg Arg Phe His  Val Gln Leu
    1070                 1075                1080

Ser Asn  Pro Lys Phe Gly Ala  His Leu Gly Gln Pro  His Ser Thr
    1085                 1090                1095

Thr Ile  Ile Ile Arg Asp Pro  Asp Glu Leu Asp Arg  Ser Phe Thr
    1100                 1105                1110

Ser Gln  Met Leu Ser Ser Gln  Pro Pro Pro His Gly  Asp Leu Gly
    1115                 1120                1125

Ala Pro  Gln Asn Pro Asn Ala  Lys Ala Ala Gly Ser  Arg Lys Ile
    1130                 1135                1140

His Phe  Asn Trp Leu Pro Pro  Ser Gly Lys Pro Met  Gly Tyr Arg
    1145                 1150                1155

Val Lys  Tyr Trp Ile Gln Gly  Asp Ser Glu Ser Glu  Ala His Leu
    1160                 1165                1170

Leu Asp  Ser Lys Val Pro Ser  Val Glu Leu Thr Asn  Leu Tyr Pro
    1175                 1180                1185

Tyr Cys  Asp Tyr Glu Met Lys  Val Cys Ala Tyr Gly  Ala Gln Gly
    1190                 1195                1200

Glu Gly  Pro Tyr Ser Ser Leu  Val Ser Cys Arg Thr  His Gln Glu
    1205                 1210                1215

Val Pro  Ser Glu Pro Gly Arg  Leu Ala Phe Asn Val  Val Ser Ser
    1220                 1225                1230

Thr Val  Thr Gln Leu Ser Trp  Ala Glu Pro Ala Glu  Thr Asn Gly
    1235                 1240                1245

Glu Ile  Thr Ala Tyr Glu Val  Cys Tyr Gly Leu Val  Asn Asp Asp
    1250                 1255                1260

Asn Arg  Pro Ile Gly Pro Met  Lys Lys Val Leu Val  Asp Asn Pro
    1265                 1270                1275

Lys Asn  Arg Met Leu Leu Ile  Glu Asn Leu Arg Glu  Ser Gln Pro
    1280                 1285                1290

Tyr Arg  Tyr Thr Val Lys Ala  Arg Asn Gly Ala Gly  Trp Gly Pro
    1295                 1300                1305

Glu Arg  Glu Ala Ile Ile Asn  Leu Ala Thr Gln Pro  Lys Arg Pro
    1310                 1315                1320

Met Ser  Ile Pro Ile Ile Pro  Asp Ile Pro Ile Val  Asp Ala Gln
    1325                 1330                1335

Ser Gly  Glu Asp Tyr Asp Ser  Phe Leu Met Tyr Ser  Asp Asp Val
    1340                 1345                1350
```

Leu Arg Ser Pro Ser Gly Ser Gln Arg Pro Ser Val Ser Asp Asp
1355 1360 1365

Thr Glu His Leu Val Asn Gly Arg Met Asp Phe Ala Phe Pro Gly
1370 1375 1380

Ser Thr Asn Ser Leu His Arg Met Thr Thr Thr Ser Ala Ala Ala
1385 1390 1395

Tyr Gly Thr His Leu Ser Pro His Val Pro His Arg Val Leu Ser
1400 1405 1410

Thr Ser Ser Thr Leu Thr Arg Asp Tyr Asn Ser Leu Thr Arg Ser
1415 1420 1425

Glu His Ser His Ser Thr Thr Leu Pro Arg Asp Tyr Ser Thr Leu
1430 1435 1440

Thr Ser Val Ser Ser His Asp Ser Arg Leu Thr Ala Gly Val Pro
1445 1450 1455

Asp Thr Pro Thr Arg Leu Val Phe Ser Ala Leu Gly Pro Thr Ser
1460 1465 1470

Leu Arg Val Ser Trp Gln Glu Pro Arg Cys Glu Arg Pro Leu Gln
1475 1480 1485

Gly Tyr Ser Val Glu Tyr Gln Leu Leu Asn Gly Gly Glu Leu His
1490 1495 1500

Arg Leu Asn Ile Pro Asn Pro Ala Gln Thr Ser Val Val Val Glu
1505 1510 1515

Asp Leu Leu Pro Asn His Ser Tyr Val Phe Arg Val Arg Ala Gln
1520 1525 1530

Ser Gln Glu Gly Trp Gly Arg Glu Arg Glu Gly Val Ile Thr Ile
1535 1540 1545

Glu Ser Gln Val His Pro Gln Ser Pro Leu Cys Pro Leu Pro Gly
1550 1555 1560

Ser Ala Phe Thr Leu Ser Thr Pro Ser Ala Pro Gly Pro Leu Val
1565 1570 1575

Phe Thr Ala Leu Ser Pro Asp Ser Leu Gln Leu Ser Trp Glu Arg
1580 1585 1590

Pro Arg Arg Pro Asn Gly Asp Ile Val Gly Tyr Leu Val Thr Cys
1595 1600 1605

Glu Met Ala Gln Gly Gly Gly Pro Ala Thr Ala Phe Arg Val Asp
1610 1615 1620

Gly Asp Ser Pro Glu Ser Arg Leu Thr Val Pro Gly Leu Ser Glu
1625 1630 1635

Asn Val Pro Tyr Lys Phe Lys Val Gln Ala Arg Thr Thr Glu Gly
1640 1645 1650

Phe Gly Pro Glu Arg Glu Gly Ile Ile Thr Ile Glu Ser Gln Asp
1655 1660 1665

Gly Gly Pro Phe Pro Gln Leu Gly Ser Arg Ala Gly Leu Phe Gln
1670 1675 1680

His Pro Leu Gln Ser Glu Tyr Ser Ser Ile Thr Thr Thr His Thr
1685 1690 1695

Ser Ala Thr Glu Pro Phe Leu Val Asp Gly Leu Thr Leu Gly Ala
1700 1705 1710

Gln His Leu Glu Ala Gly Gly Ser Leu Thr Arg His Val Thr Gln
1715 1720 1725

Glu Phe Val Ser Arg Thr Leu Thr Thr Ser Gly Thr Leu Ser Thr
1730 1735 1740

-continued

```
His Met  Asp Gln Gln Phe Phe  Gln Thr
    1745                 1750


<210> SEQ ID NO 7
<211> LENGTH: 1805
<212> TYPE: PRT
<213> ORGANISM: Homo sapiens
<220> FEATURE:
<221> NAME/KEY: misc_feature
<222> LOCATION: (1069)..(1069)
<223> OTHER INFORMATION: Phosphorylation site
<220> FEATURE:
<221> NAME/KEY: misc_feature
<222> LOCATION: (1385)..(1385)
<223> OTHER INFORMATION: Phosphorylation site
<220> FEATURE:
<221> NAME/KEY: misc_feature
<222> LOCATION: (1387)..(1387)
<223> OTHER INFORMATION: Phosphorylation site

<400> SEQUENCE: 7

Met Ala Gly Pro Arg Pro Ser Pro Trp Ala Arg Leu Leu Leu Ala Ala
1               5                   10                  15

Leu Ile Ser Val Ser Leu Ser Gly Thr Leu Ala Asn Arg Cys Lys Lys
            20                  25                  30

Ala Pro Val Lys Ser Cys Thr Glu Cys Val Arg Val Asp Lys Asp Cys
        35                  40                  45

Ala Tyr Cys Thr Asp Glu Met Phe Arg Asp Arg Arg Cys Asn Thr Gln
    50                  55                  60

Ala Glu Leu Leu Ala Ala Gly Cys Gln Arg Glu Ser Ile Val Val Met
65                  70                  75                  80

Glu Ser Ser Phe Gln Ile Thr Glu Glu Thr Gln Ile Asp Thr Thr Leu
                85                  90                  95

Arg Arg Ser Gln Met Ser Pro Gln Gly Leu Arg Val Arg Leu Arg Pro
            100                 105                 110

Gly Glu Glu Arg His Phe Glu Leu Glu Val Phe Glu Pro Leu Glu Ser
        115                 120                 125

Pro Val Asp Leu Tyr Ile Leu Met Asp Phe Ser Asn Ser Met Ser Asp
    130                 135                 140

Asp Leu Asp Asn Leu Lys Lys Met Gly Gln Asn Leu Ala Arg Val Leu
145                 150                 155                 160

Ser Gln Leu Thr Ser Asp Tyr Thr Ile Gly Phe Gly Lys Phe Val Asp
                165                 170                 175

Lys Val Ser Val Pro Gln Thr Asp Met Arg Pro Glu Lys Leu Lys Glu
            180                 185                 190

Pro Trp Pro Asn Ser Asp Pro Pro Phe Ser Phe Lys Asn Val Ile Ser
        195                 200                 205

Leu Thr Glu Asp Val Asp Glu Phe Arg Asn Lys Leu Gln Gly Glu Arg
    210                 215                 220

Ile Ser Gly Asn Leu Asp Ala Pro Glu Gly Gly Phe Asp Ala Ile Leu
225                 230                 235                 240

Gln Thr Ala Val Cys Thr Arg Asp Ile Gly Trp Arg Pro Asp Ser Thr
                245                 250                 255

His Leu Leu Val Phe Ser Thr Glu Ser Ala Phe His Tyr Glu Ala Asp
            260                 265                 270

Gly Ala Asn Val Leu Ala Gly Ile Met Ser Arg Asn Asp Glu Arg Cys
        275                 280                 285

His Leu Asp Thr Thr Gly Thr Tyr Thr Gln Tyr Arg Thr Gln Asp Tyr
    290                 295                 300
```

-continued

```
Pro Ser Val Pro Thr Leu Val Arg Leu Leu Ala Lys His Asn Ile Ile
305                 310                 315                 320

Pro Ile Phe Ala Val Thr Asn Tyr Ser Tyr Ser Tyr Tyr Glu Lys Leu
                325                 330                 335

His Thr Tyr Phe Pro Val Ser Ser Leu Gly Val Leu Gln Glu Asp Ser
            340                 345                 350

Ser Asn Ile Val Glu Leu Leu Glu Glu Ala Phe Asn Arg Ile Arg Ser
        355                 360                 365

Asn Leu Asp Ile Arg Ala Leu Asp Ser Pro Arg Gly Leu Arg Thr Glu
    370                 375                 380

Val Thr Ser Lys Met Phe Gln Lys Thr Arg Thr Gly Ser Phe His Ile
385                 390                 395                 400

Arg Arg Gly Glu Val Gly Ile Tyr Gln Val Gln Leu Arg Ala Leu Glu
                405                 410                 415

His Val Asp Gly Thr His Val Cys Gln Leu Pro Glu Asp Gln Lys Gly
            420                 425                 430

Asn Ile His Leu Lys Pro Ser Phe Ser Asp Gly Leu Lys Met Asp Ala
        435                 440                 445

Gly Ile Ile Cys Asp Val Cys Thr Cys Glu Leu Gln Lys Glu Val Arg
    450                 455                 460

Ser Ala Arg Cys Ser Phe Asn Gly Asp Phe Val Cys Gly Gln Cys Val
465                 470                 475                 480

Cys Ser Glu Gly Trp Ser Gly Gln Thr Cys Asn Cys Ser Thr Gly Ser
                485                 490                 495

Leu Ser Asp Ile Gln Pro Cys Leu Arg Glu Gly Glu Asp Lys Pro Cys
            500                 505                 510

Ser Gly Arg Gly Glu Cys Gln Cys Gly His Cys Val Cys Tyr Gly Glu
        515                 520                 525

Gly Arg Tyr Glu Gly Gln Phe Cys Glu Tyr Asp Asn Phe Gln Cys Pro
    530                 535                 540

Arg Thr Ser Gly Phe Leu Cys Asn Asp Arg Gly Arg Cys Ser Met Gly
545                 550                 555                 560

Gln Cys Val Cys Glu Pro Gly Trp Thr Gly Pro Ser Cys Asp Cys Pro
                565                 570                 575

Leu Ser Asn Ala Thr Cys Ile Asp Ser Asn Gly Gly Ile Cys Asn Gly
            580                 585                 590

Arg Gly His Cys Glu Cys Gly Arg Cys His Cys His Gln Gln Ser Leu
        595                 600                 605

Tyr Thr Asp Thr Ile Cys Glu Ile Asn Tyr Ser Ala Ile His Pro Gly
    610                 615                 620

Leu Cys Glu Asp Leu Arg Ser Cys Val Gln Cys Gln Ala Trp Gly Thr
625                 630                 635                 640

Gly Glu Lys Lys Gly Arg Thr Cys Glu Glu Cys Asn Phe Lys Val Lys
                645                 650                 655

Met Val Asp Glu Leu Lys Arg Ala Glu Glu Val Val Val Arg Cys Ser
            660                 665                 670

Phe Arg Asp Glu Asp Asp Asp Cys Thr Tyr Ser Tyr Thr Met Glu Gly
        675                 680                 685

Asp Gly Ala Pro Gly Pro Asn Ser Thr Val Leu Val His Lys Lys Lys
    690                 695                 700

Asp Cys Pro Pro Gly Ser Phe Trp Trp Leu Ile Pro Leu Leu Leu Leu
705                 710                 715                 720
```

```
Leu Leu Pro Leu Leu Ala Leu Leu Leu Leu Leu Cys Trp Lys Tyr Cys
                725                 730                 735

Ala Cys Cys Lys Ala Cys Leu Ala Leu Leu Pro Cys Cys Asn Arg Gly
            740                 745                 750

His Met Val Gly Phe Lys Glu Asp His Tyr Met Leu Arg Glu Asn Leu
        755                 760                 765

Met Ala Ser Asp His Leu Asp Thr Pro Met Leu Arg Ser Gly Asn Leu
    770                 775                 780

Lys Gly Arg Asp Val Val Arg Trp Lys Val Thr Asn Asn Met Gln Arg
785                 790                 795                 800

Pro Gly Phe Ala Thr His Ala Ala Ser Ile Asn Pro Thr Glu Leu Val
                805                 810                 815

Pro Tyr Gly Leu Ser Leu Arg Leu Ala Arg Leu Cys Thr Glu Asn Leu
            820                 825                 830

Leu Lys Pro Asp Thr Arg Glu Cys Ala Gln Leu Arg Gln Glu Val Glu
        835                 840                 845

Glu Asn Leu Asn Glu Val Tyr Arg Gln Ile Ser Gly Val His Lys Leu
    850                 855                 860

Gln Gln Thr Lys Phe Arg Gln Gln Pro Asn Ala Gly Lys Lys Gln Asp
865                 870                 875                 880

His Thr Ile Val Asp Thr Val Leu Met Ala Pro Arg Ser Ala Lys Pro
                885                 890                 895

Ala Leu Leu Lys Leu Thr Glu Lys Gln Val Glu Gln Arg Ala Phe His
            900                 905                 910

Asp Leu Lys Val Ala Pro Gly Tyr Tyr Thr Leu Thr Ala Asp Gln Asp
        915                 920                 925

Ala Arg Gly Met Val Glu Phe Gln Glu Gly Val Glu Leu Val Asp Val
    930                 935                 940

Arg Val Pro Leu Phe Ile Arg Pro Glu Asp Asp Asp Glu Lys Gln Leu
945                 950                 955                 960

Leu Val Glu Ala Ile Asp Val Pro Ala Gly Thr Ala Thr Leu Gly Arg
                965                 970                 975

Arg Leu Val Asn Ile Thr Ile Ile Lys Glu Gln Ala Arg Asp Val Val
            980                 985                 990

Ser Phe Glu Gln Pro Glu Phe Ser  Val Ser Arg Gly Asp  Gln Val Ala
        995                 1000                1005

Arg Ile  Pro Val Ile Arg Arg  Val Leu Asp Gly Gly  Lys Ser Gln
    1010                1015                1020

Val Ser  Tyr Arg Thr Gln Asp  Gly Thr Ala Gln Gly  Asn Arg Asp
    1025                1030                1035

Tyr Ile  Pro Val Glu Gly Glu  Leu Leu Phe Gln Pro  Gly Glu Ala
    1040                1045                1050

Trp Lys  Glu Leu Gln Val Lys  Leu Leu Glu Leu Gln  Glu Val Asp
    1055                1060                1065

Ser Leu  Leu Arg Gly Arg Gln  Val Arg Arg Phe His  Val Gln Leu
    1070                1075                1080

Ser Asn  Pro Lys Phe Gly Ala  His Leu Gly Gln Pro  His Ser Thr
    1085                1090                1095

Thr Ile  Ile Ile Arg Asp Pro  Asp Glu Leu Asp Arg  Ser Phe Thr
    1100                1105                1110

Ser Gln  Met Leu Ser Ser Gln  Pro Pro Pro His Gly  Asp Leu Gly
    1115                1120                1125

Ala Pro  Gln Asn Pro Asn Ala  Lys Ala Ala Gly Ser  Arg Lys Ile
```

```
    1130                1135                1140

His Phe  Asn Trp Leu Pro Pro  Ser Gly Lys Pro Met  Gly Tyr Arg
    1145                1150                1155

Val Lys  Tyr Trp Ile Gln Gly  Asp Ser Glu Ser Glu  Ala His Leu
    1160                1165                1170

Leu Asp  Ser Lys Val Pro Ser  Val Glu Leu Thr Asn  Leu Tyr Pro
    1175                1180                1185

Tyr Cys  Asp Tyr Glu Met Lys  Val Cys Ala Tyr Gly  Ala Gln Gly
    1190                1195                1200

Glu Gly  Pro Tyr Ser Ser Leu  Val Ser Cys Arg Thr  His Gln Glu
    1205                1210                1215

Val Pro  Ser Glu Pro Gly Arg  Leu Ala Phe Asn Val  Val Ser Ser
    1220                1225                1230

Thr Val  Thr Gln Leu Ser Trp  Ala Glu Pro Ala Glu  Thr Asn Gly
    1235                1240                1245

Glu Ile  Thr Ala Tyr Glu Val  Cys Tyr Gly Leu Val  Asn Asp Asp
    1250                1255                1260

Asn Arg  Pro Ile Gly Pro Met  Lys Lys Val Leu Val  Asp Asn Pro
    1265                1270                1275

Lys Asn  Arg Met Leu Leu Ile  Glu Asn Leu Arg Glu  Ser Gln Pro
    1280                1285                1290

Tyr Arg  Tyr Thr Val Lys Ala  Arg Asn Gly Ala Gly  Trp Gly Pro
    1295                1300                1305

Glu Arg  Glu Ala Ile Ile Asn  Leu Ala Thr Gln Pro  Lys Arg Pro
    1310                1315                1320

Met Ser  Ile Pro Ile Ile Pro  Asp Ile Pro Ile Val  Asp Ala Gln
    1325                1330                1335

Ser Gly  Glu Asp Tyr Asp Ser  Phe Leu Met Tyr Ser  Asp Asp Val
    1340                1345                1350

Leu Arg  Ser Pro Ser Gly Ser  Gln Arg Pro Ser Val  Ser Asp Asp
    1355                1360                1365

Thr Glu  His Leu Val Asn Gly  Arg Met Asp Phe Ala  Phe Pro Gly
    1370                1375                1380

Ser Thr  Asn Ser Leu His Arg  Met Thr Thr Thr Ser  Ala Ala Ala
    1385                1390                1395

Tyr Gly  Thr His Leu Ser Pro  His Val Pro His Arg  Val Leu Ser
    1400                1405                1410

Thr Ser  Ser Thr Leu Thr Arg  Asp Tyr Asn Ser Leu  Thr Arg Ser
    1415                1420                1425

Glu His  Ser His Ser Thr Thr  Leu Pro Arg Asp Tyr  Ser Thr Leu
    1430                1435                1440

Thr Ser  Val Ser Ser His Gly  Leu Pro Pro Ile Trp  Glu His Gly
    1445                1450                1455

Arg Ser  Arg Leu Pro Leu Ser  Trp Ala Leu Gly Ser  Arg Ser Arg
    1460                1465                1470

Ala Gln  Met Lys Gly Phe Pro  Pro Ser Arg Gly Pro  Arg Asp Ser
    1475                1480                1485

Ile Ile  Leu Ala Gly Arg Pro  Ala Ala Pro Ser Trp  Gly Pro Asp
    1490                1495                1500

Ser Arg  Leu Thr Ala Gly Val  Pro Asp Thr Pro Thr  Arg Leu Val
    1505                1510                1515

Phe Ser  Ala Leu Gly Pro Thr  Ser Leu Arg Val Ser  Trp Gln Glu
    1520                1525                1530
```

```
Pro Arg  Cys Glu Arg Pro Leu  Gln Gly Tyr Ser Val  Glu Tyr Gln
    1535                 1540                 1545

Leu Leu  Asn Gly Gly Glu Leu  His Arg Leu Asn Ile  Pro Asn Pro
    1550                 1555                 1560

Ala Gln  Thr Ser Val Val Val  Glu Asp Leu Leu Pro  Asn His Ser
    1565                 1570                 1575

Tyr Val  Phe Arg Val Arg Ala  Gln Ser Gln Glu Gly  Trp Gly Arg
    1580                 1585                 1590

Glu Arg  Glu Gly Val Ile Thr  Ile Glu Ser Gln Val  His Pro Gln
    1595                 1600                 1605

Ser Pro  Leu Cys Pro Leu Pro  Gly Ser Ala Phe Thr  Leu Ser Thr
    1610                 1615                 1620

Pro Ser  Ala Pro Gly Pro Leu  Val Phe Thr Ala Leu  Ser Pro Asp
    1625                 1630                 1635

Ser Leu  Gln Leu Ser Trp Glu  Arg Pro Arg Arg Pro  Asn Gly Asp
    1640                 1645                 1650

Ile Val  Gly Tyr Leu Val Thr  Cys Glu Met Ala Gln  Gly Gly Gly
    1655                 1660                 1665

Pro Ala  Thr Ala Phe Arg Val  Asp Gly Asp Ser Pro  Glu Ser Arg
    1670                 1675                 1680

Leu Thr  Val Pro Gly Leu Ser  Glu Asn Val Pro Tyr  Lys Phe Lys
    1685                 1690                 1695

Val Gln  Ala Arg Thr Thr Glu  Gly Phe Gly Pro Glu  Arg Glu Gly
    1700                 1705                 1710

Ile Ile  Thr Ile Glu Ser Gln  Asp Gly Gly Pro Phe  Pro Gln Leu
    1715                 1720                 1725

Gly Ser  Arg Ala Gly Leu Phe  Gln His Pro Leu Gln  Ser Glu Tyr
    1730                 1735                 1740

Ser Ser  Ile Thr Thr Thr His  Thr Ser Ala Thr Glu  Pro Phe Leu
    1745                 1750                 1755

Val Asp  Gly Leu Thr Leu Gly  Ala Gln His Leu Glu  Ala Gly Gly
    1760                 1765                 1770

Ser Leu  Thr Arg His Val Thr  Gln Glu Phe Val Ser  Arg Thr Leu
    1775                 1780                 1785

Thr Thr  Ser Gly Thr Leu Ser  Thr His Met Asp Gln  Gln Phe Phe
    1790                 1795                 1800

Gln Thr
    1805
```

<210> SEQ ID NO 8
<211> LENGTH: 1745
<212> TYPE: PRT
<213> ORGANISM: Homo sapiens
<220> FEATURE:
<221> NAME/KEY: misc_feature
<222> LOCATION: (1069)..(1069)
<223> OTHER INFORMATION: Phosphorylation site
<220> FEATURE:
<221> NAME/KEY: misc_feature
<222> LOCATION: (1385)..(1385)
<223> OTHER INFORMATION: Phosphorylation site
<220> FEATURE:
<221> NAME/KEY: misc_feature
<222> LOCATION: (1387)..(1387)
<223> OTHER INFORMATION: Phosphorylation site
<220> FEATURE:
<221> NAME/KEY: misc_feature
<222> LOCATION: (1448)..(1448)
<223> OTHER INFORMATION: Phosphorylation site

<400> SEQUENCE: 8

Met Ala Gly Pro Arg Pro Ser Pro Trp Ala Arg Leu Leu Leu Ala Ala
1               5                   10                  15

Leu Ile Ser Val Ser Leu Ser Gly Thr Leu Ala Asn Arg Cys Lys Lys
            20                  25                  30

Ala Pro Val Lys Ser Cys Thr Glu Cys Val Arg Val Asp Lys Asp Cys
        35                  40                  45

Ala Tyr Cys Thr Asp Glu Met Phe Arg Asp Arg Arg Cys Asn Thr Gln
    50                  55                  60

Ala Glu Leu Leu Ala Ala Gly Cys Gln Arg Glu Ser Ile Val Val Met
65                  70                  75                  80

Glu Ser Ser Phe Gln Ile Thr Glu Glu Thr Gln Ile Asp Thr Thr Leu
                85                  90                  95

Arg Arg Ser Gln Met Ser Pro Gln Gly Leu Arg Val Arg Leu Arg Pro
            100                 105                 110

Gly Glu Glu Arg His Phe Glu Leu Glu Val Phe Glu Pro Leu Glu Ser
        115                 120                 125

Pro Val Asp Leu Tyr Ile Leu Met Asp Phe Ser Asn Ser Met Ser Asp
    130                 135                 140

Asp Leu Asp Asn Leu Lys Lys Met Gly Gln Asn Leu Ala Arg Val Leu
145                 150                 155                 160

Ser Gln Leu Thr Ser Asp Tyr Thr Ile Gly Phe Gly Lys Phe Val Asp
                165                 170                 175

Lys Val Ser Val Pro Gln Thr Asp Met Arg Pro Glu Lys Leu Lys Glu
            180                 185                 190

Pro Trp Pro Asn Ser Asp Pro Pro Phe Ser Phe Lys Asn Val Ile Ser
        195                 200                 205

Leu Thr Glu Asp Val Asp Glu Phe Arg Asn Lys Leu Gln Gly Glu Arg
    210                 215                 220

Ile Ser Gly Asn Leu Asp Ala Pro Glu Gly Gly Phe Asp Ala Ile Leu
225                 230                 235                 240

Gln Thr Ala Val Cys Thr Arg Asp Ile Gly Trp Arg Pro Asp Ser Thr
                245                 250                 255

His Leu Leu Val Phe Ser Thr Glu Ser Ala Phe His Tyr Glu Ala Asp
            260                 265                 270

Gly Ala Asn Val Leu Ala Gly Ile Met Ser Arg Asn Asp Glu Arg Cys
        275                 280                 285

His Leu Asp Thr Thr Gly Thr Tyr Thr Gln Tyr Arg Thr Gln Asp Tyr
    290                 295                 300

Pro Ser Val Pro Thr Leu Val Arg Leu Leu Ala Lys His Asn Ile Ile
305                 310                 315                 320

Pro Ile Phe Ala Val Thr Asn Tyr Ser Tyr Ser Tyr Tyr Glu Lys Leu
                325                 330                 335

His Thr Tyr Phe Pro Val Ser Ser Leu Gly Val Leu Gln Glu Asp Ser
            340                 345                 350

Ser Asn Ile Val Glu Leu Leu Glu Glu Ala Phe Asn Arg Ile Arg Ser
        355                 360                 365

Asn Leu Asp Ile Arg Ala Leu Asp Ser Pro Arg Gly Leu Arg Thr Glu
    370                 375                 380

Val Thr Ser Lys Met Phe Gln Lys Thr Arg Thr Gly Ser Phe His Ile
385                 390                 395                 400

Arg Arg Gly Glu Val Gly Ile Tyr Gln Val Gln Leu Arg Ala Leu Glu

-continued

```
                405                 410                 415

His Val Asp Gly Thr His Val Cys Gln Leu Pro Glu Asp Gln Lys Gly
            420                 425                 430

Asn Ile His Leu Lys Pro Ser Phe Ser Asp Gly Leu Lys Met Asp Ala
        435                 440                 445

Gly Ile Ile Cys Asp Val Cys Thr Cys Glu Leu Gln Lys Glu Val Arg
    450                 455                 460

Ser Ala Arg Cys Ser Phe Asn Gly Asp Phe Val Cys Gly Gln Cys Val
465                 470                 475                 480

Cys Ser Glu Gly Trp Ser Gly Gln Thr Cys Asn Cys Ser Thr Gly Ser
                485                 490                 495

Leu Ser Asp Ile Gln Pro Cys Leu Arg Glu Gly Glu Asp Lys Pro Cys
            500                 505                 510

Ser Gly Arg Gly Glu Cys Gln Cys Gly His Cys Val Cys Tyr Gly Glu
        515                 520                 525

Gly Arg Tyr Glu Gly Gln Phe Cys Glu Tyr Asp Asn Phe Gln Cys Pro
    530                 535                 540

Arg Thr Ser Gly Phe Leu Cys Asn Asp Arg Gly Arg Cys Ser Met Gly
545                 550                 555                 560

Gln Cys Val Cys Glu Pro Gly Trp Thr Gly Pro Ser Cys Asp Cys Pro
                565                 570                 575

Leu Ser Asn Ala Thr Cys Ile Asp Ser Asn Gly Gly Ile Cys Asn Gly
            580                 585                 590

Arg Gly His Cys Glu Cys Gly Arg Cys His Cys His Gln Gln Ser Leu
        595                 600                 605

Tyr Thr Asp Thr Ile Cys Glu Ile Asn Tyr Ser Ala Ile His Pro Gly
    610                 615                 620

Leu Cys Glu Asp Leu Arg Ser Cys Val Gln Cys Gln Ala Trp Gly Thr
625                 630                 635                 640

Gly Glu Lys Lys Gly Arg Thr Cys Glu Glu Cys Asn Phe Lys Val Lys
                645                 650                 655

Met Val Asp Glu Leu Lys Arg Ala Glu Glu Val Val Val Arg Cys Ser
            660                 665                 670

Phe Arg Asp Glu Asp Asp Asp Cys Thr Tyr Ser Tyr Thr Met Glu Gly
        675                 680                 685

Asp Gly Ala Pro Gly Pro Asn Ser Thr Val Leu Val His Lys Lys Lys
    690                 695                 700

Asp Cys Pro Pro Gly Ser Phe Trp Trp Leu Ile Pro Leu Leu Leu Leu
705                 710                 715                 720

Leu Leu Pro Leu Leu Ala Leu Leu Leu Leu Leu Cys Trp Lys Tyr Cys
                725                 730                 735

Ala Cys Cys Lys Ala Cys Leu Ala Leu Leu Pro Cys Cys Asn Arg Gly
            740                 745                 750

His Met Val Gly Phe Lys Glu Asp His Tyr Met Leu Arg Glu Asn Leu
        755                 760                 765

Met Ala Ser Asp His Leu Asp Thr Pro Met Leu Arg Ser Gly Asn Leu
    770                 775                 780

Lys Gly Arg Asp Val Val Arg Trp Lys Val Thr Asn Asn Met Gln Arg
785                 790                 795                 800

Pro Gly Phe Ala Thr His Ala Ala Ser Ile Asn Pro Thr Glu Leu Val
                805                 810                 815

Pro Tyr Gly Leu Ser Leu Arg Leu Ala Arg Leu Cys Thr Glu Asn Leu
            820                 825                 830
```

```
Leu Lys Pro Asp Thr Arg Glu Cys Ala Gln Leu Arg Gln Glu Val Glu
        835                 840                 845

Glu Asn Leu Asn Glu Val Tyr Arg Gln Ile Ser Gly Val His Lys Leu
    850                 855                 860

Gln Gln Thr Lys Phe Arg Gln Gln Pro Asn Ala Gly Lys Lys Gln Asp
865                 870                 875                 880

His Thr Ile Val Asp Thr Val Leu Met Ala Pro Arg Ser Ala Lys Pro
                885                 890                 895

Ala Leu Leu Lys Leu Thr Glu Lys Gln Val Glu Gln Arg Ala Phe His
            900                 905                 910

Asp Leu Lys Val Ala Pro Gly Tyr Tyr Thr Leu Thr Ala Asp Gln Asp
        915                 920                 925

Ala Arg Gly Met Val Glu Phe Gln Glu Gly Val Glu Leu Val Asp Val
    930                 935                 940

Arg Val Pro Leu Phe Ile Arg Pro Glu Asp Asp Asp Glu Lys Gln Leu
945                 950                 955                 960

Leu Val Glu Ala Ile Asp Val Pro Ala Gly Thr Ala Thr Leu Gly Arg
                965                 970                 975

Arg Leu Val Asn Ile Thr Ile Ile Lys Glu Gln Ala Arg Asp Val Val
            980                 985                 990

Ser Phe Glu Gln Pro Glu Phe Ser  Val Ser Arg Gly Asp  Gln Val Ala
        995                 1000                1005

Arg Ile  Pro Val Ile Arg Arg  Val Leu Asp Gly Gly  Lys Ser Gln
    1010                 1015                 1020

Val Ser  Tyr Arg Thr Gln Asp  Gly Thr Ala Gln Gly  Asn Arg Asp
    1025                 1030                 1035

Tyr Ile  Pro Val Glu Gly Glu  Leu Leu Phe Gln Pro  Gly Glu Ala
    1040                 1045                 1050

Trp Lys  Glu Leu Gln Val Lys  Leu Leu Glu Leu Gln  Glu Val Asp
    1055                 1060                 1065

Ser Leu  Leu Arg Gly Arg Gln  Val Arg Arg Phe His  Val Gln Leu
    1070                 1075                 1080

Ser Asn  Pro Lys Phe Gly Ala  His Leu Gly Gln Pro  His Ser Thr
    1085                 1090                 1095

Thr Ile  Ile Ile Arg Asp Pro  Asp Glu Leu Asp Arg  Ser Phe Thr
    1100                 1105                 1110

Ser Gln  Met Leu Ser Ser Gln  Pro Pro Pro His Gly  Asp Leu Gly
    1115                 1120                 1125

Ala Pro  Gln Asn Pro Asn Ala  Lys Ala Ala Gly Ser  Arg Lys Ile
    1130                 1135                 1140

His Phe  Asn Trp Leu Pro Pro  Ser Gly Lys Pro Met  Gly Tyr Arg
    1145                 1150                 1155

Val Lys  Tyr Trp Ile Gln Gly  Asp Ser Glu Ser Glu  Ala His Leu
    1160                 1165                 1170

Leu Asp  Ser Lys Val Pro Ser  Val Glu Leu Thr Asn  Leu Tyr Pro
    1175                 1180                 1185

Tyr Cys  Asp Tyr Glu Met Lys  Val Cys Ala Tyr Gly  Ala Gln Gly
    1190                 1195                 1200

Glu Gly  Pro Tyr Ser Ser Leu  Val Ser Cys Arg Thr  His Gln Glu
    1205                 1210                 1215

Val Pro  Ser Glu Pro Gly Arg  Leu Ala Phe Asn Val  Val Ser Ser
    1220                 1225                 1230
```

-continued

Thr Val Thr Gln Leu Ser Trp Ala Glu Pro Ala Glu Thr Asn Gly
1235 1240 1245

Glu Ile Thr Ala Tyr Glu Val Cys Tyr Gly Leu Val Asn Asp Asp
1250 1255 1260

Asn Arg Pro Ile Gly Pro Met Lys Lys Val Leu Val Asp Asn Pro
1265 1270 1275

Lys Asn Arg Met Leu Leu Ile Glu Asn Leu Arg Glu Ser Gln Pro
1280 1285 1290

Tyr Arg Tyr Thr Val Lys Ala Arg Asn Gly Ala Gly Trp Gly Pro
1295 1300 1305

Glu Arg Glu Ala Ile Ile Asn Leu Ala Thr Gln Pro Lys Arg Pro
1310 1315 1320

Met Ser Ile Pro Ile Ile Pro Asp Ile Pro Ile Val Asp Ala Gln
1325 1330 1335

Ser Gly Glu Asp Tyr Asp Ser Phe Leu Met Tyr Ser Asp Asp Val
1340 1345 1350

Leu Arg Ser Pro Ser Gly Ser Gln Arg Pro Ser Val Ser Asp Asp
1355 1360 1365

Thr Glu His Leu Val Asn Gly Arg Met Asp Phe Ala Phe Pro Gly
1370 1375 1380

Ser Thr Asn Ser Leu His Arg Met Thr Thr Thr Ser Ala Ala Ala
1385 1390 1395

Tyr Gly Thr His Leu Ser Pro His Val Pro His Arg Val Leu Ser
1400 1405 1410

Thr Ser Ser Thr Leu Thr Arg Asp Tyr Asn Ser Leu Thr Arg Ser
1415 1420 1425

Glu His Ser His Ser Thr Thr Leu Pro Arg Asp Tyr Ser Thr Leu
1430 1435 1440

Thr Ser Val Ser Ser His Asp Ser Arg Leu Thr Ala Gly Val Pro
1445 1450 1455

Asp Thr Pro Thr Arg Leu Val Phe Ser Ala Leu Gly Pro Thr Ser
1460 1465 1470

Leu Arg Val Ser Trp Gln Glu Pro Arg Cys Glu Arg Pro Leu Gln
1475 1480 1485

Gly Tyr Ser Val Glu Tyr Gln Leu Leu Asn Gly Gly Glu Leu His
1490 1495 1500

Arg Leu Asn Ile Pro Asn Pro Ala Gln Thr Ser Val Val Val Glu
1505 1510 1515

Asp Leu Leu Pro Asn His Ser Tyr Val Phe Arg Val Arg Ala Gln
1520 1525 1530

Ser Gln Glu Gly Trp Gly Arg Glu Arg Glu Gly Val Ile Thr Ile
1535 1540 1545

Glu Ser Gln Val His Pro Gln Ser Pro Leu Cys Pro Leu Pro Gly
1550 1555 1560

Ser Ala Phe Thr Leu Ser Thr Pro Ser Ala Pro Gly Pro Leu Val
1565 1570 1575

Phe Thr Ala Leu Ser Pro Asp Ser Leu Gln Leu Ser Trp Glu Arg
1580 1585 1590

Pro Arg Arg Pro Asn Gly Asp Ile Val Gly Tyr Leu Val Thr Trp
1595 1600 1605

Pro Ala Thr Ala Phe Arg Val Asp Gly Asp Ser Pro Glu Ser Arg
1610 1615 1620

Leu Thr Val Pro Gly Leu Ser Glu Asn Val Pro Tyr Lys Phe Lys

```
    1625                1630                1635

Val Gln  Ala Arg Thr Thr Glu  Gly Phe Gly Pro Glu  Arg Glu Gly
    1640                1645                1650

Ile Ile  Thr Ile Glu Ser Gln  Asp Gly Gly Pro Phe  Pro Gln Leu
    1655                1660                1665

Gly Ser  Arg Ala Gly Leu Phe  Gln His Pro Leu Gln  Ser Glu Tyr
    1670                1675                1680

Ser Ser  Ile Thr Thr Thr His  Thr Ser Ala Thr Glu  Pro Phe Leu
    1685                1690                1695

Val Asp  Gly Leu Thr Leu Gly  Ala Gln His Leu Glu  Ala Gly Gly
    1700                1705                1710

Ser Leu  Thr Arg His Val Thr  Gln Glu Phe Val Ser  Arg Thr Leu
    1715                1720                1725

Thr Thr  Ser Gly Thr Leu Ser  Thr His Met Asp Gln  Gln Phe Phe
    1730                1735                1740

Gln Thr
    1745


<210> SEQ ID NO 9
<211> LENGTH: 520
<212> TYPE: PRT
<213> ORGANISM: Homo sapiens
<220> FEATURE:
<221> NAME/KEY: misc_feature
<222> LOCATION: (509)..(509)
<223> OTHER INFORMATION: Phosphorylation site

<400> SEQUENCE: 9

Met Ser Leu Ser Arg Ser Glu Glu Met His Arg Leu Thr Glu Asn Val
1               5                   10                  15

Tyr Lys Thr Ile Met Glu Gln Phe Asn Pro Ser Leu Arg Asn Phe Ile
            20                  25                  30

Ala Met Gly Lys Asn Tyr Glu Lys Ala Leu Ala Gly Val Thr Tyr Ala
        35                  40                  45

Ala Lys Gly Tyr Phe Asp Ala Leu Val Lys Met Gly Glu Leu Ala Ser
    50                  55                  60

Glu Ser Gln Gly Ser Lys Glu Leu Gly Asp Val Leu Phe Gln Met Ala
65                  70                  75                  80

Glu Val His Arg Gln Ile Gln Asn Gln Leu Glu Glu Met Leu Lys Ser
                85                  90                  95

Phe His Asn Glu Leu Leu Thr Gln Leu Glu Gln Lys Val Glu Leu Asp
            100                 105                 110

Ser Arg Tyr Leu Ser Ala Ala Leu Lys Lys Tyr Gln Thr Glu Gln Arg
        115                 120                 125

Ser Lys Gly Asp Ala Leu Asp Lys Cys Gln Ala Glu Leu Lys Lys Leu
    130                 135                 140

Arg Lys Lys Ser Gln Gly Ser Lys Asn Pro Gln Lys Tyr Ser Asp Lys
145                 150                 155                 160

Glu Leu Gln Tyr Ile Asp Ala Ile Ser Asn Lys Gln Gly Glu Leu Glu
                165                 170                 175

Asn Tyr Val Ser Asp Gly Tyr Lys Thr Ala Leu Thr Glu Glu Arg Arg
            180                 185                 190

Arg Phe Cys Phe Leu Val Glu Lys Gln Cys Ala Val Ala Lys Asn Ser
        195                 200                 205

Ala Ala Tyr His Ser Lys Gly Lys Glu Leu Leu Ala Gln Lys Leu Pro
    210                 215                 220
```

Leu Trp Gln Gln Ala Cys Ala Asp Pro Ser Lys Ile Pro Glu Arg Ala
225 230 235 240

Val Gln Leu Met Gln Gln Val Ala Ser Asn Gly Ala Thr Leu Pro Ser
245 250 255

Ala Leu Ser Ala Ser Lys Ser Asn Leu Val Ile Ser Asp Pro Ile Pro
260 265 270

Gly Ala Lys Pro Leu Pro Val Pro Pro Glu Leu Ala Pro Phe Val Gly
275 280 285

Arg Met Ser Ala Gln Glu Ser Thr Pro Ile Met Asn Gly Val Thr Gly
290 295 300

Pro Asp Gly Glu Asp Tyr Ser Pro Trp Ala Asp Arg Lys Ala Ala Gln
305 310 315 320

Pro Lys Ser Leu Ser Pro Pro Gln Ser Gln Ser Lys Leu Ser Asp Ser
325 330 335

Tyr Ser Asn Thr Leu Pro Val Arg Lys Ser Val Thr Pro Lys Asn Ser
340 345 350

Tyr Ala Thr Thr Glu Asn Lys Thr Leu Pro Arg Ser Ser Ser Met Ala
355 360 365

Ala Gly Leu Glu Arg Asn Gly Arg Met Arg Val Lys Ala Ile Phe Ser
370 375 380

His Ala Ala Gly Asp Asn Ser Thr Leu Leu Ser Phe Lys Glu Gly Asp
385 390 395 400

Leu Ile Thr Leu Leu Val Pro Glu Ala Arg Asp Gly Trp His Tyr Gly
405 410 415

Glu Ser Glu Lys Thr Lys Met Arg Gly Trp Phe Pro Phe Ser Tyr Thr
420 425 430

Arg Val Leu Asp Ser Asp Gly Ser Asp Arg Leu His Met Ser Leu Gln
435 440 445

Gln Gly Lys Ser Ser Ser Thr Gly Asn Leu Leu Asp Lys Asp Asp Leu
450 455 460

Ala Ile Pro Pro Pro Asp Tyr Gly Ala Ala Ser Arg Ala Phe Pro Ala
465 470 475 480

Gln Thr Ala Ser Gly Phe Lys Gln Arg Pro Tyr Ser Val Ala Val Pro
485 490 495

Ala Phe Ser Gln Gly Leu Asp Asp Tyr Gly Ala Arg Ser Met Ser Ser
500 505 510

Ala Asp Val Glu Val Ala Arg Phe
515 520

<210> SEQ ID NO 10
<211> LENGTH: 357
<212> TYPE: PRT
<213> ORGANISM: Homo sapiens
<220> FEATURE:
<221> NAME/KEY: misc_feature
<222> LOCATION: (345)..(345)
<223> OTHER INFORMATION: Phosphorylation site

<400> SEQUENCE: 10

Met Ala Thr Thr Val Pro Asp Gly Cys Arg Asn Gly Leu Lys Ser Lys
1 5 10 15

Tyr Tyr Arg Leu Cys Asp Lys Ala Glu Ala Trp Gly Ile Val Leu Glu
20 25 30

Thr Val Ala Thr Ala Gly Val Val Thr Ser Val Ala Phe Met Leu Thr
35 40 45

-continued

```
Leu Pro Ile Leu Val Cys Lys Val Gln Asp Ser Asn Arg Arg Lys Met
    50                  55                  60

Leu Pro Thr Gln Phe Leu Phe Leu Leu Gly Val Leu Gly Ile Phe Gly
65                  70                  75                  80

Leu Thr Phe Ala Phe Ile Ile Gly Leu Asp Gly Ser Thr Gly Pro Thr
                85                  90                  95

Arg Phe Phe Leu Phe Gly Ile Leu Phe Ser Ile Cys Phe Ser Cys Leu
            100                 105                 110

Leu Ala His Ala Val Ser Leu Thr Lys Leu Val Arg Gly Arg Lys Pro
        115                 120                 125

Leu Ser Leu Leu Val Ile Leu Gly Leu Ala Val Gly Phe Ser Leu Val
    130                 135                 140

Gln Asp Val Ile Ala Ile Glu Tyr Ile Val Leu Thr Met Asn Arg Thr
145                 150                 155                 160

Asn Val Asn Val Phe Ser Glu Leu Ser Ala Pro Arg Arg Asn Glu Asp
                165                 170                 175

Phe Val Leu Leu Leu Thr Tyr Val Leu Phe Leu Met Ala Leu Thr Phe
            180                 185                 190

Leu Met Ser Ser Phe Thr Phe Cys Gly Ser Phe Thr Gly Trp Lys Arg
        195                 200                 205

His Gly Ala His Ile Tyr Leu Thr Met Leu Leu Ser Ile Ala Ile Trp
    210                 215                 220

Val Ala Trp Ile Thr Leu Leu Met Leu Pro Asp Phe Asp Arg Arg Trp
225                 230                 235                 240

Asp Asp Thr Ile Leu Ser Ser Ala Leu Ala Ala Asn Gly Trp Val Phe
                245                 250                 255

Leu Leu Ala Tyr Val Ser Pro Glu Phe Trp Leu Leu Thr Lys Gln Arg
            260                 265                 270

Asn Pro Met Asp Tyr Pro Val Glu Asp Ala Phe Cys Lys Pro Gln Leu
        275                 280                 285

Val Lys Lys Ser Tyr Gly Val Glu Asn Arg Ala Tyr Ser Gln Glu Glu
    290                 295                 300

Ile Thr Gln Gly Phe Glu Glu Thr Gly Asp Thr Leu Tyr Ala Pro Tyr
305                 310                 315                 320

Ser Thr His Phe Gln Leu Gln Asn Gln Pro Pro Gln Lys Glu Phe Ser
                325                 330                 335

Ile Pro Arg Ala His Ala Trp Pro Ser Pro Tyr Lys Asp Tyr Glu Val
            340                 345                 350

Lys Lys Glu Gly Ser
        355


<210> SEQ ID NO 11
<211> LENGTH: 2671
<212> TYPE: PRT
<213> ORGANISM: Homo sapiens
<220> FEATURE:
<221> NAME/KEY: misc_feature
<222> LOCATION: (916)..(916)
<223> OTHER INFORMATION: Phosphorylation site

<400> SEQUENCE: 11

Met Ser Glu Met Ser Ser Phe Leu His Ile Gly Asp Ile Val Ser Leu
1               5                   10                  15

Tyr Ala Glu Gly Ser Val Asn Gly Phe Ile Ser Thr Leu Gly Leu Val
            20                  25                  30

Asp Asp Arg Cys Val Val Glu Pro Ala Ala Gly Asp Leu Asp Asn Pro
```

-continued

```
        35                  40                  45

Pro Lys Lys Phe Arg Asp Cys Leu Phe Lys Val Cys Pro Met Asn Arg
    50                  55                  60

Tyr Ser Ala Gln Lys Gln Tyr Trp Lys Ala Lys Gln Thr Lys Gln Asp
65                  70                  75                  80

Lys Glu Lys Ile Ala Asp Val Val Leu Leu Gln Lys Leu Gln His Ala
                85                  90                  95

Ala Gln Met Glu Gln Lys Gln Asn Asp Thr Glu Asn Lys Lys Val His
            100                 105                 110

Gly Asp Val Val Lys Tyr Gly Ser Val Ile Gln Leu Leu His Met Lys
        115                 120                 125

Ser Asn Lys Tyr Leu Thr Val Asn Lys Arg Leu Pro Ala Leu Leu Glu
    130                 135                 140

Lys Asn Ala Met Arg Val Thr Leu Asp Ala Thr Gly Asn Glu Gly Ser
145                 150                 155                 160

Trp Leu Phe Ile Gln Pro Phe Trp Lys Leu Arg Ser Asn Gly Asp Asn
                165                 170                 175

Val Val Val Gly Asp Lys Val Ile Leu Asn Pro Val Asn Ala Gly Gln
            180                 185                 190

Pro Leu His Ala Ser Asn Tyr Glu Leu Ser Asp Asn Ala Gly Cys Lys
        195                 200                 205

Glu Val Asn Ser Val Asn Cys Asn Thr Ser Trp Lys Ile Asn Leu Phe
    210                 215                 220

Met Gln Phe Arg Asp His Leu Glu Glu Val Leu Lys Gly Gly Asp Val
225                 230                 235                 240

Val Arg Leu Phe His Ala Glu Gln Glu Lys Phe Leu Thr Cys Asp Glu
                245                 250                 255

Tyr Lys Gly Lys Leu Gln Val Phe Leu Arg Thr Thr Leu Arg Gln Ser
            260                 265                 270

Ala Thr Ser Ala Thr Ser Ser Asn Ala Leu Trp Glu Val Glu Val Val
        275                 280                 285

His His Asp Pro Cys Arg Gly Gly Ala Gly His Trp Asn Gly Leu Tyr
    290                 295                 300

Arg Phe Lys His Leu Ala Thr Gly Asn Tyr Leu Ala Ala Glu Glu Asn
305                 310                 315                 320

Pro Ser Tyr Lys Gly Asp Ala Ser Asp Pro Lys Ala Ala Gly Met Gly
                325                 330                 335

Ala Gln Gly Arg Thr Gly Arg Arg Asn Ala Gly Glu Lys Ile Lys Tyr
            340                 345                 350

Cys Leu Val Ala Val Pro His Gly Asn Asp Ile Ala Ser Leu Phe Glu
        355                 360                 365

Leu Asp Pro Thr Thr Leu Gln Lys Thr Asp Ser Phe Val Pro Arg Asn
    370                 375                 380

Ser Tyr Val Arg Leu Arg His Leu Cys Thr Asn Thr Trp Ile Gln Ser
385                 390                 395                 400

Thr Asn Val Pro Ile Asp Ile Glu Glu Glu Arg Pro Ile Arg Leu Met
                405                 410                 415

Leu Gly Thr Cys Pro Thr Lys Glu Asp Lys Glu Ala Phe Ala Ile Val
            420                 425                 430

Ser Val Pro Val Ser Glu Ile Arg Asp Leu Asp Phe Ala Asn Asp Ala
        435                 440                 445

Ser Ser Met Leu Ala Ser Ala Val Glu Lys Leu Asn Glu Gly Phe Ile
    450                 455                 460
```

```
Ser Gln Asn Asp Arg Arg Phe Val Ile Gln Leu Leu Glu Asp Leu Val
465                 470                 475                 480

Phe Phe Val Ser Asp Val Pro Asn Asn Gly Gln Asn Val Leu Asp Ile
                485                 490                 495

Met Val Thr Lys Pro Asn Arg Glu Arg Gln Lys Leu Met Arg Glu Gln
            500                 505                 510

Asn Ile Leu Lys Gln Val Phe Gly Ile Leu Lys Ala Pro Phe Arg Glu
        515                 520                 525

Lys Gly Gly Glu Gly Pro Leu Val Arg Leu Glu Glu Leu Ser Asp Gln
    530                 535                 540

Lys Asn Ala Pro Tyr Gln His Met Phe Arg Leu Cys Tyr Arg Val Leu
545                 550                 555                 560

Arg His Ser Gln Glu Asp Tyr Arg Lys Asn Gln Glu His Ile Ala Lys
                565                 570                 575

Gln Phe Gly Met Met Gln Ser Gln Ile Gly Tyr Asp Ile Leu Ala Glu
            580                 585                 590

Asp Thr Ile Thr Ala Leu Leu His Asn Asn Arg Lys Leu Leu Glu Lys
        595                 600                 605

His Ile Thr Lys Thr Glu Val Glu Thr Phe Val Ser Leu Val Arg Lys
    610                 615                 620

Asn Arg Glu Pro Arg Phe Leu Asp Tyr Leu Ser Asp Leu Cys Val Ser
625                 630                 635                 640

Asn His Ile Ala Ile Pro Val Thr Gln Glu Leu Ile Cys Lys Cys Val
                645                 650                 655

Leu Asp Pro Lys Asn Ser Asp Ile Leu Ile Arg Thr Glu Leu Arg Pro
            660                 665                 670

Val Lys Glu Met Ala Gln Ser His Glu Tyr Leu Ser Ile Glu Tyr Ser
        675                 680                 685

Glu Glu Glu Val Trp Leu Thr Trp Thr Asp Lys Asn Asn Glu His His
    690                 695                 700

Glu Lys Ser Val Arg Gln Leu Ala Gln Glu Ala Arg Ala Gly Asn Ala
705                 710                 715                 720

His Asp Glu Asn Val Leu Ser Tyr Tyr Arg Tyr Gln Leu Lys Leu Phe
                725                 730                 735

Ala Arg Met Cys Leu Asp Arg Gln Tyr Leu Ala Ile Asp Glu Ile Ser
            740                 745                 750

Gln Gln Leu Gly Val Asp Leu Ile Phe Leu Cys Met Ala Asp Glu Met
        755                 760                 765

Leu Pro Phe Asp Leu Arg Ala Ser Phe Cys His Leu Met Leu His Val
    770                 775                 780

His Val Asp Arg Asp Pro Gln Glu Leu Val Thr Pro Val Lys Phe Ala
785                 790                 795                 800

Arg Leu Trp Thr Glu Ile Pro Thr Ala Ile Thr Ile Lys Asp Tyr Asp
                805                 810                 815

Ser Asn Leu Asn Ala Ser Arg Asp Asp Lys Lys Asn Lys Phe Ala Asn
            820                 825                 830

Thr Met Glu Phe Val Glu Asp Tyr Leu Asn Asn Val Val Ser Glu Ala
        835                 840                 845

Val Pro Phe Ala Asn Glu Glu Lys Asn Lys Leu Thr Phe Glu Val Val
    850                 855                 860

Ser Leu Ala His Asn Leu Ile Tyr Phe Gly Phe Tyr Ser Phe Ser Glu
865                 870                 875                 880
```

-continued

```
Leu Leu Arg Leu Thr Arg Thr Leu Leu Gly Ile Ile Asp Cys Val Gln
                885                 890                 895

Gly Pro Pro Ala Met Leu Gln Ala Tyr Glu Asp Pro Gly Gly Lys Asn
            900                 905                 910

Val Arg Arg Ser Ile Gln Gly Val Gly His Met Met Ser Thr Met Val
        915                 920                 925

Leu Ser Arg Lys Gln Ser Val Phe Ser Ala Pro Ser Leu Ser Ala Gly
    930                 935                 940

Ala Ser Ala Ala Glu Pro Leu Asp Arg Ser Lys Phe Glu Glu Asn Glu
945                 950                 955                 960

Asp Ile Val Val Met Glu Thr Lys Leu Lys Ile Leu Glu Ile Leu Gln
                965                 970                 975

Phe Ile Leu Asn Val Arg Leu Asp Tyr Arg Ile Ser Tyr Leu Leu Ser
            980                 985                 990

Val Phe Lys Lys Glu Phe Val Glu  Val Phe Pro Met Gln  Asp Ser Gly
        995                 1000                1005

Ala Asp  Gly Thr Ala Pro Ala  Phe Asp Ser Thr Thr  Ala Asn Met
    1010                 1015                 1020

Asn Leu  Asp Arg Ile Gly Glu  Gln Ala Glu Ala Met  Phe Gly Val
    1025                 1030                 1035

Gly Lys  Thr Ser Ser Met Leu  Glu Val Asp Asp Glu  Gly Gly Arg
    1040                 1045                 1050

Met Phe  Leu Arg Val Leu Ile  His Leu Thr Met His  Asp Tyr Ala
    1055                 1060                 1065

Pro Leu  Val Ser Gly Ala Leu  Gln Leu Leu Phe Lys  His Phe Ser
    1070                 1075                 1080

Gln Arg  Gln Glu Ala Met His  Thr Phe Lys Gln Val  Gln Leu Leu
    1085                 1090                 1095

Ile Ser  Ala Gln Asp Val Glu  Asn Tyr Lys Val Ile  Lys Ser Glu
    1100                 1105                 1110

Leu Asp  Arg Leu Arg Thr Met  Val Glu Lys Ser Glu  Leu Trp Val
    1115                 1120                 1125

Asp Lys  Lys Gly Ser Gly Lys  Gly Glu Glu Val Glu  Ala Gly Ala
    1130                 1135                 1140

Ala Lys  Asp Lys Lys Glu Arg  Pro Thr Asp Glu Glu  Gly Phe Leu
    1145                 1150                 1155

His Pro  Pro Gly Glu Lys Ser  Ser Glu Asn Tyr Gln  Ile Val Lys
    1160                 1165                 1170

Gly Ile  Leu Glu Arg Leu Asn  Lys Met Cys Gly Val  Gly Glu Gln
    1175                 1180                 1185

Met Arg  Lys Lys Gln Gln Arg  Leu Leu Lys Asn Met  Asp Ala His
    1190                 1195                 1200

Lys Val  Met Leu Asp Leu Leu  Gln Ile Pro Tyr Asp  Lys Gly Asp
    1205                 1210                 1215

Ala Lys  Met Met Glu Ile Leu  Arg Tyr Thr His Gln  Phe Leu Gln
    1220                 1225                 1230

Lys Phe  Cys Ala Gly Asn Pro  Gly Asn Gln Ala Leu  Leu His Lys
    1235                 1240                 1245

His Leu  His Leu Phe Leu Thr  Pro Gly Leu Leu Glu  Ala Glu Thr
    1250                 1255                 1260

Met Gln  His Ile Phe Leu Asn  Asn Tyr Gln Leu Cys  Ser Glu Ile
    1265                 1270                 1275

Ser Glu  Pro Val Leu Gln His  Phe Val His Leu Leu  Ala Thr His
```

```
    1280                1285                1290

Gly Arg  His Val Gln Tyr Leu  Asp Phe Leu His Thr  Val Ile Lys
    1295                1300                1305

Ala Glu  Gly Lys Tyr Val Lys  Lys Cys Gln Asp Met  Ile Met Thr
    1310                1315                1320

Glu Leu  Thr Asn Ala Gly Asp  Asp Val Val Val Phe  Tyr Asn Asp
    1325                1330                1335

Lys Ala  Ser Leu Ala His Leu  Leu Asp Met Met Lys  Ala Ala Arg
    1340                1345                1350

Asp Gly  Val Glu Asp His Ser  Pro Leu Met Tyr His  Ile Ser Leu
    1355                1360                1365

Val Asp  Leu Leu Ala Ala Cys  Ala Glu Gly Lys Asn  Val Tyr Thr
    1370                1375                1380

Glu Ile  Lys Cys Thr Ser Leu  Leu Pro Leu Glu Asp  Val Val Ser
    1385                1390                1395

Val Val  Thr His Glu Asp Cys  Ile Thr Glu Val Lys  Met Ala Tyr
    1400                1405                1410

Val Asn  Phe Val Asn His Cys  Tyr Val Asp Thr Glu  Val Glu Met
    1415                1420                1425

Lys Glu  Ile Tyr Thr Ser Asn  His Ile Trp Thr Leu  Phe Glu Asn
    1430                1435                1440

Phe Thr  Leu Asp Met Ala Arg  Val Cys Ser Lys Arg  Glu Lys Arg
    1445                1450                1455

Val Ala  Asp Pro Thr Leu Glu  Lys Tyr Val Leu Ser  Val Val Leu
    1460                1465                1470

Asp Thr  Ile Asn Ala Phe Phe  Ser Ser Pro Phe Ser  Glu Asn Ser
    1475                1480                1485

Thr Ser  Leu Gln Thr His Gln  Thr Ile Val Val Gln  Leu Leu Gln
    1490                1495                1500

Ser Thr  Thr Arg Leu Leu Glu  Cys Pro Trp Leu Gln  Gln Gln His
    1505                1510                1515

Lys Gly  Ser Val Glu Ala Cys  Ile Arg Thr Leu Ala  Met Val Ala
    1520                1525                1530

Lys Gly  Arg Ala Ile Leu Leu  Pro Met Asp Leu Asp  Ala His Ile
    1535                1540                1545

Ser Ser  Met Leu Ser Ser Gly  Ala Ser Cys Ala Ala  Ala Ala Gln
    1550                1555                1560

Arg Asn  Ala Ser Ser Tyr Lys  Ala Thr Thr Arg Ala  Phe Pro Arg
    1565                1570                1575

Val Thr  Pro Thr Ala Asn Gln  Trp Asp Tyr Lys Asn  Ile Ile Glu
    1580                1585                1590

Lys Leu  Gln Asp Ile Ile Thr  Ala Leu Glu Glu Arg  Leu Lys Pro
    1595                1600                1605

Leu Val  Gln Ala Glu Leu Ser  Val Leu Val Asp Val  Leu His Trp
    1610                1615                1620

Pro Glu  Leu Leu Phe Leu Glu  Gly Ser Glu Ala Tyr  Gln Arg Cys
    1625                1630                1635

Glu Ser  Gly Gly Phe Leu Ser  Lys Leu Ile Gln His  Thr Lys Asp
    1640                1645                1650

Leu Met  Glu Ser Glu Glu Lys  Leu Cys Ile Lys Val  Leu Arg Thr
    1655                1660                1665

Leu Gln  Gln Met Leu Leu Lys  Lys Thr Lys Tyr Gly  Asp Arg Gly
    1670                1675                1680
```

```
Asn Gln  Leu Arg Lys Met Leu  Leu Gln Asn Tyr Leu  Gln Asn Arg
    1685                 1690                 1695

Lys Ser  Thr Ser Arg Gly Asp  Leu Pro Asp Pro Ile  Gly Thr Gly
    1700                 1705                 1710

Leu Asp  Pro Asp Trp Ser Ala  Ile Ala Ala Thr Gln  Cys Arg Leu
    1715                 1720                 1725

Asp Lys  Glu Gly Ala Thr Lys  Leu Val Cys Asp Leu  Ile Thr Ser
    1730                 1735                 1740

Thr Lys  Asn Glu Lys Ile Phe  Gln Glu Ser Ile Gly  Leu Ala Ile
    1745                 1750                 1755

His Leu  Leu Asp Gly Gly Asn  Thr Glu Ile Gln Lys  Ser Phe His
    1760                 1765                 1770

Asn Leu  Met Met Ser Asp Lys  Lys Ser Glu Arg Phe  Phe Lys Val
    1775                 1780                 1785

Leu His  Asp Arg Met Lys Arg  Ala Gln Gln Glu Thr  Lys Ser Thr
    1790                 1795                 1800

Val Ala  Val Asn Met Asn Asp  Leu Gly Ser Gln Pro  His Glu Asp
    1805                 1810                 1815

Arg Glu  Pro Val Asp Pro Thr  Thr Lys Gly Arg Val  Ala Ser Phe
    1820                 1825                 1830

Ser Ile  Pro Gly Ser Ser Ser  Arg Tyr Ser Leu Gly  Pro Ser Leu
    1835                 1840                 1845

Arg Arg  Gly His Glu Val Ser  Glu Arg Val Gln Ser  Ser Glu Met
    1850                 1855                 1860

Gly Thr  Ser Val Leu Ile Met  Gln Pro Ile Leu Arg  Phe Leu Gln
    1865                 1870                 1875

Leu Leu  Cys Glu Asn His Asn  Arg Asp Leu Gln Asn  Phe Leu Arg
    1880                 1885                 1890

Cys Gln  Asn Asn Lys Thr Asn  Tyr Asn Leu Val Cys  Glu Thr Leu
    1895                 1900                 1905

Gln Phe  Leu Asp Ile Met Cys  Gly Ser Thr Thr Gly  Gly Leu Gly
    1910                 1915                 1920

Leu Leu  Gly Leu Tyr Ile Asn  Glu Asp Asn Val Gly  Leu Val Ile
    1925                 1930                 1935

Gln Thr  Leu Glu Thr Leu Thr  Glu Tyr Cys Gln Gly  Pro Cys His
    1940                 1945                 1950

Glu Asn  Gln Thr Cys Ile Val  Thr His Glu Ser Asn  Gly Ile Asp
    1955                 1960                 1965

Ile Ile  Thr Ala Leu Ile Leu  Asn Asp Ile Ser Pro  Leu Cys Lys
    1970                 1975                 1980

Tyr Arg  Met Asp Leu Val Leu  Gln Leu Lys Asp Asn  Ala Ser Lys
    1985                 1990                 1995

Leu Leu  Leu Ala Leu Met Glu  Ser Arg His Asp Ser  Glu Asn Ala
    2000                 2005                 2010

Glu Arg  Ile Leu Ile Ser Leu  Arg Pro Gln Glu Leu  Val Asp Val
    2015                 2020                 2025

Ile Lys  Lys Ala Tyr Leu Gln  Glu Glu Glu Arg Glu  Asn Ser Glu
    2030                 2035                 2040

Val Ser  Pro Arg Glu Val Gly  His Asn Ile Tyr Ile  Leu Ala Leu
    2045                 2050                 2055

Gln Leu  Ser Arg His Asn Lys  Gln Leu Gln His Leu  Leu Lys Pro
    2060                 2065                 2070
```

```
Val Lys  Arg Ile Gln Glu Glu  Glu Ala Glu Gly Ile  Ser Ser Met
    2075                 2080                 2085

Leu Ser  Leu Asn Asn Lys Gln  Leu Ser Gln Met Leu  Lys Ser Ser
    2090                 2095                 2100

Ala Pro  Ala Gln Glu Glu Glu  Glu Asp Pro Leu Ala  Tyr Tyr Glu
    2105                 2110                 2115

Asn His  Thr Ser Gln Ile Glu  Ile Val Arg Gln Asp  Arg Ser Met
    2120                 2125                 2130

Glu Gln  Ile Val Phe Pro Val  Pro Gly Ile Cys Gln  Phe Leu Thr
    2135                 2140                 2145

Glu Glu  Thr Lys His Arg Leu  Phe Thr Thr Thr Glu  Gln Asp Glu
    2150                 2155                 2160

Gln Gly  Ser Lys Val Ser Asp  Phe Phe Asp Gln Ser  Ser Phe Leu
    2165                 2170                 2175

His Asn  Glu Met Glu Trp Gln  Arg Lys Leu Arg Ser  Met Pro Leu
    2180                 2185                 2190

Ile Tyr  Trp Phe Ser Arg Arg  Met Thr Leu Trp Gly  Ser Ile Ser
    2195                 2200                 2205

Phe Asn  Leu Ala Val Phe Ile  Asn Ile Ile Ile Ala  Phe Phe Tyr
    2210                 2215                 2220

Pro Tyr  Met Glu Gly Ala Ser  Thr Gly Val Leu Asp  Ser Pro Leu
    2225                 2230                 2235

Ile Ser  Leu Leu Phe Trp Ile  Leu Ile Cys Phe Ser  Ile Ala Ala
    2240                 2245                 2250

Leu Phe  Thr Lys Arg Tyr Ser  Ile Arg Pro Leu Ile  Val Ala Leu
    2255                 2260                 2265

Ile Leu  Arg Ser Ile Tyr Tyr  Leu Gly Ile Gly Pro  Thr Leu Asn
    2270                 2275                 2280

Ile Leu  Gly Ala Leu Asn Leu  Thr Asn Lys Ile Val  Phe Val Val
    2285                 2290                 2295

Ser Phe  Val Gly Asn Arg Gly  Thr Phe Ile Arg Gly  Tyr Lys Ala
    2300                 2305                 2310

Met Val  Met Asp Met Glu Phe  Leu Tyr His Val Gly  Tyr Ile Leu
    2315                 2320                 2325

Thr Ser  Val Leu Gly Leu Phe  Ala His Glu Leu Phe  Tyr Ser Ile
    2330                 2335                 2340

Leu Leu  Phe Asp Leu Ile Tyr  Arg Glu Glu Thr Leu  Phe Asn Val
    2345                 2350                 2355

Ile Lys  Ser Val Thr Arg Asn  Gly Arg Ser Ile Leu  Leu Thr Ala
    2360                 2365                 2370

Leu Leu  Ala Leu Ile Leu Val  Tyr Leu Phe Ser Ile  Val Gly Phe
    2375                 2380                 2385

Leu Phe  Leu Lys Asp Asp Phe  Ile Leu Glu Val Asp  Arg Leu Pro
    2390                 2395                 2400

Asn Asn  His Ser Thr Ala Ser  Pro Leu Gly Met Pro  His Gly Ala
    2405                 2410                 2415

Ala Ala  Phe Val Asp Thr Cys  Ser Gly Asp Lys Met  Asp Cys Val
    2420                 2425                 2430

Ser Gly  Leu Ser Val Pro Glu  Val Leu Glu Glu Asp  Arg Glu Leu
    2435                 2440                 2445

Asp Ser  Thr Glu Arg Ala Cys  Asp Thr Leu Leu Met  Cys Ile Val
    2450                 2455                 2460

Thr Val  Met Asn His Gly Leu  Arg Asn Gly Gly Gly  Val Gly Asp
```

```
    2465                2470                2475

Ile Leu  Arg Lys Pro Ser Lys  Asp Glu Ser Leu Phe  Pro Ala Arg
    2480                2485                2490

Val Val  Tyr Asp Leu Leu Phe  Phe Phe Ile Val Ile  Ile Ile Val
    2495                2500                2505

Leu Asn  Leu Ile Phe Gly Val  Ile Ile Asp Thr Phe  Ala Asp Leu
    2510                2515                2520

Arg Ser  Glu Lys Gln Lys Lys  Glu Glu Ile Leu Lys  Thr Thr Cys
    2525                2530                2535

Phe Ile  Cys Gly Leu Glu Arg  Asp Lys Phe Asp Asn  Lys Thr Val
    2540                2545                2550

Ser Phe  Glu Glu His Ile Lys  Leu Glu His Asn Met  Trp Asn Tyr
    2555                2560                2565

Leu Tyr  Phe Ile Val Leu Val  Arg Val Lys Asn Lys  Thr Asp Tyr
    2570                2575                2580

Thr Gly  Pro Glu Ser Tyr Val  Ala Gln Met Ile Lys  Asn Lys Asn
    2585                2590                2595

Leu Asp  Trp Phe Pro Arg Met  Arg Ala Met Ser Leu  Val Ser Asn
    2600                2605                2610

Glu Gly  Glu Gly Glu Gln Asn  Glu Ile Arg Ile Leu  Gln Asp Lys
    2615                2620                2625

Leu Asn  Ser Thr Met Lys Leu  Val Ser His Leu Thr  Ala Gln Leu
    2630                2635                2640

Asn Glu  Leu Lys Glu Gln Met  Thr Glu Gln Arg Lys  Arg Arg Gln
    2645                2650                2655

Arg Leu  Gly Phe Val Asp Val  Gln Asn Cys Ile Ser  Arg
    2660                2665                2670


<210> SEQ ID NO 12
<211> LENGTH: 1729
<212> TYPE: PRT
<213> ORGANISM: Homo sapiens
<220> FEATURE:
<221> NAME/KEY: misc_feature
<222> LOCATION: (429)..(429)
<223> OTHER INFORMATION: Phosphorylation site

<400> SEQUENCE: 12

Met Lys Val Ser Thr Leu Arg Glu Ser Ser Ala Met Ala Ser Pro Leu
1               5                   10                  15

Pro Arg Glu Met Glu Glu Glu Leu Val Pro Thr Gly Ser Glu Pro Gly
            20                  25                  30

Asp Thr Arg Ala Lys Pro Pro Val Lys Pro Lys Pro Arg Ala Leu Pro
        35                  40                  45

Ala Lys Pro Ala Leu Pro Ala Lys Pro Ser Leu Leu Val Pro Val Gly
    50                  55                  60

Pro Arg Pro Pro Arg Gly Pro Leu Ala Glu Leu Pro Ser Ala Arg Lys
65                  70                  75                  80

Met Asn Met Leu Ala Gly Pro Gln Pro Tyr Gly Gly Ser Lys Arg Pro
                85                  90                  95

Leu Pro Phe Ala Pro Arg Pro Ala Val Glu Ala Ser Thr Gly Gly Glu
            100                 105                 110

Ala Thr Gln Glu Thr Gly Lys Glu Glu Ala Gly Lys Glu Glu Pro Pro
        115                 120                 125

Pro Leu Thr Pro Pro Ala Arg Cys Ala Ala Pro Gly Gly Val Arg Lys
    130                 135                 140
```

-continued

```
Ala Pro Ala Pro Phe Arg Pro Ala Ser Glu Arg Phe Ala Ala Thr Thr
145                 150                 155                 160

Val Glu Glu Ile Leu Ala Lys Met Glu Gln Pro Arg Lys Glu Val Leu
                165                 170                 175

Ala Ser Pro Asp Arg Leu Trp Gly Ser Arg Leu Thr Phe Asn His Asp
            180                 185                 190

Gly Ser Ser Arg Tyr Gly Pro Arg Thr Tyr Gly Thr Thr Thr Ala Pro
        195                 200                 205

Arg Asp Glu Asp Gly Ser Thr Leu Phe Arg Gly Trp Ser Gln Glu Gly
    210                 215                 220

Pro Val Lys Ser Pro Ala Glu Cys Arg Glu Glu His Ser Lys Thr Pro
225                 230                 235                 240

Glu Glu Arg Ser Leu Pro Ser Asp Leu Ala Phe Asn Gly Asp Leu Ala
                245                 250                 255

Lys Ala Ala Ser Ser Glu Leu Pro Ala Asp Ile Ser Lys Pro Trp Ile
            260                 265                 270

Pro Ser Ser Pro Ala Pro Ser Ser Glu Asn Gly Gly Pro Ala Ser Pro
        275                 280                 285

Gly Leu Pro Ala Glu Ala Ser Gly Ser Gly Pro Gly Ser Pro His Leu
    290                 295                 300

His Pro Pro Asp Lys Ser Ser Pro Cys His Ser Gln Leu Leu Glu Ala
305                 310                 315                 320

Gln Thr Pro Glu Ala Ser Gln Ala Ser Pro Cys Pro Ala Val Thr Pro
                325                 330                 335

Ser Ala Pro Ser Ala Ala Leu Pro Asp Glu Gly Ser Arg His Thr Pro
            340                 345                 350

Ser Pro Gly Leu Pro Ala Glu Gly Ala Pro Glu Ala Pro Arg Pro Ser
        355                 360                 365

Ser Pro Pro Pro Glu Val Leu Glu Pro His Ser Leu Asp Gln Pro Pro
    370                 375                 380

Ala Thr Ser Pro Arg Pro Leu Ile Glu Val Gly Glu Leu Leu Asp Leu
385                 390                 395                 400

Thr Arg Thr Phe Pro Ser Gly Gly Glu Glu Glu Ala Lys Gly Asp Ala
                405                 410                 415

His Leu Arg Pro Thr Ser Leu Val Gln Arg Arg Phe Ser Glu Gly Val
            420                 425                 430

Leu Gln Ser Pro Ser Gln Asp Gln Glu Lys Leu Gly Gly Ser Leu Ala
        435                 440                 445

Ala Leu Pro Gln Gly Gln Gly Ser Gln Leu Ala Leu Asp Arg Pro Phe
    450                 455                 460

Gly Ala Glu Ser Asn Trp Ser Leu Ser Gln Ser Phe Glu Trp Thr Phe
465                 470                 475                 480

Pro Thr Arg Pro Ser Gly Leu Gly Val Trp Arg Leu Asp Ser Pro Pro
                485                 490                 495

Pro Ser Pro Ile Thr Glu Ala Ser Glu Ala Ala Glu Ala Ala Glu Ala
            500                 505                 510

Gly Asn Leu Ala Val Ser Ser Arg Glu Glu Gly Val Ser Gln Gln Gly
        515                 520                 525

Gln Gly Ala Gly Ser Ala Pro Ser Gly Ser Gly Ser Ser Trp Val Gln
    530                 535                 540

Gly Asp Asp Pro Ser Met Ser Leu Thr Gln Lys Gly Asp Gly Glu Ser
545                 550                 555                 560
```

-continued

```
Gln Pro Gln Phe Pro Ala Val Pro Leu Glu Pro Leu Pro Thr Thr Glu
                565                 570                 575

Gly Thr Pro Gly Leu Pro Leu Gln Gln Ala Glu Glu Arg Tyr Glu Ser
            580                 585                 590

Gln Glu Pro Leu Ala Gly Gln Glu Ser Pro Leu Pro Leu Ala Thr Arg
        595                 600                 605

Glu Ala Ala Leu Pro Ile Leu Glu Pro Val Leu Gly Gln Glu Gln Pro
    610                 615                 620

Ala Ala Pro Asp Gln Pro Cys Val Leu Phe Ala Asp Ala Pro Glu Pro
625                 630                 635                 640

Gly Gln Ala Leu Pro Val Glu Glu Glu Ala Val Thr Leu Ala Arg Ala
                645                 650                 655

Glu Thr Thr Gln Ala Arg Thr Glu Ala Gln Asp Leu Cys Arg Ala Ser
            660                 665                 670

Pro Glu Pro Pro Gly Pro Glu Ser Ser Ser Arg Trp Leu Asp Asp Leu
        675                 680                 685

Leu Ala Ser Pro Pro Pro Ser Gly Gly Gly Ala Arg Arg Gly Ala Gly
    690                 695                 700

Ala Glu Leu Lys Asp Thr Gln Ser Pro Ser Thr Cys Ser Glu Gly Leu
705                 710                 715                 720

Leu Gly Trp Ser Gln Lys Asp Leu Gln Ser Glu Phe Gly Ile Thr Gly
                725                 730                 735

Asp Pro Gln Pro Ser Ser Phe Ser Pro Ser Ser Trp Cys Gln Gly Ala
            740                 745                 750

Ser Gln Asp Tyr Gly Leu Gly Gly Ala Ser Pro Arg Gly Asp Pro Gly
        755                 760                 765

Leu Gly Glu Arg Asp Trp Thr Ser Lys Tyr Gly Gln Gly Ala Gly Glu
    770                 775                 780

Gly Ser Thr Arg Glu Trp Ala Ser Arg Cys Gly Ile Gly Gln Glu Glu
785                 790                 795                 800

Met Glu Ala Ser Ser Ser Gln Asp Gln Ser Lys Val Ser Ala Pro Gly
                805                 810                 815

Val Leu Thr Ala Gln Asp Arg Val Val Gly Lys Pro Ala Gln Leu Gly
            820                 825                 830

Thr Gln Arg Ser Gln Glu Ala Asp Val Gln Asp Trp Glu Phe Arg Lys
        835                 840                 845

Arg Asp Ser Gln Gly Thr Tyr Ser Ser Arg Asp Ala Glu Leu Gln Asp
    850                 855                 860

Gln Glu Phe Gly Lys Arg Asp Ser Leu Gly Thr Tyr Ser Ser Arg Asp
865                 870                 875                 880

Val Ser Leu Gly Asp Trp Glu Phe Gly Lys Arg Asp Ser Leu Gly Ala
                885                 890                 895

Tyr Ala Ser Gln Asp Ala Asn Glu Gln Gly Gln Asp Leu Gly Lys Arg
            900                 905                 910

Asp His His Gly Arg Tyr Ser Ser Gln Asp Ala Asp Glu Gln Asp Trp
        915                 920                 925

Glu Phe Gln Lys Arg Asp Val Ser Leu Gly Thr Tyr Gly Ser Arg Ala
    930                 935                 940

Ala Glu Pro Gln Glu Gln Glu Phe Gly Lys Ser Ala Trp Ile Arg Asp
945                 950                 955                 960

Tyr Ser Ser Gly Gly Ser Ser Arg Thr Leu Asp Ala Gln Asp Arg Ser
                965                 970                 975

Phe Gly Thr Arg Pro Leu Ser Ser Gly Phe Ser Pro Glu Glu Ala Gln
```

-continued

```
            980                 985                 990

Gln Gln Asp Glu Glu Phe Glu Lys  Lys Ile Pro Ser Val  Glu Asp Ser
        995                 1000                1005

Leu Gly  Glu Gly Ser Arg Asp  Ala Gly Arg Pro Gly  Glu Arg Gly
    1010                 1015                 1020

Ser Gly  Gly Leu Phe Ser Pro  Ser Thr Ala His Val  Pro Asp Gly
    1025                 1030                 1035

Ala Leu  Gly Gln Arg Asp Gln  Ser Ser Trp Gln Asn  Ser Asp Ala
    1040                 1045                 1050

Ser Gln  Glu Val Gly Gly His  Gln Glu Arg Gln Gln  Ala Gly Ala
    1055                 1060                 1065

Gln Gly  Pro Gly Ser Ala Asp  Leu Glu Asp Gly Glu  Met Gly Lys
    1070                 1075                 1080

Arg Gly  Trp Val Gly Glu Phe  Ser Leu Ser Val Gly  Pro Gln Arg
    1085                 1090                 1095

Glu Ala  Ala Phe Ser Pro Gly  Gln Gln Asp Trp Ser  Arg Asp Phe
    1100                 1105                 1110

Cys Ile  Glu Ala Ser Glu Arg  Ser Tyr Gln Phe Gly  Ile Ile Gly
    1115                 1120                 1125

Asn Asp  Arg Val Ser Gly Ala  Gly Phe Ser Pro Ser  Ser Lys Met
    1130                 1135                 1140

Glu Gly  Gly His Phe Val Pro  Pro Gly Lys Thr Thr  Ala Gly Ser
    1145                 1150                 1155

Val Asp  Trp Thr Asp Gln Leu  Gly Leu Arg Asn Leu  Glu Val Ser
    1160                 1165                 1170

Ser Cys  Val Gly Ser Gly Gly  Ser Ser Glu Ala Arg  Glu Ser Ala
    1175                 1180                 1185

Val Gly  Gln Met Gly Trp Ser  Gly Gly Leu Ser Leu  Arg Asp Met
    1190                 1195                 1200

Asn Leu  Thr Gly Cys Leu Glu  Ser Gly Gly Ser Glu  Glu Pro Gly
    1205                 1210                 1215

Gly Ile  Gly Val Gly Glu Lys  Asp Trp Thr Ser Asp  Val Asn Val
    1220                 1225                 1230

Lys Ser  Lys Asp Leu Ala Glu  Val Gly Glu Gly Gly  Gly His Ser
    1235                 1240                 1245

Gln Ala  Arg Glu Ser Gly Val  Gly Gln Thr Asp Trp  Ser Gly Val
    1250                 1255                 1260

Glu Ala  Gly Glu Phe Leu Lys  Ser Arg Glu Arg Gly  Val Gly Gln
    1265                 1270                 1275

Ala Asp  Trp Thr Pro Asp Leu  Gly Leu Arg Asn Met  Ala Pro Gly
    1280                 1285                 1290

Ala Val  Cys Ser Pro Gly Glu  Ser Lys Glu Leu Gly  Val Gly Gln
    1295                 1300                 1305

Met Asp  Trp Gly Asn Asn Leu  Gly Leu Arg Asp Leu  Glu Val Thr
    1310                 1315                 1320

Cys Asp  Pro Asp Ser Gly Gly  Ser Gln Gly Leu Arg  Gly Cys Gly
    1325                 1330                 1335

Val Gly  Gln Met Asp Trp Thr  Gln Asp Leu Ala Pro  Gln Asn Val
    1340                 1345                 1350

Glu Leu  Phe Gly Ala Pro Ser  Glu Ala Arg Glu His  Gly Val Gly
    1355                 1360                 1365

Gly Val  Ser Gln Cys Pro Glu  Pro Gly Leu Arg His  Asn Gly Ser
    1370                 1375                 1380
```

Leu Ser Pro Gly Leu Glu Ala Arg Asp Pro Leu Glu Ala Arg Glu
1385 1390 1395

Leu Gly Val Gly Glu Thr Ser Gly Pro Glu Thr Gln Gly Glu Asp
1400 1405 1410

Tyr Ser Ser Ser Ser Leu Glu Pro His Pro Ala Asp Pro Gly Met
1415 1420 1425

Glu Thr Gly Glu Ala Leu Ser Phe Gly Ala Ser Pro Gly Arg Cys
1430 1435 1440

Pro Ala Arg Pro Pro Pro Ser Gly Ser Gln Gly Leu Leu Glu Glu
1445 1450 1455

Met Leu Ala Ala Ser Ser Ser Lys Ala Val Ala Arg Arg Glu Ser
1460 1465 1470

Ala Ala Ser Gly Leu Gly Gly Leu Leu Glu Glu Glu Gly Ala Gly
1475 1480 1485

Ala Gly Ala Ala Gln Glu Glu Val Leu Glu Pro Gly Arg Asp Ser
1490 1495 1500

Pro Pro Ser Trp Arg Pro Gln Pro Asp Gly Glu Ala Ser Gln Thr
1505 1510 1515

Glu Asp Val Asp Gly Thr Trp Gly Ser Ser Ala Ala Arg Trp Ser
1520 1525 1530

Asp Gln Gly Pro Ala Gln Thr Ser Arg Arg Pro Ser Gln Gly Pro
1535 1540 1545

Pro Ala Arg Ser Pro Ser Gln Asp Phe Ser Phe Ile Glu Asp Thr
1550 1555 1560

Glu Ile Leu Asp Ser Ala Met Tyr Arg Ser Arg Ala Asn Leu Gly
1565 1570 1575

Arg Lys Arg Gly His Arg Ala Pro Val Ile Arg Pro Gly Gly Thr
1580 1585 1590

Leu Gly Leu Ser Glu Ala Ala Asp Ser Asp Ala His Leu Phe Gln
1595 1600 1605

Asp Ser Thr Glu Pro Arg Ala Ser Arg Val Pro Ser Ser Asp Glu
1610 1615 1620

Glu Val Val Glu Glu Pro Gln Ser Arg Arg Thr Arg Met Ser Leu
1625 1630 1635

Gly Thr Lys Gly Leu Lys Val Asn Leu Phe Pro Gly Leu Ser Pro
1640 1645 1650

Ser Ala Leu Lys Ala Lys Leu Arg Pro Arg Asn Arg Ser Ala Glu
1655 1660 1665

Glu Gly Glu Leu Ala Glu Ser Lys Ser Ser Gln Lys Glu Ser Ala
1670 1675 1680

Val Gln Arg Ser Lys Ser Cys Lys Val Pro Gly Leu Gly Lys Pro
1685 1690 1695

Leu Thr Leu Pro Pro Lys Pro Glu Lys Ser Ser Gly Ser Glu Gly
1700 1705 1710

Ser Ser Pro Asn Trp Leu Gln Ala Leu Lys Leu Lys Lys Lys Lys
1715 1720 1725

Val

<210> SEQ ID NO 13
<211> LENGTH: 1173
<212> TYPE: PRT
<213> ORGANISM: Homo sapiens
<220> FEATURE:
<221> NAME/KEY: misc_feature

```
<222> LOCATION: (1101)..(1101)
<223> OTHER INFORMATION: Phosphorylation site

<400> SEQUENCE: 13

Met Val Thr Val Gly Thr Asn Ile Leu Pro Ser Arg Pro Ala Ala Ser
1               5                   10                  15

Ala Asn Thr Ala Arg Glu Asp Ala Ala Leu Phe Ser Arg Arg Ile Pro
            20                  25                  30

Pro Arg His Lys Asn Gly Ala Ala Gln Pro Gly Ala Ala Pro Gly Pro
        35                  40                  45

Gly Ala Pro Gly Ala Asn Met Gly Asn Ala His Ser Lys Ser Gly Asp
    50                  55                  60

Arg His Ser Ala Leu Pro Gly Arg Pro Glu Leu Ser Phe Tyr Gly Ser
65                  70                  75                  80

Phe Pro Arg Lys Trp Ser Glu Asn Val Phe Leu Asp Asn Glu Leu Leu
                85                  90                  95

Thr Ser Lys Ile Leu Ser Val Leu Arg Pro Gln Ser Glu Arg Gly Phe
            100                 105                 110

Arg Ala Gly Asp Leu Arg Tyr Pro Thr His Phe Leu Ser Thr Asn Ser
        115                 120                 125

Val Leu Ala Ser Val Thr Ala Ser Leu Lys Glu His Pro Arg Gly Thr
    130                 135                 140

Leu Leu Ser Asp Gly Ser Pro Ala Leu Ser Arg Asn Val Gly Met Thr
145                 150                 155                 160

Val Ser Gln Lys Gly Gly Pro Gln Pro Thr Pro Ser Pro Ala Gly Pro
                165                 170                 175

Gly Thr Gln Leu Gly Pro Ile Thr Gly Glu Met Asp Glu Ala Asp Ser
            180                 185                 190

Ala Phe Leu Lys Phe Lys Gln Thr Ala Asp Asp Ser Leu Ser Leu Thr
        195                 200                 205

Ser Pro Asn Thr Glu Ser Ile Phe Val Glu Asp Pro Tyr Thr Ala Ser
    210                 215                 220

Leu Arg Ser Glu Ile Glu Ser Asp Gly His Glu Phe Glu Ala Glu Ser
225                 230                 235                 240

Trp Ser Leu Ala Val Asp Ala Ala Tyr Ala Lys Lys Gln Lys Arg Glu
                245                 250                 255

Val Val Lys Arg Gln Asp Val Leu Tyr Glu Leu Met Gln Thr Glu Val
            260                 265                 270

His His Val Arg Thr Leu Lys Ile Met Leu Lys Val Tyr Ser Arg Ala
        275                 280                 285

Leu Gln Glu Glu Leu Gln Phe Ser Ser Lys Ala Ile Gly Arg Leu Phe
    290                 295                 300

Pro Cys Ala Asp Asp Leu Leu Glu Thr His Ser His Phe Leu Ala Arg
305                 310                 315                 320

Leu Lys Glu Arg Arg Gln Glu Ser Leu Glu Glu Gly Ser Asp Arg Asn
                325                 330                 335

Tyr Val Ile Gln Lys Ile Gly Asp Leu Leu Val Gln Gln Phe Ser Gly
            340                 345                 350

Glu Asn Gly Glu Arg Met Lys Glu Lys Tyr Gly Val Phe Cys Ser Gly
        355                 360                 365

His Asn Glu Ala Val Ser His Tyr Lys Leu Leu Leu Gln Gln Asn Lys
    370                 375                 380

Lys Phe Gln Asn Leu Ile Lys Lys Ile Gly Asn Phe Ser Ile Val Arg
385                 390                 395                 400
```

```
Arg Leu Gly Val Gln Glu Cys Ile Leu Leu Val Thr Gln Arg Ile Thr
                405                 410                 415

Lys Tyr Pro Val Leu Val Glu Arg Ile Ile Gln Asn Thr Glu Ala Gly
            420                 425                 430

Thr Glu Asp Tyr Glu Asp Leu Thr Gln Ala Leu Asn Leu Ile Lys Asp
        435                 440                 445

Ile Ile Ser Gln Val Asp Ala Lys Val Ser Glu Cys Glu Lys Gly Gln
    450                 455                 460

Arg Leu Arg Glu Ile Ala Gly Lys Met Asp Leu Lys Ser Ser Ser Lys
465                 470                 475                 480

Leu Lys Asn Gly Leu Thr Phe Arg Lys Glu Asp Met Leu Gln Arg Gln
                485                 490                 495

Leu His Leu Glu Gly Met Leu Cys Trp Lys Thr Thr Ser Gly Arg Leu
            500                 505                 510

Lys Asp Ile Leu Ala Ile Leu Leu Thr Asp Val Leu Leu Leu Leu Gln
        515                 520                 525

Glu Lys Asp Gln Lys Tyr Val Phe Ala Ser Val Asp Ser Lys Pro Pro
    530                 535                 540

Val Ile Ser Leu Gln Lys Leu Ile Val Arg Glu Val Ala Asn Glu Glu
545                 550                 555                 560

Lys Ala Met Phe Leu Ile Ser Ala Ser Leu Gln Gly Pro Glu Met Tyr
                565                 570                 575

Glu Ile Tyr Thr Ser Ser Lys Glu Asp Arg Asn Ala Trp Met Ala His
            580                 585                 590

Ile Gln Arg Ala Val Glu Ser Cys Pro Asp Glu Glu Glu Gly Pro Phe
        595                 600                 605

Ser Leu Pro Glu Glu Glu Arg Lys Val Val Glu Ala Arg Ala Thr Arg
    610                 615                 620

Leu Arg Asp Phe Gln Glu Arg Leu Ser Met Lys Asp Gln Leu Ile Ala
625                 630                 635                 640

Gln Ser Leu Leu Glu Lys Gln Gln Ile Tyr Leu Glu Met Ala Glu Met
                645                 650                 655

Gly Gly Leu Glu Asp Leu Pro Gln Pro Arg Gly Leu Phe Arg Gly Gly
            660                 665                 670

Asp Pro Ser Glu Thr Leu Gln Gly Glu Leu Ile Leu Lys Ser Ala Met
        675                 680                 685

Ser Glu Ile Glu Gly Ile Gln Ser Leu Ile Cys Arg Gln Leu Gly Ser
    690                 695                 700

Ala Asn Gly Gln Ala Glu Asp Gly Gly Ser Ser Thr Gly Pro Pro Arg
705                 710                 715                 720

Arg Ala Glu Thr Phe Ala Gly Tyr Asp Cys Thr Asn Ser Pro Thr Lys
                725                 730                 735

Asn Gly Ser Phe Lys Lys Lys Val Ser Ser Thr Asp Pro Arg Pro Arg
            740                 745                 750

Asp Trp Arg Gly Pro Pro Asn Ser Pro Asp Leu Lys Leu Ser Asp Ser
        755                 760                 765

Asp Ile Pro Gly Ser Ser Glu Glu Ser Pro Gln Val Val Glu Ala Pro
    770                 775                 780

Gly Thr Glu Ser Asp Pro Arg Leu Pro Thr Val Leu Glu Ser Glu Leu
785                 790                 795                 800

Val Gln Arg Ile Gln Thr Leu Ser Gln Leu Leu Leu Asn Leu Gln Ala
                805                 810                 815
```

```
Val Ile Ala His Gln Asp Ser Tyr Val Glu Thr Gln Arg Ala Ala Ile
            820                 825                 830

Gln Glu Arg Glu Lys Gln Phe Arg Leu Gln Ser Thr Arg Gly Asn Leu
        835                 840                 845

Leu Leu Glu Gln Glu Arg Gln Arg Asn Phe Glu Lys Gln Arg Glu Glu
    850                 855                 860

Arg Ala Ala Leu Glu Lys Leu Gln Ser Gln Leu Arg His Glu Gln Gln
865                 870                 875                 880

Arg Trp Glu Arg Glu Arg Gln Trp Gln His Gln Glu Leu Glu Arg Ala
                885                 890                 895

Gly Ala Arg Leu Gln Glu Arg Glu Gly Glu Ala Arg Gln Leu Arg Glu
            900                 905                 910

Arg Leu Glu Gln Glu Arg Ala Glu Leu Glu Arg Gln Arg Gln Ala Tyr
        915                 920                 925

Gln His Asp Leu Glu Arg Leu Arg Glu Ala Gln Arg Ala Val Glu Arg
    930                 935                 940

Glu Arg Glu Arg Leu Glu Leu Leu Arg Arg Leu Lys Lys Gln Asn Thr
945                 950                 955                 960

Ala Pro Gly Ala Leu Pro Pro Asp Thr Leu Ala Glu Ala Gln Pro Pro
                965                 970                 975

Ser His Pro Pro Ser Phe Asn Gly Glu Gly Leu Glu Gly Pro Arg Val
            980                 985                 990

Ser Met Leu Pro Ser Gly Val Gly  Pro Glu Tyr Ala Glu  Arg Pro Glu
        995                 1000                1005

Val Ala  Arg Arg Asp Ser Ala  Pro Thr Glu Asn Arg  Leu Ala Lys
    1010                1015                1020

Ser Asp  Val Pro Ile Gln Leu  Leu Ser Ala Thr Asn  Gln Phe Gln
    1025                1030                1035

Arg Gln  Ala Ala Val Gln Gln  Gln Ile Pro Thr Lys  Leu Ala Ala
    1040                1045                1050

Ser Thr  Lys Gly Gly Lys Asp  Lys Gly Gly Lys Ser  Arg Gly Ser
    1055                1060                1065

Gln Arg  Trp Glu Ser Ser Ala  Ser Phe Asp Leu Lys  Gln Gln Leu
    1070                1075                1080

Leu Leu  Asn Lys Leu Met Gly  Lys Asp Glu Ser Thr  Ser Arg Asn
    1085                1090                1095

Arg Arg  Ser Leu Ser Pro Ile  Leu Pro Gly Arg His  Ser Pro Ala
    1100                1105                1110

Pro Pro  Pro Asp Pro Gly Phe  Pro Ala Pro Ser Pro  Pro Pro Ala
    1115                1120                1125

Asp Ser  Pro Ser Glu Gly Phe  Ser Leu Lys Ala Gly  Gly Thr Ala
    1130                1135                1140

Leu Leu  Pro Gly Pro Pro Ala  Pro Ser Pro Leu Pro  Ala Thr Pro
    1145                1150                1155

Leu Ser  Ala Lys Glu Asp Ala  Ser Lys Glu Asp Val  Ile Phe Phe
    1160                1165                1170


<210> SEQ ID NO 14
<211> LENGTH: 1015
<212> TYPE: PRT
<213> ORGANISM: Homo sapiens
<220> FEATURE:
<221> NAME/KEY: misc_feature
<222> LOCATION: (943)..(943)
<223> OTHER INFORMATION: Phosphorylation site
```

<400> SEQUENCE: 14

```
Met Thr Val Ser Gln Lys Gly Gly Pro Gln Pro Thr Pro Ser Pro Ala
1               5                   10                  15

Gly Pro Gly Thr Gln Leu Gly Pro Ile Thr Gly Glu Met Asp Glu Ala
            20                  25                  30

Asp Ser Ala Phe Leu Lys Phe Lys Gln Thr Ala Asp Asp Ser Leu Ser
        35                  40                  45

Leu Thr Ser Pro Asn Thr Glu Ser Ile Phe Val Glu Asp Pro Tyr Thr
    50                  55                  60

Ala Ser Leu Arg Ser Glu Ile Glu Ser Asp Gly His Glu Phe Glu Ala
65                  70                  75                  80

Glu Ser Trp Ser Leu Ala Val Asp Ala Ala Tyr Ala Lys Lys Gln Lys
                85                  90                  95

Arg Glu Val Val Lys Arg Gln Asp Val Leu Tyr Glu Leu Met Gln Thr
            100                 105                 110

Glu Val His His Val Arg Thr Leu Lys Ile Met Leu Lys Val Tyr Ser
        115                 120                 125

Arg Ala Leu Gln Glu Glu Leu Gln Phe Ser Ser Lys Ala Ile Gly Arg
    130                 135                 140

Leu Phe Pro Cys Ala Asp Asp Leu Leu Glu Thr His Ser His Phe Leu
145                 150                 155                 160

Ala Arg Leu Lys Glu Arg Arg Gln Glu Ser Leu Glu Glu Gly Ser Asp
                165                 170                 175

Arg Asn Tyr Val Ile Gln Lys Ile Gly Asp Leu Leu Val Gln Gln Phe
            180                 185                 190

Ser Gly Glu Asn Gly Glu Arg Met Lys Glu Lys Tyr Gly Val Phe Cys
        195                 200                 205

Ser Gly His Asn Glu Ala Val Ser His Tyr Lys Leu Leu Leu Gln Gln
    210                 215                 220

Asn Lys Lys Phe Gln Asn Leu Ile Lys Lys Ile Gly Asn Phe Ser Ile
225                 230                 235                 240

Val Arg Arg Leu Gly Val Gln Glu Cys Ile Leu Leu Val Thr Gln Arg
                245                 250                 255

Ile Thr Lys Tyr Pro Val Leu Val Glu Arg Ile Ile Gln Asn Thr Glu
            260                 265                 270

Ala Gly Thr Glu Asp Tyr Glu Asp Leu Thr Gln Ala Leu Asn Leu Ile
        275                 280                 285

Lys Asp Ile Ile Ser Gln Val Asp Ala Lys Val Ser Glu Cys Glu Lys
    290                 295                 300

Gly Gln Arg Leu Arg Glu Ile Ala Gly Lys Met Asp Leu Lys Ser Ser
305                 310                 315                 320

Ser Lys Leu Lys Asn Gly Leu Thr Phe Arg Lys Glu Asp Met Leu Gln
                325                 330                 335

Arg Gln Leu His Leu Glu Gly Met Leu Cys Trp Lys Thr Thr Ser Gly
            340                 345                 350

Arg Leu Lys Asp Ile Leu Ala Ile Leu Leu Thr Asp Val Leu Leu Leu
        355                 360                 365

Leu Gln Glu Lys Asp Gln Lys Tyr Val Phe Ala Ser Val Asp Ser Lys
    370                 375                 380

Pro Pro Val Ile Ser Leu Gln Lys Leu Ile Val Arg Glu Val Ala Asn
385                 390                 395                 400

Glu Glu Lys Ala Met Phe Leu Ile Ser Ala Ser Leu Gln Gly Pro Glu
                405                 410                 415
```

-continued

```
Met Tyr Glu Ile Tyr Thr Ser Ser Lys Glu Asp Arg Asn Ala Trp Met
            420                 425                 430

Ala His Ile Gln Arg Ala Val Glu Ser Cys Pro Asp Glu Glu Glu Gly
        435                 440                 445

Pro Phe Ser Leu Pro Glu Glu Glu Arg Lys Val Val Glu Ala Arg Ala
    450                 455                 460

Thr Arg Leu Arg Asp Phe Gln Glu Arg Leu Ser Met Lys Asp Gln Leu
465                 470                 475                 480

Ile Ala Gln Ser Leu Leu Glu Lys Gln Gln Ile Tyr Leu Glu Met Ala
                485                 490                 495

Glu Met Gly Gly Leu Glu Asp Leu Pro Gln Pro Arg Gly Leu Phe Arg
            500                 505                 510

Gly Gly Asp Pro Ser Glu Thr Leu Gln Gly Glu Leu Ile Leu Lys Ser
        515                 520                 525

Ala Met Ser Glu Ile Glu Gly Ile Gln Ser Leu Ile Cys Arg Gln Leu
    530                 535                 540

Gly Ser Ala Asn Gly Gln Ala Glu Asp Gly Gly Ser Ser Thr Gly Pro
545                 550                 555                 560

Pro Arg Arg Ala Glu Thr Phe Ala Gly Tyr Asp Cys Thr Asn Ser Pro
                565                 570                 575

Thr Lys Asn Gly Ser Phe Lys Lys Lys Val Ser Ser Thr Asp Pro Arg
            580                 585                 590

Pro Arg Asp Trp Arg Gly Pro Pro Asn Ser Pro Asp Leu Lys Leu Ser
        595                 600                 605

Asp Ser Asp Ile Pro Gly Ser Ser Glu Glu Ser Pro Gln Val Val Glu
    610                 615                 620

Ala Pro Gly Thr Glu Ser Asp Pro Arg Leu Pro Thr Val Leu Glu Ser
625                 630                 635                 640

Glu Leu Val Gln Arg Ile Gln Thr Leu Ser Gln Leu Leu Leu Asn Leu
                645                 650                 655

Gln Ala Val Ile Ala His Gln Asp Ser Tyr Val Glu Thr Gln Arg Ala
            660                 665                 670

Ala Ile Gln Glu Arg Glu Lys Gln Phe Arg Leu Gln Ser Thr Arg Gly
        675                 680                 685

Asn Leu Leu Leu Glu Gln Glu Arg Gln Arg Asn Phe Glu Lys Gln Arg
    690                 695                 700

Glu Glu Arg Ala Ala Leu Glu Lys Leu Gln Ser Gln Leu Arg His Glu
705                 710                 715                 720

Gln Gln Arg Trp Glu Arg Glu Arg Gln Trp Gln His Gln Glu Leu Glu
                725                 730                 735

Arg Ala Gly Ala Arg Leu Gln Glu Arg Glu Gly Glu Ala Arg Gln Leu
            740                 745                 750

Arg Glu Arg Leu Glu Gln Glu Arg Ala Glu Leu Glu Arg Gln Arg Gln
        755                 760                 765

Ala Tyr Gln His Asp Leu Glu Arg Leu Arg Glu Ala Gln Arg Ala Val
    770                 775                 780

Glu Arg Glu Arg Glu Arg Leu Glu Leu Leu Arg Arg Leu Lys Lys Gln
785                 790                 795                 800

Asn Thr Ala Pro Gly Ala Leu Pro Pro Asp Thr Leu Ala Glu Ala Gln
                805                 810                 815

Pro Pro Ser His Pro Pro Ser Phe Asn Gly Glu Gly Leu Glu Gly Pro
            820                 825                 830
```

```
Arg Val Ser Met Leu Pro Ser Gly Val Gly Pro Glu Tyr Ala Glu Arg
        835                 840                 845

Pro Glu Val Ala Arg Arg Asp Ser Ala Pro Thr Glu Asn Arg Leu Ala
    850                 855                 860

Lys Ser Asp Val Pro Ile Gln Leu Leu Ser Ala Thr Asn Gln Phe Gln
865                 870                 875                 880

Arg Gln Ala Ala Val Gln Gln Gln Ile Pro Thr Lys Leu Ala Ala Ser
                885                 890                 895

Thr Lys Gly Gly Lys Asp Lys Gly Gly Lys Ser Arg Gly Ser Gln Arg
            900                 905                 910

Trp Glu Ser Ser Ala Ser Phe Asp Leu Lys Gln Gln Leu Leu Leu Asn
        915                 920                 925

Lys Leu Met Gly Lys Asp Glu Ser Thr Ser Arg Asn Arg Arg Ser Leu
    930                 935                 940

Ser Pro Ile Leu Pro Gly Arg His Ser Pro Ala Pro Pro Pro Asp Pro
945                 950                 955                 960

Gly Phe Pro Ala Pro Ser Pro Pro Pro Ala Asp Ser Pro Ser Glu Gly
                965                 970                 975

Phe Ser Leu Lys Ala Gly Gly Thr Ala Leu Leu Pro Gly Pro Pro Ala
            980                 985                 990

Pro Ser Pro Leu Pro Ala Thr Pro  Leu Ser Ala Lys Glu  Asp Ala Ser
        995                 1000                1005

Lys Glu  Asp Val Ile Phe Phe
    1010                1015


<210> SEQ ID NO 15
<211> LENGTH: 1030
<212> TYPE: PRT
<213> ORGANISM: Homo sapiens
<220> FEATURE:
<221> NAME/KEY: misc_feature
<222> LOCATION: (943)..(943)
<223> OTHER INFORMATION: Phosphorylation site

<400> SEQUENCE: 15

Met Thr Val Ser Gln Lys Gly Gly Pro Gln Pro Thr Pro Ser Pro Ala
1               5                   10                  15

Gly Pro Gly Thr Gln Leu Gly Pro Ile Thr Gly Glu Met Asp Glu Ala
            20                  25                  30

Asp Ser Ala Phe Leu Lys Phe Lys Gln Thr Ala Asp Asp Ser Leu Ser
        35                  40                  45

Leu Thr Ser Pro Asn Thr Glu Ser Ile Phe Val Glu Asp Pro Tyr Thr
    50                  55                  60

Ala Ser Leu Arg Ser Glu Ile Glu Ser Asp Gly His Glu Phe Glu Ala
65                  70                  75                  80

Glu Ser Trp Ser Leu Ala Val Asp Ala Ala Tyr Ala Lys Lys Gln Lys
                85                  90                  95

Arg Glu Val Val Lys Arg Gln Asp Val Leu Tyr Glu Leu Met Gln Thr
            100                 105                 110

Glu Val His His Val Arg Thr Leu Lys Ile Met Leu Lys Val Tyr Ser
        115                 120                 125

Arg Ala Leu Gln Glu Glu Leu Gln Phe Ser Ser Lys Ala Ile Gly Arg
    130                 135                 140

Leu Phe Pro Cys Ala Asp Asp Leu Leu Glu Thr His Ser His Phe Leu
145                 150                 155                 160

Ala Arg Leu Lys Glu Arg Arg Gln Glu Ser Leu Glu Glu Gly Ser Asp
```

-continued

```
                165                 170                 175

Arg Asn Tyr Val Ile Gln Lys Ile Gly Asp Leu Leu Val Gln Gln Phe
            180                 185                 190

Ser Gly Glu Asn Gly Glu Arg Met Lys Glu Lys Tyr Gly Val Phe Cys
        195                 200                 205

Ser Gly His Asn Glu Ala Val Ser His Tyr Lys Leu Leu Leu Gln Gln
    210                 215                 220

Asn Lys Lys Phe Gln Asn Leu Ile Lys Lys Ile Gly Asn Phe Ser Ile
225                 230                 235                 240

Val Arg Arg Leu Gly Val Gln Glu Cys Ile Leu Leu Val Thr Gln Arg
                245                 250                 255

Ile Thr Lys Tyr Pro Val Leu Val Glu Arg Ile Ile Gln Asn Thr Glu
            260                 265                 270

Ala Gly Thr Glu Asp Tyr Glu Asp Leu Thr Gln Ala Leu Asn Leu Ile
        275                 280                 285

Lys Asp Ile Ile Ser Gln Val Asp Ala Lys Val Ser Glu Cys Glu Lys
    290                 295                 300

Gly Gln Arg Leu Arg Glu Ile Ala Gly Lys Met Asp Leu Lys Ser Ser
305                 310                 315                 320

Ser Lys Leu Lys Asn Gly Leu Thr Phe Arg Lys Glu Asp Met Leu Gln
                325                 330                 335

Arg Gln Leu His Leu Glu Gly Met Leu Cys Trp Lys Thr Thr Ser Gly
            340                 345                 350

Arg Leu Lys Asp Ile Leu Ala Ile Leu Leu Thr Asp Val Leu Leu Leu
        355                 360                 365

Leu Gln Glu Lys Asp Gln Lys Tyr Val Phe Ala Ser Val Asp Ser Lys
    370                 375                 380

Pro Pro Val Ile Ser Leu Gln Lys Leu Ile Val Arg Glu Val Ala Asn
385                 390                 395                 400

Glu Glu Lys Ala Met Phe Leu Ile Ser Ala Ser Leu Gln Gly Pro Glu
                405                 410                 415

Met Tyr Glu Ile Tyr Thr Ser Ser Lys Glu Asp Arg Asn Ala Trp Met
            420                 425                 430

Ala His Ile Gln Arg Ala Val Glu Ser Cys Pro Asp Glu Glu Glu Gly
        435                 440                 445

Pro Phe Ser Leu Pro Glu Glu Glu Arg Lys Val Val Glu Ala Arg Ala
    450                 455                 460

Thr Arg Leu Arg Asp Phe Gln Glu Arg Leu Ser Met Lys Asp Gln Leu
465                 470                 475                 480

Ile Ala Gln Ser Leu Leu Glu Lys Gln Gln Ile Tyr Leu Glu Met Ala
                485                 490                 495

Glu Met Gly Gly Leu Glu Asp Leu Pro Gln Pro Arg Gly Leu Phe Arg
            500                 505                 510

Gly Gly Asp Pro Ser Glu Thr Leu Gln Gly Glu Leu Ile Leu Lys Ser
        515                 520                 525

Ala Met Ser Glu Ile Glu Gly Ile Gln Ser Leu Ile Cys Arg Gln Leu
    530                 535                 540

Gly Ser Ala Asn Gly Gln Ala Glu Asp Gly Gly Ser Ser Thr Gly Pro
545                 550                 555                 560

Pro Arg Arg Ala Glu Thr Phe Ala Gly Tyr Asp Cys Thr Asn Ser Pro
                565                 570                 575

Thr Lys Asn Gly Ser Phe Lys Lys Lys Val Ser Ser Thr Asp Pro Arg
            580                 585                 590
```

-continued

```
Pro Arg Asp Trp Arg Gly Pro Pro Asn Ser Pro Asp Leu Lys Leu Ser
        595                 600                 605

Asp Ser Asp Ile Pro Gly Ser Ser Glu Glu Ser Pro Gln Val Val Glu
    610                 615                 620

Ala Pro Gly Thr Glu Ser Asp Pro Arg Leu Pro Thr Val Leu Glu Ser
625                 630                 635                 640

Glu Leu Val Gln Arg Ile Gln Thr Leu Ser Gln Leu Leu Leu Asn Leu
                645                 650                 655

Gln Ala Val Ile Ala His Gln Asp Ser Tyr Val Glu Thr Gln Arg Ala
            660                 665                 670

Ala Ile Gln Glu Arg Glu Lys Gln Phe Arg Leu Gln Ser Thr Arg Gly
        675                 680                 685

Asn Leu Leu Leu Glu Gln Glu Arg Gln Arg Asn Phe Glu Lys Gln Arg
    690                 695                 700

Glu Glu Arg Ala Ala Leu Glu Lys Leu Gln Ser Gln Leu Arg His Glu
705                 710                 715                 720

Gln Gln Arg Trp Glu Arg Glu Arg Gln Trp Gln His Gln Glu Leu Glu
                725                 730                 735

Arg Ala Gly Ala Arg Leu Gln Glu Arg Glu Gly Glu Ala Arg Gln Leu
            740                 745                 750

Arg Glu Arg Leu Glu Gln Glu Arg Ala Glu Leu Glu Arg Gln Arg Gln
        755                 760                 765

Ala Tyr Gln His Asp Leu Glu Arg Leu Arg Glu Ala Gln Arg Ala Val
    770                 775                 780

Glu Arg Glu Arg Glu Arg Leu Glu Leu Leu Arg Arg Leu Lys Lys Gln
785                 790                 795                 800

Asn Thr Ala Pro Gly Ala Leu Pro Pro Asp Thr Leu Ala Glu Ala Gln
                805                 810                 815

Pro Pro Ser His Pro Pro Ser Phe Asn Gly Glu Gly Leu Glu Gly Pro
            820                 825                 830

Arg Val Ser Met Leu Pro Ser Gly Val Gly Pro Glu Tyr Ala Glu Arg
        835                 840                 845

Pro Glu Val Ala Arg Arg Asp Ser Ala Pro Thr Glu Asn Arg Leu Ala
    850                 855                 860

Lys Ser Asp Val Pro Ile Gln Leu Leu Ser Ala Thr Asn Gln Phe Gln
865                 870                 875                 880

Arg Gln Ala Ala Val Gln Gln Gln Ile Pro Thr Lys Leu Ala Ala Ser
                885                 890                 895

Thr Lys Gly Gly Lys Asp Lys Gly Gly Lys Ser Arg Gly Ser Gln Arg
            900                 905                 910

Trp Glu Ser Ser Ala Ser Phe Asp Leu Lys Gln Gln Leu Leu Leu Asn
        915                 920                 925

Lys Leu Met Gly Lys Asp Glu Ser Thr Ser Arg Asn Arg Arg Ser Leu
    930                 935                 940

Ser Pro Ile Leu Pro Gly Arg His Ser Pro Ala Pro Pro Pro Asp Pro
945                 950                 955                 960

Gly Phe Pro Ala Pro Ser Pro Pro Pro Ala Asp Ser Pro Ser Glu Gly
                965                 970                 975

Phe Ser Leu Lys Ala Gly Gly Thr Ala Leu Leu Pro Gly Pro Pro Ala
            980                 985                 990

Pro Ser Pro Leu Pro Ala Arg Trp  Arg Arg Gln His Leu  Ser Pro Glu
        995                 1000                1005
```

```
Ser Gly  Arg Ile His Phe Pro  Asn Arg Ala Pro Arg  Arg Phe Thr
    1010                 1015                 1020

Met Asn  Leu Arg Val Arg Glu
    1025                 1030


<210> SEQ ID NO 16
<211> LENGTH: 828
<212> TYPE: PRT
<213> ORGANISM: Homo sapiens
<220> FEATURE:
<221> NAME/KEY: misc_feature
<222> LOCATION: (102)..(102)
<223> OTHER INFORMATION: Phosphorylation site

<400> SEQUENCE: 16

Met Asp Ser Glu Ala Phe Gln Ser Ala Arg Asp Phe Leu Asp Met Asn
1               5                   10                  15

Phe Gln Ser Leu Ala Met Lys His Met Asp Leu Lys Gln Met Glu Leu
            20                  25                  30

Asp Thr Ala Ala Ala Lys Val Asp Glu Leu Thr Lys Gln Leu Glu Ser
        35                  40                  45

Leu Trp Ser Asp Ser Pro Ala Pro Pro Gly Pro Gln Ala Gly Pro Pro
    50                  55                  60

Ser Arg Pro Pro Arg Tyr Ser Ser Ser Ser Ile Pro Glu Pro Phe Gly
65                  70                  75                  80

Ser Arg Gly Ser Pro Arg Lys Ala Ala Thr Asp Gly Ala Asp Thr Pro
                85                  90                  95

Phe Gly Arg Ser Glu Ser Ala Pro Thr Leu His Pro Tyr Ser Pro Leu
            100                 105                 110

Ser Pro Lys Gly Arg Pro Ser Ser Pro Arg Thr Pro Leu Tyr Leu Gln
        115                 120                 125

Pro Asp Ala Tyr Gly Ser Leu Asp Arg Ala Thr Ser Pro Arg Pro Arg
    130                 135                 140

Ala Phe Asp Gly Ala Gly Ser Ser Leu Gly Arg Ala Pro Ser Pro Arg
145                 150                 155                 160

Pro Gly Pro Gly Pro Leu Arg Gln Gln Gly Pro Pro Thr Pro Phe Asp
                165                 170                 175

Phe Leu Gly Arg Ala Gly Ser Pro Arg Gly Ser Pro Leu Ala Glu Gly
            180                 185                 190

Pro Gln Ala Phe Phe Pro Glu Arg Gly Pro Ser Pro Arg Pro Pro Ala
        195                 200                 205

Thr Ala Tyr Asp Ala Pro Ala Ser Ala Phe Gly Ser Ser Leu Leu Gly
    210                 215                 220

Ser Gly Gly Ser Ala Phe Ala Pro Pro Leu Arg Ala Gln Asp Asp Leu
225                 230                 235                 240

Thr Leu Arg Arg Arg Pro Pro Lys Ala Trp Asn Glu Ser Asp Leu Asp
                245                 250                 255

Val Ala Tyr Glu Lys Lys Pro Ser Gln Thr Ala Ser Tyr Glu Arg Leu
            260                 265                 270

Asp Val Phe Ala Arg Pro Ala Ser Pro Ser Leu Gln Leu Leu Pro Trp
        275                 280                 285

Arg Glu Ser Ser Leu Asp Gly Leu Gly Gly Thr Gly Lys Asp Asn Leu
    290                 295                 300

Thr Ser Ala Thr Leu Pro Arg Asn Tyr Lys Val Ser Pro Leu Ala Ser
305                 310                 315                 320

Asp Arg Arg Ser Asp Ala Gly Ser Tyr Arg Arg Ser Leu Gly Ser Ala
```

-continued

```
                325                 330                 335

Gly Pro Ser Gly Thr Leu Pro Arg Ser Trp Gln Pro Val Ser Arg Ile
            340                 345                 350

Pro Met Pro Pro Ser Ser Pro Gln Pro Arg Gly Ala Pro Arg Gln Arg
        355                 360                 365

Pro Ile Pro Leu Ser Met Ile Phe Lys Leu Gln Asn Ala Phe Trp Glu
    370                 375                 380

His Gly Ala Ser Arg Ala Met Leu Pro Gly Ser Pro Leu Phe Thr Arg
385                 390                 395                 400

Ala Pro Pro Pro Lys Leu Gln Pro Gln Pro Gln Pro Gln Pro Gln Pro
                405                 410                 415

Gln Ser Gln Pro Gln Pro Gln Leu Pro Pro Gln Pro Gln Thr Gln Pro
            420                 425                 430

Gln Thr Pro Thr Pro Ala Pro Gln His Pro Gln Gln Thr Trp Pro Pro
        435                 440                 445

Val Asn Glu Gly Pro Pro Lys Pro Pro Thr Glu Leu Glu Pro Glu Pro
    450                 455                 460

Glu Ile Glu Gly Leu Leu Thr Pro Val Leu Glu Ala Gly Asp Val Asp
465                 470                 475                 480

Glu Gly Pro Val Ala Arg Pro Leu Ser Pro Thr Arg Leu Gln Pro Ala
                485                 490                 495

Leu Pro Pro Glu Ala Gln Ser Val Pro Glu Leu Glu Glu Val Ala Arg
            500                 505                 510

Val Leu Ala Glu Ile Pro Arg Pro Leu Lys Arg Arg Gly Ser Met Glu
        515                 520                 525

Gln Ala Pro Ala Val Ala Leu Pro Pro Thr His Lys Lys Gln Tyr Gln
    530                 535                 540

Gln Ile Ile Ser Arg Leu Phe His Arg His Gly Gly Pro Gly Pro Gly
545                 550                 555                 560

Gly Pro Glu Pro Glu Leu Ser Pro Ile Thr Glu Gly Ser Glu Ala Arg
                565                 570                 575

Ala Gly Pro Pro Ala Pro Ala Pro Pro Ala Pro Ile Pro Pro Pro Ala
            580                 585                 590

Pro Ser Gln Ser Ser Pro Pro Glu Gln Pro Gln Ser Met Glu Met Arg
        595                 600                 605

Ser Val Leu Arg Lys Ala Gly Ser Pro Arg Lys Ala Arg Arg Ala Arg
    610                 615                 620

Leu Asn Pro Leu Val Leu Leu Leu Asp Ala Ala Leu Thr Gly Glu Leu
625                 630                 635                 640

Glu Val Val Gln Gln Ala Val Lys Glu Met Asn Asp Pro Ser Gln Pro
                645                 650                 655

Asn Glu Glu Gly Ile Thr Ala Leu His Asn Ala Ile Cys Gly Ala Asn
            660                 665                 670

Tyr Ser Ile Val Asp Phe Leu Ile Thr Ala Gly Ala Asn Val Asn Ser
        675                 680                 685

Pro Asp Ser His Gly Trp Thr Pro Leu His Cys Ala Ala Ser Cys Asn
    690                 695                 700

Asp Thr Val Ile Cys Met Ala Leu Val Gln His Gly Ala Ala Ile Phe
705                 710                 715                 720

Ala Thr Thr Leu Ser Asp Gly Ala Thr Ala Phe Glu Lys Cys Asp Pro
                725                 730                 735

Tyr Arg Glu Gly Tyr Ala Asp Cys Ala Thr Tyr Leu Ala Asp Val Glu
            740                 745                 750
```

```
Gln Ser Met Gly Leu Met Asn Ser Gly Ala Val Tyr Ala Leu Trp Asp
        755                 760                 765

Tyr Ser Ala Glu Phe Gly Asp Glu Leu Ser Phe Arg Glu Gly Glu Ser
    770                 775                 780

Val Thr Val Leu Arg Arg Asp Gly Pro Glu Glu Thr Asp Trp Trp Trp
785                 790                 795                 800

Ala Ala Leu His Gly Gln Glu Gly Tyr Val Pro Arg Asn Tyr Phe Gly
                805                 810                 815

Leu Phe Pro Arg Val Lys Pro Gln Arg Ser Lys Val
            820                 825


<210> SEQ ID NO 17
<211> LENGTH: 607
<212> TYPE: PRT
<213> ORGANISM: Homo sapiens
<220> FEATURE:
<221> NAME/KEY: misc_feature
<222> LOCATION: (269)..(269)
<223> OTHER INFORMATION: Phosphorylation site

<400> SEQUENCE: 17

Met Ser Ser Gly Leu Arg Ala Ala Asp Phe Pro Arg Trp Lys Arg His
1               5                   10                  15

Ile Ser Glu Gln Leu Arg Arg Arg Asp Arg Leu Gln Arg Gln Ala Phe
            20                  25                  30

Glu Glu Ile Ile Leu Gln Tyr Asn Lys Leu Leu Glu Lys Ser Asp Leu
        35                  40                  45

His Ser Val Leu Ala Gln Lys Leu Gln Ala Glu Lys His Asp Val Pro
    50                  55                  60

Asn Arg His Glu Ile Ser Pro Gly His Asp Gly Thr Trp Asn Asp Asn
65                  70                  75                  80

Gln Leu Gln Glu Met Ala Gln Leu Arg Ile Lys His Gln Glu Glu Leu
                85                  90                  95

Thr Glu Leu His Lys Lys Arg Gly Glu Leu Ala Gln Leu Val Ile Asp
            100                 105                 110

Leu Asn Asn Gln Met Gln Arg Lys Asp Arg Glu Met Gln Met Asn Glu
        115                 120                 125

Ala Lys Ile Ala Glu Cys Leu Gln Thr Ile Ser Asp Leu Glu Thr Glu
    130                 135                 140

Cys Leu Asp Leu Arg Thr Lys Leu Cys Asp Leu Glu Arg Ala Asn Gln
145                 150                 155                 160

Thr Leu Lys Asp Glu Tyr Asp Ala Leu Gln Ile Thr Phe Thr Ala Leu
                165                 170                 175

Glu Gly Lys Leu Arg Lys Thr Thr Glu Glu Asn Gln Glu Leu Val Thr
            180                 185                 190

Arg Trp Met Ala Glu Lys Ala Gln Glu Ala Asn Arg Leu Asn Ala Glu
        195                 200                 205

Asn Glu Lys Asp Ser Arg Arg Arg Gln Ala Arg Leu Gln Lys Glu Leu
    210                 215                 220

Ala Glu Ala Ala Lys Glu Pro Leu Pro Val Glu Gln Asp Asp Asp Ile
225                 230                 235                 240

Glu Val Ile Val Asp Glu Thr Ser Asp His Thr Glu Glu Thr Ser Pro
                245                 250                 255

Val Arg Ala Ile Ser Arg Ala Ala Thr Lys Arg Leu Ser Gln Pro Ala
            260                 265                 270
```

```
Gly Gly Leu Leu Asp Ser Ile Thr Asn Ile Phe Gly Arg Arg Ser Val
        275                 280                 285

Ser Ser Phe Pro Val Pro Gln Asp Asn Val Asp Thr His Pro Gly Ser
    290                 295                 300

Gly Lys Glu Val Arg Val Pro Ala Thr Ala Leu Cys Val Phe Asp Ala
305                 310                 315                 320

His Asp Gly Glu Val Asn Ala Val Gln Phe Ser Pro Gly Ser Arg Leu
                325                 330                 335

Leu Ala Thr Gly Gly Met Asp Arg Arg Val Lys Leu Trp Glu Val Phe
            340                 345                 350

Gly Glu Lys Cys Glu Phe Lys Gly Ser Leu Ser Gly Ser Asn Ala Gly
        355                 360                 365

Ile Thr Ser Ile Glu Phe Asp Ser Ala Gly Ser Tyr Leu Leu Ala Ala
    370                 375                 380

Ser Asn Asp Phe Ala Ser Arg Ile Trp Thr Val Asp Asp Tyr Arg Leu
385                 390                 395                 400

Arg His Thr Leu Thr Gly His Ser Gly Lys Val Leu Ser Ala Lys Phe
                405                 410                 415

Leu Leu Asp Asn Ala Arg Ile Val Ser Gly Ser His Asp Arg Thr Leu
            420                 425                 430

Lys Leu Trp Asp Leu Arg Ser Lys Val Cys Ile Lys Thr Val Phe Ala
        435                 440                 445

Gly Ser Ser Cys Asn Asp Ile Val Cys Thr Glu Gln Cys Val Met Ser
    450                 455                 460

Gly His Phe Asp Lys Lys Ile Arg Phe Trp Asp Ile Arg Ser Glu Ser
465                 470                 475                 480

Ile Val Arg Glu Met Glu Leu Leu Gly Lys Ile Thr Ala Leu Asp Leu
                485                 490                 495

Asn Pro Glu Arg Thr Glu Leu Leu Ser Cys Ser Arg Asp Asp Leu Leu
            500                 505                 510

Lys Val Ile Asp Leu Arg Thr Asn Ala Ile Lys Gln Thr Phe Ser Ala
        515                 520                 525

Pro Gly Phe Lys Cys Gly Ser Asp Trp Thr Arg Val Val Phe Ser Pro
    530                 535                 540

Asp Gly Ser Tyr Val Ala Ala Gly Ser Ala Glu Gly Ser Leu Tyr Ile
545                 550                 555                 560

Trp Ser Val Leu Thr Gly Lys Val Glu Lys Val Leu Ser Lys Gln His
                565                 570                 575

Ser Ser Ser Ile Asn Ala Val Ala Trp Ser Pro Ser Gly Ser His Val
            580                 585                 590

Val Ser Val Asp Lys Gly Cys Lys Ala Val Leu Trp Ala Gln Tyr
        595                 600                 605
```

<210> SEQ ID NO 18
<211> LENGTH: 470
<212> TYPE: PRT
<213> ORGANISM: Homo sapiens
<220> FEATURE:
<221> NAME/KEY: misc_feature
<222> LOCATION: (269)..(269)
<223> OTHER INFORMATION: Phosphorylation site

<400> SEQUENCE: 18

```
Met Ser Ser Gly Leu Arg Ala Ala Asp Phe Pro Arg Trp Lys Arg His
1               5                   10                  15

Ile Ser Glu Gln Leu Arg Arg Arg Asp Arg Leu Gln Arg Gln Ala Phe
```

-continued

```
            20                  25                  30

Glu Glu Ile Ile Leu Gln Tyr Asn Lys Leu Leu Glu Lys Ser Asp Leu
        35                  40                  45

His Ser Val Leu Ala Gln Lys Leu Gln Ala Glu Lys His Asp Val Pro
    50                  55                  60

Asn Arg His Glu Ile Ser Pro Gly His Asp Gly Thr Trp Asn Asp Asn
65                  70                  75                  80

Gln Leu Gln Glu Met Ala Gln Leu Arg Ile Lys His Gln Glu Glu Leu
                85                  90                  95

Thr Glu Leu His Lys Lys Arg Gly Glu Leu Ala Gln Leu Val Ile Asp
            100                 105                 110

Leu Asn Asn Gln Met Gln Arg Lys Asp Arg Glu Met Gln Met Asn Glu
        115                 120                 125

Ala Lys Ile Ala Glu Cys Leu Gln Thr Ile Ser Asp Leu Glu Thr Glu
    130                 135                 140

Cys Leu Asp Leu Arg Thr Lys Leu Cys Asp Leu Glu Arg Ala Asn Gln
145                 150                 155                 160

Thr Leu Lys Asp Glu Tyr Asp Ala Leu Gln Ile Thr Phe Thr Ala Leu
                165                 170                 175

Glu Gly Lys Leu Arg Lys Thr Thr Glu Glu Asn Gln Glu Leu Val Thr
            180                 185                 190

Arg Trp Met Ala Glu Lys Ala Gln Glu Ala Asn Arg Leu Asn Ala Glu
        195                 200                 205

Asn Glu Lys Asp Ser Arg Arg Arg Gln Ala Arg Leu Gln Lys Glu Leu
    210                 215                 220

Ala Glu Ala Ala Lys Glu Pro Leu Pro Val Glu Gln Asp Asp Asp Ile
225                 230                 235                 240

Glu Val Ile Val Asp Glu Thr Ser Asp His Thr Glu Glu Thr Ser Pro
                245                 250                 255

Val Arg Ala Ile Ser Arg Ala Ala Thr Lys Arg Leu Ser Gln Pro Ala
            260                 265                 270

Gly Gly Leu Leu Asp Ser Ile Thr Asn Ile Phe Gly Arg Arg Ser Val
        275                 280                 285

Ser Ser Phe Pro Val Pro Gln Asp Asn Val Asp Thr His Pro Gly Ser
    290                 295                 300

Gly Lys Glu Val Arg Val Pro Ala Thr Ala Leu Cys Val Phe Asp Ala
305                 310                 315                 320

His Asp Gly Glu Val Asn Ala Val Gln Phe Ser Pro Gly Ser Arg Leu
                325                 330                 335

Leu Ala Thr Gly Gly Met Asp Arg Arg Val Lys Leu Trp Glu Val Phe
            340                 345                 350

Gly Glu Lys Cys Glu Phe Lys Gly Ser Leu Ser Gly Ser Asn Ala Gly
        355                 360                 365

Ile Thr Ser Ile Glu Phe Asp Ser Ala Gly Ser Tyr Leu Leu Ala Ala
    370                 375                 380

Ser Asn Asp Phe Ala Ser Arg Ile Trp Thr Val Asp Asp Tyr Arg Leu
385                 390                 395                 400

Arg His Thr Leu Thr Gly His Ser Gly Lys Val Leu Ser Ala Lys Phe
                405                 410                 415

Leu Leu Asp Asn Ala Arg Ile Val Ser Gly Ser His Asp Arg Thr Leu
            420                 425                 430

Lys Leu Trp Asp Leu Arg Ser Lys Val Cys Glu Glu Ile Gln Ser Leu
        435                 440                 445
```

```
Cys Leu Cys Ile Cys Leu Asp Val Ser Val Glu Val Cys Val Cys Thr
    450                 455                 460

Ser Glu Pro Ala Phe Met
465                 470


<210> SEQ ID NO 19
<211> LENGTH: 428
<212> TYPE: PRT
<213> ORGANISM: Homo sapiens
<220> FEATURE:
<221> NAME/KEY: misc_feature
<222> LOCATION: (125)..(125)
<223> OTHER INFORMATION: Phosphorylation site

<400> SEQUENCE: 19

Met Ser Ser Gly Leu Arg Ala Ala Asp Phe Pro Arg Trp Lys Arg His
1               5                   10                  15

Ile Ser Glu Gln Leu Arg Arg Arg Asp Arg Leu Gln Arg Gln Ala Phe
            20                  25                  30

Glu Glu Ile Ile Leu Gln Tyr Asn Lys Leu Leu Glu Lys Ser Asp Leu
        35                  40                  45

His Ser Val Leu Ala Gln Lys Leu Gln Ala Glu Lys His Asp Val Pro
    50                  55                  60

Asn Arg His Glu Ile Arg Arg Arg Gln Ala Arg Leu Gln Lys Glu Leu
65                  70                  75                  80

Ala Glu Ala Ala Lys Glu Pro Leu Pro Val Glu Gln Asp Asp Asp Ile
                85                  90                  95

Glu Val Ile Val Asp Glu Thr Ser Asp His Thr Glu Glu Thr Ser Pro
            100                 105                 110

Val Arg Ala Ile Ser Arg Ala Ala Thr Lys Arg Leu Ser Gln Pro Ala
        115                 120                 125

Gly Gly Leu Leu Asp Ser Ile Thr Asn Ile Phe Gly Arg Arg Ser Val
    130                 135                 140

Ser Ser Phe Pro Val Pro Gln Asp Asn Val Asp Thr His Pro Gly Ser
145                 150                 155                 160

Gly Lys Glu Val Arg Val Pro Ala Thr Ala Leu Cys Val Phe Asp Ala
                165                 170                 175

His Asp Gly Glu Val Asn Ala Val Gln Phe Ser Pro Gly Ile Thr Ser
            180                 185                 190

Ile Glu Phe Asp Ser Ala Gly Ser Tyr Leu Leu Ala Ala Ser Asn Asp
        195                 200                 205

Phe Ala Ser Arg Ile Trp Thr Val Asp Asp Tyr Arg Leu Arg His Thr
    210                 215                 220

Leu Thr Gly His Ser Gly Lys Val Leu Ser Ala Lys Phe Leu Leu Asp
225                 230                 235                 240

Asn Ala Arg Ile Val Ser Gly Ser His Asp Arg Thr Leu Lys Leu Trp
                245                 250                 255

Asp Leu Arg Ser Lys Val Cys Ile Lys Thr Val Phe Ala Gly Ser Ser
            260                 265                 270

Cys Asn Asp Ile Val Cys Thr Glu Gln Cys Val Met Ser Gly His Phe
        275                 280                 285

Asp Lys Lys Ile Arg Phe Trp Asp Ile Arg Ser Glu Ser Ile Val Arg
    290                 295                 300

Glu Met Glu Leu Leu Gly Lys Ile Thr Ala Leu Asp Leu Asn Pro Glu
305                 310                 315                 320
```

-continued

```
Arg Thr Glu Leu Leu Ser Cys Ser Arg Asp Asp Leu Leu Lys Val Ile
                325                 330                 335

Asp Leu Arg Thr Asn Ala Ile Lys Gln Thr Phe Ser Ala Pro Gly Phe
            340                 345                 350

Lys Cys Gly Ser Asp Trp Thr Arg Val Val Phe Ser Pro Asp Gly Ser
        355                 360                 365

Tyr Val Ala Ala Gly Ser Ala Glu Gly Ser Leu Tyr Ile Trp Ser Val
    370                 375                 380

Leu Thr Gly Lys Val Glu Lys Val Leu Ser Lys Gln His Ser Ser Ser
385                 390                 395                 400

Ile Asn Ala Val Ala Trp Ser Pro Ser Gly Ser His Val Val Ser Val
                405                 410                 415

Asp Lys Gly Cys Lys Ala Val Leu Trp Ala Gln Tyr
            420                 425


<210> SEQ ID NO 20
<211> LENGTH: 206
<212> TYPE: PRT
<213> ORGANISM: Homo sapiens
<220> FEATURE:
<221> NAME/KEY: misc_feature
<222> LOCATION: (161)..(161)
<223> OTHER INFORMATION: Phosphorylation site

<400> SEQUENCE: 20

Met Asp Ser Ala Gly Gln Asp Ile Asn Leu Asn Ser Pro Asn Lys Gly
1               5                   10                  15

Leu Leu Ser Asp Ser Met Thr Asp Val Pro Val Asp Thr Gly Val Ala
            20                  25                  30

Ala Arg Thr Pro Ala Val Glu Gly Leu Thr Glu Ala Glu Glu Glu Glu
        35                  40                  45

Leu Arg Ala Glu Leu Thr Lys Val Glu Glu Glu Ile Val Thr Leu Arg
    50                  55                  60

Gln Val Leu Ala Ala Lys Glu Arg His Cys Gly Glu Leu Lys Arg Arg
65                  70                  75                  80

Leu Gly Leu Ser Thr Leu Gly Glu Leu Lys Gln Asn Leu Ser Arg Ser
                85                  90                  95

Trp His Asp Val Gln Val Ser Ser Ala Tyr Val Lys Thr Ser Glu Lys
            100                 105                 110

Leu Gly Glu Trp Asn Glu Lys Val Thr Gln Ser Asp Leu Tyr Lys Lys
        115                 120                 125

Thr Gln Glu Thr Leu Ser Gln Ala Gly Gln Lys Thr Ser Ala Ala Leu
    130                 135                 140

Ser Thr Val Gly Ser Ala Ile Ser Arg Lys Leu Gly Asp Met Arg Asn
145                 150                 155                 160

Ser Ala Thr Phe Lys Ser Phe Glu Asp Arg Val Gly Thr Ile Lys Ser
                165                 170                 175

Lys Val Val Gly Asp Arg Glu Asn Gly Ser Asp Asn Leu Pro Ser Ser
            180                 185                 190

Ala Gly Ser Gly Asp Lys Pro Leu Ser Asp Pro Ala Pro Phe
        195                 200                 205


<210> SEQ ID NO 21
<211> LENGTH: 186
<212> TYPE: PRT
<213> ORGANISM: Homo sapiens
<220> FEATURE:
<221> NAME/KEY: misc_feature
```

<222> LOCATION: (141)..(141)
<223> OTHER INFORMATION: Phosphorylation site

<400> SEQUENCE: 21

```
Met Asp Ser Ala Gly Gln Asp Ile Asn Leu Asn Ser Pro Asn Lys Gly
1               5                   10                  15

Leu Leu Ser Asp Ser Met Thr Asp Val Pro Val Asp Thr Gly Val Ala
            20                  25                  30

Ala Arg Thr Pro Ala Val Glu Gly Leu Thr Glu Ala Glu Glu Glu Glu
        35                  40                  45

Leu Arg Ala Glu Leu Thr Lys Val Glu Glu Glu Ile Val Thr Leu Arg
    50                  55                  60

Gln Val Leu Ala Ala Lys Glu Arg His Cys Gly Glu Leu Lys Arg Arg
65                  70                  75                  80

Leu Gly Leu Ser Thr Leu Gly Glu Leu Lys Gln Asn Leu Ser Arg Ser
                85                  90                  95

Trp His Asp Val Gln Val Ser Ser Ala Tyr Lys Lys Thr Gln Glu Thr
            100                 105                 110

Leu Ser Gln Ala Gly Gln Lys Thr Ser Ala Ala Leu Ser Thr Val Gly
        115                 120                 125

Ser Ala Ile Ser Arg Lys Leu Gly Asp Met Arg Asn Ser Ala Thr Phe
    130                 135                 140

Lys Ser Phe Glu Asp Arg Val Gly Thr Ile Lys Ser Lys Val Val Gly
145                 150                 155                 160

Asp Arg Glu Asn Gly Ser Asp Asn Leu Pro Ser Ser Ala Gly Ser Gly
                165                 170                 175

Asp Lys Pro Leu Ser Asp Pro Ala Pro Phe
            180                 185
```

<210> SEQ ID NO 22
<211> LENGTH: 14
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: Phosphorylated-Ser

<400> SEQUENCE: 22

```
Asp Tyr Ser Thr Leu Thr Ser Val Ser Ser His Asp Ser Arg
1               5                   10
```

<210> SEQ ID NO 23
<211> LENGTH: 12
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Phosphorylated-Ser

<400> SEQUENCE: 23

```
Ser Met Ser Ser Ala Asp Val Glu Val Ala Arg Phe
1               5                   10
```

<210> SEQ ID NO 24
<211> LENGTH: 14
<212> TYPE: PRT
<213> ORGANISM: Homo sapiens
<220> FEATURE:
<221> NAME/KEY: MOD_RES
<222> LOCATION: (11)..(11)

<223> OTHER INFORMATION: Phosphorylated-Ser

<400> SEQUENCE: 24

Met Asp Phe Ala Phe Pro Gly Ser Thr Asn Ser Leu His Arg
1 5 10

<210> SEQ ID NO 25
<211> LENGTH: 14
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Thr

<400> SEQUENCE: 25

Met Asp Phe Ala Phe Pro Gly Ser Thr Asn Ser Leu His Arg
1 5 10

<210> SEQ ID NO 26
<211> LENGTH: 14
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: Phosphorylated-Ser

<400> SEQUENCE: 26

Leu Leu Glu Leu Gln Glu Val Asp Ser Leu Leu Arg Gly Arg
1 5 10

<210> SEQ ID NO 27
<211> LENGTH: 14
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: Phosphorylated-Ser

<400> SEQUENCE: 27

Ala His Ala Trp Pro Ser Pro Tyr Lys Asp Tyr Glu Val Lys
1 5 10

<210> SEQ ID NO 28
<211> LENGTH: 16
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Phosphorylated-Ser

<400> SEQUENCE: 28

Ser Ile Gln Gly Val Gly His Met Met Ser Thr Met Val Leu Ser Arg
1 5 10 15

<210> SEQ ID NO 29
<211> LENGTH: 16
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Ser

<400> SEQUENCE: 29

Arg Phe Ser Glu Gly Val Leu Gln Ser Pro Ser Gln Asp Gln Glu Lys
1 5 10 15

<210> SEQ ID NO 30
<211> LENGTH: 9
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Phosphorylated-Ser

<400> SEQUENCE: 30

Ser Leu Ser Pro Ile Leu Pro Gly Arg
1 5

<210> SEQ ID NO 31
<211> LENGTH: 16
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Ser

<400> SEQUENCE: 31

Ser Glu Ser Ala Pro Thr Leu His Pro Tyr Ser Pro Leu Ser Pro Lys
1 5 10 15

<210> SEQ ID NO 32
<211> LENGTH: 19
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Phosphorylated-Ser

<400> SEQUENCE: 32

Arg Leu Ser Gln Pro Ala Gly Gly Leu Leu Asp Ser Ile Thr Asn Ile
1 5 10 15

Phe Gly Arg

<210> SEQ ID NO 33
<211> LENGTH: 12
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Phosphorylated-Ser

<400> SEQUENCE: 33

Phe Leu Gly Asp Met Arg Asn Ser Ala Thr Phe Lys
1 5 10

<210> SEQ ID NO 34
<211> LENGTH: 13
<212> TYPE: PRT
<213> ORGANISM: Homo sapiens

<400> SEQUENCE: 34

Phe Asn Ala Asp Glu Phe Glu Asp Met Val Ala Glu Lys
1 5 10

<210> SEQ ID NO 35
<211> LENGTH: 18

<212> TYPE: PRT
<213> ORGANISM: Homo sapiens

<400> SEQUENCE: 35

Phe Thr Pro Gly Thr Phe Thr Asn Gln Ile Gln Ala Ala Phe Arg Glu
1 5 10 15

Pro Arg

<210> SEQ ID NO 36
<211> LENGTH: 9
<212> TYPE: PRT
<213> ORGANISM: Homo sapiens

<400> SEQUENCE: 36

His Gly Ser Leu Gly Phe Leu Pro Arg
1 5

<210> SEQ ID NO 37
<211> LENGTH: 9
<212> TYPE: PRT
<213> ORGANISM: Homo sapiens

<400> SEQUENCE: 37

His Met Tyr His Ser Leu Tyr Leu Lys
1 5

<210> SEQ ID NO 38
<211> LENGTH: 16
<212> TYPE: PRT
<213> ORGANISM: Homo sapiens

<400> SEQUENCE: 38

Ile Leu Asp Ser Val Gly Ile Glu Ala Asp Asp Asp Arg Leu Asn Lys
1 5 10 15

<210> SEQ ID NO 39
<211> LENGTH: 12
<212> TYPE: PRT
<213> ORGANISM: Homo sapiens

<400> SEQUENCE: 39

Asn Ile Glu Asp Val Ile Ala Gln Gly Ile Gly Lys
1 5 10

<210> SEQ ID NO 40
<211> LENGTH: 15
<212> TYPE: PRT
<213> ORGANISM: Homo sapiens

<400> SEQUENCE: 40

Thr Ile Ala Glu Cys Leu Ala Asp Glu Leu Ile Asn Ala Ala Lys
1 5 10 15

<210> SEQ ID NO 41
<211> LENGTH: 16
<212> TYPE: PRT
<213> ORGANISM: Homo sapiens

<400> SEQUENCE: 41

Val Cys Thr Leu Ala Ile Ile Asp Pro Gly Asp Ser Asp Ile Ile Arg
1 5 10 15